United States Patent
Lee et al.

(10) Patent No.: US 10,975,390 B2
(45) Date of Patent: *Apr. 13, 2021

(54) TARGETED MODIFICATION OF RAT GENOME

(71) Applicant: Regeneron Pharmaceuticals, Inc., Tarrytown, NY (US)

(72) Inventors: Jeffrey D. Lee, New York, NY (US); Alexander O. Mujica, Elmsford, NY (US); Wojtek Auerbach, Ridgewood, NJ (US); Ka-Man Venus Lai, Seattle, WA (US); David M. Valenzuela, Yorktown Heights, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/451,859

(22) Filed: Jun. 25, 2019

(65) Prior Publication Data

US 2019/0323032 A1    Oct. 24, 2019

Related U.S. Application Data

(60) Continuation of application No. 15/410,252, filed on Jan. 19, 2017, now Pat. No. 10,385,359, which is a division of application No. 14/254,715, filed on Apr. 16, 2014, now abandoned.

(60) Provisional application No. 61/812,319, filed on Apr. 16, 2013, provisional application No. 61/914,768, filed on Dec. 11, 2013.

(51) Int. Cl.
| | | |
|---|---|---|
| *C12N 15/85* | (2006.01) |
| *A61D 19/04* | (2006.01) |
| *A01K 67/027* | (2006.01) |
| *C07K 14/715* | (2006.01) |
| *C07K 14/775* | (2006.01) |
| *C12N 15/90* | (2006.01) |

(52) U.S. Cl.
CPC ...... *C12N 15/8509* (2013.01); *A01K 67/0276* (2013.01); *A01K 67/0278* (2013.01); *A61D 19/04* (2013.01); *C07K 14/7155* (2013.01); *C07K 14/775* (2013.01); *C12N 15/907* (2013.01); *A01K 2217/07* (2013.01); *A01K 2227/105* (2013.01); *A01K 2267/0362* (2013.01); *A01K 2267/0381* (2013.01); *C12N 2015/8527* (2013.01); *C12N 2800/30* (2013.01); *C12N 2810/00* (2013.01)

(58) Field of Classification Search
CPC .............. C12N 15/8509; C12N 15/907; C12N 2800/30; C12N 2015/8527; C12N 2810/00; A01K 67/0276; A01K 67/0278; A01K 2267/0362; A01K 2267/0381; A01K 2217/07; A01K 2227/105; C07K 14/7155; C07K 14/775; A61D 19/04

See application file for complete search history.

(56) References Cited

U.S. PATENT DOCUMENTS

| | | | |
|---|---|---|---|
| 6,136,566 A | 10/2000 | Sands et al. |
| 6,372,956 B1 | 4/2002 | Goldsmith et al. |
| 6,566,579 B1 | 5/2003 | Jaisser et al. |
| 7,294,754 B2 | 11/2007 | Poueymirou et al. |
| 7,771,967 B2 | 8/2010 | Huang et al. |
| 8,338,179 B2 | 12/2012 | Enenkel et al. |
| 8,502,018 B2 | 8/2013 | Murphy et al. |
| 8,558,055 B2 | 10/2013 | Ostertag et al. |
| 8,628,957 B2 | 1/2014 | Teratani et al. |
| 8,697,359 B1 | 4/2014 | Zhang |
| 8,703,485 B2 | 4/2014 | Buelow |
| 8,722,964 B2 | 5/2014 | Ostertag et al. |
| 8,907,157 B2 | 12/2014 | Buelow |
| 8,921,332 B2 | 12/2014 | Choulika et al. |
| 9,228,208 B2 | 1/2016 | Frendewey et al. |

(Continued)

FOREIGN PATENT DOCUMENTS

| | | |
|---|---|---|
| EP | 1 726 640 A1 | 11/2005 |
| EP | 2336329 A1 | 6/2011 |

(Continued)

OTHER PUBLICATIONS

Zhang et al., "The CRISPR/Cas9 system produces specific and homozygous targeted gene editing in rice in one generation," Plant Biotechnol. J., vol. 12(6), pp. 797-807, May 23, 2014.

(Continued)

*Primary Examiner* — Thaian N. Ton
(74) *Attorney, Agent, or Firm* — Elysa Goldberg; Yongjin Choi; Alston & Bird LLP

(57) ABSTRACT

Compositions and methods are provided for modifying a rat genomic locus of interest using a large targeting vector (LTVEC) comprising various endogenous or exogenous nucleic acid sequences as described herein. Compositions and methods for generating a genetically modified rat comprising one or more targeted genetic modifications in their germline are also provided. Compositions and methods are provided which comprise a genetically modified rat or rat cell comprising a targeted genetic modification in the rat interleukin-2 receptor gamma locus, the rat ApoE locus, the rat Rag2 locus, the rat Rag1 locus and/or the rat Rag2/Rag1 locus. The various methods and compositions provided herein allows for these modified loci to be transmitted through the germline.

46 Claims, 43 Drawing Sheets
(27 of 43 Drawing Sheet(s) Filed in Color)
Specification includes a Sequence Listing.

(56) References Cited

U.S. PATENT DOCUMENTS

| | | | |
|---|---|---|---|
| 10,329,582 B2* | 6/2019 | Lee | C12N 15/8218 |
| 10,385,359 B2* | 8/2019 | Lee | C12N 15/907 |
| 2003/0134318 A1 | 7/2003 | Case et al. | |
| 2003/0175968 A1 | 9/2003 | Golic et al. | |
| 2004/0018626 A1 | 1/2004 | Murphy et al. | |
| 2004/0197317 A1 | 10/2004 | Rao et al. | |
| 2005/0144655 A1 | 6/2005 | Economides et al. | |
| 2007/0186293 A1 | 8/2007 | Teratani et al. | |
| 2008/0014638 A1 | 1/2008 | Smith et al. | |
| 2008/0066197 A1 | 3/2008 | Ying et al. | |
| 2008/0113437 A1 | 5/2008 | Joly et al. | |
| 2008/0299580 A1 | 12/2008 | DeKelver et al. | |
| 2009/0055943 A1 | 2/2009 | Economides et al. | |
| 2010/0041137 A1 | 2/2010 | Smith et al. | |
| 2010/0047805 A1 | 2/2010 | Wang | |
| 2010/0076057 A1 | 3/2010 | Sontheimer et al. | |
| 2010/0218264 A1 | 8/2010 | Cui et al. | |
| 2011/0041197 A1 | 2/2011 | Frendewey et al. | |
| 2011/0207221 A1 | 8/2011 | Cost et al. | |
| 2011/0263028 A1 | 10/2011 | Cabaniols et al. | |
| 2011/0307968 A1 | 12/2011 | Auerbach et al. | |
| 2012/0142092 A1 | 6/2012 | Teratani et al. | |
| 2012/0272349 A1 | 10/2012 | Ochiya et al. | |
| 2012/0315670 A1 | 12/2012 | Jacobson et al. | |
| 2013/0309670 A1 | 11/2013 | Frendewey et al. | |
| 2014/0068797 A1 | 3/2014 | Doudna et al. | |
| 2014/0179770 A1 | 6/2014 | Zhang et al. | |
| 2014/0186843 A1 | 7/2014 | Zhang et al. | |
| 2014/0186958 A1 | 7/2014 | Zhang et al. | |
| 2014/0235933 A1 | 8/2014 | Lee et al. | |
| 2014/0242702 A1 | 8/2014 | Chen et al. | |
| 2014/0248702 A1 | 9/2014 | Zhang et al. | |
| 2014/0256046 A1 | 9/2014 | Zhang et al. | |
| 2014/0273037 A1 | 9/2014 | Wu | |
| 2014/0273226 A1 | 9/2014 | Wu | |
| 2014/0273231 A1 | 9/2014 | Zhang et al. | |
| 2014/0273232 A1 | 9/2014 | Zhang et al. | |
| 2014/0273233 A1 | 9/2014 | Chen et al. | |
| 2014/0273234 A1 | 9/2014 | Zhang et al. | |
| 2014/0301990 A1 | 10/2014 | Gregory et al. | |
| 2014/0309487 A1 | 10/2014 | Lee et al. | |
| 2014/0310828 A1 | 10/2014 | Lee et al. | |
| 2014/0315985 A1 | 10/2014 | May et al. | |
| 2014/0335063 A1 | 11/2014 | Cannon et al. | |
| 2014/0342456 A1 | 11/2014 | Mali et al. | |
| 2014/0342458 A1 | 11/2014 | Mali et al. | |
| 2014/0349400 A1 | 11/2014 | Jakimo et al. | |
| 2014/0359795 A1 | 12/2014 | Fahrenkrug et al. | |
| 2015/0024500 A1 | 1/2015 | Yu et al. | |
| 2015/0031132 A1 | 1/2015 | Church et al. | |
| 2015/0031133 A1 | 1/2015 | Church et al. | |
| 2015/0071889 A1 | 3/2015 | Musunuru et al. | |
| 2015/0079680 A1 | 3/2015 | Bradley et al. | |
| 2015/0110762 A1 | 4/2015 | Holmes et al. | |
| 2015/0140664 A1 | 5/2015 | Byrne et al. | |
| 2015/0152436 A1 | 6/2015 | Musunuru et al. | |
| 2015/0159174 A1 | 6/2015 | Frendewey et al. | |
| 2015/0159175 A1 | 6/2015 | Frendewey et al. | |
| 2015/0176013 A1 | 6/2015 | Musunuru et al. | |
| 2015/0184199 A1 | 7/2015 | Horwitz et al. | |
| 2015/0232881 A1 | 8/2015 | Glucksmann et al. | |
| 2015/0232883 A1 | 8/2015 | Dahlman et al. | |
| 2015/0240263 A1 | 8/2015 | Holmes et al. | |
| 2015/0252358 A1 | 9/2015 | Maeder et al. | |
| 2015/0267205 A1 | 9/2015 | Froelich et al. | |
| 2015/0283265 A1 | 10/2015 | Peyman | |
| 2015/0291965 A1 | 10/2015 | Zhang et al. | |
| 2015/0291966 A1 | 10/2015 | Zhang et al. | |
| 2015/0291969 A1 | 10/2015 | Nair et al. | |
| 2015/0368670 A1 | 12/2015 | Quake et al. | |
| 2015/0376583 A1 | 12/2015 | Quake et al. | |
| 2015/0376650 A1 | 12/2015 | Auerbach et al. | |
| 2015/0376651 A1 | 12/2015 | Frendewey et al. | |
| 2016/0017301 A1 | 1/2016 | Khalili et al. | |
| 2016/0024529 A1 | 1/2016 | Carstens | |
| 2016/0032292 A1 | 2/2016 | Storici et al. | |
| 2016/0040155 A1 | 2/2016 | Maizels et al. | |
| 2016/0046960 A1 | 2/2016 | Frendewey et al. | |
| 2016/0060637 A1 | 3/2016 | Hommelsheim et al. | |
| 2016/0060655 A1 | 3/2016 | Quake et al. | |
| 2016/0060657 A1 | 3/2016 | Frendewey et al. | |
| 2016/0074535 A1 | 3/2016 | Ranganathan et al. | |
| 2016/0090607 A1 | 3/2016 | Conway et al. | |
| 2016/0108360 A1 | 4/2016 | Lee et al. | |
| 2016/0108369 A1 | 4/2016 | Kuno et al. | |
| 2016/0122774 A1 | 5/2016 | Duchateau et al. | |
| 2016/0138045 A1 | 5/2016 | Koshland et al. | |
| 2016/0138046 A1 | 5/2016 | Wu | |
| 2016/0145646 A1 | 5/2016 | Frendewey et al. | |
| 2016/0151491 A1 | 6/2016 | Rabinovich et al. | |
| 2016/0153003 A1 | 6/2016 | Joung et al. | |
| 2016/0153004 A1 | 6/2016 | Zhang et al. | |
| 2016/0153005 A1 | 6/2016 | Zhang et al. | |
| 2016/0153006 A1 | 6/2016 | Zhang et al. | |
| 2016/0160210 A1 | 6/2016 | Mali et al. | |
| 2016/0175462 A1 | 6/2016 | Zhang et al. | |
| 2016/0177278 A1 | 6/2016 | Wolfe et al. | |
| 2016/0177339 A1 | 6/2016 | Voronina et al. | |
| 2016/0184362 A1 | 6/2016 | Duchateau et al. | |
| 2016/0186213 A1 | 6/2016 | Zhang et al. | |
| 2016/0201072 A1 | 7/2016 | Cigan et al. | |
| 2016/0208243 A1 | 7/2016 | Zhang et al. | |
| 2016/0208288 A1 | 7/2016 | Liu et al. | |
| 2016/0208319 A1 | 7/2016 | Berman et al. | |
| 2016/0215276 A1 | 7/2016 | Liu et al. | |
| 2016/0215300 A1 | 7/2016 | May et al. | |
| 2016/0250300 A1 | 9/2016 | Khalili et al. | |
| 2016/0257967 A1 | 9/2016 | Russell et al. | |
| 2016/0264995 A1 | 9/2016 | Yamamoto et al. | |
| 2016/0281111 A1 | 9/2016 | Cotta-Ramusino et al. | |
| 2017/0037429 A1 | 2/2017 | Lee et al. | |
| 2017/0204430 A1 | 7/2017 | Lee et al. | |
| 2019/0316149 A1 | 10/2019 | Lee et al. | |

FOREIGN PATENT DOCUMENTS

| | | |
|---|---|---|
| EP | 2152880 B1 | 8/2011 |
| EP | 1360287 B1 | 9/2012 |
| EP | 2508595 A1 | 10/2012 |
| EP | 2602323 A1 | 6/2013 |
| EP | 3009511 A2 | 4/2016 |
| EP | 3064585 A1 | 9/2016 |
| GB | 2 436 737 A | 10/2007 |
| WO | WO 97/30151 A1 | 8/1997 |
| WO | WO 1997/030151 A1 | 8/1997 |
| WO | WO 2002/036789 A2 | 5/2002 |
| WO | WO 2002/066630 A1 | 8/2002 |
| WO | WO 2003/087341 A2 | 10/2003 |
| WO | WO 2006/028723 A1 | 3/2006 |
| WO | WO 2006/044962 A1 | 4/2006 |
| WO | WO 2007/113505 A2 | 10/2007 |
| WO | WO 2007/117410 A2 | 10/2007 |
| WO | WO 2008/015418 A2 | 2/2008 |
| WO | WO 2008/151081 A1 | 12/2008 |
| WO | WO 2010/077955 A1 | 7/2010 |
| WO | WO 2011/020005 A1 | 2/2011 |
| WO | WO 2011/051390 A1 | 5/2011 |
| WO | WO 2011/078665 A1 | 6/2011 |
| WO | WO 2011/146121 A1 | 11/2011 |
| WO | WO 2011/154927 A2 | 12/2011 |
| WO | WO 2012/012667 A2 | 1/2012 |
| WO | WO 2012/018726 A1 | 9/2012 |
| WO | WO 2012/129198 A1 | 9/2012 |
| WO | WO 2012/168307 A2 | 12/2012 |
| WO | WO 2013/063361 A1 | 5/2013 |
| WO | WO 2013/141680 A1 | 9/2013 |
| WO | WO 2013/142578 A1 | 9/2013 |
| WO | WO 2013/163394 A1 | 10/2013 |
| WO | WO 2013/169802 A1 | 11/2013 |
| WO | WO 2013/176772 A1 | 11/2013 |
| WO | WO 2013/188522 A2 | 12/2013 |
| WO | WO 2014/018423 A2 | 1/2014 |
| WO | WO 2014/065596 A1 | 5/2014 |
| WO | WO 2014/089290 A1 | 6/2014 |

(56) References Cited

FOREIGN PATENT DOCUMENTS

| | | |
|---|---|---|
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/127287 A1 | 8/2014 |
| WO | WO 2014/130706 A1 | 8/2014 |
| WO | WO 2014/130955 A1 | 8/2014 |
| WO | WO 2014/131833 A1 | 9/2014 |
| WO | WO 2014/143381 A1 | 9/2014 |
| WO | WO 2014/150624 A1 | 9/2014 |
| WO | WO 2014/165825 A2 | 10/2014 |
| WO | WO 2014/172458 A1 | 10/2014 |
| WO | WO 2014/172470 A2 | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/186585 A2 | 11/2014 |
| WO | WO 2014/191128 A1 | 12/2014 |
| WO | WO 2014/191518 A1 | 12/2014 |
| WO | WO 2014/201015 A2 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2015/006290 A1 | 1/2015 |
| WO | WO 2015/006294 A2 | 1/2015 |
| WO | WO 2015/006498 A2 | 1/2015 |
| WO | WO 2015/010114 A1 | 1/2015 |
| WO | WO 2015/013583 A2 | 1/2015 |
| WO | WO 2015/026885 A1 | 2/2015 |
| WO | WO 2015/035139 A2 | 3/2015 |
| WO | WO 2015/035162 A2 | 3/2015 |
| WO | WO 2015/040402 A1 | 3/2015 |
| WO | WO 2015/048690 A1 | 4/2015 |
| WO | WO 2015/052231 A2 | 4/2015 |
| WO | WO 2015/057980 A1 | 4/2015 |
| WO | WO 2015/070083 A1 | 5/2015 |
| WO | WO 2015/077290 A2 | 5/2015 |
| WO | WO 2015/079057 A2 | 6/2015 |
| WO | WO 2015/086798 A2 | 6/2015 |
| WO | WO 2015/088643 A1 | 6/2015 |
| WO | WO 2015/089351 A1 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/095804 A1 | 6/2015 |
| WO | WO 2015/112790 A2 | 7/2015 |
| WO | WO 2015/116969 A2 | 8/2015 |
| WO | WO 2015/117041 A1 | 8/2015 |
| WO | WO 2015/123339 A1 | 8/2015 |
| WO | WO 2015/127439 A1 | 8/2015 |
| WO | WO 2015/138510 A1 | 9/2015 |
| WO | WO 2015/138739 A2 | 9/2015 |
| WO | WO 2015/139008 A1 | 9/2015 |
| WO | WO 2015/143046 A2 | 9/2015 |
| WO | WO 2045/134812 A1 | 9/2015 |
| WO | WO 2015/148761 A1 | 10/2015 |
| WO | WO 2015/159086 A1 | 10/2015 |
| WO | WO 2015/163733 A1 | 10/2015 |
| WO | WO 2015/166272 A2 | 11/2015 |
| WO | WO 2015/173436 A1 | 11/2015 |
| WO | WO 2015/184259 A1 | 12/2015 |
| WO | WO 2015/184262 A1 | 12/2015 |
| WO | WO 2015/184268 A1 | 12/2015 |
| WO | WO 2015/188109 A1 | 12/2015 |
| WO | WO 2015/200805 A2 | 12/2015 |
| WO | WO 2016/011210 A2 | 1/2016 |
| WO | WO 2016/011428 A1 | 1/2016 |
| WO | WO 2016/033246 A1 | 3/2016 |
| WO | WO 2016/033315 A2 | 3/2016 |
| WO | WO 2016/036754 A1 | 3/2016 |
| WO | WO 2016/037161 A2 | 3/2016 |
| WO | WO 2016/037162 A1 | 3/2016 |
| WO | WO 2016/049024 A2 | 3/2016 |
| WO | WO 2016/049163 A2 | 3/2016 |
| WO | WO 2016/049258 A2 | 3/2016 |
| WO | WO 2016/054032 A1 | 4/2016 |
| WO | WO 2016/054326 A1 | 4/2016 |
| WO | WO 2016/057821 A2 | 4/2016 |
| WO | WO 2016/057961 A1 | 4/2016 |
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO 2016/065364 A1 | 4/2016 |
| WO | WO 2016/073955 A2 | 5/2016 |
| WO | WO 2016/073990 A1 | 5/2016 |
| WO | WO 2016/081923 A2 | 5/2016 |
| WO | WO 2016/084084 A1 | 6/2016 |
| WO | WO 2016/089866 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/097751 A1 | 6/2016 |
| WO | WO 2016/100819 A1 | 6/2016 |
| WO | WO 2016/106338 A2 | 6/2016 |
| WO | WO 2015/105928 A1 | 7/2016 |
| WO | WO 2016/108926 A1 | 7/2016 |
| WO | WO 2016/112242 A1 | 7/2016 |
| WO | WO 2016/112351 A1 | 7/2016 |
| WO | WO 2016/114972 A1 | 7/2016 |
| WO | WO 2016/115326 A1 | 7/2016 |
| WO | WO 2016/130697 A1 | 8/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/142719 A1 | 9/2016 |
| WO | WO 2016/154579 A2 | 9/2016 |
| WO | WO 2016/138574 A1 | 6/2019 |

OTHER PUBLICATIONS

"Stem Cells: Scientific Progress and Future Research Directions," National Institute of Health, Department of Health and Human Services, (2001).
Abudayyeh et al., "C2c2 is a single-component programmable RNA-guided RNA-targeting CRISPR effector," Science, vol. 353(6299), Jun. 2, 2016.
Aitman et al., "Progress and prospects in rat genetics: a community view," Nature Genetics, vol. 40(5), pp. 516-522, May 2008.
Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.
Baker, M., "Gene editing at CRISPR speed," Nature Biotechnology (2014), vol. 32(4), p. 309-312.
Barrangou, "RNA-mediated programmable DNA cleavage," Nature Biotechnology, 2012, vol. 30(9), pp. 836-838.
Bassett, A.R., et al., "CRISPR/Cas9 and Genome Editing in *Drosophila*," Journal of Genetics and Genomics (2014), vol. 41, pp. 7-19.
Benders et al., "Cloning whole bacterial genomes in yeast," Nucleic Acids Res., vol. 38(8), pp. 2558-2569, Mar. 7, 2010.
Berdien, et al., "TALEN-mediated editing of endogenous T-cell receptors facilitates efficient reprogramming of T lymphocytes by lentiviral gene transfer," Gene Therapy, 21, 539-548.
Bernardini et al., "Site-specific genetic engineering of the Anopheles gambiae Y chromosome," Proc. Natl. Acad. Sci. USA, vol. 111(21), pp. 7600-7605, May 12, 2014.

(56) References Cited

OTHER PUBLICATIONS

Beumer et al., "Donor DNA Utilization During Gene Targeting with Zinc-Finger Nucleases," Genes Genomes Genetics, vol. 3, pp. 657-664, Apr. 2013.
Blair et al., "Culture parameters for stable expansion, genetic modification and germline transmission of rat pluripotent stem cells," Biol. Open, vol. 1(1): pp. 58-65, Nov. 1, 2011.
Brouns, S.J.J., "A Swiss Army Knife of Immunity," Science (2012), vol. 337, pp. 808-809.
Buehr et al., "Capture of Authentic Embryonic Stem Cells from Rat Blastocysts," Cell, vol. 135, pp. 1287-1298, 2008.
Byrne et al., "Multi-kilobase homozygous targeted gene replacement in human induced pluripotent stem cells," Nucleic Acids Research, Vo. 43(3), p. e21, 2014 (epub Nov. 20, 2014).
Carlson, et al., "Targeting DNA with Fingers TALENs," Molecular Therapy-Nucleic Acids, 2012, 1:e3.
Carroll, "Staying on target with CRISPR-Cas," Nature Biotechnolgy, 2013, vol. 31(9), pp. 807-809.
Carroll, "Zinc-Finger Nucleases as Gene Therapy Agents", Gene Ther., Nov. 15, 2008:(22):1463-1468.
Cartwright et al., "LIF/STAT3 controls ES cell self-renewal and pluripotency by a Myc-dependent mechanism," Development, vol. 132(5), pp. 885-896, 2005.
Casanova et al., "Cross-Species Genome Wide Expression Analysis during Pluripotent Cell Determination in Mouse and Rat Preimplantation Embryos," PLoS One, vol. 7(10), e47107, 2012.
Cathomen, et al., "Zinc-finger nucleases: the next generation emerges," Molecular Therapy, 208, vol. 16(7), pp. 1200-1207 (Jul. 2008).
Chang et al., "Genome editing with RNA-guided Cas9 nuclease in Zebrafish embryos," Cell Research, vol. 23, pp. 465-472, 2013. (published Mar. 2013).
Chari et al., "Unraveling CRISPR-Cas9 genome engineering parameters via a library-on-library approach," Nature Methods, vol. 12(9): 823-826 plus Supplementary Figures, Jul. 13, 2015.
Chen et al., "High-frequency genome editing using ssDNA oligonucleotides with zinc-finger nucleases," Nature Methods, vol. 8(9), pp. 753-755, 2011. (Jul. 17, 2011).
Chen et al., "Highly Efficient Mouse Genome Editing by CRISPR Ribonucleoprotein Electroporation of Zygotes," J. Biol. Chem., May 5, 2016.
Cho, et al., "Targeting genome engineering in human cells with the Cas9 RNA-guided endonuclease," Nature Biotechnology, 2013, vol. 31(3):233-239.
Choulika et al., "Induction of Homologous Recombination in Mammalian Chromosomes by Using the I-SceI System of *Saccharomyces cerevisiae*," Mol. Cell. Biol., vol. 15(4), pp. 1968-1973, 1995.
Christian M., et al., "Targeting DNA Double-Strand Breaks with TAL Effector Nucleases," Genetics (2010), vol. 186, pp. 757-761.
Chu et al., "Increasing the efficiency of homology-directed repair for CRISPR-Cas9-induced precise gene editing in mammalian cells," Nature Biotech., vol. 33(5), pp. 543-548, 2015. (published Mar. 2015).
Cobb and Zhao, "Direct cloning of large genomic sequences," Nature Biotechnology, 2012, vol. 30(5), pp. 405-406.
Cohen, et al., "A trangenic Alzheimer Rat with Plaques, Tau Pathology, Behavioral Impairment, Oligomeric Aβ, and Frank Neuronal Loss," J. Neurosci. 33(15):6245-6256, (2013).
Cong et al., "Multiplex Genome Engineering Using CRISPR/Cas Systems," Science, vol. 339(6121), pp. 819-823 plus Supplemental Materials, Jan. 3, 2013.
Cui, et al., "Targeted integration in rat and mouse embryos with zinc-finger nucleases," Nature Biotechnology, vol. 29, No. 1, 64-68 (Dec. 12, 2010).
Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.
Ding et al., "Enhanced Efficiency of Human Pluripotent Stem Cell Genome Editing through Replacing TALENs with CRISPRs," Cell Stem Cell, vol. 12, pp. 393-394 plus supplemental materials, 2013 (Apr. 4, 2013).
Ding, et al., "A TALEN genome-editing system for generating human stem cell-based disease models," Cell Stem Cell, 2013, vol. 12, pp. 238-251.
Donoho et al., "Analysis of Gene Targeting and Intrachromosomal Homologous Recombination Stimulated by Genomic Double-Strand Breaks in Mouse Embryonic Stem Cells," Mol. Cell. Biol., vol. 18(7), pp. 4070-4078, 1998.
Doudna et al., "The new frontier of genome engineering with CRISPR-Cas9," Science, vol. 346(6213), pp. 1258096-1-1258096-9, Nov. 28, 2014.
EMD-Millipore, Certificate of Analysis for Recombinant Human Leukemia Inhibitory Factor, retrieved from internet on Apr. 25, 2015 at <http://www.emdmillipore.com/US/en/product/Leukemia-Inhibitory-Factor-Protein%2C-Recombinant-human,MM_NF-LIF1010#documentation>.
EMD-Millipore, "Product Information sheet for Rat ESGRO," retrieved from internet on Apr. 25, 2015 at <http://www.emdmillipore.com/US/en/product/Rat-ESGRO%C2%AE%2C-1-million-units1-mL,MM_NF-ESG2206#anchor_COA>.
EP Application No. 14754746.7, Extended European Search Report dated Jun. 13, 2016.
EP Application No. 14784879.0, Extended European Search Report dated Sep. 19, 2016.
EP Application No. 18187581.6 Extended European Search Report dated Feb. 18, 2019.
Evers et al., "CRISPR knockout screening outperforms shRNA and CRISPRi in identifying essential genes," Nature Biotechnology, vol. 24(6), pp. 631-633, Apr. 25, 2016.
Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.
Flisikowska, et al., "Efficient Immunoglobulin Gene Disruption and Targeted Replacement in Rabbit Using Zinc Finger Nucleases," Plos one, vol. 6 Issue 6 (Jun. 2011).
Frendewey, "VelociGene: Large-scale Modification of Rodent Genomes," Wellcome Trust Advanced Course: Genetic Engineering of Mammalian Stem Cells, Feb. 20, 2015.
Frendewey, "VelociGene: Large-scale Modification of Rodent Genomes," Wellcome Trust Advanced Course: Genetic Engineering of Mammalian Stem Cells, Mar. 13, 2014.
Frokjaer-Jensen C., "Exciting Prospects for Precise Engineering of Caenorhabditis elegans Genomes with CRISPR/Cas9," Genetics (2013), vol. 195, pp. 635-642.
Fu, et al., "High-frequency off-target mutagenesis induced by CRISPR-Cas nucleases in human cells," Nature Biotechnology, 2013, vol. 31(9), pp. 822-826.
Fujii et al., "Efficient generation of genome-modified mice via offset-nicking by CRISPR/Cas system," Biochemical and Biophysical Research Communications, vol. 445(4), pp. 791-794 plus Supplementary Information, Jan. 31, 2014.
Fujii W., et al., "Efficient generation of large-scale genome-modified mice using gRNA and CAS9 endonuclease," Nucleic Acids Research (2013), vol. 41(20), p. e187.
Gaj et al., "ZFN, TALEN, and CRISPR/Cas-based methods for genome engineering," Trends Biotech., vol. 31(7), pp. 397-405, 2013.
Gao et al., "DNA-guided genome editing using the Natronobacterium gregoryi Argonaute," Nature Biotechnology, vol. 34(7), pp. 768-773, May 2, 2016.
Garg, A., et al., "Engineering synthetic TAL effectors with orthogonal target sites," Nucleic Acids Research (2012), vol. 40(15), p. 7584-7595.
Gasiunas, G., et al., "Cas9-crRNA ribonucleoprotein complex mediates specific DNA cleavage for adaptive immunity in bacteria," PNAS, 2012, vol. 108, pp. 10098-10103.

(56) References Cited

OTHER PUBLICATIONS

Gennequin, et al., "CRISPR/Cas-induced double-strand breaks boost the frequency of gene replacement for humanizing the mouse Cnr2 gene," Biochem. Biophys. Res. Commun., (2013), http://dx.doi.org/10.1016/j.bbrc.2013.10.138.
Gibco Data Sheet for "Recombinant Mouse Leukemia Inhibitory Factor (LIF), PMC4054," pp. 1-2, 2011.
Gibson, D., et al., "Enzymatic assembly of DNA molecules up to several hundred kilobases," Nature Methods, 2009, vol. 6(5), pp. 343-345.
Gibson, Daniel G., "Enzymatic Assembly of Overlapping DNA Fragments," Methods in Enzymology, 2011, vol. 498, pp. 349-361.
Graf et al., "The Role of the Leukemia Inhibitory Factor (LIF)—Pathway in Derivation and Maintenance of Murine Pluripotent Stem Cells," Genes, vol. 2, pp. 280-297, 2011.
Gratz et al., "Genome Engineering of *Drosophila* with the CRISPR RNA-Guided Cas9 Nuclease," Genetics, vol. 194, pp. 1029-1035, 2013. (published May 2013).
Gratz et al., "Highly Specific and Efficient CRISPR/Cas9-Catalyzed Homology-Directed Repair in *Drosophila*," Genetics, vol. 196(4), pp. 961-971 plus Supporting Information, Jan. 29, 2014.
Harrison, M.M., et al., "A CRISPR view of development," Genes & Development (2014), vol. 28(17), pp. 1859-1872.
Hirabayashi et al., "Establishment of Rat Embryonic Stem Cell Lines That Can Participate in Germline Chimerae at High Efficiency," Mol. Reprod. Dev., vol. 77, p. 94, 2010.
Hirano et al., "Human and Mouse Induced Pluripotent Stem Cells Are Differentially Reprogrammed in Response to Kinase Inhibitors," Stem Cells and Development, vol. 21(8), pp. 1287-1298, May 20, 2012.
Horvath, P., et al., "CRISPR/Cas, the Immune System of Bacteria and Archaea," Science, 2010, vol. 327, pp. 167-170.
Hsu, et al., "DNA targeting specificity of RNA-guided Cas9 nucleases," Nature Biotechnology, 2013, vol. 31(9), pp. 827-832.
Hsu, P.D., et al., "Development and Applications of CRISPR-Cas9 for Genome Engineering," Cell (2014), vol. 157, pp. 1262-1278.
Hwang et al., "Efficient In Vivo Genome Editing Using RNA-Guided Nucleases," Nat. Biotechnol., vol. 31(3), pp. 227-229 (plus supplemental materials), 2013.
Iiannaccone, P., et al., "Pluripotent Embryonic Stem Cells from the Rat Are Capable of Producing Chimeras," Developmental Biology, 1994, vol. 163, pp. 288-292.
Jallepalli et al., "Securin is required for chromosomal stability in human cells," Cell, vol. 105(4), pp. 445-457, May 18, 2001.
Jao et al., "Efficient multiplex biallelic zebrafish genome editing using a CRISPR nuclease system," Proc. Natl. Acad. Sci. U.S.A., vol. 110(34), pp. 13904-13909 plus Supporting Information, Aug. 5, 2013.
Jasin, et al., "Repair of Strand Breaks by Homologous Recombination," Cold Spring Harb. Perspect. Biol., vol. 5(11), p. a012740, Nov. 1, 2013.
Jiang, et al., "RNA-guided editing of bacterial genomes using CRISPR-Cas systems," Nature Biotechnology, 2013, vol. 31(3), pp. 233-239.
Jinek et al., "A Programmable Dual-RNA-Guided DNA Endonuclease in Adaptive Bacterial Immunity," Science, vol. 337, pp. 816-821 plus Supplemental Materials, Jun. 28, 2012.
Johnson, et al., "A rapid assay to quantify the cleavage efficiency of custom-designed nucleases in planta," Plant Mol Biol, 82:207-221 (2013).
Kashimada et al., "Sry: the master switch in mammalian sex determination," Development, vol. 137(23), pp. 3921-3930, Dec. 2, 2010.
Kato et al., "Production of Sly knockout mouse using TALEN via oocyte injection," Scientific Reports, vol. 3, p. 3136, 2013 (published Nov. 5, 2013).
Kawamata et al., "Two distinct knockout approaches highlight a critical role for p53 in rat development," Sci. Rep., vol. 2, p. 945, 2012.
Kawamata, et al., "Generation of genetically modified rats from embryonic stem cells," PNAS, vol. 107, No. 32, pp. 14223-14228 (Aug. 10, 2010).
Kawamata, M., et al., "Establishment of Embryonic Stem Cells from Rat Blastocysts," Methods Mol. Biol., 2010, vol. 597, pp. 169-177.
Kim et al., "Targeted genome editing in human cells with zinc finger nucleases constructed via modular assembly," Genome Res., vol. 19(7), pp. 1279-1288, 2009.
Kobayashi et al., "Identification of Rat Rosa26 Locus Enables Generation of Knock-In Rat Lines Ubiquitously Expressing tdTomato," Stem Cells and Development, vol. 21(16), pp. 2981-2986, May 7, 2012.
Komor et al, "Programmable editing of a target base in genomic DNA without double-stranded cleavage," Nature, vol. 533(7603), pp. 420-424, Apr. 20, 2016.
Kondo, et al., "Highly Improved Gene Targeting by Germline-Specific Cas9 Expression in *Drosophila*," Genetics, vol. 195, pp. 715-721, Sep. 3, 2013.
Konermann et al., "Genome-scale transcriptional activation by an engineered CRISPR-Cas9 complex," Nature, vol. 517(7536), pp. 583-588, published online Dec. 10, 2014.
Kosicki et al., "Repair of double-strand breaks induced by CRISPR-Cas9 leads to large deletions and complex rearrangements," Nat. Biotechnol., 36(8): 765-771, (Jul. 16, 2018).
Krivokharchenko, A., et al., "In Vitro Formation of Tetraploid Rat Blastocysts After Fusion of Two-Cell Embryos," Molecular Reproduction and Development, 2002, vol. 61, pp. 460-465.
Kuijpers et al., "One-step assembly and targeted integration of multigene constructs assisted by the I-SceI meganuclease in *Saccharomyces cerevisiae*," FEMS Yeast Res., vol. 13(8), pp. 769-781, Oct. 7, 2013.
Kuno et al., "Generation of fertile and fecund F0 XY female mice from XY ES cells," Transgenic Research, vol. 24(1), pp. 19-29, 2014 (epub Aug. 3, 2014).
Kuroiwa, et al., "Sequential targeting of the genes encoding immunoglobulin-µand prion protein in cattle," Nature Genetics, vol. 36, No. 7, (Jul. 2004).
Li et al., "Derivation of Germline Competent Rat Embryonic Stem Cells from DA Rats," J. Genet. Genomics, vol. 39, pp. 603-606, 2012.
Li et al., "Germline Competent Embryonic Stem Cells Derived from Rat Blastocysts," Cell, vol. 135, pp. 1299-1310, 2008.
Li et al., "Genetic modification and screening in rat using haploid embryonic stem cells," Cell Stem Cell, vol. 14(3); pp. 404-414, 2013 (epub Dec. 19, 2013).
Li et al., "Optimization of Genome Engineering Approaches with the CRISPR/Cas9 System," PLoS One, vol. 9(8), p. e105779, Aug. 28, 2014.
Li, D., et al., "Heritable gene targeting in the mouse and rat using a CRISPR-Cas system," Nature Biotechnology, 2013, vol. 31(8), pp. 681-683.
Li, et al., "Modularly assembled designer TAL effector nucleases for targeted gene knockout and gene replacement in eukaryotes," Nucleic Acids Research, 2011, vol. 39(14), pp. 6315-6325.
Li, M., et al., "A Cut above the Rest: Targeted Genome Editing Technologies in Human Pluripotent Stem Cells," Journal of Biological Chemistry (2014), vol. 289((8), pp. 4594-4599.
Lin et al., "Enhanced homology-directed human genome engineering by controlled timing of CRISPR/Cas9 delivery," eLife, vol. 3, e04766, 2014. (published Dec. 15, 2014).
Lin, S.-C., et al., "Strategies for gene disruption in *Drosophila*," Cell & Bioscience (2014), vol. 4(1), p. 63.
Liu et al., "A one-step cloning method for the construction of somatic cell gene targeting vectors: application to production of human knockout cell lines," BMC Biotechnol., vol. 12, p. 71, Oct. 9, 2012.
Lombardo, et al., "Gene editing in human stem cells using zinc finger nucleases and integrase-defective lentiviral vector delivery," Nature Biotechnology, 2007, vol. 25(11), pp. 1298-1306.
Ma et al., "Heritable multiplex genetic engineering in rats using CRISPR/Cas9," PLoS ONE, vol. 9(3), p. e89413, Mar. 5, 2014.

(56) References Cited

OTHER PUBLICATIONS

MacDonald, et al., "Precise and in situ genetic humanization of 6 Mb of mouse immunoglobulin genes," PNAS, vol. 111, No. 14: 5147-5152, (Apr. 8, 2014).
Mali et al., "RNA-Guided Human Genome Engineering via Cas9," Science, vol. 339(6121), pp. 823-826 plus Supplemental Materials, Jan. 3, 2013.
Mali et al., "CAS9 transcriptional activators for target specificity screening and paired nickases for cooperative genome engineering," Nature Biotechnology, vol. 31(9), pp. 833-838 plus Supplementary Information, Aug. 1, 2013.
Mali, et al., "Cas9 as a versatile tool for engineering biology," Nature Methods, vol. 10(10), pp. 957-963, 2013.
Manjunath, et al., "Newer Gene Editing Technologies toward HIV Gene Therapy," Viruses (2013), vol. 5, pp. 2748-2766.
Maruyama et al., "Increasing the efficiency of precise genome editing with CRISPR-Cas9 by inhibition of nonhomologous end joining," Nature Biotech., vol. 33(5), pp. 538-542, 2015. (published Mar. 2015).
Mashiko et al., "Generation of mutant mice by pronuclear injection of circular plasmid expressing Cas9 and single guided RNA," Sci. Rep., vol. 3, p. 3355, Nov. 27, 2013.
Mashimo et al., "Generation of knockout rats with X-linked severe combined immunodeficiency (X-SCID) using zinc finger nucleases," PLoS One, vol. 5(1), p. e8870, 2010.
Matsuda et al., "STAT3 activation is sufficient to maintain an undifferentiated state of mouse embryonic stem cells," The EMBO Journal, vol. 18(15), pp. 4261-4269, 1999.
Meek et al., "Efficient Gene Targeting by Homologous Recombination in Rat Embryonic Stem Cells," PLoS One, vol. 5(12), p. e14225, 2010.
Men et al., "Germline Transmission of a Novel Rat Embryonic Stem Cell Line Derived from Transgenic Rats," Stem Cells Dev., vol. 21(14), pp. 2606-2612, 2012.
Miller, et al., "A TALE nuclease architecture for efficient genome editing," Nature Biotechnology, 2011, vol. 29(2), pp. 143-148.
Moehle et al., "Targeted gene addition into a specified location in the human genome using designed zinc finger nucleases," Proc. Natl. Acad. Sci. U.S.A., vol. 104(9), pp. 3055-3060, 2007 (epub Feb. 20, 2007).
Morgens et al., "Systematic comparison of CRISPR/Cas9 and RNAi screens for essential genes," Nature Biotechnology, vol. 34(6), pp. 634-636, May 9, 2016.
Moscou and Bogdanove, "A simple cipher governs DNA recognition by TAL effectors," Science, 2009, vol. 326, p. 1501.
Musser, "Rodent," Brittanica. Retrieved from the Internet May 31, 2016: http://www.brittanica.com/animal/rodent.
Mussolino, et al., "TALE nucleases: tailored genome engineering made easy," Curr. Opin. Biotechnol., vol. 23(5), pp. 644-650, 2012. (epub Feb. 17, 2012).
Narsinh, et al., "Gene Correction in Human Embryonic and Induced Pluripotent Stem Cells: Promise and Challenges Ahead", Molecular Therapy, vol. 18, No. 6, pp. 1061-1063, (Jun. 2010).
News Feature "Move over ZFNs," Nature Biotechnology, 2011, vol. 29(8), pp. 681-684.
Ota, S., et al., "Zebrafish: A model vertebrate suitable for the analysis of human genetic disorders," Congenital Anomalies (2014), vol. 54, pp. 8-11.
Parikh et al., "Detailed Phenotypic and Molecular Analyses of Genetically Modified Mice Generated by CRISPR-Cas9-Mediated Editing," PLoS One, vol. 10(1), p. e0116484, Jan. 14, 2015.
Pattanayak,"High-throughput profiling of off-target DNA cleavage reveals RNA-programmed Cas9 nuclease specificity," Nature Biotechnology, 2013, vol. 31(9), pp. 839-843.
PCT International Preliminary Report on Patentability for application PCT/US2013/038165 dated Oct. 28, 2014.
PCT International Preliminary Report on Patentability for application PCT/US2014/017452 dated Aug. 25, 2015.
PCT International Preliminary Report on Patentability for application PCT/US2014/034412 dated Oct. 30, 2015.
PCT International Preliminary Report on Patentability for application PCT/US2014/060788 dated Jun. 23, 2016.
PCT International Search Report and Written Opinion of the International Searching Authority for application PCT/US2014/060788 dated Jan. 26, 2015.
PCT International Search Report and Written Opinion of the International Searching Authority for application PCT/US2015/038001 dated Feb. 25, 2016.
PCT International Search Report and Written Opinion of the International Searching Authority for application PCT/US2015/062023 dated May 13, 2016.
PCT International Search Report and Written Opinion of the International Searching Authority for application PCT/US2015/066681 dated Mar. 29, 2016.
PCT International Search Report for application PCT/US2015/034503 dated Sep. 8, 2015.
PCT Written Opinion of the International Searching Authority for application PCT/US2015/034503 dated Sep. 8, 2015.
PCT/US2013/038165 International Search Report and Written Opinion dated Jul. 12, 2013.
PCT/US2014/017452 International Search Report and Written Opinion of the Searching Authority dated May 14, 2014.
PCT/US2014/034412 International Search Report and Written Opinion of the Searching Authority dated Oct. 9, 2014.
PCT/US2015/038001 Invitation of Pay Additional Fees dated Nov. 13, 2015.
PCT/US2015/062023 Invitation of Pay Additional Fees dated Feb. 8, 2016.
Peng, Y., et al., "Making designer mutants in model organisms," Development (2014), vol. 141, pp. 4042-4054.
Pennisi, E., "Beyond TALENs," Science (2012), vol. 338, p. 1411.
Perez et al., "Establishment of HIV-1 resistance in CD4+ T cells by genome editing using zinc finger nucleases," Nature Biotech., vol. 26(7), pp. 808-816, 2008.
Piatkevich et al., "Guide to Red Fluorescent Proteins and Biosensors for Flow Cytometry," Methods Cell Biol., vol. 102, pp. 431-461, 2011.
Platt et al., "CRISPR-Cas9 Knockin Mice for Genome Editing and Cancer Modeling," Cell, vol. 159, pp. 1-16, Sep. 25, 2014.
Port et al., "Optimized CRISPR/Cas tools for efficient germline and somatic genome engineering in *Drosophila*," Proc. Natl. Acad. Sci. U.S.A., vol. 111(29), pp. E2967-E2976 plus Supporting Information, Jul. 7, 2014.
Porteus, et al., "Gene targeting using zinc finger nucleases," Nature Biotechnology, vol. 23(8), pp. 967-973, 2005.
Poueymirou et al., "F0 generation mice fully derived from gene-targeted embryonic stem cells allowing immediate analysis," Nature Biotechnology, Epub Dec. 24, 2006, vol. 25(1):91-99.
Qi, et al., "Repurposing CRISPR as an RNA-guided platform for sequence-specific control of gene expression," Cell, 2013, vol. 152, pp. 1173-1183.
Quinn et al., "A Site-Specific, Single-Copy Transgenesis Strategy to Identify 5' Regulatory Sequences of the Mouse Testis-Determining Gene Sry," PLoS One, vol. 9(4), p. e94813, Apr. 2014.
Ramirez et al., "Engineered zinc finger nickases induce homology-directed repair with reduced mutagenic effects," Nucleic Acids Research, vol. 40(12), pp. 5560-5568, 2012. (published Feb. 2012).
Ran et al., "Double nicking by RNA-guided CRISPR Cas9 for enhanced genome editing specificity," Cell, vol. 154, pp. 1380-1389, 2013.
Ran et al., "Genome engineering using the CRISPR-Cas9 system," Nature Protocols, vol. 8(11), pp. 2281-2308, Oct. 24, 2013.
Ran et al., "In vivo genomAprile editing using *Staphylococcus aureus* Cas9," Nature, vol. 520(7546) pp. 186-191, Apr. 1, 2015.
Rathjen et al., "Differentiation Inhibiting Activity Is Produced in Matrix-Associated and Diffusible Forms That Are Generated by Alternate Promoter Usage," Cell, vol. 62, pp. 1105-1114, 1990.
Ruhnke, M., et al., "Long-Term Culture and Differentiation of Rat Embryonic Stem Cell-Like Cells into Neuronal, Glial, Endothelial, and Hepatic Lineages," Stem Cells, 2003, vol. 21, pp. 428-436.
Sadhu et al., "CRISPR-directed mitotic recombination enables genetic mapping without crosses," Science, vol. 352(6289): 1113-1116, May 5, 2016.

(56) References Cited

OTHER PUBLICATIONS

Scharenberg, A.M., et al., "Genome Engineering with TAL-Effector Nucleases and Alternative Modular Nuclease Technologies," Current Gene Therapy (2013), vol. 13, pp. 291-303.
Schwank, G., et al., "Functional Repair of CFTR by CRISPR/Cas9 in Intestinal Stem Cell Organoids of Cystic Fibrosis Patients," Cell Stem Cell (2013), vol. 13, pp. 653-658.
Shan et al., "Targeted genome modification of crop plants using a CRISPR-Cas system," Nature Biotechnology, vol. 31(8), pp. 686-688, Aug. 1, 2013.
Shao et al., "CRISPR/Cas-mediated genome editing in the rat via direct injection of one-cell embryos," Nature Protocols, vol. 9(10), pp. 2493-2512, 2014 (epub Sep. 25, 2014).
Shen, H, et al., "The heterogeneity and dynamic equilibrium of rat embryonic stem cells," Cell Research (2011), vol. 21, pp. 1143-1147.
Siao et al., "Single-step homozygous humanization induced by dual CRISPR/Cas9 cleavage," Oct. 28, 2015.
Sigma-Aldrich, "Product Information sheet for Leukemia Inhibitory Factor human," retrieved from internet on Apr. 25, 2015 at http://www.sigmaaldrich.com/content/dam/sigma-aldrich/docs/Sigma/Datasheet/4/I5283dat.pdf.
Singh et al., "A Mouse Geneticist's Practical Guide to CRISPR Applications," Genetics, vol. 199, pp. 1-15, (2015).
Stemgent Product Specification Sheet, PD0325901, pp. 1-2 (2012).
Straub A., et al., "Zinc Fingers, TAL Effectors, or Cas9-Based DNA Binding Proteins: What's Best for Targeting Desired Genome Loci?," Molecular Plant (2013), vol. 6(5), pp. 1384-1387.
Tong et al., "Production of p53 gene knockout rats by homologous recombination in embryonic stem cells," Nature, vol. 467(7312), pp. 211-213, 2010.
Tong et al., "Generating gene knockout rats by homologous recombination in embryonic stem cells," Nature Protocols, vol. 6(6), pp. 827-844, 2011 (epub May 26, 2011).
U.S. Appl. No. 13/870,280 Final Rejection dated Oct. 15, 2015.
U.S. Appl. No. 13/870,280, Advisory Action dated Jan. 5, 2016.
U.S. Appl. No. 13/870,280, Requirement for Restriction/Election dated Jul. 22, 2014.
U.S. Appl. No. 14/185,703 Non-Final Office Action dated Dec. 3, 2015.
U.S. Appl. No. 14/185,703, Requirement for Restriction/Election dated Sep. 4, 2015.
U.S. Appl. No. 14/252,025, Notice of Allowance and Interview Summary dated Feb. 6, 2019.
U.S. Appl. No. 14/254,715 Final Office Action dated Nov. 30, 2015.
U.S. Appl. No. 14/254,715, Advisory Action dated Dec. 9, 2016.
U.S. Appl. No. 14/254,715, Final Office Action dated Sep. 19, 2016.
U.S. Appl. No. 14/254,715, Non-Final Office Action dated Apr. 21, 2016.
U.S. Appl. No. 14/254,715, Non-Final Office Action dated Aug. 12, 2015.
U.S. Appl. No. 14/314,866, Advisory Action dated Aug. 12, 2015.
U.S. Appl. No. 14/314,866, Advisory Action dated Aug. 15, 2016.
U.S. Appl. No. 14/314,866, Final Office Action dated Apr. 26, 2016.
U.S. Appl. No. 14/314,866, Final Office Action dated Jun. 4, 2015.
U.S. Appl. No. 14/314,866, Non-Final Office Action dated Sep. 19, 2016.
U.S. Appl. No. 14/314,866, Non-Final Office Action dated Dec. 26, 2014.
U.S. Appl. No. 14/314,866, Non-Final Office Action dated Nov. 27, 2015.
U.S. Appl. No. 14/314,866, Requirement for Restriction/Election dated Sep. 22, 2014.
U.S. Appl. No. 14/515,503, Non-Final Office Action dated May 20, 2016.
U.S. Appl. No. 14/515,503, Notice of Allowance dated Sep. 23, 2016.
U.S. Application No. 14/515,503, Requirement for Restriction/Election dated Mar. 4, 2016.
U.S. Appl. No. 14/578,291, Non-Final Office Action dated Mar. 10, 2015.
U.S. Appl. No. 14/578,291, Notice of Allowance dated Aug. 26, 2015.
U.S. Appl. No. 14/731,914, Non-Final Office Action dated Jun. 17, 2016.
U.S. Appl. No. 14/731,914, Requirement for Restriction/Election dated Dec. 31, 2015.
U.S. Appl. No. 14/751,807, Requirement for Restriction/Election dated Aug. 26, 2016.
U.S. Appl. No. 14/926,773, Non-Final Office Action dated May 6, 2016.
U.S. Appl. No. 14/926,773, Requirement for Restriction/Election dated Feb. 16, 2016.
U.S. Appl. No. 14/928,134, Advisory Action dated Jul. 15, 2016.
U.S. Appl. No. 14/928,134, Final Office Action dated Apr. 14, 2016.
U.S. Appl. No. 14/928,180, Advisory Action dated Aug. 22, 2016.
U.S. Appl. No. 14/928,180, Final Office Action dated Jun. 6, 2016.
U.S. Appl. No. 14/928,180, Non-Final Office Action dated Jan. 5, 2016.
U.S. Appl. No. 15/242,025, Final Office Action dated Nov. 29, 2018.
U.S. Appl. No. 15/242,025, Non-Final Office Action dated Feb. 6, 2017.
U.S. Appl. No. 15/242,025, Non-Final Office Action dated May 3, 2018.
U.S. Appl. No. 15/410,252 Non-Final Office Action dated May 18, 2018.
U.S. Appl. No. 15/410,252, Notice of Allowability dated Mar. 4, 2019.
U.S. Appl. No. 15/410,252, Notice of Allowance dated Jan. 23, 2019.
U.S. Appl. No. 15/410,252, Notice of Allowance dated Apr. 18, 2019.
U.S. Appl. No. 13/870,280, Non-Final Office Action dated Mar. 13, 2015.
U.S. Appl. No. 14/185,703, Final Office Action dated Apr. 20, 2016.
U.S. Appl. No. 14/254,715, Requirement for Restriction/Election dated Jun. 4, 2015.
Ueda et al., "Establishment of Rat Embryonic Stem Cells and Making of Chimera Rats," PLoS One, vol. 3(7), p. e2800, 2008.
U.S. Appl. No. 14/928,134 Non-Final Office Action dated Feb. 1, 2016.
Valenzuela, et al., "High-throughput engineering of the mouse genome coupled with high-resolution expression analysis," Nature Biotechnology, vol. 21, No. 6, pp. 652-659, (Jun. 2003).
Van Der Oost, "New tool for genome surgery," Science, 2013, vol. 339(6121), pp. 768-770.
Varlakhanova et al., "Myc Maintains Embryonic Stem Cell Pluripotency and Self-Renewal," Differentiation, vol. 80(1), pp. 9-19, 2010.
Vechkanov et al., "Fundamentals of Cell Engineering: A Study Guide", Rostov-on-Don, pp. 15 and 46-47, Full English translation (2012).
Verkhovskaya et al, "The action of alkoxy-substituted glycerin on the morphofunctional properties of a passaged cell culture," Cryobiology 1:30-33; Full English translation (1990).
Wang et al., "One-Step Generation of Mice Carrying Mutations in Multiple Genes by CRISPR/Cas-Mediated Genome Engineering," Cell, vol. 153, pp. 910-918 plus supplemental materials, 2013. (published May 2013).
Wang et al., "TALEN-mediated editing of the mouse Y chromosome," Nature Biotechnology, vol. 31(6), p. 530-532, 2013 (epub May 12, 2013).
Wen et al., "Completely ES Cell-Derived Mice Produced by Tetraploid Complementation Using Inner Cell Mass (ICM) Deficient Blastocysts," PLoS One, vol. 9(4), e94730, Apr. 14, 2014.
Whitworth et al., "Use of the CRISPR/Cas9 System to Produce Genetically Engineered Pigs from In Vitro-Derived Oocytes and Embryos," Biology of Reproduction, vol. 91(3), p. 78, Aug. 6, 2014.
Wu, Y., et al., "Correction of a Genetic Disease in Mouse via Use of CRISPR-Cas9," Cell Stem Cell (2013), vol. 13, pp. 659-662.
Xu, T., et al., "Cas9-Based Tools for Targeted Genome Editing and Transcriptional Control," Applied and Environmental Microbiology (2014), vol. 80(5), pp. 1544-1552.

(56) References Cited

OTHER PUBLICATIONS

Yamamoto et al., "Derivation of rat embryonic stem cells and generation of protease-activated receptor-2 knockout rats," Transgenic Res., vol. 21, pp. 743-755, 2012.

Yang et al., "One-step generation of mice carrying reporter and conditional alleles by CRISPR/Cas-mediated genome engineering," Cell, vol. 154(6), pp. 1370-1379, Aug. 29, 2013.

Yang et al., "Optimization of scarless human stem cell genome editing," Nucleic Acids Res., vol. 41(19), pp. 9049-9061, 2013 (epub Jul. 31, 2013).

Yang et al., "Targeted and genome-wide sequencing reveal single nucleotide variations impacting specificity of Cas9 in human stem cells," Nat. Commun., vol. 5, p. 5507, (2014).

Yang, S., et al., "Derivation and Genetic Modification of Embryonic Stem Cells from Disease-Model Inbred Rat Strains," Stem Cells and Development, 2013, vol. 22(20), Abstract only.

Yang, S., et al., Retraction of "Derivation and Genetic Modification of Embryonic Stem Cells from Disease-Model Inbred Rat Strains," Stem Cells and Development, 2013, vol. 22(20), 2813.

Yen et al., "Somatic mosaicism and allele complexity induced by CRISPR/Cas9 RNA injections in mouse zygotes," Dev. Biol., vol. 393(1), pp. 3-9, Jun. 28, 2014.

Yoshimi et al., "Allele-specific genome editing and correction of disease-associated phenotypes in rats using the CRISPR-Cas platform," Nature Communications, vol. 5, p. 4240 plus Supplementary Information, Jun. 26, 2014.

Yoshimi et al., "ssODN-mediated knock-in with CRISPR-Cas for large genomic regions in zygotes," Nat. Commun., vol. 7, p. 10431, Jan. 20, 2016.

Yu et al., "Highly Efficient Genome Modifications Mediated by CRISPR/Cas9 in *Drosophila*," Genetics, vol. 195, pp. 289-291 plus supporting information, Sep. 2013.

Zetsche et al., "Cpf1 is a Single RNA-Guided Endonuclease of a Class 2 CRISPR-Cas System," Cell, vol. 163, pp. 1-13, 2015 (available online Sep. 25, 2015).

Zhang et al., "Biallelic targeting of expressed genes in mouse embryonic stem cells using the Cas9 system," Methods, vol. 69(2), pp. 171-178, Jun. 12, 2014.

Zhao et al., "Derivation of embryonic stem cells from Brown Norway rats blastocysts," J. Genet. Genomics, vol. 37, pp. 467-473, 2010.

Zhou et al., "Dual sgRNAs facilitate CRISPR/Cas9-mediated mouse genome targeting," FEBS J., vol. 281(7), pp. 1717-1725, Feb. 26, 2014.

Zhou, H., et al., "Large chromosomal deletions and heritable small genetic changes induced by CRISPR/Cas9 in rice," Nucleic Acids Research (2014), vol. 42(17), pp. 10903-10914.

Declaration of Jeffrey D. Lee filed in U.S. Appl. No. 14/314,866, filed Mar. 26, 2015.

EP 19178517.9 Extended European Search Report dated Jul. 18, 2019.

Henderson et al., "MEK inhibitor PD0325901 significantly reduces the growth of papillary thyroid carcinoma cells in vitro and in vivo," Mol. Cancer Ther., 9(7):1968-1976, (2010).

Hirabayashi et al., "Effect of leukemia inhibitory factor and forskolin on establishment of rat embryonic stem cell lines," J. Reprod. Dev., 60(1.):78-82, (2014).

Ma et al., "Generation of eGFP and Cre knockin rats by CRISPR/Cas9," FEBS J., 281(17):3779-3790, (2014).

Ma et al., "Generating rats with conditional alleles using CRISPR/Cas9," Cell Res. 24(1):122-125, (2014).

U.S. Appl. No. 16/401,539 Final Office Action dated Jun. 17, 2020.

U.S. Appl. No. 16/401,539, Non-Final Office Action dated Dec. 30, 2019.

\* cited by examiner

*Cell Results: 42,XX*

*X, Y:*

*Label - Slide/Cell met-4 - S01-01*

Cell Results: 42,XY

X, Y:

Label - Slide/Cell  met-1 - SD1-01

Cell Results: 42,XX

Label - Slide/Cell met-4 - S01-01

X, Y:

Rat ApoE ZFNs: improved targeting efficiency

| DNA: | Colonies Screened | Heterozygous Targeted | Homozygous targeted | "Mixed" doubles | Cut/ untargeted |
|---|---|---|---|---|---|
| vector | 330 | 184 | 15 (8.2%) | 0 | 0 | N/A |
| vector + ZFN 1 | 560 | 192 | 132 (68.8%) | 6 (3.1%) | 18 (9.4%) | 17 (8.9%) |
| vector + ZFN 2 | 410 | 192 | 136 (70.8%) | 2 (1.0%) | 6 (3.1%) | 18 (9.4%) |

Heterozygous targeted: 1 copy of LOA U & D lost; 1 copy of ZFN probe lost
Mixed doubles: 1 copy of LOA U & D lost; 2 copies of ZFN probe lost
Homozygous targeted: 2 copies of LOA U & D lost; 2 copies of ZFN probe lost

FIG. 11

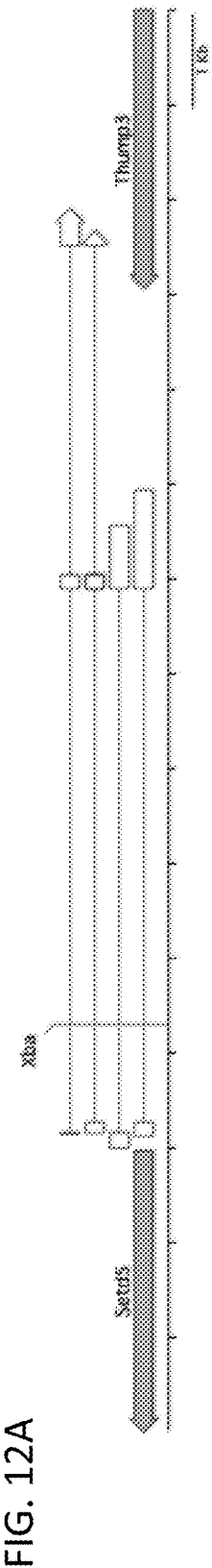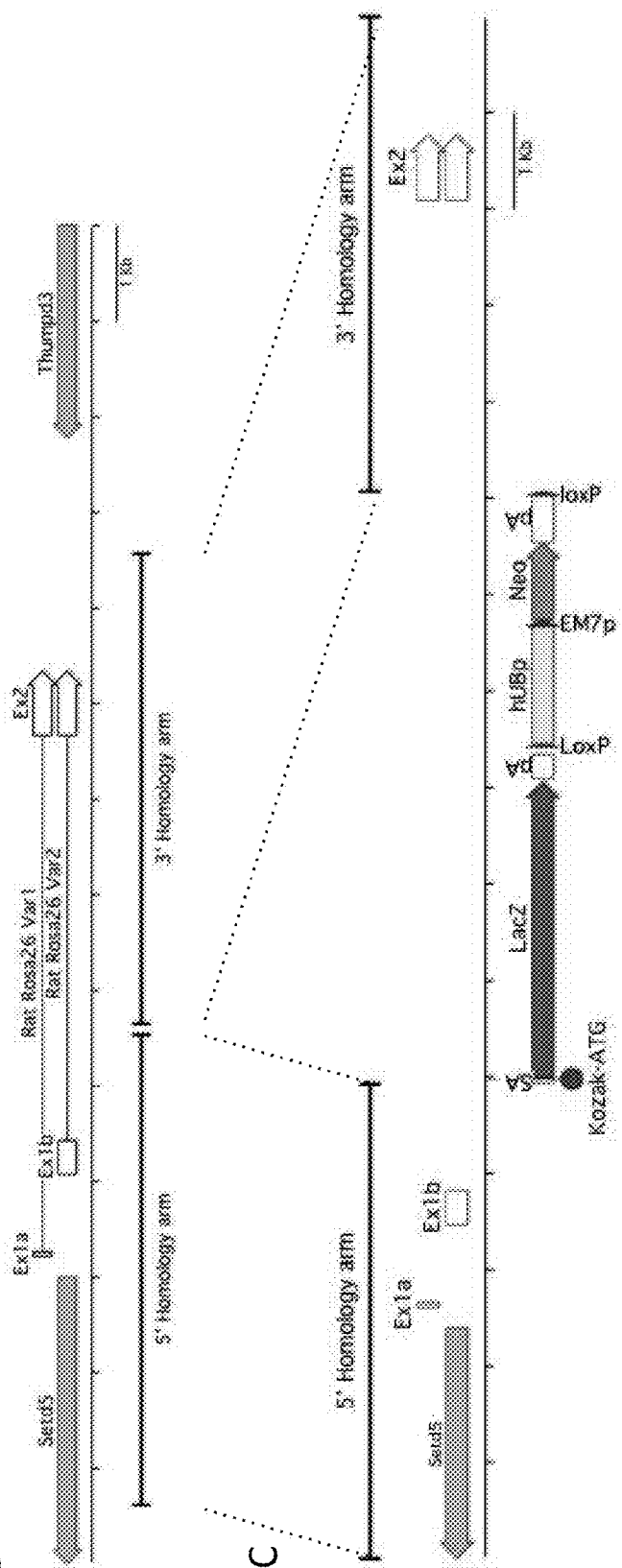
FIG. 12A
FIG. 12B
FIG. 12C

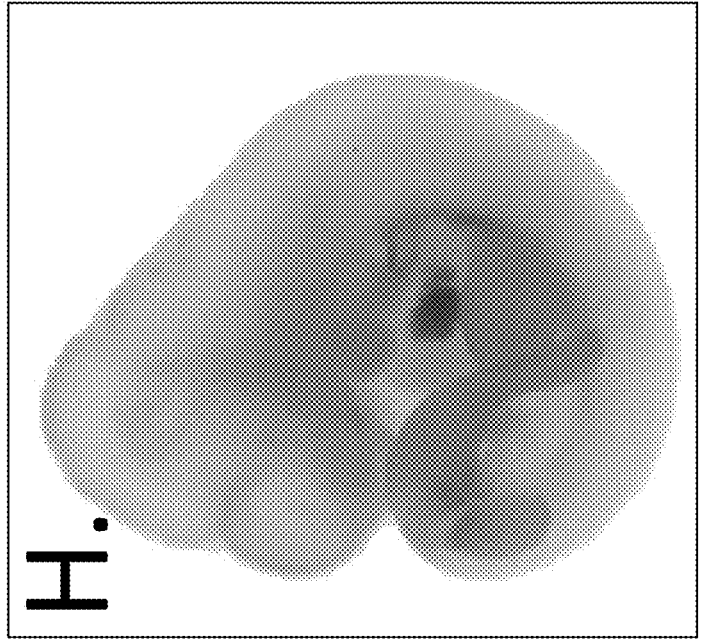

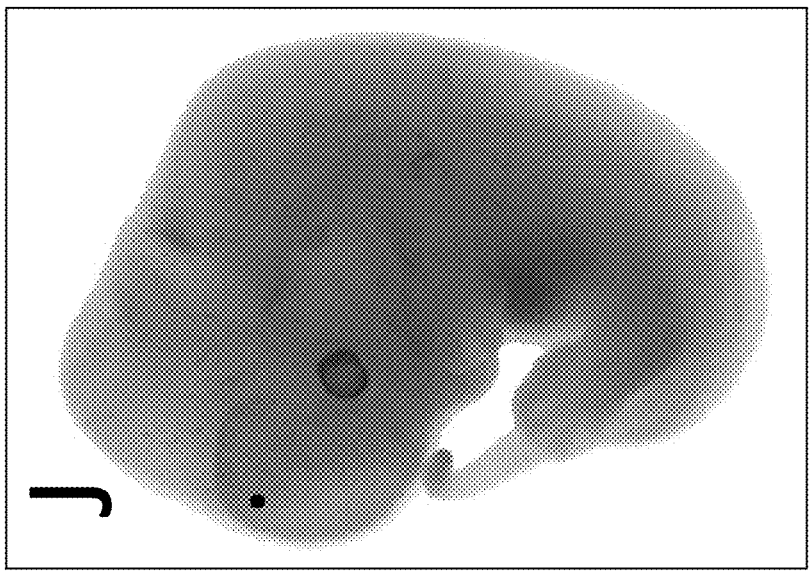
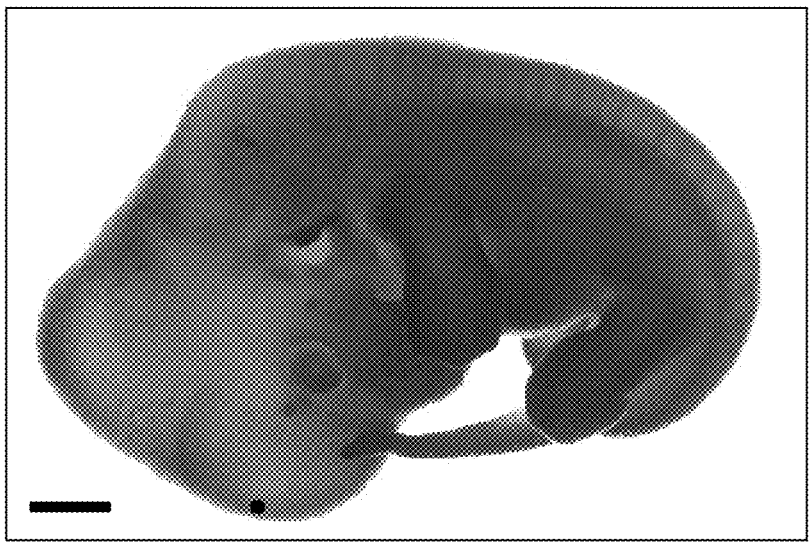

| Clone | Pups | Chimeras |
|---|---|---|
| ApoE-ZFN1-AB5 (homozyous targeted) | 12 | 4 (90, 90, 80, 80) |
| ApoE-ZFN1-AE5 (homozygous targeted) | 6 | 3 (90, 80, 70) |

ApoE-ZFN1-AB5 chimeras

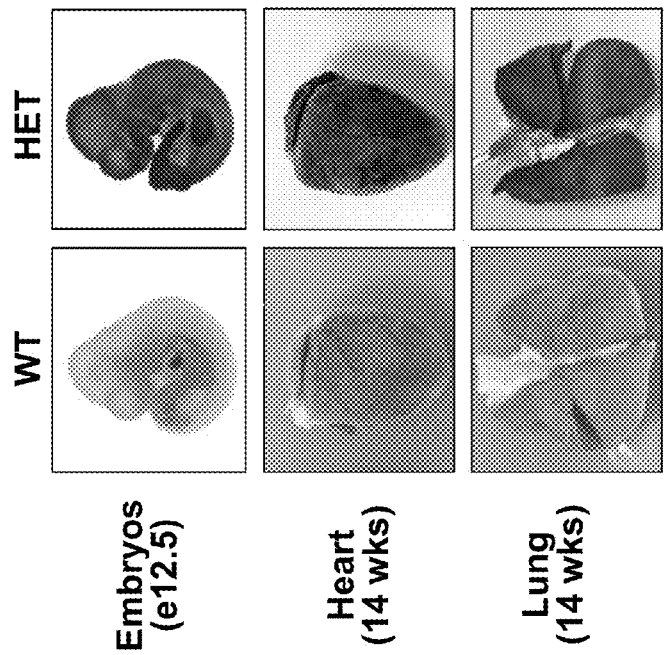
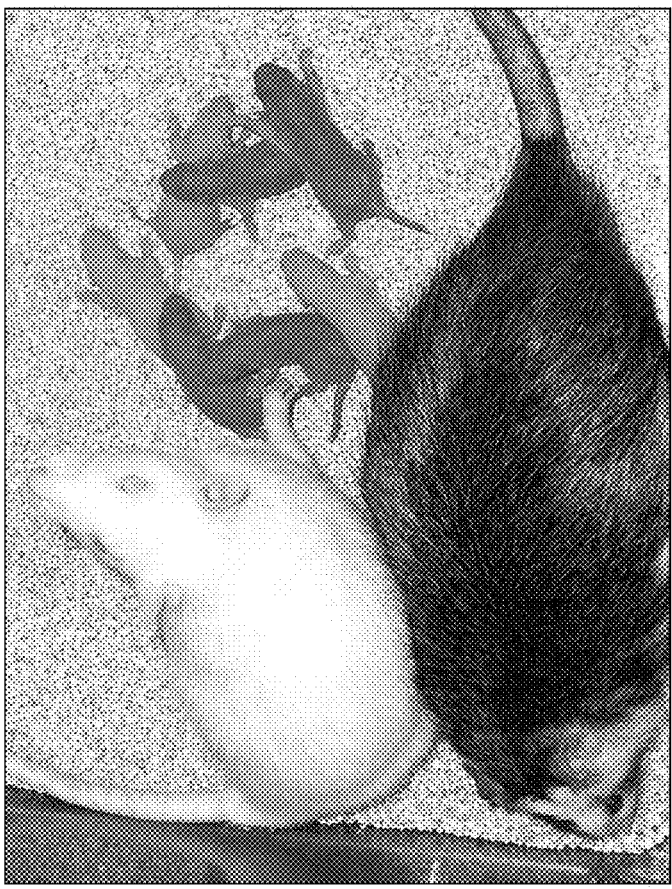
FIG. 25

TARGETED MODIFICATION OF RAT GENOME

CROSS-REFERENCE TO RELATED APPLICATIONS

This application is a continuation application of U.S. application Ser. No. 15/410,252, filed Jan. 19, 2017, which is a divisional application of U.S. application Ser. No. 14/254,715, filed Apr. 16, 2014, which claims the benefit of U.S. Provisional Application No. 61/812,319, filed Apr. 16, 2013, and U.S. Provisional Application No. 61/914,768, filed Dec. 11, 2013, all of which are hereby incorporated herein in their entirety by reference.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 532676SEQLIST.TXT, created on Jun. 25, 2019, and having a size of 15.1 kilobytes, and is filed concurrently with the specification. The sequence listing contained in this ASCII formatted document is part of the specification and is herein incorporated by reference in its entirety.

FIELD OF INVENTION

Isolated non-human totipotent or pluripotent stem cells, in particular rat embryonic stem cells, that are capable of sustaining pluripotency following one or more serial genetic modifications in vitro, and that are capable of transmitting the targeted genetic modifications to subsequent generations through germline. Compositions and methods for modifying a rat genomic locus of interest via bacterial homologous recombination (BHR) in a prokaryotic cell. Compositions and methods for genetically modifying a rat genomic locus of interest using a large targeting vector (LTVEC) in combination with endonucleases. Compositions and methods for producing a genetically modified rat comprising one or more targeted genetic modifications.

BACKGROUND OF THE INVENTION

While rats have been regarded as an important animal model system that can recapitulate the pathology of various human diseases, including, but not limited to, cardiovascular (e.g., hypertension), metabolic (e.g., obesity, diabetes), neurological (e.g., pain pathologies), and a variety of cancers, the use of rats in modeling human diseases has been limited as compared to mice, due in part to unavailability of germline-transmittable pluripotent rat cells, which can sustain their pluripotency following a series of genetic modifications in vitro, e.g., one or more serial electroporations, and due in part to lack of efficient targeting technologies that allow introduction or deletion of large genomic DNA sequences, or replacement of large endogenous genomic DNA sequences with exogenous nucleic acid sequences in pluripotent rat cells.

There is a need in the art for compositions and methods that allow precise targeted changes in the genome of a rat, which can open or expand current areas of target discovery and validate therapeutic agents more quickly and easily.

SUMMARY

Methods are provided for modifying a genomic locus of interest in a pluripotent cell via targeted genetic modification. Such a method comprises (a) introducing into the pluripotent cell a large targeting vector (LTVEC) comprising an insert nucleic acid flanked with a 5' homology arm and a 3' homology arm; and (b) identifying a genetically modified pluripotent cell comprising the targeted genetic modification at the genomic locus of interest, wherein the targeted genetic modification is capable of being transmitted through the germline.

In one embodiment, the pluripotent cell is derived from a non-human animal, including, but not limited to, a rodent, a human, a rat, a mouse, a hamster, a rabbit, a pig, a bovine, a deer, a sheep, a goat, a chicken, a cat, a dog, a ferret, a primate (e.g., marmoset, rhesus monkey), a domesticated mammal or an agricultural mammal, or any other organism of interest.

In one embodiment, the pluripotent cell is a non-human pluripotent cell. In one embodiment, the non-human pluripotent cell is a mammalian pluripotent cell. In one embodiment, the mammalian pluripotent cell is a rodent pluripotent cell. In one embodiment, the rodent pluripotent cell is a rat or mouse pluripotent cell. In one embodiment, the pluripotent cell is a human induced pluripotent stem (iPS) cell.

In one embodiment, the pluripotent cell is a non-human fertilized egg at the single cell stage. In one embodiment, the non-human fertilized egg is a mammalian fertilized egg. In one embodiment, the mammalian fertilized egg is a rodent fertilized egg at the single cell stage. In one embodiment, the mammalian fertilized egg is a rat or mouse fertilized egg at the single cell stage.

In some embodiments, the sum total of the 5' and the 3' homology arms of the LTVEC is at least 10 kb. In some embodiments, the sum total of the 5' and the 3' homology arms of the LTVEC is at least 10 kb but less than 100 kb or the sum total of the 5' and the 3' homology arms of the LTVEC is at least 10 kb but less than 150 kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

In some such embodiments, the targeted genetic modification is biallelic.

In some embodiments, the pluripotent cell is a pluripotent rat cell. In one embodiment, the pluripotent rat cell is a rat embryonic stem cell. In one embodiment, the pluripotent rat cell is derived from a DA strain or an ACI strain. In some embodiments, the pluripotent rat cell is characterized by expression of at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof. In some such methods, the pluripotent rat cell is characterized by one of more of the following characteristics: (a) lack of expression of one or more pluripotency markers comprising c-Myc, Ecat1, and/or Rexo1; (b) lack of expression of mesodermal markers comprising Brachyury and/or Bmpr2; (c) lack of expression of one or more endodermal markers comprising Gata6, Sox17 and/or Sox7; or (d) lack of expression of one or more neural markers comprising Nestin and/or Pax6. Such methods provide that the sum total of the 5' and the 3' homology arms of the LTVEC is from about 10 kb to about 30 kb, from about 20 kb to about 40 kb, from about 40 kb to about 60 kb, from about 60 kb to about 80 kb, or from about 80 kb to about 100 kb, from about 100 kb to about 120 kb, from about 120 kb to about 150 kb, or from about 10 kb but less than about 150 kb. In some embodiments, the sum total of the 5' and the 3' homology arms of the LTVEC is from about 16 Kb to about 100 Kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

The methods further provide that targeted genetic modification (a) comprises a replacement of an endogenous rat nucleic acid sequence with a homologous or an orthologous mammalian nucleic acid sequence; (b) comprises a deletion of an endogenous rat nucleic acid sequence; (c) comprises a deletion of an endogenous rat nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) comprises an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (e) comprises an exogenous nucleic acid sequence comprising a homologous or an orthologous nucleic acid sequence; (f) comprises a chimeric nucleic acid sequence comprising a human and a rat nucleic acid sequence; (g) ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (h) comprises a conditional allele flanked with site-specific recombinase target sequences; or, (i) comprises a reporter gene operably linked to a promoter active in a rat cell.

Further provided is a method for modifying a genomic locus of interest in a pluripotent rat cell via targeted genetic modification, wherein the genomic locus of interest comprises (i) a first nucleic acid sequence that is complementary to the 5' rat homology arm; and (ii) a second nucleic acid sequence that is complementary to the 3' rat homology arm. In some such embodiments, the first and the second nucleic acid sequence is separated by at least 5 kb. In some embodiments, the first and the second nucleic acid sequence is separated by at least 5 kb but less than 3 Mb. In some such methods, the first and the second nucleic acid sequence is separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, at least about 2.5 Mb but less than about 3 Mb, at least about 1 Mb but less than about 2 Mb, at least about 2 Mb but less than about 3 Mb.

In some embodiments, the introducing step further comprises introducing a second nucleic acid encoding a nuclease agent that promotes a homologous recombination between the targeting construct and the genomic locus of interest in the pluripotent rat cell. In some such embodiments, the nuclease agent comprises (a) a chimeric protein comprising a zinc finger-based DNA binding domain fused to a FokI endonuclease; or, (b) a chimeric protein comprising a Transcription Activator-Like Effector Nuclease (TALEN) fused to a FokI endonuclease.

In some methods, the introducing step further comprises introducing into the pluripotent rat cell: (i) a first expression construct comprising a first promoter operably linked to a first nucleic acid sequence encoding a Clustered Regularly Interspaced Short Palindromic Repeats (CRISPR)-associated (Cas) protein, (ii) a second expression construct comprising a second promoter operably linked to a second nucleic acid sequence encoding a genomic target sequence operably linked to a guide RNA (gRNA), wherein the genomic target sequence is immediately flanked on the 3' end by a Protospacer Adjacent Motif (PAM) sequence. In one embodiment, the genomic locus of interest comprises the nucleotide sequence of SEQ ID NO: 1. In one embodiment, the gRNA comprises a third nucleic acid sequence encoding a Clustered Regularly Interspaced Short Palindromic Repeats (CRISPR) RNA (crRNA) and a trans-activating CRISPR RNA (tracrRNA). In another embodiment, the genome of the pluripotent rat cell comprises a target DNA region complementary to the genomic target sequence. In some such methods, the Cas protein is Cas9. In some such methods the gRNA comprises (a) the chimeric RNA of the nucleic acid sequence of SEQ ID NO: 2; or, (b) the chimeric RNA of the nucleic acid sequence of SEQ ID NO: 3. In some such methods, the crRNA comprises the sequence set forth in SEQ ID NO: 4, SEQ ID NO: 5, or SEQ ID NO: 6. In some such methods, the tracrRNA comprises the sequence set forth in SEQ ID NO: 7 or SEQ ID NO: 8.

Further provided is a rat genomic locus comprising (i) an insertion of a homologous or orthologous human nucleic acid sequence; (ii) a replacement of an endogenous rat nucleic acid sequence with the homologous or orthologous human nucleic acid sequence; or (iii) a combination thereof, wherein the rat genomic locus is capable of being transmitted through the germline. In some such rat genomic locus, the size of the insertion or replacement is from about 5 kb to about 400 kb. In some such rat genomic locus, the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb, at least about 200 kb but less than about 300 kb, at least about 300 kb but less than about 400 kb, at least about 400 kb but less than about 500 kb, at least about 500 kb but less than about 1 Mb, at least about 1.1 Mb but less than about 2 Mb, at least about 2 Mb but less than about 3 Mb.

Further provided is a method for making a humanized rat, comprising: (a) targeting a genomic locus of interest in a pluripotent rat cell with a targeting construct comprising a human insert nucleic acid to form a genetically modified pluripotent rat cell; (b) introducing the genetically modified pluripotent rat cell into a host rat embryo; and (c) gestating the host rat embryo in a surrogate mother; wherein the surrogate mother produces rat progeny comprising, a modified genomic locus that comprises: (i) an insertion of a human nucleic acid sequence; (ii) a replacement of the rat nucleic acid sequence at the genomic locus of interest with a homologous or orthologous human nucleic acid sequence; (iii) a chimeric nucleic acid sequence comprising a human and a rat nucleic acid sequence; or (iv) a combination thereof, wherein the modified genomic locus is capable of being transmitted through the germline.

In some such methods, the targeting construct is a large targeting vector (LTVEC), and the sum total of the 5' and the 3' homology arms of the LTVEC is at least 10 kb but less than 100 kb or the sum total of the 5' and the 3' homology arms of the LTVEC is at least 10 kb but less than 150 kb. In some such methods, the sum total of the 5' and the 3' homology arms of the targeting construct is from about 10 kb to about 30 kb, from about 20 kb to 40 kb, from about 40 kb to about 60 kb, from about 60 kb to about 80 kb, from about 80 kb to about 100 kb, from about 100 kb to about 120 kb, or from about 120 kb to about 150 kb. In some such methods, the human nucleic acid sequence is at least 5 kb but less than 400 kb. In some such methods, the human nucleic acid sequence is at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, at least 150 kb but less than 200 kb, at least 200 kb but less than 250 kb, at least 250 kb but less than 300 kb, at least 300 kb but less than 350 kb, or at least 350 kb but less than 400 kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

In some methods for making a humanized rat, the pluripotent rat cell is a rat embryonic stem (ES) cell. In some such methods, the pluripotent rat cell is derived from a DA strain or an ACI strain. In some such methods, the pluripotent rat cell is characterized by expression of at least one pluripotency marker comprises Dnmt3L, Eras, Err-beta, Fbxo15, Fgf4, Gdf3, Klf4, Lef1, LIF receptor, Lin28, Nanog, Oct4, Sox15, Sox2, Utf1, and/or a combination thereof. In some such methods, the pluripotent rat cell is characterized by one or more of the following features: (a) lack of expression of one or more pluripotency markers comprising c-Myc, Ecat1, and/or Rexo1; (b) lack of expression of one or more mesodermal markers comprising Brachyury and/or Bmpr2; (c) lack of expression of one or more endodermal markers comprising Gata6, Sox17, and/or Sox7; or (d) lack of expression of one or more neural markers comprising Nestin and/or Pax6.

Further provided is a genetically modified rat comprising a humanized genomic locus, wherein the genetically modified rat comprises: (i) an insertion of a homologous or orthologous human nucleic acid sequence; (ii) a replacement of a rat nucleic acid sequence with a homologous or orthologous human nucleic acid sequence at an endogenous genomic locus with a homologous or orthologous human nucleic acid sequence; (iii) a chimeric nucleic acid sequence comprising a human and a rat nucleic acid sequence; or, (iv) a combination thereof, wherein the humanized genomic locus is capable of being transmitted through the germline. In some such genetically modified rats, the humanized genomic locus comprises a chimeric nucleic acid sequence comprising a human and a rat nucleic acid sequence.

Methods for modifying a target genomic locus of a rat via bacterial homologous recombination (BHR) are also provided and comprise: introducing into a prokaryotic cell a large targeting vector (LTVEC) comprising an insert nucleic acid flanked with a 5' rat homology arm and a 3' rat homology arm, wherein the prokaryotic cell comprises a rat nucleic acid and is capable of expressing a recombinase that mediates the BHR at the target locus, and wherein the sum total of the 5' and 3' homology arms of the LTVEC is at least 10 kb but less than 100 kb or the sum total of the 5' and the 3' homology arms of the LTVEC is at least 10 kb but less than 150 kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

In some such methods, the target locus of the rat nucleic acid comprises a first nucleic acid sequence that is complementary to the 5' homology arm and a second nucleic acid sequence that is complementary to the 3' homology arm. In some such methods, the first and the second nucleic acid sequence is separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1.1 Mb but less than about 2 Mb, at least about 2 Mb but less than about 3 Mb.

In some such methods, introducing the targeting vector into the prokaryotic cell leads to: (i) a deletion of an endogenous rat nucleic acid sequence from the target genomic locus; (ii) an addition of an exogenous nucleic acid sequence at the target genomic locus; (iii) a replacement of the endogenous rat nucleic acid sequence with the exogenous nucleic acid sequence at the target locus; or (iv) a combination thereof. In some such methods, the insert nucleic acid comprises (a) a polynucleotide that is homologous or orthologous to the rat nucleic acid sequence at the target genomic locus; or (b) a conditional allele flanked with site-specific recombination recognition sequences.

Further provided is a host prokaryotic cell comprising a targeting vector comprising an insert nucleic acid flanked with a 5' rat homology arm and a 3' rat homology arm, wherein the insert nucleic acid ranges from about 5 k to about 400 kb. In some host prokaryotic cells the size of the insert nucleic acid is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from 350 kb to about 400 kb. In some host prokaryotic cells, the prokaryotic cell comprises a recombinase gene operably linked to a constitutively active promoter or an inducible promoter.

Methods are also provided for modifying a genomic locus of interest in a cell via targeted genetic modification comprising introducing into the cell
(a) a large targeting vector (LTVEC) comprising an insert nucleic acid flanked with a 5' homology arm and a 3' homology arm, wherein the sum total of the 5' and 3' homology arms of the LTVEC is at least 10 kb; and
(b) (i) a first expression construct comprising a first promoter operably linked to a first nucleic acid sequence encoding a Clustered Regularly Interspaced Short Palindromic Repeats (CRISPR)-associated (Cas) protein, (ii) a second expression construct comprising a second promoter operably linked to a second nucleic acid sequence encoding a genomic target sequence operably linked to a guide RNA (gRNA); and identifying a genetically modified pluripotent cell comprising the targeted genetic modification at the genomic locus of interest.

In one embodiment, the genomic locus of interest comprises the nucleotide sequence set forth in SEQ ID NO: 1, wherein the gRNA comprises a third nucleic acid sequence encoding a Clustered Regularly Interspaced Short Palindromic Repeats (CRISPR) RNA (crRNA) and a trans-activating CRISPR RNA (tracrRNA), and wherein the genome of the cell comprises a target DNA region complementary to the genomic target sequence. In some such methods, the Cas protein is Cas9. In such methods, the cell can be a pluripotent cell (such as an embryonic stem cell) or a prokaryotic cell. In one embodiment, the pluripotent cell is from non-human animal, a non-human mammal, a rodent, a human, a rat, a mouse, a hamster a rabbit, a pig, a bovine, a deer, a sheep, a goat, a chicken, a cat, a dog, a ferret, a primate (e.g.,  marmoset, rhesus monkey), domesticated mammal or an agricultural mammal or any other organism of interest. In another embodiment, the prokaryotic cell is from bacteria, such as, *E. coli*.

In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

In one embodiment, the pluripotent cell is a non-human pluripotent cell. In one embodiment, the non-human pluripotent cell is a mammalian pluripotent cell. In one embodiment, the mammalian pluripotent cell is a rodent pluripotent cell. In one embodiment, the rodent pluripotent cell is a rat or mouse pluripotent cell. In one embodiment, the pluripotent cell is a human induced pluripotent stem (iPS) cell.

In one embodiment, the pluripotent cell is a non-human fertilized egg at the single cell stage. In one embodiment, the non-human fertilized egg is a mammalian fertilized egg. In one embodiment, the mammalian fertilized egg is a rodent fertilized egg at the single cell stage. In one embodiment, the mammalian fertilized egg is a rat or mouse fertilized egg at the single cell stage.

Further provided is a rat or rat cell comprising a targeted genetic modification in its genomic locus, wherein the genomic locus is an Interleukin-2 receptor gamma locus, an ApoE locus, a Rag1 locus, a Rag2 locus, or a Rag2/Rag1 locus, wherein the targeted genetic modification comprises: (a) a deletion of an endogenous rat nucleic acid sequence at the genomic locus; (b) an insertion of a homologous nucleic acid, an orthologous nucleic acid, or a chimeric nucleic acid comprising a human and a rat nucleic acid sequence; or (c) a combination thereof. In such a rat or rat cell, the targeted genetic modification is transmissible through the germline of the rat or a rat propagated from the rat cell.

In some such rats or rat cells the deletion of the endogenous rat nucleic acid at the genomic locus is at least about 10 kb, or the insertion of the exogenous nucleic acid sequence at the genomic locus is at least about 5 kb.

Further provided is a rat or rat cell, wherein (a) the targeted genetic modification at the Interleukin-2 receptor gamma locus results in a decrease in or absence of Interleukin-2 receptor gamma protein activity; (b) the targeted genetic modification at the ApoE locus results in a decrease in or absence of ApoE protein activity; (c) the targeted genetic modification at the Rag1 locus results in a decrease in or absence of Rag1 protein activity; (d) the targeted genetic modification at the Rag2 locus results in a decrease in or absence of Rag2 protein activity; or, (e) the targeted genetic modification at the Rag2/Rag1 locus results in a decrease in or absence of Rag2 protein activity and Rag1 activity.

In some embodiments, the targeted genetic modification of the Interleukin-2 receptor gamma locus comprises: (a) a deletion of the entire rat Interleukin-2 receptor gamma coding region or a portion thereof; (b) a replacement of the entire rat Interleukin-2 receptor gamma coding region or a portion thereof with a human Interleukin-2 receptor gamma coding region or a portion thereof; (c) a replacement of an ecto-domain of the rat Interleukin-2 receptor gamma coding region with the ecto-domain of a human Interleukin-2 receptor gamma; or, (d) at least a 3 kb deletion of the Interleukin-2 receptor gamma locus. In other such rats or rat cells the targeted genetic modification of the ApoE locus comprises: (a) a deletion of the entire ApoE coding region or a portion thereof; or, (b) at least a 1.8 kb deletion of the ApoE locus comprising the ApoE coding region.

Further provided is a rat or rat cell, wherein the targeted genetic modification of the Rag2 locus comprises: (a) a deletion of the entire Rag2 coding region or a portion thereof; or (b) at least a 5.7 kb deletion of the Rag2 locus comprising the Rag2 coding region. In some embodiments, the targeted genetic modification of the Rag2/Rag1 locus comprises: (a) a deletion of the entire Rag2 coding region or a portion thereof and a deletion of the entire Rag1 coding region or portion thereof; or, (b) a deletion of at least 16 kb of the Rag2/Rag1 locus comprising the Rag2 coding region.

Further provided is a rat or rat cell, wherein the targeted genetic modification comprises an insertion of an expression cassette comprising a selective marker at the Interleukin-2 receptor gamma locus, the ApoE locus, the Rag1 locus, the Rag2 locus, or the Rag2/Rag1 locus. In some such rats or rat cells the expression cassette comprises a lacZ gene operably linked to the endogenous promoter at the genomic locus and a human ubiquitin promoter operably linked to a selective marker.

Further provided is a rat or rat cell, wherein the targeted genetic modification in the Interleukin-2 receptor gamma locus, the ApoE locus, the Rag1 locus, the Rag2 locus or the Rag2/Rag1 locus comprises the insertion of a self-deleting selection cassette. In some such rats or rat cells, the self-deleting selection cassette comprises a selective marker gene operably linked to a promoter active in the rat cell and a recombinase gene operably linked to a male germ cell-specific promoter, wherein the self-deleting cassette is flanked by recombination recognition sites recognized by the recombinase. In some such rats or rat cells, the male germ cell-specific promoter is a Protamine-1 promoter; the recombinase gene encodes Cre, and the recombination recognition sites are loxP sites. In one embodiment, the Protamine-1 promoter is a mouse or a rat Protamine-1 promoter.

Further provided is a rat or rat cell, wherein the insertion of the exogenous nucleic acid sequence at the genomic locus comprises a reporter nucleic acid operably linked to an endogenous Interleukin-2 receptor gamma promoter, an endogenous ApoE promoter, an endogenous Rag1 promoter, or an endogenous Rag2 promoter. In some such rats or rat cells, the reporter nucleic acid encodes a reporter comprising β-galactosidase, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, or a combination thereof.

Further provided is a rat cell, wherein the rat cell is a pluripotent rat cell or a rat embryonic stem (ES) cell. In some such rat cells, the pluripotent rat cell or the rat embryonic stem (ES) cell (a) is derived from a DA strain or an ACI strain; (b) is characterized by expression of at least one pluripotency marker comprising Dnmt3L, Eras, Errbeta, Fbxo15, Fgf4, Gdf3, Klf4, Lef1, LIF receptor, Lin28, Nanog, Oct4, Sox15, Sox2, Utf1, or a combination thereof; or (c) is characterized by one or more of the following characteristics: (i) lack of expression of one or more pluripotency markers comprising c-Myc, Ecat1, and Rexo1; (ii) lack of expression of mesodermal markers comprising Brachyury and Bmpr2; (iii) lack of expression of one or more endodermal markers comprising Gata6, Sox17 and Sox7; or (iv) lack of expression of one or more neural markers comprising Nestin and Pax6.

Further provided is a method for modifying a target genomic locus in an Interleukin-2 receptor gamma locus, an ApoE locus, a Rag1 locus, a Rag2 locus or a Rag2/Rag1 locus in a pluripotent rat cell, the method comprising: (a) introducing into the pluripotent rat cell a targeting vector comprising an insert nucleic acid flanked with 5' and 3' rat homology arms homologous to the target genomic locus; and (b) identifying a genetically modified pluripotent rat cell comprising a targeted genetic modification at the target genomic locus, wherein the targeted genetic modification is capable of being transmitted through the germline of a rat propagated from the pluripotent rat cell. In some such methods, the targeting vector is a large targeting vector (LTVEC), wherein the sum total of the 5' and the 3' rat homology arms is at least about 10 kb. In some embodiments, the sum total of the 5' and the 3' rat homology arms is at least 10 kb but less than 150 kb. In some embodiments, the sum total of the 5' and the 3' rat homology arms is at least about 10 kb but less than about 100 kb. In some embodiments, introducing the targeting vector into the pluripotent rat cell leads to: (i) a deletion of an endogenous rat nucleic acid sequence at the target genomic locus; (ii) an insertion of an exogenous nucleic acid sequence at the target genomic locus; or (iii) a combination thereof.

In some embodiments, the deletion of the endogenous rat nucleic acid at the genomic locus is at least about 10 kb; the deletion of an endogenous rat nucleic acid sequence at the genomic locus ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; the insertion of an exogenous nucleic acid sequence at the genomic locus is at least about 5 kb; or the insertion of an exogenous nucleic acid sequence ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

In some embodiments, (a) the targeted genetic modification at the Interleukin-2 receptor gamma locus results in a decrease in or absence of Interleukin-2 receptor gamma protein activity; (b) the targeted genetic modification at the ApoE locus results in a decrease in or absence of ApoE protein activity; (c) the targeted genetic modification at the Rag1 locus results in a decrease in or absence of Rag1 protein activity; (d) the targeted genetic modification at the Rag2 locus results in a decrease in or absence of Rag2 protein activity; or, (e) the targeted genetic modification at the Rag2/Rag1 locus results in a decrease in or absence of Rag2 protein activity and Rag1 protein activity.

In some embodiments, the targeted genetic modification at the Interleukin-2 receptor gamma locus comprises (a) a deletion of the entire rat Interleukin-2 receptor gamma coding region or a portion thereof; (b) a replacement of the entire rat Interleukin-2 receptor gamma coding region or a portion thereof with a human Interleukin-2 receptor gamma coding region or a portion thereof; (c) a replacement of an ecto-domain of the rat Interleukin-2 receptor gamma coding region with the ecto-domain of a human Interleukin-2 receptor gamma; or, (d) at least a 3 kb deletion of the Interleukin-2 receptor gamma locus comprising the Interleukin-2 receptor gamma coding region.

In some embodiments, the targeted genetic modification at the ApoE locus comprises: (a) a deletion of the entire ApoE coding region or a portion thereof; or, (b) at least a 1.8 kb deletion of the ApoE locus comprising the ApoE coding region.

In some embodiments, the targeted genetic modification at the Rag2 locus comprises: (a) a deletion of the entire Rag2 coding region or a portion thereof; or, (b) at least a 5.7 kb deletion of the Rag2 locus comprising the Rag2 coding region. In other methods, the targeted genetic modification of the Rag1/Rag2 locus comprises: (a) a deletion of the entire Rag2 coding region or a portion thereof and a deletion of the entire Rag1 coding region or portion thereof; or, (b) a deletion of at least 16 kb of the Rag2/Rag1 locus comprising the Rag2 and Rag1 coding regions.

In some such embodiments for modifying a target genomic locus, the insert nucleic acid comprises an expression cassette comprising a polynucleotide encoding a selective marker. In some such embodiments, the expression cassette comprises a lacZ gene operably linked to an endogenous promoter at the genomic locus and a human ubiquitin promoter operably linked to a selective marker gene.

In some embodiments, the insert nucleic acid comprises a self-deleting selection cassette. In some such embodiments, the self-deleting selection cassette comprises a selective marker operably linked to a promoter active in the rat pluripotent cell and a polynucleotide encoding a recombinase operably linked to a male germ cell-specific promoter, wherein the self-deleting cassette is flanked by recombination recognition sites recognized by the recombinase. In some such embodiments, the male germ cell-specific promoter is a Protamine-1 promoter; or, the recombinase gene encodes Cre and the recombination recognition sites are loxP sites. In some embodiments, the Protamine-1 promoter is a mouse or a rat Protamine-1 promoter.

In other methods, the insertion of the exogenous nucleic acid sequence at the genomic locus comprises a reporter nucleic acid sequence operably linked to the endogenous Interleukin-2 receptor gamma promoter, the endogenous ApoE promoter, the endogenous Rag1 promoter, or the endogenous Rag2 promoter. In some such embodiments, the reporter nucleic acid sequence encodes a reporter comprising β-galactosidase, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, or a combination thereof.

In some embodiments for modifying a target genomic locus, the pluripotent rat cell is a rat embryonic stem (ES) cell. In some such embodiments, the pluripotent rat cell (a) is derived from a DA strain or an ACI strain; (b) is characterized by expression of a pluripotency marker comprising Oct-4, Sox-2, alkaline phosphatase, or a combination thereof; or, (c) is characterized by one or more of the following characteristics: (i) lack of expression of one or more pluripotency markers comprising c-Myc, Ecat1, and Rexo1; (ii) lack of expression of mesodermal markers comprising Brachyury and Bmpr2; (iii) lack of expression of one or more endodermal markers comprising Gata6, Sox17 and Sox7; or (iv) lack of expression of one or more neural markers comprising Nestin and Pax6.

In some embodiments, the method further comprises identifying the targeted genetic modification at the target genomic locus, wherein the identification step employs a quantitative assay for assessing a modification of allele (MOA) at the target genomic locus.

In some embodiments, the introducing step further comprises introducing a second nucleic acid encoding a nuclease agent that promotes a homologous recombination between the targeting vector and the target genomic locus in the pluripotent rat cell. In some such embodiments, the nuclease agent comprises a chimeric protein comprising a zinc finger-based DNA binding domain fused to a FokI endonuclease. Some such methods result in bi-allelic modification of the target genomic locus.

In some embodiments, the introducing step of the method further comprises introducing into the pluripotent rat cell: a first expression construct comprising a first promoter operably linked to a first nucleic acid sequence encoding a Clustered Regularly Interspaced Short Palindromic Repeats (CRISPR)-associated (Cas) protein, and a second expression construct comprising a second promoter operably linked to a second nucleic acid sequence encoding a genomic target sequence operably linked to a guide RNA (gRNA), wherein the genomic target sequence is immediately flanked on the 3' end by a Protospacer Adjacent Motif (PAM) sequence. In one embodiment, the genomic target sequence comprises the nucleotide sequence set forth in SEQ ID NO: 1. In one embodiment the gRNA comprises a third nucleic acid sequence encoding a Clustered Regularly Interspaced Short Palindromic Repeats (CRISPR) RNA (crRNA) and a trans-activating CRISPR RNA (tracrRNA). In some such embodiments, the Cas protein is Cas9. In some such embodiments, (a) the gRNA is the chimeric RNA of the nucleic acid sequence set forth in SEQ ID NO: 2; (b) the gRNA is the chimeric RNA of the nucleic acid sequence set forth in SEQ ID NO: 3; (c) the crRNA comprises a sequence set forth in SEQ ID NO: 4, SEQ ID NO: 5, SEQ ID NO: 6; or, (d) the tracrRNA comprises the sequence set forth in SEQ ID NO: 7 and/or SEQ ID NO: 8.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A depicts Oct-4 (green); FIG. 2B depicts Sox-2 (red); FIG. 2C depicts DAPI (blue); FIG. 2D depicts an overlay of pluripotency markers expressed by rESCs.

FIG. 11 provides a summary of the ApoE targeting efficiency when performed in the presence of zinc finger nucleases (ZFN1 or ZFN2)

FIGS. 12A-12C depict targeting of the rat Rosa 26 locus, which lies between the Setd5 and Thumpd3 genes as in mouse, with the same spacing. FIG. 12A shows the structure of the mouse Rosa 26 locus. Mouse Rosa26 transcripts consist of 2 or 3 exons. FIG. 12B depicts the structure of the rat Rosa26 locus; the rat locus contains a second exon 1 (Ex1b) in addition to the homologous exon to mouse exon1 (Ex1a); no third exon has been identified in rat. FIG. 12C depicts a targeted rat Rosa26 allele; homology arms of 5 kb each were cloned by PCR using genomic DNA from DA rESC; the targeted allele contains a Splicing Acceptor (SA)-lacZ-hUB-neo cassette replacing a 117 bp deletion in the rat Rosa26 intron.

FIGS. 13G and 13H depict LacZ expression in E12.5 rat embryos. In contrast to the wild-type control embryo (FIG. 13H), which shows a low level of background LacZ staining, the rRosa26 heterozygous embryo exhibited ubiquitous expression of the LacZ reporter throughout the embryo (FIG. 13G).

FIGS. 13I and 13J depict LacZ expression in E14.5 rat embryos. In contrast to the wild-type control embryo (FIG. 13J), which shows a low level of background LacZ staining, the rRosa26 heterozygous rat embryo exhibited ubiquitous expression of the LacZ reporter throughout the embryo (FIG. 13I).

FIG. 25 provides a summary of the germ-line transmitting, targetable rat embryonic stem cell lines.

DETAILED DESCRIPTION OF THE INVENTION

Glossary

Figure 1:
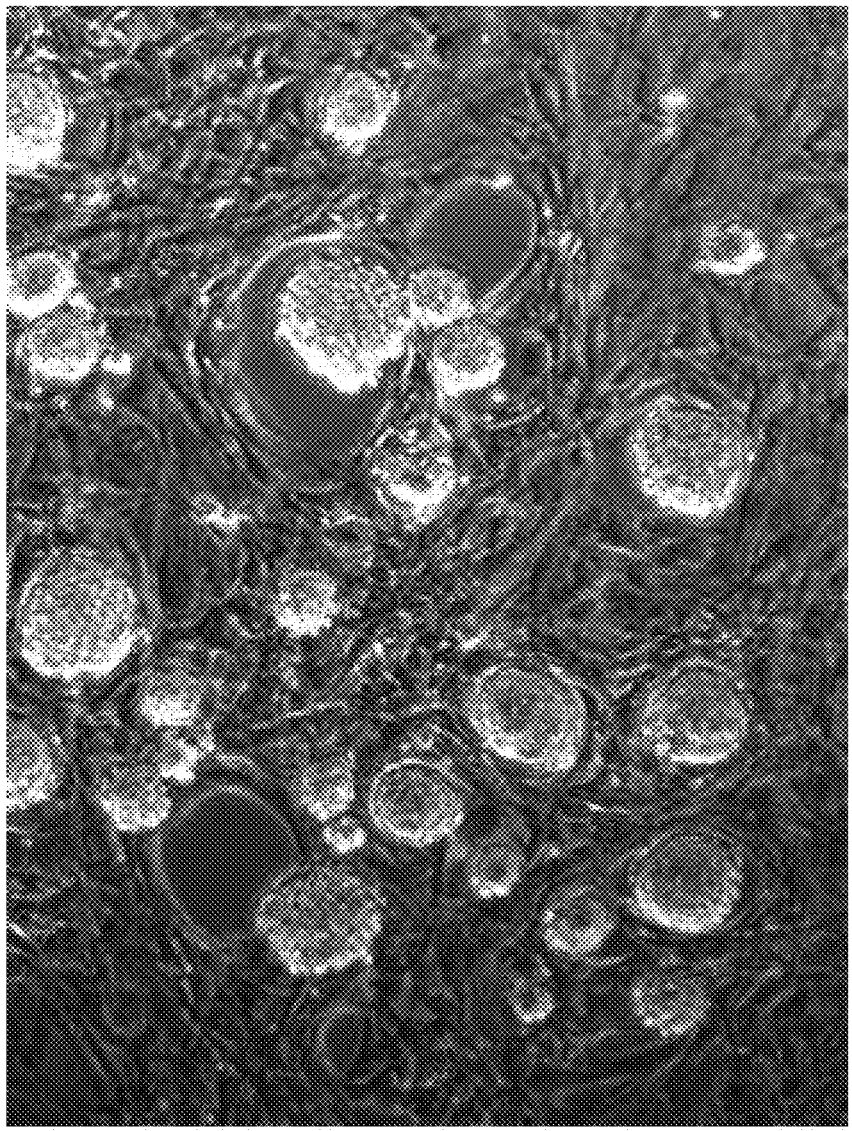
FIG. 1 depicts rat ESCs, which grow as compact spherical colonies that routinely detach and float in the dish.

The term "embryonic stem cell" or "ES cell" as used herein includes an embryo-derived totipotent or pluripotent cell that is capable of contributing to any tissue of the developing embryo upon introduction into an embryo. The term "pluripotent cell" as used herein includes an undifferentiated cell that possesses the ability to develop into more than one differentiated cell types.

The term "homologous nucleic acid" as used herein includes a nucleic acid sequence that is either identical or substantially similar to a known reference sequence. In one embodiment, the term "homologous nucleic acid" is used to characterize a sequence having amino acid sequence that is at least 70%, at least 75%, at least 80%, at least 85%, at least 90%, at least 95%, at least 96%, at least 97%, at least 98%, at least 99%, or even 100% identical to a known reference sequence.

The term "orthologous nucleic acid" as used herein includes a nucleic acid sequence from one species that is functionally equivalent to a known reference sequence in another species.

The term "large targeting vector" or "LTVEC" as used herein includes large targeting vectors for eukaryotic cells that are derived from fragments of cloned genomic DNA larger than those typically used by other approaches intended to perform homologous gene targeting in eukaryotic cells. Examples of LTVEC, include, but are not limited to, bacterial homologous chromosome (BAC) and yeast artificial chromosome (YAC).

The term "modification of allele" (MOA) as used herein includes the modification of the exact DNA sequence of one allele of a gene(s) or chromosomal locus (loci) in a genome. Examples of "modification of allele (MOA)" as described herein includes, but is not limited to, deletions, substitutions, or insertions of as little as a single nucleotide or deletions of many kilobases spanning a gene(s) or chromosomal locus (loci) of interest, as well as any and all possible modifications between these two extremes.

The term "recombination site" as used herein includes a nucleotide sequence that is recognized by a site-specific recombinase and that can serve as a substrate for a recombination event.

"Serial" genetic modifications include two or more modifications to, e.g., a rat ES cell, conducted independently. For example, a first modification is made to a rat ES cell genome employing a suitable first nucleic acid construct. The first modification may be achieved by electroporation, or any other method known in the art. Then a second modification is made to the same rat ES cell genome employing a suitable second nucleic acid construct. The second modification may be achieved by a second electroporation, or any other method known in the art. In various embodiments, following the first and the second genetic modifications of the same rat ES cell, a third, a fourth, a fifth, a sixth, and so on, serial genetic modifications (one following another) may be achieved using, e.g., serial electroporation or any other suitable method (serially) known in the art.

The term "site-specific recombinase" as used herein includes a group of enzymes that can facilitate recombination between "recombination sites" where the two recombination sites are physically separated within a single nucleic acid molecule or on separate nucleic acid molecules. Examples of "site-specific recombinase" include, but are not limited to, Cre, Flp, and Dre recombinases.

The term "germline" in reference to a nucleic acid sequence includes a nucleic acid sequence that can be passed to progeny.

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. Heavy chain variable domains are encoded by variable region nucleotide sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found in IMGT database, which is accessible via the internet on the world wide web (www) at the URL "imgt.org."

The phrase "light chain" includes an immunoglobulin light chain sequence from any organism, and unless otherwise specified includes human kappa (κ) and lambda (λ) light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by the light chain variable region nucleotide sequence, which generally comprises light chain $V_L$ and light chain $J_L$ gene segments, derived from a repertoire of light chain V and J gene segments present in the germline. Sequences, locations and nomenclature for light chain V and J gene segments for various organisms can be found in IMGT database, which is accessible via the internet on the world wide web (www) at the URL "imgt.org." Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

The phrase "operably linked" comprises a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

1. Target Locus Comprising a Rat Nucleic Acid

Various methods and compositions are provided, which allow for the integration of at least one insert nucleic acid at a target locus. As used herein, a "genomic locus of interest" comprises any segment or region of DNA within the genome that one desires to integrate an insert nucleic acid. The terms "genomic locus of interest" and "target genomic locus of interest" can be used interchangeable. The genomic locus of interest can be native to the cell, or alternatively can comprise a heterologous or exogenous segment of DNA that was integrated into the genome of the cell. Such heterologous or exogenous segments of DNA can include transgenes, expression cassettes, polynucleotide encoding selection makers, or heterologous or exogenous regions of genomic DNA. The term "locus" is a defined herein as a segment of DNA within the genomic DNA. Genetic modifications as described herein can include one or more deletions from a locus of interest, additions to a locus of interest, replacement of a locus of interest, and/or any combination thereof. The locus of interest can comprise coding regions or non-coding regulatory regions.

The genomic locus of interest can further comprise any component of a targeted integration system including, for example, a recognition site, a selection marker, a previously integrated insert nucleic acid, polynucleotides encoding nuclease agents, promoters, etc. Alternatively, the genomic locus of interest can be located within a yeast artificial chromosome (YAC), bacterial artificial chromosome (BAC), a human artificial chromosome, or any other engineered genomic region contained in an appropriate host cell. In various embodiments, the targeted locus can comprise native, heterologous, or exogenous nucleic acid sequence from a prokaryote, a eukaryote, yeast, bacteria, a non-human mammal, a non-human cell, a rodent, a human, a rat, a mouse, a hamster, a rabbit, a pig, a bovine, a deer, a sheep, a goat, a chicken, a cat, a dog, a ferret, a primate (e.g., marmoset, rhesus monkey), domesticated mammal or an agricultural mammal or any other organism of interest or a combination thereof.

In specific embodiments, the genomic locus of interest comprises a target locus of a "rat nucleic acid". Such a region comprises a nucleic acid from a rat that is integrated within the genome of a cell.

Non-limiting examples of the target locus include a genomic locus that encodes a protein expressed in a B cell, a genomic locus that expresses a polypeptide in an immature B cell, a genomic locus that expresses a polypeptide in a mature B cell, an immunoglobulin (Ig) loci, or a T cell receptor loci, including, for example, a T cell receptor alpha locus. Additional examples of target genomic locus include an FcER1a locus, a TLR4 locus, a PRLR locus, a Notch4 locus, an Accn2 locus, an Adamts5 locus, a TRPA1 locus, FolH1 locus, an LRP5 locus, an IL2 receptor locus, including, for example, an IL2 Receptor gamma (IL2Rg) locus, an ApoE locus, a Rag1 locus, a Rag2 locus, a Rag1/Rag2 locus, and an ERBB4 locus. Any such target locus can be from a rat.

In one embodiment, the target locus encodes a mammalian immunoglobulin heavy chain variable region amino acid sequence. In one embodiment, the target locus encodes a rat immunoglobulin heavy chain variable region amino acid sequence. In one embodiment, the target locus comprises a genomic DNA sequence comprising an unrearranged rat, mouse, or human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a rat, mouse, or human immunoglobulin heavy chain constant region nucleic acid sequence selected from a CH1, a hinge, a CH2, a CH3, and a combination thereof. In one embodiment, the heavy chain constant region nucleic acid sequence comprises a CH1-hinge-CH2-CH3. In one embodiment, the target locus comprises a rearranged rat, mouse, or human immunoglobulin heavy chain variable region nucleic acid sequence operably linked to an immunoglobulin heavy chain constant region nucleic acid sequence. In one embodiment, the immunoglobulin heavy chain constant region nucleic acid sequence is a rat, mouse, or human immunoglobulin heavy chain constant region nucleic acid sequence selected from a CH1, a hinge, a CH2, a CH3, and a combination thereof. In one embodiment, the heavy chain constant region nucleic acid sequence comprises a CH1-hinge-CH2-CH3.

In one embodiment, the target locus comprises a genomic DNA sequence that encodes a mammalian immunoglobulin light chain variable region amino acid sequence. In one embodiment, the genomic DNA sequence comprises an unrearranged mammalian λ and/or κ light chain variable region nucleic acid sequence.

In one embodiment, the genomic DNA sequence comprises a rearranged mammalian λ and/or κ light chain variable region nucleic acid sequence. In one embodiment, the unrearranged λ or κ light chain variable region nucleic acid sequence is operably linked to a mammalian immunoglobulin light chain constant region nucleic acid sequence selected from a λ light chain constant region nucleic acid sequence and a κ light chain constant region nucleic acid sequence. In one embodiment, the mammalian immunoglobulin light chain constant region nucleic acid sequence is a rat immunoglobulin light chain constant region nucleic acid sequence. In one embodiment, the mammalian immunoglobulin light chain constant region nucleic acid sequence is a mouse immunoglobulin light chain constant region nucleic acid sequence. In one embodiment, the mammalian immunoglobulin light chain constant region nucleic acid sequence is a human immunoglobulin light chain constant region nucleic acid sequence.

As used herein, a rat ApoE locus, a rat interleukin-2 receptor gamma (Il-2rg) locus, a rat Rag2 locus, a rat Rag1 locus and/or a rat Rag2/Rag1 locus comprise the respective regions of the rat genome in which each of these genes or gene combinations are located. Modifying any one of the rat ApoE locus, the rat interleukin-2 receptor gamma locus, the rat Rag2 locus, the rat Rag1 locus and/or the combined rat Rag2/Rag1 locus can comprise any desired alteration to the given locus. Non-limiting examples of modification to the given rat locus are discussed in further detail herein.

For example, in specific embodiments, one or more of the rat ApoE locus, the rat interleukin-2 receptor gamma locus, the Rag2 locus, and/or the Rag2/Rag1 locus is modified such that the activity and/or level of the encoded ApoE protein or the interleukin-2 receptor gamma protein or the Rag1 protein or the Rag2 protein or a combination of the Rag1 and Rag2 proteins are decreased. In other embodiments, the activity of the ApoE protein, the interleukin-2 receptor gamma protein, the Rag1 protein, or the Rag2 protein, or a combination of the Rag1 and Rag2 proteins is absent.

By "decreased" is intended any decrease in the level or activity of the gene/protein encoded at the locus of interest. For example, a decrease in activity can comprise either (1) a statistically significant decrease in the overall level or activity of a given protein (i.e., ApoE, interleukin-2 receptor gamma, Rag2, Rag2 or a combination of Rag1 and Rag2) including, for example, a decreased level or activity of 0.5%, 1%, 5%, 10%, 20%, 30%, 40%, 50%, 60%, 70%, 80%, 90%, 100%, 120% or greater when compared to an appropriate control. Methods to assay for a decrease in the concentration and/or the activity of anyone of ApoE, interleukin-2 receptor gamma, Rag1 and Rag2 are known in the art.

In other embodiments, one or more of the rat ApoE locus, the rat interleukin-2 receptor gamma locus, the rat Rag2 locus, the rat Rag1 locus and/or rat Rag2/Rag1 locus comprise a modification such that the activity and/or level of the encoded ApoE polypeptide, the interleukin-2 receptor gamma polypeptide, the Rag2 polypeptide, the Rag1 polypeptide, or both the Rag1 and Rag2 polypeptide is increased. By "increased" is intended any increase in the level or activity of the gene/polypeptide encoded at the locus of interest. For example, an increase in activity can comprise either (1) a statistically significant increase in the overall level or activity of a given protein (i.e., ApoE, interleukin-2 receptor gamma, Rag1, Rag2 or Rag1 and Rag2) including, for example, an increased level or activity of 0.5%, 1%, 5%, 10%, 20%, 30%, 40%, 50%, 60%, 70%, 80%, 90%, 100%, 120% or greater when compared to an appropriate control. Methods to assay for an increase in the concentration and/or the activity of anyone of the ApoE, Rag1, Rag2 and interleukin-2 receptor gamma proteins are known in the art.

The genetic modification to the rat ApoE locus, the rat interleukin-2 receptor gamma locus, the rat Rag2 locus, the rat Rag1 locus and/or rat Rag2/Rag1 locus can comprise a deletion of an endogenous rat nucleic acid sequence at the genomic locus, an insertion of an exogenous nucleic acid at the genomic locus, or a combination thereof. The deletion and/or insertion can occur anywhere within the given locus as discussed elsewhere herein.

Further embodiments provided herein comprise the modification of one or more of the rat ApoE locus, the rat interleukin-2 receptor gamma locus, the rat Rag2 locus, the rat Rag1 locus and/or the rat Rag2/Rag1 locus through the replacement of a portion of the rat ApoE locus, the interleukin-2 receptor gamma locus, Rag2 locus, Rag1 locus and/or Rag2/Rag1 locus with the corresponding homologous or orthologous portion of an ApoE locus, an interleukin-2 receptor gamma locus, a Rag2 locus, a Rag1 locus and/or a Rag2/Rag1 locus from another organism.

Still other embodiments, the modification of one or more of the rat ApoE locus, the rat interleukin-2 receptor gamma locus, Rag2 locus, Rag1 locus, and/or Rag2/Rag1 locus is carried out through the replacement of a portion of the rat ApoE locus, the rat interleukin-2 receptor gamma locus and/or the rat Rag2 locus, and/or the Rag1 locus and/or Rag2/Rag1 locus with an insert polynucleotide sharing across its full length least 80%, 85%, 90%, 91%, 92%, 93%, 94%, 95%, 96%, 97%, 98%, 99% to a portion of an ApoE locus, an interleukin-2 receptor gamma locus, a Rag2 locus, a Rag1 locus and/or a Rag2/Rag1 locus it is replacing.

The given insert polynucleotide and/or the corresponding region of the rat locus being deleted can be a coding region, an intron, an exon, an untranslated region, a regulatory region, a promoter, or an enhancer or any combination thereof or any portion thereof. Moreover, the given insert polynucleotide and/or the region of the rat locus being deleted can be of any desired length, including for example, between 10-100 nucleotides in length, 100-500 nucleotides in length, 500-1 kb nucleotide in length, 1 Kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other instances, the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 300 kb to about 400 kb, from about 400 kb to about 500 kb, from about 500 kb to 1 Mb, from about 1 Mb to about 1.5 Mb, from about 1.5 Mb to about 2 Mb, from about 2 Mb to about 2.5 Mb, from about 2.5 Mb to about 2.8 Mb, from about 2.8 Mb to about 3 Mb. In other embodiments, the given insert polynucleotide and/or the region of the rat locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

The given insert polynucleotide can be from any organism, including, for example, a rodent, a rat, a mouse, a hamster, a mammal, a non-human mammal, a human, an agricultural animal or a domestic animal.

As discussed in further detail herein, various methods are provided to generate targeted modifications of any rat locus of interest, including for example, targeted modifications in the rat ApoE locus, the rat interleukin-2 receptor gamma locus, the rat Rag2 locus, the rat Rag1 locus, and/or the rat Rag2/Rag1 locus. Further provided are genetically modified rats or genetically modified pluripotent rat cells (e.g., an rat ES cells), which comprise a deletion, an insertion, a replacement and/or any combination thereof at the interleukin-2 receptor gamma locus, at the ApoE locus, at the rat Rag2 locus, at the rat Rag1 locus, and/or at the rat Rag2/Rag1 locus. Such genetic modifications (including those that result in an absence, a decrease, an increase or a modulation in activity of the target locus) and are also capable of being transmitted through the germline. In specific embodiments, the genetic modifications result in a knockout of the desired target locus. Such rats find use in in a variety of experimental systems as discussed elsewhere herein.

For example, ApoE (Apolipoprotein E) knockouts in rats offer an animal model to study endothelial function, including, but not limited to, plaque formation, transcriptional changes (Whole Transcriptome Shotgun Sequencing (RNA-Seq), and ex vivo function. Moreover, the larger size of rats facilitate all these assays and potentially improve the quality of the RNA-Seq data. ApoE is an important transport molecule and can transport lipids, such as cholesterol, through the bloodstream. ApoE can also function in the nervous system, for example, to clear β-amyloid from the brain. Modifications in ApoE have been implicated in various conditions, including, for example, atherosclerosis, hyperlipidemia, and Alzheimer's disease. ApoE knockout animals display impaired clearing of lipoproteins from the blood and develop atherosclerosis. Thus, ApoE knockout animals provide a model to study conditions and/or processes such as, for example, endothelia function, plaque formation, transcriptional changes (RNA-Seq), hyperlipidemia, atherosclerosis and Alzheimer's disease. Assays to measure ApoE activity are known in the art. For example, a decrease in ApoE activity can be measured by assaying for a decrease in the ApoE levels in a blood sample obtained from a subject by immunoassays, such as by ELISA or by Immunoblotting techniques. Moreover, the large size of rats facilitates all these assays and improves the quality of the data.

RAG1 (Recombination-Activating Gene 1) and RAG2 (Recombination-Activating Gene 2) are enzymes that are part of a multi-subunit complex having VDJ recombination activity and play an important role in the rearrangement and recombination of immunoglobulin and T-cell receptor genes in lymphocytes. RAG1 and RAG2 induce a double stranded DNA cleavage to facilitate recombination and join of segments of the T cell receptor and B cell receptor (i.e. immunoglobulin) genes. Knockout of RAG1 and/or RAG2 causes a loss of B cells and T cells in the animal resulting in severe immunodeficiency. RAG1 and/or RAG2 knockout animals find use, for example, in studies of xenografts (i.e. human cell xenografts in rats), cancer, vaccine development, autoimmune disease, infectious disease and graft versus host disease (GVHD). Various assays to measure RAG1 and/or RAG2 activity are known in the art and include, for example, measuring recombination efficiency or assaying for the presence or absence of B cells and/or T cells in a subject. Moreover, the large size of rats facilitates all these assays and potentially improves the quality of the data.

The IL-2 receptor (IL-2R) is expressed on the surface of certain immune cells and binds to the cytokine interleukin-2 (IL-2). The IL-2R is an integral membrane protein comprising at least three separate subunit chains, including, an alpha chain (IL-2Ra, CD25), a beta chain (IL-2Rb, CD122) and a gamma chain (IL2-Rg, CD132). The IL-2 receptor gamma (also referred to as IL2r-γ or IL2Rg) chain is a common gamma chain that is shared by various cytokine receptors, including, for example, the receptors for IL-2, IL-4, IL-7, IL-9, IL-15 and IL-21. IL-2Rg comprises an ectodomain on the extracellular surface of the cell, which contributes to the binding of the ligand, a transmembrane domain, and an intracellular domain which can interact with various molecules to induce intracellular signal transduction pathways. The Il2rg gene is found on the X-chromosome in mammals and certain mutations in the gamma chain gene in humans can cause human X-linked severe combined immunodeficiency (XSCID) characterized by a profound T-cell defect. In addition, the gamma chain ecto-domain can be shed off of the transmembrane receptor and released as a soluble gamma chain receptor. The soluble gamma chain receptor can be detected in the blood of a subject and can function to regulate cytokine signaling.

In some embodiments, the rat IL-2Rg chain is replaced with the human IL2-Rg chain such that the rat expresses a fully human IL-2Rg chain. In other instances, it may be useful to replace only the ectodomain of the rat IL-2Rg chain with the ectodomain of the human IL-2Rg chain. In such cases, the resulting humanized IL-2Rg chain expressed in a rat comprises a human ectodomain, with the remainder of the molecule being from the rat.

The full-length humanization of IL-2Rg is useful because rats having this modified locus will produce human IL-2Rg. This will allow for the detection of human IL-2Rg in rats with antibodies specific to human IL-2Rg. The ecto-humanization (i.e., replacing the rat ecto-domain of IL-2Rg with the human ecto-domain of IL-2Rg) will result in an IL-2Rg polypeptide that will bind the human ligands for IL2-Rg, but because the cytoplasmic domain is still rat, it ecto-humanized form of IL-2Rg will also interact with the rat signaling machinery.

2. Modifying a Rat Target Locus

A. Targeting Vectors and Insert Nucleic Acids i. Insert Nucleic Acid

As used herein, the "insert nucleic acid" comprises a segment of DNA that one desires to integrate at the target locus. In one embodiment, the insert nucleic acid comprises one or more polynucleotides of interest. In other embodiments, the insert nucleic acid can comprise one or more expression cassettes. A given expression cassette can comprise a polynucleotide of interest, a polynucleotide encoding a selection marker and/or a reporter gene along with the various regulatory components that influence expression. Non-limiting examples of polynucleotides of interest, selection markers, and reporter genes that can be included within the insert nucleic acid are discussed in detail elsewhere herein.

In specific embodiments, the insert nucleic acid can comprise a nucleic acid from rat, which can include a segment of genomic DNA, a cDNA, a regulatory region, or any portion or combination thereof. In other embodiments, the insert nucleic acid can comprise a nucleic acid from a non-human mammal, a rodent, a human, a rat, a mouse, a hamster a rabbit, a pig, a bovine, a deer, a sheep, a goat, a chicken, a cat, a dog, a ferret, a primate (e.g., marmoset, rhesus monkey), domesticated mammal or an agricultural mammal or any other organism of interest. As outlined in further detail herein, the insert nucleic acid employed in the various methods and compositions can result in the "humanization" of the a target locus comprising a rat nucleic acid.

In one embodiment, the insert nucleic acid comprises a knock-in allele of at least one exon of an endogenous gene. In one embodiment, the insert nucleic acid comprises a knock-in allele of the entire endogenous gene (i.e., "gene-swap knock-in").

In one embodiment, the insert nucleic acid comprises a regulatory element, including for example, a promoter, an enhancer, or a transcriptional repressor-binding element.

In further embodiments, the insert nucleic acid comprises a conditional allele. In one embodiment, the conditional allele is a multifunctional allele, as described in US 2011/0104799, which is incorporated by reference in its entirety. In specific embodiments, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

The insert nucleic acid ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

In one embodiment, the insert nucleic acid comprises a deletion of a rat genomic DNA sequence ranging from about 1 kb to about 200 kb, from about 2 kb to about 20 kb, or from about 0.5 kb to about 3 Mb. In one embodiment, the extent of the deletion of the genomic DNA sequence is greater than a total length of the 5' homology arm and the 3' homology arm. In one embodiment, the extent of the deletion of the genomic DNA sequence ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In one embodiment, the insert nucleic acid comprises an insertion or a replacement of a rat nucleic acid sequence with a homologous or orthologous human nucleic acid sequence. In one embodiment, the insert nucleic acid comprises an insertion or replacement of a rat DNA sequence with a homologous or orthologous human nucleic acid sequence at an endogenous rat locus that comprises the corresponding rat DNA sequence.

In one embodiment, the genetic modification is an addition of a nucleic acid sequence. In one embodiment, the added nucleotide sequence ranges from 5 kb to 200 kb.

In one embodiment, the insert nucleic acid comprises a genetic modification in a coding sequence. In one embodiment, the genetic modification comprises a deletion mutation of a coding sequence. In one embodiment, the genetic modification comprises a fusion of two endogenous coding sequences.

In one embodiment, the insert nucleic acid comprises an insertion or a replacement of a rat nucleic acid sequence with a homologous or orthologous human nucleic acid sequence. In one embodiment, the insert nucleic acid comprises an insertion or replacement of a rat DNA sequence with a homologous or orthologous human nucleic acid sequence at an endogenous rat locus that comprises the corresponding rat DNA sequence.

In one embodiment, the genetic modification comprises a deletion of a non-protein-coding sequence, but does not comprise a deletion of a protein-coding sequence. In one embodiment, the deletion of the non-protein-coding sequence comprises a deletion of a regulatory element. In one embodiment, the genetic modification comprises a deletion of a promoter. In one embodiment, the genetic modification comprises an addition of a promoter or a regulatory element. In one embodiment, the genetic modification comprises a replacement of a promoter or a regulatory element.

In one embodiment, the nucleic acid sequence of the targeting vector can comprise a polynucleotide that when integrated into the genome will produce a genetic modification of a region of the rat ApoE locus, wherein the genetic modification at the ApoE locus results in a decrease in ApoE activity, increase in ApoE activity, or a modulation of ApoE activity. In one embodiment, an ApoE knockout ("null allele") is generated.

In one embodiment, the nucleic acid sequence of the targeting vector can comprise a polynucleotide that when integrated into the genome will produce a genetic modification of a region of the rat interleukin-2 receptor locus, wherein the genetic modification at the interleukin-2 receptor locus results in a decrease in interleukin-2 receptor activity. In one embodiment, an interleukin-2 receptor knockout ("null allele") is generated.

In further embodiments, the insert nucleic acid results in the replacement of a portion of the rat ApoE locus, the interleukin-2 receptor gamma locus and/or Rag2 locus, and/or Rag1 locus and/or Rag2/Rag1 locus with the corresponding homologous or orthologous portion of an ApoE locus, an interleukin-2 receptor gamma locus, a Rag2 locus, a Rag1 locus and/or a Rag2/Rag1 locus from another organism.

Still other embodiments, the insert nucleic acid comprises a polynucleotide sharing across its full length least 80%, 85%, 90%, 91%, 92%, 93%, 94%, 95%, 96%, 97%, 98%, 99% to a portion of an ApoE locus, an interleukin-2 receptor gamma locus, a Rag2 locus, a Rag1 locus and/or a Rag2/Rag1 locus it is replacing.

The given insert polynucleotide and the corresponding region of the rat locus being replaced can be a coding region, an intron, an exon, an untranslated region, a regulatory region, a promoter, or an enhancer or any combination thereof. Moreover, the given insert polynucleotide and/or the region of the rat locus being deleted can be of any desired length, including for example, between 10-100 nucleotides in length, 100-500 nucleotides in length, 500-1 kb nucleotide in length, 1 Kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other instances, the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb. In other embodiments, the given insert polynucleotide and/or the region of the rat locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

In one embodiment, the promoter is constitutively active promoter.

In one embodiment, the promoter is an inducible promoter. In one embodiment, the inducible promoter is a chemically-regulated promoter. In one embodiment, the chemically-regulated promoter is an alcohol-regulated promoter. In one embodiment, the alcohol-regulated promoter is an alcohol dehydrogenase (alcA) gene promoter. In one embodiment, the chemically-regulated promoter is a tetracycline-regulated promoter. In one embodiment, the tetracycline-regulated promoter is a tetracycline-responsive promoter. In one embodiment, the tetracycline-regulated promoter is a tetracycline operator sequence (tetO). In one embodiment, the tetracycline-regulated promoter is a tet-On promoter. In one embodiment, the tetracycline-regulated promoter a tet-Off promoter. In one embodiment, the chemically-regulated promoter is a steroid regulated promoter. In one embodiment, the steroid regulated promoter is a promoter of a rat glucocorticoid receptor. In one embodiment, the steroid regulated promoter is a promoter of an estrogen receptor. In one embodiment, the steroid-regulated promoter is a promoter of an ecdysone receptor. In one embodiment, the chemically-regulated promoter is a metal-regulated promoter. In one embodiment, the metal-regulated promoter is a metalloprotein promoter. In one embodiment, the inducible promoter is a physically-regulated promoter. In one embodiment, the physically-regulated promoter is a temperature-regulated promoter. In one embodiment, the temperature-regulated promoter is a heat shock promoter. In one embodiment, the physically-regulated promoter is a light-regulated promoter. In one embodiment, the light-regulated promoter is a light-inducible promoter. In one embodiment, the light-regulated promoter is a light-repressible promoter.

In one embodiment, the promoter is a tissue-specific promoter. In one embodiment, the promoter is a neuron-specific promoter. In one embodiment, the promoter is a glia-specific promoter. In one embodiment, the promoter is a muscle cell-specific promoter. In one embodiment, the promoter is a heart cell-specific promoter. In one embodiment, the promoter is a kidney cell-specific promoter. In one embodiment, the promoter is a bone cell-specific promoter. In one embodiment, the promoter is an endothelial cell-specific promoter. In one embodiment, the promoter is an immune cell-specific promoter. In one embodiment, the immune cell promoter is a B cell promoter. In one embodiment, the immune cell promoter is a T cell promoter.

In one embodiment, the promoter is a developmentally-regulated promoter. In one embodiment, the developmentally-regulated promoter is active only during an embryonic stage of development. In one embodiment, the developmentally-regulated promoter is active only in an adult cell.

In some embodiments, the insert nucleic acid comprises a nucleic acid flanked with site-specific recombination target sequences. It is recognized the while the entire insert nucleic acid can be flanked by such site-specific recombination target sequences, any region or individual polynucleotide of interest within the insert nucleic acid can also be flanked by such sites. The site-specific recombinase can be introduced into the cell by any means, including by introducing the recombinase polypeptide into the cell or by introducing a polynucleotide encoding the site-specific recombinase into the host cell. The polynucleotide encoding the site-specific recombinase can be located within the insert nucleic acid or within a separate polynucleotide. The site-specific recombinase can be operably linked to a promoter active in the cell including, for example, an inducible promoter, a promoter that is endogenous to the cell, a promoter that is heterologous to the cell, a cell-specific promoter, a tissue-specific promoter, or a developmental stage-specific promoter. Site-specific recombination target sequences, which can flank the insert nucleic acid or any polynucleotide of interest in the insert nucleic acid can include, but are not limited to, loxP, lox511, lox2272, lox66, lox71, loxM2, lox5171, FRT, FRT11, FRT71, attp, att, FRT, rox, and a combination thereof.

In some embodiments, the site-specific recombination sites flank a polynucleotide encoding a selection marker and/or a reporter gene contained within the insert nucleic acid. In such instances following integration of the insert nucleic acid at the targeted locus the sequences between the site-specific recombination sites can be removed.

In one embodiment, the insert nucleic acid comprises a polynucleotide encoding a selection marker. The selection marker can be contained in a selection cassette. Such selection markers include, but are not limited, to neomycin phosphotransferase ($neo^r$), hygromycin B phosphotransferase ($hyg^r$), puromycin-N-acetyltransferase ($puro^r$), blasticidin S deaminase (bse), xanthine/guanine phosphoribosyl transferase (gpt), or herpes simplex virus thymidine kinase (HSV-k), or a combination thereof. In one embodiment, the polynucleotide encoding the selection marker is operably linked to a promoter active in the cell, rat cell, pluripotent rat cell or the ES rat cell. When serially stacking polynucleotides of interest into a targeted locus, the selection marker can comprise a recognition site for a nuclease agent, as outlined above. In one embodiment, the polynucleotide encoding the selection marker is flanked with a site-specific recombination target sequences.

The insert nucleic acid can further comprise a reporter gene operably linked to a promoter, wherein the reporter gene encodes a reporter protein selected from the group consisting of or comprising LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and/or a combination thereof. Such reporter genes can be operably linked to a promoter active in the cell. Such promoters can be an inducible promoter, a promoter that is endogenous to the reporter gene or the cell, a promoter that is heterologous to the reporter gene or to the cell, a cell-specific promoter, a tissue-specific promoter, or a developmental stage-specific promoter.

In one embodiment, nucleic acid insert can comprise a mammalian nucleic acid comprises a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the mammalian nucleic acid comprises a genomic locus that encodes a protein expressed in a bone marrow or a bone marrow-derived cell. In one embodiment, the nucleic acid comprises a genomic locus that encodes a protein expressed in a spleen cell.

In one embodiment, the mammalian nucleic acid comprises a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the mammalian nucleic acid comprises a genomic locus that encodes a protein expressed in a bone marrow or a bone marrow-derived cell. In one embodiment, the nucleic acid comprises a genomic locus that encodes a protein expressed in a spleen cell. In one embodiment, the genomic locus comprises a mouse genomic DNA sequence, a rat genomic DNA sequence a human genomic DNA sequence, or a combination thereof. In one embodiment, the genomic locus comprises, in any order, rat and human genomic DNA sequences. In one embodiment, the genomic locus comprises, in any order, mouse and human genomic DNA sequences. In one embodiment, the genomic locus comprises, in any order, mouse and rat genomic DNA sequences. In one embodiment, the genomic locus comprises, in any order, rat, mouse, and human genomic DNA sequences.

In one embodiment, the genomic locus comprises a mouse genomic DNA sequence, a rat genomic DNA sequence a human genomic DNA sequence, or a combination thereof. In one embodiment, the genomic locus comprises, in any order, rat and human genomic DNA sequences. In one embodiment, the genomic locus comprises, in any order, mouse and human genomic DNA sequences. In one embodiment, the genomic locus comprises, in any order, mouse and rat genomic DNA sequences. In one embodiment, the genomic locus comprises, in any order, rat, mouse, and human genomic DNA sequences.

In one embodiment, the genetic modification comprises at least one human disease allele of a human gene. In one embodiment, the human disease is a neurological disease. In one embodiment, the human disease is a cardiovascular disease. In one embodiment, the human disease is a kidney disease. In one embodiment, the human disease is a muscle disease. In one embodiment, the human disease is a blood disease. In one embodiment, the human disease is a cancer. In one embodiment, the human disease is an immune system disease.

In one embodiment, the human disease allele is a dominant allele. In one embodiment, the human disease allele is a recessive allele. In one embodiment, the human disease allele comprises a single nucleotide polymorphism (SNP) allele.

In one embodiment, the genetic modification produces a mutant form of a protein with an altered binding characteristic, altered localization, altered expression, and/or altered expression pattern.

In one embodiment, the insert nucleic acid comprises a selection cassette. In one embodiment, the selection cassette comprises a nucleic acid sequence encoding a selective marker, wherein the nucleic acid sequence is operably linked to a promoter active in rat ES cells. In one embodiment, the selective marker is selected from or comprises a hygromycin resistance gene or a neomycin resistance gene.

In one embodiment, the nucleic acid comprises a genomic locus that encodes a protein expressed in a B cell. In one embodiment, the nucleic acid comprises a genomic locus that encodes a protein expressed in an immature B cell. In one embodiment, the nucleic acid comprises a genomic locus that encodes a protein expressed in a mature B cell.

In one embodiment, the insert nucleic acid comprises a regulatory element. In one embodiment, the regulatory element is a promoter. In one embodiment, the regulatory element is an enhancer. In one embodiment, the regulatory element is a transcriptional repressor-binding element.

In one embodiment, the genetic modification comprises a deletion of a non-protein-coding sequence, but does not comprise a deletion of a protein-coding sequence. In one embodiment, the deletion of the non-protein-coding sequence comprises a deletion of a regulatory element. In one embodiment, the genetic modification comprises a deletion of a regulatory element. In one embodiment, the genetic modification comprises an addition of a promoter or a regulatory element. In one embodiment, the genetic modification comprises a replacement of a promoter or a regulatory element.

ii. Expression Cassettes

Provided herein are polynucleotides or nucleic acid molecules comprising the various components employed in a targeted genomic integration system provided herein (i.e. any one of or any combination of nuclease agents, recognition sites, insert nucleic acids, polynucleotides of interest, targeting vectors, selection markers, and other components).

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Polynucleotides can comprise deoxyribonucleotides and ribonucleotides include both naturally occurring molecules and synthetic analogues, and any combination these. The polynucleotides provided herein also encompass all forms of sequences including, but not limited to, single-stranded forms, double-stranded forms, hairpins, stem-and-loop structures, and the like.

Further provided are recombinant polynucleotides comprising the various components of the targeted genomic integration system. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that is used to transform the host cells as is well known to those skilled in the art. For example, a plasmid vector can be used. Genetic elements required to successfully transform, select, and propagate host cells comprising any of the isolated nucleic acid fragments provided herein are also provided. Screening may be accomplished by Southern analysis of DNA, Northern analysis of mRNA expression, immunoblotting analysis of protein expression, or phenotypic analysis, among others.

In specific embodiments, one or more of the components of the targeted genomic integration system described herein can be provided in an expression cassette for expression in a prokaryotic cell, a eukaryotic cell, a bacterial, a yeast cell, or a mammalian cell or other organism or cell type of interest. The cassette can include 5' and 3' regulatory sequences operably linked to a polynucleotide provided herein. "Operably linked" comprises a relationship wherein the components operably linked function in their intended manner. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, operably linked means that the coding regions are in the same reading frame. In another instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

The cassette may additionally contain at least one additional polynucleotide of interest to be co-introduced into the organism. Alternatively, the additional polynucleotide of interest can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selection marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in mammalian cell or a host cell of interest. The regulatory regions (i.e., promoters, transcriptional regulatory regions, and translational termination regions) and/or a polynucleotide provided herein may be native/analogous to the host cell or to each other. Alternatively, the regulatory regions and/or a polynucleotide provided herein may be heterologous to the host cell or to each other. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the host cell, or may be derived from another source (i.e., foreign or heterologous) to the promoter, the recombinant polynucleotide, the host cell, or any combination thereof.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

The expression cassette containing the polynucleotides provided herein can also comprise a selection marker gene for the selection of transformed cells. Selectable marker genes are utilized for the selection of transformed cells or tissues.

Where appropriate, the sequences employed in the methods and compositions (i.e., the polynucleotide of interest, the nuclease agent, etc.) may be optimized for increased expression in the cell. That is, the genes can be synthesized using codons preferred in a given cell of interest including, for example, mammalian-preferred codons, human-preferred codons, rodent-preferred codon, mouse-preferred codons, rat-preferred codons, etc. for improved expression.

The various methods and compositions provided herein can employ selection markers. Various selection markers can be used in the methods and compositions disclosed herein. Such selection markers can, for example, impart resistance to an antibiotic such as G418, hygromycin, blasticidin, neomycin, or puromycin. Such selection markers include neomycin phosphotransferase (neo$^r$), hygromycin B phosphotransferase (hyg$^r$), puromycin-N-acetyltransferase (puro$^r$), and blasticidin S deaminase (bsr$^r$). In still other embodiments, the selection marker is operably linked to an inducible promoter and the expression of the selection marker is toxic to the cell. Non-limiting examples of such selection markers include xanthine/guanine phosphoribosyl transferase (gpt), hahypoxanthine-guanine phosphoribosyltransferase (HGPRT) or herpes simplex virus thymidine kinase (HSV-TK). The polynucleotide encoding the selection markers are operably linked to a promoter active in the cell.

iii. Targeting Vectors

Targeting vectors are employed to introduce the insert nucleic acid into the target locus of the rat nucleic acid. The targeting vector comprises the insert nucleic acid and further comprises a 5' and a 3' homology arm, which flank the insert nucleic acid. The homology arms, which flank the insert nucleic acid, correspond to regions within the target locus of the rat nucleic acid. For ease of reference, the corresponding cognate genomic regions within the targeted genomic locus are referred to herein as "target sites". For example, a targeting vector can comprise a first insert nucleic acid flanked by a first and a second homology arm complementary to a first and a second target site. As such, the targeting vector thereby aids in the integration of the insert nucleic acid into the target locus of the rat nucleic acid through a homologous recombination event that occurs between the homology arms and the complementary target sites within the genome of the cell.

In one embodiment, the target locus of the rat nucleic acid comprises a first nucleic acid sequence that is complementary to the 5' homology arm and a second nucleic acid sequence that is complementary to the 3' homology arm. In one embodiment, the first and the second nucleic acid sequences are separated by at least 5 kb. In another embodiment, the first and the second nucleic acid sequences are separated by at least 5 kb but less than 200 kb. In one embodiment, the first and the second nucleic acid sequences are separated by at least 10 kb. In one embodiment, the first and the second nucleic acid sequences are separated by at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. In still further embodiments, the first and the second nucleic acid sequence is separated by at least 5 kb but less than 10 kb, at least 5 kb but less than 3 Mb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1.5 Mb but less than about 2 Mb, at least about 1 Mb but less than about 1.5 Mb, at least about 2 Mb but less than 2.5 Mb, at least about 2.5 Mb but less than 3 Mb, or at least about 2 Mb but less than about 3 Mb.

A homology arm of the targeting vector can be of any length that is sufficient to promote a homologous recombination event with a corresponding target site, including for example, at least 5-10 kb, 5-15 kb, 10-20 kb, 20-30 kb, 30-40 kb, 40-50 kb, 50-60 kb, 60-70 kb, 70-80 kb, 80-90 kb, 90-100 kb, 100-110 kb, 110-120 kb, 120-130 kb, 130-140 kb, 140-150 kb, 150-160 kb, 160-170 kb, 170-180 kb, 180-190 kb, 190-200 kb in length or greater. As outlined in further detail below, large targeting vectors can employ targeting arms of greater length. In a specific embodiment, the sum total of the 5' homology arm and the 3' homology arm is at least 10 kb or the sum total of the 5' homology arm and the 3' homology arm is at least about 16 kb to about 100 kb or about 30 kb to about 100 kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

When nuclease agents are employed, the cognate genomic regions corresponding to the 5' and 3' homology arms of a targeting vector are "located in sufficient proximity" to nuclease target sites so as to promote the occurrence of a homologous recombination event between the cognate genomic regions and the homology arms upon a nick or double-strand break at the recognition site. For example, the nuclease target sites can be located anywhere between the cognate genomic regions corresponding to the 5' and 3' homology arms. In specific embodiments, the recognition site is immediately adjacent to at least one or both of the cognate genomic regions.

As used herein, a homology arm and a target site (i.e., cognate genomic region) "complement" or are "complementary" to one another when the two regions share a sufficient level of sequence identity to one another to act as substrates for a homologous recombination reaction. By "homology" is meant DNA sequences that are either identical or share sequence identity to a corresponding or "complementary" sequence. The sequence identity between a given target site and the corresponding homology arm found on the targeting vector can be any degree of sequence identity that allows for homologous recombination to occur. For example, the amount of sequence identity shared by the homology arm of the targeting vector (or a fragment thereof) and the target site (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a complementary region of homology between the homology arm and the complementary target site can be of any length that is sufficient to promote homologous recombination at the cleaved recognition site. For example, a given homology arm and/or complementary target site can comprise complementary regions of homology that are at least 5-10 kb, 5-15 kb, 10-20 kb, 20-30 kb, 30-40 kb, 40-50 kb, 50-60 kb, 60-70 kb, 70-80 kb, 80-90 kb, 90-100 kb, 100-110 kb, 110-120 kb, 120-130 kb, 130-140 kb, 140-150 kb, 150-160 kb, 160-170 kb, 170-180 kb, 180-190 kb, 190-200 kb in length or greater (such as described in the LTVEC vectors described elsewhere herein) such that the homology arm has sufficient homology to undergo homologous recombination with the corresponding target sites within the genome of the cell. For ease of reference the homology arms are referred to herein as a 5' and a 3' homology arm. This terminology relates to the relative position of the homology arms to the insert nucleic acid within the targeting vector.

The homology arms of the targeting vector are therefore designed to be complementary to a target site with the targeted locus. Thus, the homology arms can be complementary to a locus that is native to the cell, or alternatively they can be complementary to a region of a heterologous or exogenous segment of DNA that was integrated into the genome of the cell, including, but not limited to, transgenes, expression cassettes, or heterologous or exogenous regions of genomic DNA. Alternatively, the homology arms of the targeting vector can be complementary to a region of a human artificial chromosome or any other engineered genomic region contained in an appropriate host cell. Still further, the homology arms of the targeting vector can be complementary to or be derived from a region of a BAC library, a cosmid library, or a P1 phage library. Thus, in specific embodiments, the homology arms of the targeting vector are complementary to a rat genomic locus that is native, heterologous or exogenous to a given cell. In further embodiments, the homology arms are complementary to a rat genomic locus that is not targetable using a conventional method or can be targeted only incorrectly or only with significantly low efficiency, in the absence of a nick or double-strand break induced by a nuclease agent. In one embodiment, the homology arms are derived from a synthetic DNA.

In still other embodiments, the 5' and 3' homology arms are complementary to the same genome as the targeted genome. In one embodiment, the homology arms are from a related genome, e.g., the targeted genome is a rat genome of a first strain, and the targeting arms are from a rat genome of a second strain, wherein the first strain and the second strain are different. In other embodiments, the homology arms are from the genome of the same animal or are from the genome of the same strain, e.g., the targeted genome is a rat genome of a first strain, and the targeting arms are from a rat genome from the same rat or from the same strain.

The targeting vector (such as a large targeting vector) can also comprise a selection cassette or a reporter gene as discussed elsewhere herein. The selection cassette can comprise a nucleic acid sequence encoding a selection marker, wherein the nucleic acid sequence is operably linked to a promoter. The promoter can be active in a prokaryotic cell of interest and/or active in a eukaryotic cell of interest. Such promoters can be an inducible promoter, a promoter that is endogenous to the reporter gene or the cell, a promoter that is heterologous to the reporter gene or to the cell, a cell-specific promoter, a tissue-specific promoter or a developmental stage-specific promoter. In one embodiment, the selection marker is selected from or comprises neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and/or a combination thereof. The selection marker of the targeting vector can be flanked by the 5' and 3' homology arms or found either 5' or 3' to the homology arms.

In one embodiment, the targeting vector (such as a large targeting vector) comprises a reporter gene operably linked to a promoter, wherein the reporter gene encodes a reporter protein selected from the group consisting of or comprises LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and/or a combination thereof. Such reporter genes can be operably linked to a promoter active in the cell. Such promoters can be an inducible promoter, a promoter that is endogenous to the report gene or the cell, a promoter that is heterologous to the reporter gene or to the cell, a cell-specific promoter, a tissue-specific promoter or a developmental stage-specific promoter.

In one embodiment, combined use of the targeting vector (including, for example, a large targeting vector) with the nuclease agent results in an increased targeting efficiency compared to use of the targeting vector alone. In one embodiment, when the targeting vector is used in conjunction with the nuclease agent, targeting efficiency of the targeting vector is increased at least by two-fold, at least three-fold, or at least 4-fold when compared to when the targeting vector is used alone.

When employing a targeting vector, the vector design can be such as to allow for the insertion of a given sequence that is from about 5 kb to about 200 kb as described herein. In one embodiment, the insertion is from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

When employing a targeting vector, the vector design can be such as to allow for the replacement of a given sequence that is from about 5 kb to about 200 kb or from about 5 kb to about 3.0 Mb as described herein. In one embodiment, the replacement is from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In one embodiment, the targeting vector comprises a site-specific recombinase gene. In one embodiment, the site-specific recombinase gene encodes a Cre recombinase. In one embodiment, the Cre recombinase gene is Crei, wherein two exons encoding the Cre recombinase are separated by an intron to prevent its expression in a prokaryotic cell.

In one embodiment, the Cre recombinase gene further comprises a nuclear localization signal to facilitate localization of Cre (or any recombinase or nuclease agent) to the nucleus (e.g., the gene is an NL-Cre gene). In a specific embodiment, the Cre recombinase gene further comprises a nuclear localization signal and an intron (e.g., NL-Crei).

In various embodiments, a suitable promoter for expression of the nuclease agent (including the Cre or Crei recombinase discussed above) is selected from or comprises a Prm1, Blimp1, Gata6, Gata4, Igf2, Lhx2, Lhx5, and/or Pax3. In a specific embodiment, the promoter is the Gata6 or Gata4 promoter. The various promoters can be from any organism, including for example, a rodent such as a mouse or a rat. In another specific embodiment, the promoter is a Prm1 promoter. In another specific embodiment, the promoter is a rat Prm1 promoter. In another specific embodiment, the promoter is a mouse Prm1 promoter. In another specific embodiment, the promoter is a Blimp1 promoter or a fragment thereof, e.g., a 1 kb or 2 kb fragment of a Blimp1 promoter. See, for example, U.S. Pat. No. 8,697,851 and U.S. Application Publication 2013-0312129, both of which are herein incorporated by reference in their entirety.

iv. Large Targeting Vectors

The term "large targeting vector" or "LTVEC" as used herein comprises large targeting vectors that comprise homology arms that correspond to and are derived from nucleic acid sequences larger than those typically used by other approaches intended to perform homologous targeting in cells and/or comprising insert nucleic acids comprising nucleic acid sequences larger than those typically used by other approaches intended to perform homologous recombination targeting in cells. For example, the LTVEC make possible the modification of large loci that cannot be accommodated by traditional plasmid-based targeting vectors because of their size limitations. In specific embodiments, the homology arms and/or the insert nucleic acid of the LTVEC comprises genomic sequence of a eukaryotic cell. The size of the LTVEC is too large to enable screening of targeting events by conventional assays, e.g., southern blotting and long-range (e.g., 1 kb-5 kb) PCR. Examples of the LTVEC, include, but are not limited to, vectors derived from a bacterial artificial chromosome (BAC), a human artificial chromosome or a yeast artificial chromosome (YAC). Non-limiting examples of LTVECs and methods for making them are described, e.g., in U.S. Pat. Nos. 6,586,251, 6,596,541, 7,105,348, and WO 2002/036789 (PCT/US01/45375), and US 2013/0137101, each of which is herein incorporated by reference.

The LTVEC can be of any length, including, but not limited to, from about 20 kb to about 400 kb, from about 20 kb to about 30 kb, from about 30 kb to about 40 kb, from about 40 kb to about 50 kb, from about 50 kb to about 75 kb, from about 75 kb to about 100 kb, from about 100 kb to about 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb, from about 200 kb to about 300 kb, from about 300 kb to about 350 kb, from about 350 kb to about 400 kb, from about 350 kb to about 550 kb. In one embodiment, the LTVEC is about 100 kb.

In one embodiment, the LTVEC comprises an insert nucleic acid ranging from about 5 kb to about 200 kb, from about 5 kb to about 10 kb, from about 10 kb to about 20 kb, from about 20 kb to about 30 kb, from about 0.5 kb to about 30 kb, from about 0.5 kb to about 40 kb, from about 30 kb to about 150 kb, from about 0.5 kb to about 150 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb;

When employing a LTVEC, the vector design can be such as to allow for the replacement of a given sequence that is from about 5 kb to about 200 kb or from about 5 kb to about 3 Mb as described herein. In one embodiment, the replacement is from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In one embodiment, the homology arms of the LTVEC are derived from a BAC library, a cosmid library, or a P1 phage library. In other embodiments, the homology arms are derived from the targeted genomic locus of the cell and in some instances the target genomic locus, which the LTVEC is designed to target is not targetable using a conventional method. In still other embodiments, the homology arms are derived from a synthetic DNA.

In one embodiment, a sum total of the 5' homology arm and the 3' homology arm in the LTVEC is at least 10 kb. In other embodiments, the sum total of the 5' and the 3' homology arms of the LTVEC is from about 10 kb to about 30 kb, from about 20 kb to about 40 kb, from about 40 kb to about 60 kb, from about 60 kb to about 80 kb, from about 80 kb to about 100 kb, from 100 kb to about 120 kb, from about 120 kb to about 140 kb, from about 140 kb to about 160 kb, from about 160 kb to about 180 kb, from about 180 kb to about 200 kb. In one embodiment the sum total of the 5' and the 3' homology arms of the LTVEC is from about 30 kb to about 100 kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

In other embodiments, the 5' homology arm ranges from about 5 kb to about 100 kb. In one embodiment, the 3' homology arm ranges from about 5 kb to about 100 kb. In other embodiments, the sum total of the 5' and 3' homology arms are from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, or from about 30 kb to about 100 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb.

In one embodiment, the LTVEC comprises an insert nucleic acid that is homologous or orthologous to a rat nucleic acid sequence flanked by the LTVEC homology arms. In one embodiment, the insert nucleic acid sequence is from a species other than a rat. In one embodiment, the insert nucleic acid that is homologous or orthologous to the rat nucleic acid sequence is a mammalian nucleic acid. In one embodiment, the mammalian nucleic acid is a mouse nucleic acid. In one embodiment, the mammalian nucleic acid is a human nucleic acid. In one embodiment, the insert nucleic acid is a genomic DNA. In one embodiment, the insert is from 5 kb to 200 kb as described above.

In one embodiment, the LTVEC comprises a selection cassette or a reporter gene. Various forms of the selection cassette and reporter gene that can be employed are discussed elsewhere herein.

As described elsewhere herein, the LTVEC can also be used in the methods provided herein in combination with a nuclease agent that promotes a homologous recombination between the targeting vector and the target locus of a rat nucleic acid in a pluripotent rat cell.

In one embodiment, the large targeting vector (LTVEC) comprises a site-specific recombinase gene. In one embodiment, the site-specific recombinase gene encodes a Cue recombinase. In one embodiment, the Cre recombinase gene is Crei, wherein two exons encoding the Cre recombinase are separated by an intron to prevent its expression in a prokaryotic cell. In one embodiment, the Cre recombinase gene further comprises a nuclear localization signal to facilitate localization of Cre (or any recombinase or nuclease agent) to the nucleus (e.g., the gene is an NL-Cre gene). In a specific embodiment, the Cre recombinase gene further comprises a nuclear localization signal and an intron (e.g., NL-Crei)

In various embodiments, a suitable promoter for expression of the nuclease agent (including the Cre or Crei recombinase discussed above) is selected from or comprises a Prm1, Blimp1, Gata6, Gata4, Igf2, Lhx2, Lhx5, and/or Pax3. In a specific embodiment, the promoter is the Gata6 or Gata4 promoter. The various promoters can be from any organism, including for example, a rodent such as a mouse or a rat. In another specific embodiment, the promoter is a Prm1 promoter. In another specific embodiment, the promoter is a rat Prm1 promoter. In another specific embodiment, the promoter is a mouse Prm1 promoter. In another specific embodiment, the promoter is a Blimp1 promoter or a fragment thereof, e.g., a 1 kb or 2 kb fragment of a Blimp1 promoter. See, for example, U.S. Pat. No. 8,697,851 and U.S. Application Publication 2013-0312129, both of which are herein incorporated by reference in their entirety.

In one embodiment, the LTVEC comprises an insert nucleic acid that can produce a deletion, addition, replacement or a combination thereof of a region of the rat ApoE locus, the IL-2Rg locus, the Rag2 locus, the Rag1 locus and/or the Rag2/Rag1 locus as discussed in detail elsewhere herein. In specific embodiments, the genetic modification at the ApoE locus results in a decrease, an increase or a modulation in ApoE activity, IL-2Rg activity, Rag2 activity, Rag1 activity and/or Rag2 and Rag1 activity. In one embodiment, an ApoE knockout, and IL-2Rg knockout, a Rag2 knockout, a Rag1 knockout, a Rag2/Rag1 knockout is generated. As discussed below, nuclease agents can be employed with any of the LTVEC targeting systems to target any genomic locus of interest.

v. Nuclease Agents and Recognition Sites for Nuclease Agents

As outlined in detail above, nuclease agents may be utilized in the methods and compositions disclosed herein to aid in the modification of the target locus both in a prokaryotic cell or within a pluripotent rat cell. Such a nuclease agent may promote homologous recombination between the targeting vector and the target locus. In one embodiment, the nuclease agent comprises an endonuclease agent.

As used herein, the term "recognition site for a nuclease agent" comprises a DNA sequence at which a nick or double-strand break is induced by a nuclease agent. The recognition site for a nuclease agent can be endogenous (or native) to the cell or the recognition site can be exogenous to the cell. In specific embodiments, the recognition site is exogenous to the cell and thereby is not naturally occurring in the genome of the cell. In still further embodiments, the recognition site is exogenous to the cell and to the polynucleotides of interest that one desired to be positioned at the target genomic locus. In further embodiments, the exogenous or endogenous recognition site is present only once in the genome of the host cell. In specific embodiments, an endogenous or native site that occurs only once within the genome is identified. Such a site can then be used to design nuclease agents that will produce a nick or double-strand break at the endogenous recognition site.

The length of the recognition site can vary, and includes, for example, recognition sites that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length. In one embodiment, each monomer of the nuclease agent recognizes a recognition site of at least 9 nucleotides. In other embodiments, the recognition site is from about 9 to about 12 nucleotides in length, from about 12 to about 15 nucleotides in length, from about 15 to about 18 nucleotides in length, or from about 18 to about 21 nucleotides in length, and any combination of such subranges (e.g., 9-18 nucleotides). The recognition site could be palindromic, that is, the sequence on one strand reads the same in the opposite direction on the complementary strand. It is recognized that a given nuclease agent can bind the recognition site and cleave that binding site or alternatively, the nuclease agent can bind to a sequence that is the different from the recognition site. Moreover, the term recognition site comprises both the nuclease agent binding site and the nick/cleavage site irrespective whether the nick/cleavage site is within or outside the nuclease agent binding site. In another variation, the cleavage by the nuclease agent can occur at nucleotide positions immediately opposite each other to produce a blunt end cut or, in other cases, the incisions can be staggered to produce single-stranded overhangs, also called "sticky ends", which can be either 5' overhangs, or 3' overhangs.

Any nuclease agent that induces a nick or double-strand break into a desired recognition site can be used in the methods and compositions disclosed herein. A naturally-occurring or native nuclease agent can be employed so long as the nuclease agent induces a nick or double-strand break in a desired recognition site. Alternatively, a modified or engineered nuclease agent can be employed. An "engineered nuclease agent" comprises a nuclease that is engineered (modified or derived) from its native form to specifically recognize and induce a nick or double-strand break in the desired recognition site. Thus, an engineered nuclease agent can be derived from a native, naturally-occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

Active variants and fragments of the exemplified recognition sites are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by a nuclease agent in a sequence-specific manner. Assays to measure the double-strand break of a recognition site by a nuclease agent are known in the art and generally measure the ability of a nuclease to cut the recognition site.

The recognition site of the nuclease agent can be positioned anywhere in or near the target locus. The recognition site can be located within a coding region of a gene, or within regulatory regions, which influence expression of the gene. Thus, a recognition site of the nuclease agent can be located in an intron, an exon, a promoter, an enhancer, a regulatory region, or any non-protein coding region.

In one embodiment, the nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res.* (2010) doi:10.1093/nar/gkq704; and Miller et al. (2011) *Nature Biotechnology* 29:143-148; all of which are herein incorporated by reference.

Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference). In various embodiments, TAL effector nucleases are engineered that cut in or near a target nucleic acid sequence in, e.g., a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In one embodiment, each monomer of the TALEN comprises 12-25 TAL repeats, wherein each TAL repeat binds a 1bp subsite. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by about 6 bp to about 40 bp cleavage site, and wherein the FokI nucleases dimerize and make a double strand break at a target sequence.

In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by a 5 bp or 6 bp cleavage site, and wherein the FokI nucleases dimerize and make a double strand break.

The nuclease agent employed in the various methods and compositions disclosed herein can further comprise a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site or about a 5 bp to about 6 bp cleavage site, and wherein the FokI nucleases dimerize and make a double strand break. See, for example, US20060246567; US20080182332; US20020081614; US20030021776; WO/2002/057308A2; US20130123484; US20100291048; and, WO/2011/017293A2, each of which is herein incorporated by reference.

In one embodiment of the methods provided herein, the nuclease agent comprises (a) a chimeric protein comprising a zinc finger-based DNA binding domain fused to a FokI endonuclease; or, (b) a chimeric protein comprising a Transcription Activator-Like Effector Nuclease (TALEN) fused to a FokI endonuclease.

In still another embodiment, the nuclease agent is a meganuclease. Meganucleases have been classified into four families based on conserved sequence motifs, the families are the LAGLIDADG (SEQ ID NO: 16), GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) Q *Rev Biophys* 38:49-95; and Moure et al., (2002) *Nat Struct Biol* 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mot Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG (SEQ ID NO: 16) family of homing nuclease. In one embodiment, the LAGLIDADG (SEQ ID NO: 16) family of homing nuclease is selected from I-SceI, I-CreI, and I-DmoI.

Nuclease agents can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in *Mobile DNA II*, pp. 761-783, Eds. Craigie et al., (ASM Press, Washington, D.C.).

The nuclease agent employed in the various methods and compositions can also comprise a CRISPR/Cas system. Such systems can employ, for example, a Cas9 nuclease, which in some instances, is codon-optimized for the desired cell type in which it is to be expressed. The system further employs a fused crRNA-tracrRNA construct that functions with the codon-optimized Cas9. This single RNA is often referred to as a guide RNA or gRNA. Within a gRNA, the crRNA portion is identified as the 'target sequence' for the given recognition site and the tracrRNA is often referred to as the 'scaffold'. Briefly, a short DNA fragment containing the target sequence is inserted into a guide RNA expression plasmid. The gRNA expression plasmid comprises the target sequence (in some embodiments around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid. The gRNA expression cassette and the Cas9 expression cassette is then introduced into the cell. See, for example, Mali P et al. (2013) *Science* 2013 Feb. 15; 339(6121):823-6; Jinek M et al. *Science* 2012 Aug. 17; 337(6096):816-21; Hwang W Y et al. *Nat Biotechnol* 2013 March; 31(3):227-9; Jiang W et al. *Nat Biotechnol* 2013 March; 31(3):233-9; and, Cong L et al. *Science* 2013 Feb. 15; 339(6121):819-23, each of which is herein incorporated by reference.

In one embodiment, the method for modifying a genomic locus of interest in a pluripotent rat cell further comprises introducing into the pluripotent rat cell: (a) a first expression construct comprising a first promoter operably linked to a first nucleic acid sequence encoding a Clustered Regularly Interspaced Short Palindromic Repeats (CRISPR)-associated (Cas) protein; (b) a second expression construct comprising a second promoter operably linked to a genomic target sequence linked to a guide RNA (gRNA), wherein the genomic target sequence is flanked on the 3' end by a Protospacer Adjacent Motif (PAM) sequence. In one embodiment, the genomic target sequence comprises the nucleotide sequence of GNNNNNNNNNNNNNNNNNNNGG ($GN_{1-20}GG$; SEQ ID NO: 1). In one embodiment, the genomic target sequence comprises SEQ ID NO:23, wherein N is between 1 and 20 nucleotides in length. In another embodiment, the genomic target sequence comprises between 14 and 20 nucleotides in length of SEQ ID NO:1.

In one embodiment, the gRNA comprises a third nucleic acid sequence encoding a Clustered Regularly Interspaced Short Palindromic Repeats (CRISPR) RNA (crRNA) and a trans-activating CRISPR RNA (tracrRNA). In specific embodiments, the Cas protein is Cas9.

In some embodiments, the gRNA comprises (a) the chimeric RNA of the nucleic acid sequence 5'-GUUUUA-GAGCUAGAAAUAGCAAGUUAAAAU AAGGCUA-GUCCGUUAUCAACUUGAAAAAGUGGCACCGAGUCG-GUGCUUUU-3' (SEQ ID NO: 2); or, (b) the chimeric RNA of the nucleic acid sequence 5'-GUUUUAGAGCUA-GAAAUAGCAAGUUAAAAUAAGGCUAGUCCG-3' (SEQ NO: 3).

In another embodiment, the crRNA comprises 5'-GUUUUAGAGCUAGAAAUAGCAAGUUAAAAU-3' (SEQ ID NO: 4); 5'-GUUUUAGAGCUA-GAAAUAGCAAGUUAAAAUAAG (SEQ ID NO: 5); or 5'-GAGUCCGAGCAGAAGAAGAAGUUUUA-3' (SEQ ID NO: 6).

In yet other embodiments, the tracrRNA comprises. 5'-AAGGCUAGUCCG-3' (SEQ ID NO: 7) or 5'-AAGGC-UAGUCCGU UAUCAACUUGAAAAAGUGGCACCGA-GUCGGUGCUUUU-3' (SEQ ID NO: 8).

In one embodiment, the Cas protein is a type I Cas protein. In one embodiment, the Cas protein is a type II Cas protein. In one embodiment, the type II Cas protein is Cas9. In one embodiment, the first nucleic acid sequence encodes a human codon-optimized Cas protein.

In one embodiment, the first nucleic acid comprises a mutation that disrupts at least one amino acid residue of nuclease active sites in the Cas protein, wherein the mutant Cas protein generates a break in only one strand of the target DNA region, and wherein the mutation diminishes nonhomologous recombination in the target DNA region.

In one embodiment, the first nucleic acid that encodes the Cas protein further comprises a nuclear localization signal (NLS). In one embodiment, the nuclear localization signal is a SV40 nuclear localization signal.

In one embodiment, the second promoter that drives the expression of the genomic target sequence and the guide RNA (gRNA) is an RNA polymerase III promoter. In one embodiment, the RNA polymerase III promoter is a human U6 promoter. In one embodiment, the RNA polymerase III promoter is a rat U6 polymerase III promoter. In one embodiment, the RNA polymerase III promoter is a mouse U6 polymerase III promoter.

In one embodiment, the nucleic acid sequences encoding crRNA and the tracrRNA are linked via a synthetic loop, wherein, upon expression, the crRNA and the tracrRNA forms a crRNA:tracrRNA duplex.

In one embodiment, the first expression construct and the second expression construct are expressed from a same plasmid.

In one embodiment, the first and the second expression constructs are introduced together with the LTVEC. In one embodiment, the first and the second expression constructs are introduced separately from the LTVEC over a period of time.

In one embodiment, the method comprises introducing a plurality of the second construct and a plurality of the LTVEC for multiplex editing of distinct target loci as described herein.

Active variants and fragments of nuclease agents (i.e. an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

The nuclease agent may be introduced into the cell by any means known in the art. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally or constitutively expressed within the cell. Thus, the polynucleotide encoding the nuclease agent can be contained in an expression cassette and be operably linked to a conditional promoter, an inducible promoter, a constitutive promoter, or a tissue-specific promoter. Such promoters of interest are discussed in further detail elsewhere herein. Alternatively, the nuclease agent is introduced into the cell as an mRNA encoding or comprising a nuclease agent.

In one embodiment, the crRNA and the tracrRNA are expressed as separate RNA transcripts.

In specific embodiments, the polynucleotide encoding the nuclease agent is stably integrated in the genome of the cell and operably linked to a promoter active in the cell. In other embodiments, the polynucleotide encoding the nuclease agent is in the same targeting vector comprising the insert nucleic acid, while in other instances the polynucleotide encoding the nuclease agent is in a vector or a plasmid that is separate from the targeting vector comprising the insert nucleic acid.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example the polynucleotide encoding the nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

In one embodiment, the endonuclease agent is introduced together with the LTVEC. In one embodiment, the endonuclease agent is introduced separately from the LTVEC over a period of time. In one embodiment, the endonuclease agent is introduced prior to the introduction of the LTVEC. In one embodiment, the endonuclease agent is introduced into the rat ES cell following introduction of the LTVEC.

In one embodiment, the endonuclease agent is an expression construct comprising a nucleic acid sequence encoding an endonuclease, wherein the nucleic acid sequence is operably linked to a promoter. In one embodiment, the promoter is a constitutively active promoter. In one embodiment, the promoter is an inducible promoter. In one embodiment, the promoter is active in the pluripotent rat cell. In one embodiment, the endonuclease agent is an mRNA encoding an endonuclease.

B. Methods for Integrating a Polynucleotide of Interest into a Target Locus

Methods for modifying a target locus of interest are provided. In one embodiment, a target locus in a pluripotent rat cell is targeted for genetic modification. Such a method comprises: (a) introducing into the pluripotent rat cell a targeting vector comprising an insert nucleic acid flanked with a 5' rat homology arm and a 3' rat homology arm; and (b) identifying a genetically modified pluripotent rat cell comprising the targeted genetic modification at the target locus, wherein the targeted genetic modification is capable of being transmitted through the germline. In specific embodiments, the sum total of the 5' homology arm and the 3' homology arm is at east 10 kb and/or a large targeting vector is employed.

In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

The pluripotent rat cell can be a rat embryonic stem cell. In a specific embodiment, (a) the rat ES cell is derived from a DA strain or an ACI strain; or, (b) the rat ES cell is characterized by expression of a pluripotency marker comprising Oct-4, Sox-2, alkaline phosphatase, or a combination thereof. In other instances, the rat embryonic stem cell employed comprises a rat ES cell as described in US 2014-0235933, herein incorporated by reference in its entirety.

As described elsewhere herein, the insert nucleic acid can be any nucleic acid sequence. In non-limiting embodiments, (a) the insert nucleic acid comprises a replacement of an endogenous rat nucleic acid sequence with a homologous or a orthologous mammalian nucleic acid sequence; (b) the insert nucleic acid comprises a deletion of an endogenous rat nucleic acid sequence; (c) the insert nucleic acid comprises a deletion of an endogenous rat nucleic acid sequence, wherein the deletion ranges from 5 kb to 200 kb or from 5 kb to 3 Mb (as discussed in detail elsewhere herein); (d) the insert nucleic acid comprises an addition of an exogenous nucleic acid sequence (including for example an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb); (e) the insert nucleic add comprises an exogenous nucleic acid sequence comprising a homologous or an orthologous nucleic acid sequence; (f) the homologous or the orthologous nucleic acid sequence of (a) wherein the nucleic acid sequence is a human nucleic acid sequence; (g) the insert nucleic acid comprises the homologous or the orthologous nucleic acid sequence of (a) wherein the nucleic acid sequence is a chimeric nucleic acid sequence comprising a human and a rat nucleic acid sequence; (h) the insert nucleic acid comprises the exogenous nucleic acid sequence of (e), wherein the insert nucleic acid ranges from about 5 kb to about 200 kb; (i) the insert nucleic acid comprises a conditional allele flanked with site-specific recombinase target sequences; (j) the insert nucleic acid comprises a reporter gene operably linked to a promoter; (k) the insert nucleic acid comprises one or more unrearranged human immunoglobulin heavy chain $V_H$ gene segments, one or more unrearranged human immunoglobulin heavy chain D gene segments, and one or more unrearranged human immunoglobulin heavy chain $J_H$ gene segments, which are operably linked to a rodent heavy chain constant region nucleic acid sequence; (l) the insert nucleic acid comprises a rearranged human immunoglobulin heavy chain variable region nucleic acid sequence operably linked to a rodent heavy chain constant region nucleic acid sequence; (m) the insert nucleic acid comprises one or more unrearranged human immunoglobulin $V_\kappa$ or $V_\lambda$ gene segments and one or more unrearranged human immunoglobulin $J_\kappa$ or $J_\lambda$ gene segments, which are operably linked to a mammalian immunoglobulin λ or κ light chain light chain constant region nucleic acid sequence; (n) the insert nucleic acid comprises a rearranged human immunoglobulin λ or κ light chain variable region nucleic acid sequence operably linked to a mammalian immunoglobulin λ or κ light chain light chain constant region nucleic acid sequence; (o) the mammalian heavy chain constant region nucleic acid sequence of (k) and/or (l) comprises a rat constant region nucleic acid sequence, a human constant region nucleic acid sequence, or a combination thereof; or, (p) the mammalian immunoglobulin λ or κ light chain constant region nucleic acid of (m) and/or (n) comprises a rat constant region nucleic acid sequence, a human constant region nucleic acid sequence, or a combination thereof.

In one embodiment, the insert nucleic acid comprises one or more functional human $V_H$ gene segments comprising $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, or a combination thereof.

In one embodiment, the insert nucleic acid comprises one or more functional human D gene segments comprising D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, or a combination thereof.

In one embodiment, the insert nucleic acid comprises one or more functional $J_H$ gene segments comprising $J_H1$, $J_H2$, $J_H3$, $J_H4$, $J_H5$, $J_H6$, or a combination thereof. In one embodiment, the insert nucleic acid comprises one or more human Vκ gene segments comprising Vκ4-1, Vκ7-3, Vκ2-4, Vκ1-5, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, or a combination thereof.

In one embodiment, the insert nucleic acid comprises one or more human Vλ gene segments comprising Vλ3-1, Vλ2-8, Vλ3-10, Vλ2-11, Vλ3-12, Vλ2-14, Vλ2-16, Vλ2-18, Vλ3-19, Vλ3-21, Vλ3-22, Vλ2-23, Vλ3-25, Vλ3-27 or a combination thereof.

In one embodiment, the insert nucleic acid comprises one or more human Jκ gene segments comprising Jκ1, Jκ2, Jκ3, Jκ4, Jκ5, or a combination thereof.

In specific embodiments, upon modification of the target locus in a pluripotent rat cell, the genetic modification is transmitted through the germline.

In one embodiment, the insert nucleic acid sequence comprises a polynucleotide that when integrated into the genome will produce a genetic modification of a region of the rat ApoE locus, wherein the genetic modification at the ApoE locus results in a decrease in ApoE activity, an increase in ApoE activity or a modulation of ApoE activity. In one embodiment, an ApoE knockout is generated.

In one embodiment, the insert nucleic acid sequence comprises a polynucleotide that when integrated into the genome will produce a genetic modification of a region of the rat interleukin-2 receptor gamma locus, wherein the genetic modification at the interleukin-2 receptor gamma locus results in a decrease in interleukin-2 receptor activity, an increase in interleukin-2 receptor gamma activity, or a modulation of interleukin-2 receptor activity. In one embodiment, an interleukin-2 receptor knockout is generated.

In still another embodiment, the insert nucleic acid sequence comprises a polynucleotide that when integrated into the genome will produce a genetic modification of a region of the rat Rag1 locus, the rat Rag2 locus and/or the rat Rag2/Rag1 locus, wherein the genetic modification at the rat Rag1, Rag2 and/or Rag2/Rag1 locus results in a decrease in in Rag1, Rag2 or Rag1 and Rag2 protein activity, an increase in Rag1, Rag2 or Rag1 and Rag2 protein activity, or a modulation in Rag1, Rag2 or Rag 1 and Rag2 protein activity. In one embodiment, a Rag1, Rag2 or Rag2/Rag1 knockout is generated.

In further embodiments, the insert nucleic acid results in the replacement of a portion of the rat ApoE locus, the interleukin-2 receptor gamma locus and/or Rag2 locus, and/or Rag1 locus and/or Rag2/Rag1 locus with the corresponding orthologous portion of an ApoE locus, an interleukin-2 receptor gamma locus, a Rag2 locus, a Rag1 locus and/or a Rag2/Rag1 locus from another organism.

Still other embodiments, the insert nucleic acid comprises a polynucleotide sharing across its full length least 80%, 85%, 90%, 91%, 92%, 93%, 94%, 95%, 96%, 97%, 98%, 99% to a portion of an ApoE locus, an interleukin-2 receptor gamma locus, a Rag2 locus, a Rag1 locus and/or a Rag2/Rag1 locus it is replacing.

The given insert polynucleotide and the corresponding region of the rat locus being replaced can be a coding region, an intron, an exon, an untranslated region, a regulatory region, a promoter, or an enhancer or any combination thereof. Moreover, the given insert polynucleotide and/or the region of the rat locus being replaced can be of any desired length, including for example, between 10-100 nucleotides in length, 100-500 nucleotides in length, 500-1 kb nucleotide in length, 1 Kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other instances, the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb. In other embodiments, the given insert polynucleotide and/or the region of the rat locus being replaced is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

i. Methods for Modifying a Target Locus of a Rat Nucleic Acid Via Bacterial Homologous Recombination (BHR)

Methods and compositions are provided for modifying a target locus of a rat nucleic acid via bacterial homologous recombination (BHR) in a prokaryotic cell. Such methods find use in utilizing bacterial homologous recombination in a prokaryotic cell to genetically modify a target locus of a rat nucleic acid in order to create a targeting vector. Such a targeting vector comprising the genetically modified target locus can be introduced into a eukaryotic cell, for example, a pluripotent rat cell. "Homologous recombination" includes the exchange of DNA fragments between two DNA molecules at cross-over sites within regions of homology. Thus, "bacterial homologous recombination" or "BHR" includes homologous recombination that occurs in bacteria.

Methods for modifying a target locus of a rat nucleic acid via bacterial homologous recombination (BHR) are provided that comprise introducing into a prokaryotic cell a targeting vector comprising an insert nucleic acid flanked with a 5' rat homology arm and a 3' rat homology arm, wherein the prokaryotic cell comprises a rat nucleic acid and is capable of expressing a recombinase that mediates the BHR at the target locus. Such targeting vectors can include any of the large targeting vectors described herein.

In one embodiment, the method comprises introducing into a prokaryotic cell: (i) a first construct comprising a rat nucleic acid having a DNA sequence of interest; (ii) a second targeting construct comprising an insert nucleic acid flanked with a rat 5' homology arm and a rat 3' homology arm, and (iii) a third construct encoding a recombinase that mediates bacterial homologous recombination. In one embodiment, the first, the second, and the third construct are introduced into the prokaryotic cell separately over a period of time. In one embodiment, the prokaryotic cell comprises a nucleic acid that encodes the recombinase, and the method does not require introduction of the third construct. In one embodiment, the recombinase is expressed under the control of an inducible promoter.

In one embodiment the first construct comprising the rat nucleic acid is derived from a bacterial artificial chromosome (BAC) or yeast artificial chromosome (YAC).

A prokaryotic cell comprising the insert nucleic acid at the target genomic locus can be selected. This method can be serially repeated as disclosed herein to allow the introduction of multiple insert nucleic acids at the targeted rat locus in the prokaryotic cell. Once the target rat nucleic acid locus is "built" within the prokaryotic cell, a targeting vector comprising the modified rat target locus can be isolated from the prokaryotic cell and introduced into a target genomic locus within a mammalian cell (i.e., a rat cell, a pluripotent rat cell, or a rat embryonic stem cell).

Preferred rat cells for receiving targeting vectors are described in US 2014-0235933, the contents of which are summarized herein. These rat cells are pluripotent rat cells capable of sustaining their pluripotency following one or more targeted genetic modifications in vitro, and are capable of transmitting the targeted genetic modifications through the germline.

Electroporated pluripotent rat cells are plated at a high density for the selection of drug-resistant cells comprising the targeting vector. The drug selection process removes the majority of the plated cells (~99%), leaving behind individual colonies, each of which is a clone derived from a single cell. Of the remaining cells, most cells (~80-100%) contain the targeting vector (comprising a drug selection cassette) integrated at a random location in the genome. Therefore, the colonies are picked individually and genotyped to identify rat ES cells harboring the targeting vector at the correct genomic location (e.g., using the modification of allele assay described below).

A high-throughput quantitative assay, namely, modification of allele (MOA) assay, can be used for genotyping. Such an assay allows a large-scale screening of a modified allele(s) in a parental chromosome following a genetic modification. The MOA assay can be carried out via various analytical techniques, including, but not limited to, a quantitative PCR, e.g., a real-time PCR (qPCR). For example, the real-time PCR comprises a first primer set that recognizes the target locus and a second primer set that recognizes a non-targeted reference locus. In addition, the primer set comprises a fluorescent probe that recognizes the amplified sequence. In one embodiment, the quantitative assay is carried out via Invader Probes®. In one embodiment, the quantitative assay is carried out via MMP Assays®. In one embodiment, the quantitative assay is carried out via TaqMan® Molecular Beacon. In one embodiment, the quantitative assay is carried out via Eclipse™ probe technology. (See, for example, US2005/0144655, which is incorporated by reference herein in its entirety).

The selected pluripotent rat cell or the rat ES cells comprising the targeted genetic modification can then be introduced into a host rat embryo, for example, a pre-morula stage or blastocyst stage rat embryo, and implanted in the uterus of a surrogate mother to generate a founder rat (F0 rat). Subsequently, the founder rat can be bred to a wild-type rat to create F1 progeny heterozygous for the genetic modification. Mating of the heterozygous F1 rat can produce progeny homozygous for the genetic modification. Mating of the heterozygous F1 rat can produce progeny homozygous for the genetic modification. In some embodiments, various genetic modifications of the target loci described herein can be carried out using a large targeting vector (LTVEC) as described in detail elsewhere herein. For example, an LTVEC can be derived from Bacterial Artificial Chromosome (BAC) DNA using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, Nature Biotechnology 21(6): 652-659, which is incorporated herein by reference in their entireties).

Use of bacterial homologous recombination (BHR) to generate a large targeting vector (LTVEC) circumvents the limitations of plasmids in accommodating a large genomic DNA fragment and consequent low efficiency of introducing a targeted modification into an endogenous locus in pluripotent rat cells. One or more targeted genetic modifications can be performed in generating a LTVEC. An exemplary LTVEC produced in the prokaryotic cell can comprises an insert nucleic acid that carries a rat genomic sequence with one or more genetic modifications or an exogenous nucleic acid (e.g., a homolog or ortholog of a rat nucleic acid), which is flanked by rat homologous arms complementary to specific genomic regions.

Host prokaryotic cells comprising the various targeting vectors described herein are also provided. Such prokaryotic cells include, but are not limited to, bacteria such as *E. coli*. In one embodiment, a host prokaryotic cell comprises a targeting vector comprising an insert nucleic acid flanked with a 5' rat homology arm and a 3' rat homology arm, wherein the insert nucleic acid ranges from about 5 kb to about 200 kb.

The host prokaryotic cell can further comprise a nucleic acid that encodes a recombinase polypeptide or the nucleic acid that encodes the recombinase polypeptide is operably linked to an inducible promoter.

Further provided are various methods and compositions, which employ the LTVEC as described herein in combination with a prokaryotic cell in order to produce targeted genetic modifications, Such compositions and methods are discussed elsewhere herein.

Methods for modifying a target locus of a nucleic acid via bacterial homologous recombination (BHR) are provided that comprise introducing into a prokaryotic cell a targeting vector comprising an insert nucleic acid flanked with a 5' homology arm and a 3' homology arm, wherein the prokaryotic cell comprises nucleic acids corresponding to the 5' and 3' homology arms and the prokaryotic cell is capable of expressing a recombinase that mediates the BHR at the target locus. Such targeting vectors can include any of the large targeting vectors described herein. Such methods can employ a LTVEC as discussed in detail herein and further employ the CRISPR/Cas system as discussed elsewhere herein.

ii. Methods for Modifying a Target Locus of Interest in a Pluripotent Rat Cell

Further provided is a method for modifying a target locus of interest in a pluripotent rat cell via targeted genetic modification, comprising (a) introducing into the pluripotent rat cell a targeting vector comprising an insert nucleic acid flanked with a 5' rat homology arm and a 3' rat homology arm, wherein the sum total of the 5' homology arm and the 3' homology arm is at least 10 kb; and (b) identifying a genetically modified pluripotent rat cell comprising the targeted genetic modification at the target locus of interest. In one embodiment; the sum total of the 5' homology arm and the 3' homology arm is at least about 16 kb to about 30 kb. In specific embodiments, the targeted genetic modification is capable of being transmitted through the germline. Such targeting vectors can include any of the large targeting vectors described herein.

In one aspect, a method for modifying a genomic locus of interest in a pluripotent rat cell via targeted genetic modification is provided, comprising: (a) providing a pluripotent rat cell that is able to sustain its pluripotency following at least one targeted genetic modification of its genome and is able to transmit the targeted modification to a germline of an F1 generation; (b) introducing a large targeting vector (LTVEC) into the pluripotent rat cell, wherein the LTVEC comprises an insert nucleic acid flanked with a 5' homology arm and a 3' homology arm, wherein the 5' homology arm and the 3' homology arm comprise a rat genomic DNA fragment; and (c) identifying a genetically modified pluripotent rat cell comprising the targeted genetic modification.

Various methods can be used to identify cells having the insert nucleic acid integrated at the target locus of interest. Insertion of the insert nucleic acid at the target locus of interest results in a "modification of allele". The term "modification of allele" and methods for the detection of the modified allele are discussed in further detail elsewhere herein.

In one aspect, a method for modifying a genomic locus of interest in a pluripotent rat cell via endonuclease-mediated gene targeting is provided, the method comprising: (a) providing an isolated pluripotent rat cell that is able to transmit the genetically modified genome to a germline of an F1 generation; (b) introducing into the pluripotent rat cell an endonuclease agent; wherein the endonuclease agent makes a nick or a double strand break at a target DNA sequence located in the genomic locus of interest, and wherein the nick or the double strand break at the target DNA sequence in the rat ES cell induces: (i) non-homologous end joining (NHEJ)-mediated DNA repair of the nick or the double strand break, wherein the NHEJ-mediated DNA repair generates a mutant allele comprising an insertion or a deletion of a nucleic acid sequence at the target DNA sequence; or (ii) homologous recombination-mediated DNA repair that results in restoration of a wild-type nucleic acid sequence; and (c) identifying the modified genomic locus of interest.

In one aspect, a method for modifying a genomic locus of interest in an isolated rat embryonic stem cell (ES) via a nuclease agent is provided, comprising: (a) providing an isolated rat ES cell that is able to transmit the targeted genetic modification to a germline of an F1 generation; (b) introducing into the rat ES cell: (i) a large targeting vector (LTVEC) comprising an insert nucleic acid flanked with a rat 5' homology arm and a rat 3' homology arm, wherein the insert is a nucleic acid sequence that is at least 5 kb; and (ii) an endonuclease agent, wherein the endonuclease agent makes a nick or a double strand break at a target DNA sequence located in the genomic locus of interest, and wherein the target sequence is not present in the insert nucleic acid; and (c) identifying the targeted genetic modification in the rat embryonic stem (ES) cell.

In one aspect, a method for modifying a genomic locus of interest in a pluripotent rat cell via RNA-guided genome engineering is provided, the method comprising: (a) providing a pluripotent rat cell that is able to transmit the genetically modified genome to a germline of an F1 generation; (b) introducing into the pluripotent rat cell: (i) a first expression construct comprising a first promoter operably linked to a first nucleic acid sequence encoding a Clustered Regularly Interspaced Short Palindromic Repeats (CRISPR)-associated (Cas) protein, (ii) a second expression construct comprising a second promoter operably linked to a genomic target sequence linked to a guide RNA (gRNA), wherein the genomic target sequence is flanked on the 3' end by a Protospacer Adjacent Motif (PAM) sequence. In one embodiment, the genomic target sequence comprises the nucleotide sequence of GNNNNNNNNNNNNNNNNNN-NNNGG ($GN_{1-20}GG$; SEQ ID NO: 1). In one embodiment, the genomic target sequence comprises SEQ ID NO:1, wherein N is between 14 and 20 nucleotides in length. In one embodiment, the gRNA comprises a third nucleic acid sequence encoding a Clustered Regularly Interspaced Short Palindromic Repeats (CRISPR) RNA (crRNA) and a fourth nucleic acid sequence encoding a trans-activating CRISPR RNA (tracrRNA). In one embodiment, upon expression, the Cas protein forms a CRISPR-Cas complex comprising the crRNA and the tracrRNA, and the CRISPR-Cas complex makes a nick or a double strand break at a target DNA sequence located in the genomic locus of interest, and wherein the nick or the double strand break at the target DNA sequence in the pluripotent rat cell induces: (i) non-homologous end joining (NHEJ)-mediated DNA repair of the nick or the double strand break created by the CRISPR-Cas complex, wherein the NHEJ generates a mutant allele comprising an insertion or a deletion of a nucleic acid sequence at the target DNA sequence; or (ii) homologous recombination-mediated DNA repair that results in restoration of a wild-type nucleic acid sequence; and (c) identifying the modified genomic locus of interest.

In one embodiment, the pluripotent rat cell is an induced rat pluripotent stem cell (iPS). In one embodiment, the pluripotent rat cell is a developmentally restricted progenitor cell.

The presence of a nick or a double-strand break in the recognition site within the selection marker, in various embodiments, increases the efficiency and/or frequency of recombination between a targeting vector (such as a LTVEC) and the targeted locus of interest. In one embodiment, the recombination is homologous recombination. In another embodiment, the recombination is an insertion by non-homologous end joining. In various embodiments, in the presence of the nick or double strand break, targeting efficiency of a targeting vector (such as a LTVEC) at the target genomic locus is at least about 2-fold higher, at least about 3-fold higher, at least about 4-fold higher than in the absence of the nick or double-strand break (using, e.g., the same targeting vector and the same homology arms and corresponding target sites at the genomic locus of interest but in the absence of an added nuclease agent that makes the nick or double strand break).

In one embodiment, the targeted genetic modification at the target locus is biallelic. By "biallelic" is meant that both alleles of a gene comprise the targeted genetic modification. In certain embodiments, the combined use of a targeting vector (including, for example, an LTVEC) with a nuclease agent results in biallelic targeted genetic modification of the genomic locus of interest in a cell as compared to use of the targeting vector alone. When the targeting vector is used in conjunction with a nuclease agent, biallelic targeting efficiency is increased at least by two-fold, at least three-fold, at least 4-fold or more as compared to when the targeting vector is used alone. In further embodiments, the biallelic targeting efficiency is at least 0.2%, 0.3%, 0.4%, 0.5%, 0.6%, 0.7%, 0.8%, 0.9%, 1%, 2%, 3%, 4% or 5% or higher.

Compositions are provided which comprise a genetically modified rat having a targeted genetic modification in the interleukin-2 receptor gamma locus or in the ApoE locus. The various methods and compositions provided herein allows for these modified loci to be transmitted through the germline.

In specific embodiments, a genetically modified rat or a genetically modified pluripotent rat cell comprises a genomic locus having a targeted genetic modification in the interleukin-2 gamma receptor locus or having a targeted genetic modification in the ApoE locus, wherein the interleukin-2 gamma receptor genomic locus or the ApoE locus comprise: (i) a deletion of at least a portion of the interleukin-2 gamma receptor locus or at least a portion of the ApoE locus; (ii) an insertion of a heterologous nucleic acid sequence into the ApoE locus or into the interleukin-2 gamma receptor locus; or (iii) a combination thereof, wherein the genetically modified genomic locus is capable of being transmitted through the germline.

Methods are further provided that allow for such genetically modified rats and for such genetically modified pluripotent rat cells to be made. Such methods include a method for modifying an ApoE genomic locus or an interleukin-2 gamma receptor locus in a pluripotent rat cell via targeted genetic modification. The method comprises (a) introducing into the pluripotent rat cell a targeting vector comprising an insert nucleic acid flanked with a 5' rat homology arm to the ApoE locus and a 3' rat homology arm to the ApoE locus, (b) identifying a genetically modified pluripotent rat cell comprising the targeted genetic modification at the ApoE genomic locus of interest, wherein the targeted genetic modification is capable of being transmitted through germline.

Additional methods include (a) introducing into the pluripotent rat cell a targeting vector comprising an insert nucleic acid flanked with a 5' rat homology arm to the interleukin-2 receptor gamma locus and a 3' rat homology arm to the interleukin-2 receptor gamma locus, (b) identifying a genetically modified pluripotent rat cell comprising the targeted genetic modification at the interleukin-2 receptor gamma locus, wherein the targeted genetic modification is capable of being transmitted through germline.

iii. Methods of Integrating Multiple Polynucleotides of Interest at the Targeted Locus The various methods and compositions provided herein allow for the targeted integration of multiple polynucleotides of interest with a given target locus. The various methods set forth above can be sequentially repeated to allow for the targeted integration of any number of insert nucleic acids into a given targeted locus. Thus, the various methods provide for the insertion of at least 1, 2, 3, 4, 5, 6, 7, 8, 9, 10, 11, 12, 13, 14, 15, 16, 17, 18, 19, 20 or more insert nucleic acids into the target locus. In particular embodiments, such sequential stacking methods allow for the reconstruction of large genomic regions from a mammalian cell (i.e., a human, a non-human, a rodent, a mouse, a monkey, a rat, a hamster, a domesticated mammal or an agricultural animal) into a targeted locus. In such instances, the transfer and reconstruction of genomic regions that include both coding and non-coding regions allow for the complexity of a given region to be preserved by retaining, at least in part, the coding regions, the non-coding regions and the copy number variations found within the native genomic region. Thus, the various methods provide, for example, methods to generate "heterologous" or "exogenous" genomic regions within any mammalian cell or animal of interest, particularly within a prokaryotic host cell or within a pluripotent rat cell or a rat ES cell. In one non-limiting example, a "humanized" genomic region within a non-human animal (i.e., within a rat) is generated.

3. A Humanized Genomic Locus

Provided herein are various methods and compositions comprising a humanized rat locus. As used herein, by "humanized" genomic locus is meant a region of a non-human genome comprising at least one human nucleic acid sequence. A "humanized rat locus" comprises a region of rat DNA that has a human DNA sequence inserted therein. The human DNA sequence can be a naturally occurring human DNA sequence or it can be modified from its native form. In specific embodiments, the human DNA shares at least 85%, 90%, 91%, 92%, 93%, 94%, 95%, 96%, 97%, 98%, or 99% sequence identity to a native human sequence. If a human sequence is not a native human sequence it at least has greater sequence identity to a native human sequence than it does to an orthologous rat sequence. Moreover, the human DNA sequence can comprise a cDNA, a region of human genomic DNA, a non-coding regulatory region, or any portion of a coding, genomic, or regulatory region of the human DNA. The human DNA sequence inserted into the rat locus can comprise any of the insert polynucleotides as described elsewhere herein. In specific embodiments, the human DNA sequence is orthologous to the rat target locus, while in other instances, the human DNA sequence is homologous to the rat target locus.

In one embodiment, the targeted genetic modification is an insertion or a replacement of an endogenous rat nucleic acid sequence with a homologous or orthologous human nucleic acid sequence. In one embodiment, the targeted genetic modification comprises an insertion or replacement of an endogenous rat nucleic acid sequence with a homologous or orthologous human nucleic acid sequence at an endogenous rat locus that comprises the corresponding rat nucleic acid sequence.

Methods for making a humanized rat locus (or a rat or rat cell comprising the humanized rat locus) comprise introducing into the target locus comprising a rat nucleic acid a human nucleic acid sequence. In one embodiment, a method of making a humanized rat is provided. Such a method comprises (a) modifying a genome of a pluripotent rat cell with a targeting vector comprising an insert nucleic acid that comprises a human nucleic acid sequence to form a donor cell; (b) introducing the donor cell into a host rat embryo; and (c) gestating the host rat embryo in a surrogate mother; wherein the surrogate mother produces a rat progeny that comprises the human nucleic acid sequence. In specific embodiments, the humanized rat locus is capable of being transmitted through the germline. In a further embodiment, the targeting vector comprises a large targeting vector (LTVEC) and the insert nucleic acid that comprises a human nucleic acid sequence is at least 5 kb.

In other methods, the humanized rat locus is made by modifying a target locus of a rat nucleic acid via bacterial homologous recombination (BHR). The method comprises introducing into a prokaryotic cell a targeting vector comprising an insert nucleic acid flanked with a 5' rat homology arm and a 3' rat homology arm, wherein the insert nucleic acid comprises a human nucleic acid sequence, and wherein the prokaryotic cell comprises a rat nucleic acid and is capable of expressing a recombinase that mediates the BHR at the target locus.

The humanized rat genomic locus can comprise (a) an insertion of a homologous or orthologous human nucleic acid sequence; (b) a replacement of an endogenous rat nucleic acid sequence with a homologous or orthologous human nucleic acid sequence; or (c) a combination thereof. In specific embodiments, the humanized rat genomic locus is capable of being transmitted through the germline. In still other embodiments, the human orthologous sequence replaces the corresponding sequence found in the rat.

Any human nucleic acid sequence can be used in the methods and compositions provided herein. Non-limiting examples of human nucleic acid sequences that can be used in the methods and compositions are discussed in detail elsewhere herein.

The human nucleic acid sequence for insertion into the rat locus of interest can be any size. In one embodiment, the human nucleic acid sequence can be from about 500 nucleotides to about 200 kb, from about 500 nucleotides to about 5 kb, from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 11.0 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. In a specific embodiment, the human nucleic acid sequence is at least 5 kb.

In one embodiment, a rat genomic locus is provided wherein the homologous or orthologous human nucleic acid sequence comprises (a) one or more unrearranged human immunoglobulin heavy chain $V_H$ gene segments, one or more unrearranged human immunoglobulin heavy chain D gene segments, and one or more unrearranged human immunoglobulin heavy chain $J_H$ gene segments, which are operably linked to a mammalian heavy chain constant region nucleic acid sequence; (b) a rearranged human immunoglobulin heavy chain variable region nucleic acid sequence operably linked to a mammalian immunoglobulin heavy chain constant region nucleic acid sequence; (c) one or more unrearranged human immunoglobulin $V_\kappa$ or $V_\lambda$ gene segments and one or more unrearranged human immunoglobulin $J_\kappa$ or $J_\lambda$ gene segments, which are operably linked to a mammalian, immunoglobulin λ or κ light chain light chain constant region nucleic acid sequence; or, (d) a rearranged human immunoglobulin λ or κ light chain variable region nucleic acid sequence operably linked to a mammalian immunoglobulin λ or κ light chain light chain constant region nucleic acid sequence.

In another embodiment, a rat genomic locus is provided wherein (a) the mammalian immunoglobulin heavy chain constant region nucleic acid sequence is a rat constant region nucleic acid sequence, a human constant region nucleic acid sequence, or a combination thereof; or, (b) the mammalian immunoglobulin λ or κ Light chain light chain constant region nucleic acid sequence is a rat constant region nucleic acid sequence, a human constant region nucleic acid sequence, or a combination thereof.

In a specific embodiment, a rat genomic locus is provided wherein the immunoglobulin heavy chain constant region nucleic acid sequence is selected from or comprises a CH1, a hinge, a CH2, a CH3, and/or a combination thereof.

In one embodiment, the rat genomic locus comprises one or more functional human $V_H$ gene segments comprising $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, or a combination thereof.

In one embodiment, the rat genomic locus comprises one or more functional human D gene segments comprising D1-1, D1-7, D1-14, D1-20, D1-26, D2-2, D2-8, D2-15, D2-21; D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, or a combination thereof.

In one embodiment, the rat genomic locus comprises one or more functional $J_H$ gene segments comprising $J_H1$, $J_H2$, $J_H3$, $J_H4$, $J_H5$, $J_H6$, and/or a combination thereof. In one embodiment, the insert nucleic acid comprises one or more human Vκ gene segments comprises Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ2-14, Vκ3-15, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, or a combination thereof.

In one embodiment, the rat genomic locus comprises one or more human Vλ gene segments comprising Vλ3-1, Vλ4-3, Vλ2-8, Vλ3-10, Vλ2-11, Vλ3-12, Vλ2-14, Vλ3-16, Vλ2-18, Vλ3-22, Vλ2-23, Vλ3-25, Vλ3-27, or a combination thereof.

In one embodiment, the rat genomic locus comprises one or more human Jκ gene segments comprising Jκ1, Jκ2, Jκ3, Jκ4, Jκ5, or a combination thereof.

In yet another embodiment, the rat genomic locus comprises a humanized genomic locus comprising a human interleukin-2 receptor (IL2R) nucleic acid sequence or a variant or a fragment thereof is provided. In specific embodiments, the IL2R nucleic acid sequence comprises an interleukin-2 receptor alpha, an interleukin-2 receptor beta, or an interleukin-2 receptor gamma nucleic acid sequence or variants or fragments thereof.

In further embodiments, a rat genomic locus comprises a humanized genomic locus comprising of a portion of the human ApoE locus, the human interleukin-2 receptor gamma locus, the human Rag2 locus, the human Rag1 locus and/or the human Rag2/Rag1 locus replacing the corresponding homologous or orthologous portion of the rat ApoE locus, the rat interleukin-2 receptor gamma locus, the rat Rag2 locus, the rat Rag1 locus and/or the rat Rag2/Rag1 locus. In one embodiment, the rat ecto-domain of IL-2Rg is replaced with the ecto-domain of human IL-2Rg, with the remainder of the molecule being from the rat.

In another embodiment, a genetically modified rat comprising a humanized genomic locus is provided, Such genetically modified rats comprise (a) an insertion of a homologous or orthologous human nucleic acid sequence; (b) a replacement of rat nucleic acid sequence with a homologous or orthologous human nucleic acid sequence at an endogenous genomic locus; or (c) a combination thereof, wherein the humanized genomic locus is capable of being transmitted through the germline.

Genetically modified rats comprising any of the various humanized genomic loci provided herein and described above are also provided.

4. Polynucleotides of Interest

Any polynucleotide of interest may be contained in the various insert nucleic acids and thereby integrated at the target locus. The methods disclosed herein, provide for at least 1, 2, 3, 4, 5, 6 or more polynucleotides of interest to be integrated into the targeted genomic locus.

The polynucleotide of interest within the insert nucleic acid when integrated at the target genomic locus can introduce one or more genetic modifications into the cell. The genetic modification can comprise a deletion of an endogenous nucleic acid sequence and/or the addition of an exogenous or heterologous or orthologous polynucleotide into the target genomic locus. In one embodiment, the genetic modification comprises a replacement of an endogenous nucleic acid sequence with an exogenous polynucleotide of interest at the target genomic locus. Thus, methods provided herein allow for the generation of a genetic modification comprising a knockout, a deletion, an insertion, a replacement ("knock-in"), a point mutation, a domain swap, an exon swap, an intron swap, a regulatory sequence swap, a gene swap, or a combination thereof. Such modifications may occur upon integration of the first, second, third, fourth, fifth, six, seventh, or any subsequent insert nucleic acids into the target genomic locus.

The polynucleotide of interest within the insert nucleic acid and/or integrated at the target locus can comprise a sequence that is native to the cell it is introduced into; the polynucleotide of interest can be heterologous to the cell it is introduced to; the polynucleotide of interest can be exogenous to the cell it is introduced into; the polynucleotide of interest can be orthologous to the cell it is introduced into; or the polynucleotide of interest can be from a different species than the cell it is introduced into. As used herein "native" in reference to a sequence inserted at the target locus is a sequence that is native to the cell having the target locus or native to the cell from which the target locus was derived (i.e., from a rat). As used herein, "heterologous" in reference to a sequence includes a sequence that originates from a foreign species, or, if from the same species, is substantially different or modified from its native form in composition and/or genomic locus by deliberate human intervention. As used herein, "exogenous" in reference to a sequence is a sequence that originates from a foreign species. The polynucleotide of interest can be from any organism of interest including, but not limited to, non-human, a rodent, a hamster, a mouse, a rat, a human, a monkey, an agricultural mammal or a non-agricultural mammal. The polynucleotide of interest can further comprise a coding region, a non-coding region, a regulatory region, or a genomic DNA. Thus, the 1st, 2nd, 3rd, 4th, 5th, 6th, 7th, and/or any of the subsequent insert nucleic acids can comprise such sequences.

In one embodiment, the polynucleotide of interest within the insert nucleic acid and/or integrated at the target locus is native to a mouse nucleic acid sequence, a human nucleic acid, a non-human nucleic acid, a rodent nucleic acid, a rat nucleic acid, a hamster nucleic acid, a monkey nucleic acid, an agricultural mammal nucleic acid, or a non-agricultural mammal nucleic acid. In still further embodiments, the polynucleotide of interest integrated at the target locus is a fragment of a genomic nucleic acid. In one embodiment, the genomic nucleic acid is a mouse genomic nucleic acid, a human genomic nucleic acid, a non-human nucleic acid, a rodent nucleic acid, a rat nucleic acid, a hamster nucleic acid, a monkey nucleic acid, an agricultural mammal nucleic acid or a non-agricultural mammal nucleic acid or a combination thereof.

In one embodiment, the polynucleotide of interest can range from about 500 nucleotides to about 200 kb as described above. The polynucleotide of interest can be from about 500 nucleotides to about 5 kb, from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 1.00 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

The polynucleotide of interest within the insert nucleic acid and/or inserted at the target genomic locus can encode a polypeptide, can encode an miRNA, or it can comprise any regulatory regions or non-coding regions of interest including, for example, a regulatory sequence, a promoter sequence, an enhancer sequence, a transcriptional repressor-binding sequence, or a deletion of a non-protein-coding sequence, but does not comprise a deletion of a protein-coding sequence. In addition, the polynucleotide of interest within the insert nucleic acid and/or inserted at the target genomic locus can encode a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the polynucleotide of interest within the insert nucleic acid and/or inserted at the target genomic locus encodes a protein expressed in a bone marrow or a bone marrow-derived cell. In one embodiment, the polynucleotide of interest within the insert nucleic add and/or integrated at the target locus encodes a protein expressed in a spleen cell. In still further embodiments, the polynucleotide of interest within the insert nucleic acid and/or inserted at the target locus encodes a protein expressed in a B cell, encodes a protein expressed in an immature B cell or encodes a protein expressed in a mature B cell.

The polynucleotide of interest within the insert polynucleotide can comprise a portion of an ApoE locus, an IL-2-Rg locus, a Rag1 locus, a Rag2 locus and/or a Rag2/Rag1 locus. Such portions of these given loci are discussed elsewhere herein, as are the various homologous and orthologous regions from any organism of interest that can be employed.

In one embodiment, polynucleotide of interest within the insert nucleic acid and/or inserted at the target locus comprises a genomic nucleic acid sequence that encodes an immunoglobulin heavy chain variable region amino acid sequence. The phrase "heavy chain," or "immunoglobulin heavy chain" are described elsewhere herein.

In one embodiment, the polynucleotide of interest within the insert nucleic acid and/or integrated at the target locus comprises a genomic nucleic acid sequence that encodes a human immunoglobulin heavy chain variable region amino acid sequence.

In one embodiment, the genomic nucleic acid sequence comprises one or more unrearranged human immunoglobulin heavy chain gene segments, one or more unrearranged human immunoglobulin heavy chain D gene segments, and one or more unrearranged human immunoglobulin heavy chain $J_H$ gene segments, which are operably linked to a mammalian heavy chain constant region nucleic acid sequence. In one embodiment, the genomic nucleic acid sequence comprises a rearranged human immunoglobulin heavy chain variable region nucleic acid sequence operably linked to a mammalian heavy chain constant region nucleic acid sequence. In one embodiment, the genomic nucleic acid sequence comprises one or more unrearranged human immunoglobulin $V_\kappa$ or $V_\lambda$ gene segments and one or more unrearranged human immunoglobulin $J_\kappa$ or $J_\lambda$ gene segments, which are operably linked to a mammalian immunoglobulin λ or κ light chain light chain constant region nucleic acid sequence. In one embodiment, the genomic nucleic acid sequence comprises a rearranged human immunoglobulin λ or κ light chain variable region nucleic acid sequence operably linked to a mammalian immunoglobulin λ or κ light chain light chain constant region nucleic acid sequence. In one embodiment, the heavy chain constant region nucleic acid sequence comprises a rat constant region nucleic acid sequence, a human constant region nucleic acid sequence, or a combination thereof. In one embodiment, the immunoglobulin λ or κ light chain constant region nucleic acid comprises a rat constant region nucleic acid sequence, a human constant region nucleic acid sequence, or a combination thereof.

In one embodiment, the immunoglobulin heavy chain constant region nucleic acid sequence is selected from or comprises a CH1, a hinge, a CH2, a CH3, and/or a combination thereof. In one embodiment, the heavy chain constant region nucleic acid sequence comprises a CH1-hinge-CH2-CH3.

In one embodiment, the polynucleotide of interest within the insert nucleic acid and/or integrated at the target locus comprises a genomic nucleic acid sequence that encodes an immunoglobulin light chain variable region amino acid sequence. The phrase "light chain" includes an immunoglobulin light chain sequence from any organism, and is described elsewhere herein.

In one embodiment, the polynucleotide of interest within the insert nucleic acid and/or integrated at the target genomic locus comprises a genomic nucleic acid sequence that encodes a human immunoglobulin light chain variable region amino acid sequence.

In one embodiment, the genomic nucleic acid sequence comprises one or more unrearranged human immunoglobulin $V_\kappa$ or $V_\lambda$ gene segments and one or more unrearranged human immunoglobulin $J_\kappa$ or $J_\lambda$ gene segments, which are operably linked to a rodent immunoglobulin λ or κ light chain light chain constant region nucleic acid sequence. In one embodiment, the genomic nucleic acid sequence comprises a rearranged human immunoglobulin λ or κ light chain variable region nucleic acid sequence operably linked to a rodent immunoglobulin λ or κ light chain light chain constant region nucleic acid sequence. In one embodiment, the light chain constant region nucleic acid sequence comprises a rat constant region nucleic acid sequence, a human constant region nucleic acid sequence, or a combination thereof. In one embodiment, the immunoglobulin λ or κ light chain constant region nucleic acid comprises a rat constant region nucleic acid sequence, a human constant region nucleic acid sequence, or a combination thereof.

The polynucleotide of interest within the insert nucleic acid and/or integrated at the target locus can encode an extracellular protein or a ligand for a receptor. In specific embodiments, the encoded ligand is a cytokine. Cytokines of interest includes a chemokine selected from or comprising CCL, CXCL, CX3CL, and/or XCL. The cytokine can also comprise a tumor necrosis factor (TNF). In still other embodiments, the cytokine is an interleukin (IL). In one embodiment, the interleukin is selected from or comprises IL-1, IL-2, IL-3, IL-4, IL-5, IL-6, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or IL-36. In one embodiment, the interleukin is IL-2. In specific embodiments, such polynucleotides of interest within the insert nucleic acid and/or integrated at the target genomic locus are from a human and, in more specific embodiments, can comprise human genomic sequence.

The polynucleotide of interest within the insert nucleic acid and/or integrated at the target genomic locus can encode Apolipoprotein E (ApoE).

The polynucleotide of interest within the insert nucleic acid and/or integrated at the target locus can encode a cytoplasmic protein or a membrane protein. In one embodiment, the membrane protein is a receptor, such as, a cytokine receptor, an interleukin receptor, an interleukin 2 receptor-alpha, an interleukin-2 receptor beta, an interleukin-2 receptor gamma or receptor tyrosine kinase. In other instances, the polynucleotide of interest within the insert nucleic acid and/or integrated at the target locus can comprise an orthologous or homologous region of the target locus.

The polynucleotide of interest within the insert nucleic acid and/or integrated at the target locus can comprise a polynucleotide encoding at least a region of a T cell receptor, including the T cell receptor alpha. In specific methods each of the insert nucleic acids comprise a genomic region of the T cell receptor locus (i.e. the T cell receptor alpha locus) such that upon completion of the serial integration, a portion or the entirety of the genomic T cell receptor locus has been integrated at the target locus. Such insert nucleic acids can comprise at least one or more of a variable segment or a joining segment of a T cell receptor locus (i.e. of the T cell receptor alpha locus). In still further embodiments, the polynucleotide of interest encoding the region of the T cell receptor can be from, for example, a mammal, a non-human mammal, rodent, mouse, rat, a human, a monkey, an agricultural mammal or a domestic mammal polynucleotide encoding a mutant protein.

In other embodiments, the polynucleotide of interest integrated at the target locus encodes a nuclear protein. In one embodiment, the nuclear protein is a nuclear receptor. In specific embodiments, such polynucleotides of interest within the insert nucleic acid and/or integrated at the target locus are from a human and, in more specific embodiments, can comprise human genomic sequence.

The polynucleotide of interest within the insert nucleic acid and/or integrated at the target genomic locus can comprise a genetic modification in a coding sequence. Such genetic modifications include, but are not limited to, a deletion mutation of a coding sequence or the fusion of two coding sequences.

The polynucleotide of interest within the insert nucleic acid and/or integrated at the target locus can comprise a polynucleotide encoding a mutant protein, including, for example, a human mutant protein. In one embodiment, the mutant protein is characterized by an altered binding characteristic, altered localization, altered expression, and/or altered expression pattern. In one embodiment, the polynucleotide of interest within the insert nucleic acid and/or integrated at the target locus comprises at least one disease allele, including for example, an allele of a neurological disease, an allele of a cardiovascular disease, an allele of a kidney disease, an allele of a muscle disease, an allele of a blood disease, an allele of a cancer-causing gene, or an allele of an immune system disease. In such instances, the disease allele can be a dominant allele or the disease allele is a recessive allele. Moreover, the disease allele can comprises a single nucleotide polymorphism (SNP) allele. The polynucleotide of interest encoding the mutant protein can be from any organism, including, but not limited to, a mammal, a non-human mammal, rodent, mouse, rat, a human, a monkey, an agricultural mammal or a domestic mammal polynucleotide encoding a mutant protein.

In one embodiment, the genetic modification produces a mutant form of a protein with an altered binding characteristic, altered localization, altered expression, and/or altered expression pattern.

In one embodiment, the genetic modification produces a deletion, addition, replacement or a combination thereof of a region of the rat ApoE locus, wherein the genetic modification at the ApoE locus results in a decrease in ApoE activity. In one embodiment, an ApoE knockout is generated.

In one embodiment, the genetic modification produces a deletion, addition, replacement or a combination thereof of a region of the rat Rag1 locus, wherein the genetic modification at the Rag1 locus results in a decrease in Rag1 activity. In one embodiment, a Rag1 knockout is generated. In one embodiment, the genetic modification produces a deletion, addition, replacement or a combination thereof of a region of the rat Rag2 locus, wherein the genetic modification at the Rag2 locus results in a decrease in Rag2 activity. In one embodiment, a Rag2 knockout is generated. In one embodiment, the genetic modification produces a deletion, addition, replacement or a combination thereof of a region of the rat Rag1/Rag2 locus, wherein the genetic modification at the Rag1/Rag2 locus results in a decrease in Rag1 activity and a decrease in Rag2 activity. In one embodiment, a Rag1/Rag2 knockout is generated.

In one embodiment, the genetic modification produces a deletion, addition, replacement or a combination thereof of a region of the rat interleukin-2 receptor gamma locus, wherein the genetic modification at the interleukin-2 receptor gamma locus results in a decrease in interleukin-2 receptor gamma. In one embodiment, an interleukin-2 receptor gamma knockout is generated.

As discussed elsewhere herein, further embodiments provided herein comprises one or more of the rat ApoE locus, the rat interleukin-2 receptor gamma locus, the Rag2 locus, the Rag1 locus and/or the Rag2/Rag1 locus is modified through the replacement of a portion of the rat ApoE locus, the interleukin-2 receptor gamma locus, the Rag2 locus, the Rag1 locus and/or Rag2/Rag1 locus with the corresponding orthologous portion of an ApoE locus, an interleukin-2 receptor gamma locus, a Rag2 locus, a Rag1 locus and/or a Rag2/Rag1 locus from another organism.

In one embodiment, multiple genetic modifications are generated. In one embodiment, a genetic modification produces a deletion, addition, replacement or a combination thereof of a region of the rat interleukin-2 receptor gamma locus, wherein the genetic modification at the interleukin-2 receptor gamma locus results in a decrease in interleukin-2 receptor gamma and a second genetic modification produces a deletion, addition, replacement or a combination thereof of a region of the rat Rag2 locus, wherein the genetic modification at the Rag2 locus results in a decrease in Rag2 activity. In one embodiment, an interleukin-2 receptor gamma/Rag2 knockout is generated. Such a rat has a SCID phenotype.

In one embodiment, the mammalian nucleic acid comprises a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In one embodiment, the mammalian nucleic acid comprises a genomic locus that encodes a protein expressed in a bone marrow or a bone marrow-derived cell. In one embodiment, the nucleic acid comprises a genomic locus that encodes a protein expressed in a spleen cell. In one embodiment, the genomic locus comprises a mouse genomic DNA sequence, a rat genomic DNA sequence a human genomic DNA sequence, or a combination thereof. In one embodiment, the genomic locus comprises, in any order, rat and human genomic DNA sequences. In one embodiment, the genomic locus comprises, in any order, mouse and human genomic DNA sequences. In one embodiment, the genomic locus comprises, in any order, mouse and rat genomic DNA sequences. In one embodiment, the genomic locus comprises, in any order, rat, mouse, and human genomic DNA sequences.

In one embodiment, the insert nucleic acid comprises a genetic modification in a coding sequence of a gene. In one embodiment, the genetic modification comprises a deletion mutation in the coding sequence. In one embodiment, the genetic modification comprises a fusion of two endogenous coding sequences.

In one embodiment, the genetic modification comprises a deletion of a non-protein-coding sequence, but does not comprise a deletion of a protein-coding sequence. In one embodiment, the deletion of the non-protein-coding sequence comprises a deletion of a regulatory element. In one embodiment, the genetic modification comprises an addition of a promoter. In one embodiment, the genetic modification comprises a replacement of a promoter or regulatory element. In one embodiment, the regulatory element is an enhancer. In one embodiment, the regulatory element is a transcriptional repressor-binding element.

In one embodiment, the genetic modification comprises placement of a human nucleic acid sequence encoding a mutant human protein. In one embodiment, the genetic modification comprises at least one human disease allele of a human gene. In one embodiment, the human disease is a neurological disease. In one embodiment, the human disease is a cardiovascular disease. In one embodiment, the human disease is a kidney disease. In one embodiment, the human disease is a muscle disease. In one embodiment, the human disease is a blood disease. In one embodiment, the human disease is a cancer. In one embodiment, the human disease is an immune system disease. In one embodiment, the human disease allele is a dominant allele. In one embodiment, the human disease allele is a recessive allele. In one embodiment, the human disease allele comprises a single nucleotide polymorphism (SNP) allele.

The polynucleotide of interest within the insert nucleic acid and/or integrated at the target locus can also comprise a regulatory sequence, including for example, a promoter sequence, an enhancer sequence, or a transcriptional repressor-binding sequence. In specific embodiments, the polynucleotide of interest within the insert nucleic acid and/or integrated at the target genomic locus comprises a polynucleotide having a deletion of a non-protein-coding sequence, but does not comprise a deletion of a protein-coding sequence. In one embodiment, the deletion of the non-protein-coding sequence comprises a deletion of a regulatory sequence. In another embodiment, the deletion of the regulatory element comprises a deletion of a promoter sequence. In one embodiment, the deletion of the regulatory element comprises a deletion of an enhancer sequence. Such a polynucleotide of interest can be from any organism, including, but not limited to, a mammal, a non-human mammal, rodent, mouse, rat, a human, a monkey, an agricultural mammal or a domestic mammal polynucleotide encoding a mutant protein.

5. Methods of Introducing Sequences and Generation of Transgenic Animals

As outlined above, methods and compositions are provided herein to allow for the targeted integration of one or more polynucleotides of interest into a target locus. Such systems employ a variety of components and for ease of reference, herein the term "targeted integration system" generically comprises all the components required for an integration event (i.e. in non-limiting examples, the various nuclease agents, recognition sites, insert DNA polynucleotides, targeting vectors, target genomic locus, and/or polynucleotides of interest).

The methods provided herein comprise introducing into a cell one or more polynucleotides or polypeptide constructs comprising the various components of the targeted genomic integration system. "Introducing" means presenting to the cell the sequence (polypeptide or polynucleotide) in such a manner that the sequence gains access to the interior of the cell. The methods provided herein do not depend on a particular method for introducing any component of the targeted genomic integration system into the cell, only that the polynucleotide gains access to the interior of a least one cell. Methods for introducing polynucleotides into various cell types are known in the art and include, but are not limited to, stable transfection methods, transient transfection methods, and virus-mediated methods.

In some embodiments, the cells employed in the methods and compositions have a DNA construct stably incorporated into their genome. "Stably incorporated" or "stably introduced" means the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

Transfection protocols as well as protocols for introducing polypeptides or polynucleotide sequences into cells may vary. Non-limiting transfection methods include chemical-based transfection methods include the use of liposomes; nanoparticles; calcium phosphate (Graham et al. (1973). Virology 52 (2): 456-67, Bacchetti et al. (1977) Proc Natl Acad Sci USA 74 (4): 1590-4 and, Kriegler, M (1991). Transfer and Expression: A Laboratory Manual. New York: W. H. Freeman and Company. pp. 96-97); dendrimers; or cationic polymers such as DEAE-dextran or polyethylenimine. Non chemical methods include electroporation; Sono-poration; and optical transfection Particle-based transfection include the use of a gene gun, magnet assisted transfection (Bertram, J. (2006) Current Pharmaceutical Biotechnology 7, 277-28). Viral methods can also be used for transfection.

In one embodiment, the introducing one or more of the polynucleotides into a cell is mediated by electroporation, by intracytoplasmic injection, by a viral infection, by an adenovirus, by lentivirus, by retrovirus, by transfection, by lipid-mediated transfection or is mediated via Nucleofection™.

In one embodiment, introduction one or more of the polynucleotides into a cell further comprises: introducing an expression construct comprising a nucleic acid sequence of interest operably linked to a promoter. In one embodiment, the promoter is a constitutively-active promoter. In one embodiment, the promoter is an inducible promoter. In one embodiment, the promoter is active in the rat embryonic stem cell.

In one embodiment, the expression construct is introduced together with the LTVEC. In one embodiment, the expression construct is introduced separately from the LTVEC over a period of time.

In one embodiment, the introduction of the one or more polynucleotides into the cell can be performed multiple times over a period of time. In one embodiment, the introduction of the one or more polynucleotides into the cell are performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

In one embodiment, the nuclease agent is introduced into the c ell simultaneously with the targeting vector or the large targeting vector (LTVEC). Alternatively, the nuclease agent is introduced separately from the targeting vector or the LTVEC over a period of time. In one embodiment, the nuclease agent is introduced prior to the introduction of the targeting vector or the LTVEC, while in other embodiments, the nuclease agent is introduced following introduction of the targeting vector or the LTVEC.

In one embodiment, screening step comprises a quantitative assay for assessing modification of allele (MOA) of a parental chromosome. In one embodiment, the quantitative assay is carried out via a quantitative PCR. In one embodiment, the quantitative PCR is a real-time PCR (qPCR). In one embodiment, the real-time PCR comprises a first primer set that recognizes the target locus and a second primer set that recognizes a non-targeted reference locus. In one embodiment, the primer set comprises a fluorescent probe that recognizes the amplified sequence. In one embodiment, the quantitative assay is carried out via fluorescence-mediated in situ hybridization (FISH). In one embodiment, the quantitative assay is carried out via comparative genomic hybridization. In one embodiment, the quantitative assay is carried out via isothermic DNA amplification. In one embodiment, the quantitative assay is carried out via isothermic DNA amplification. In one embodiment, the quantitative assay is carried out via quantitative hybridization to an immobilized probe(s). In one embodiment, the quantitative assay is carried out via Invader Probes®. In one embodiment, the quantitative assay is carried out via MMP Assays®. In one embodiment, the quantitative assay is carried out via TaqMan® Molecular Beacon. In one embodiment, the quantitative assay is carried out via Eclipse™ probe technology. (See, for example, US2005/0144655, which is incorporated by reference herein in its entirety).

Further provided is a method for making a humanized rat, comprising: (a) modifying a genome of a pluripotent rat cell with a targeting vector comprising an insert nucleic acid that comprises a human nucleic acid sequence to form a donor cell; (b) introducing the donor cell into a host rat embryo; and (c) gestating the host rat embryo in a surrogate mother; wherein the surrogate mother produces a rat progeny that comprises the human nucleic acid sequence. In one embodiment, the donor cell is introduced into a host rat embryo that is at the blastocyst stage or at a pre-morula stage (i.e., a 4 cell stage or an 8 cell stage). Moreover, step (a) can also be performed with a large targeting vector (LTVEC) and/or a human nucleic acid sequence at least 5 Kb in length. In still further embodiments, the genetic modification is capable of being transmitted through the germline.

Genetically modified rats can be generated employing the various methods disclosed herein. Such methods comprise (1) integrating one or more polynucleotide of interest at the target locus of a pluripotent rat cell to generate a genetically modified pluripotent rat cell comprising the insert nucleic acid in the targeted genomic locus employing the methods disclosed herein; (2) selecting the genetically modified pluripotent rat cell having the one or more polynucleotides of interest at the target genomic locus; (3) introducing the genetically modified pluripotent rat cell into a rat host embryo; and (4) implanting the host rat embryo comprising the genetically modified pluripotent rat cell into a surrogate mother. A progeny from the genetically modified pluripotent rat cell is generated. In one embodiment, the donor cell is introduced into a rat host embryo at the blastocyst stage or at the pre-morula stage (i.e., the 4 cell stage or the 8 cell stage). Progeny that are capable of transmitting the genetic modification though the germline are generated. The pluripotent rat cell can be a rat ES cell as discussed elsewhere herein.

Nuclear transfer techniques can also be used to generate the genetically modified rats. Briefly, methods for nuclear transfer include the steps of: (1) enucleating oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes can be matured in a variety of medium known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal. See, for example, US20080092249, WO/1999/005266A2, US20040177390, WO/2008/017234A1, and U.S. Pat. No. 7,612,250, each of which is herein incorporated by reference.

In one aspect, a method for making a genetically modified rat is provided, comprising modifying a genomic locus of interest in a pluripotent rat cell employing endonuclease-mediated gene targeting to introduce a modification at a rat genomic locus of interest to form a modified pluripotent rat cell, maintaining the modified pluripotent rat cell under conditions sufficient to maintain pluripotency, employing the modified pluripotent rat cell as a donor cell in a rat host embryo, and gestating the host embryo comprising the modified pluripotent rat cell in a surrogate mother, wherein the host embryo is gestated by the surrogate mother and a genetically modified rat progeny is born.

In one embodiment, the target sequence is located in an intron. In one embodiment, the target sequence is located in an exon. In one embodiment, the target sequence is located in a promoter. In one embodiment, the target sequence is located in a promoter regulatory region. In one embodiment, the target sequence is located in an enhancer region.

In one embodiment, introducing step is performed multiple times over a period of time using a plurality of endonucleases that recognize distinct target sequences. In one embodiment, step is performed at least two times over a period of time using a plurality of endonucleases that recognize distinct target sequences, at least three times over a period of time using a plurality of endonucleases that recognize distinct target sequences, at least four times over a period of time using a plurality of endonucleases that recognize distinct target sequences, at least five times over a period of time using a plurality of endonucleases that recognize distinct target sequences, at least six times over a period of time using a plurality of endonucleases that recognize distinct target sequences, at least seven times over a period of time using a plurality of endonucleases that recognize distinct target sequences, at least eight times over a period of time using a plurality of endonucleases that recognize distinct target sequences, at least nine times over a period of time using a plurality of endonucleases that recognize distinct target sequences, at least ten times over a period of time using a plurality of endonucleases that recognize distinct target sequences, at least eleven times over a period of time using a plurality of endonucleases that recognize distinct target sequences, at least twelve times over a period of time using a plurality of endonucleases that recognize distinct target sequences, at least thirteen times over a period of time using a plurality of endonucleases that recognize distinct target sequences, at least fourteen times over a period of time using a plurality of endonucleases that recognize distinct target sequences, at least fifteen times over a period of time using a plurality of endonucleases that recognize distinct target sequences, at least sixteen times over a period of time using a plurality of endonucleases that recognize distinct target sequences, at least seventeen times over a period of time using a plurality of endonucleases that recognize distinct target sequences, at least eighteen times over a period of time using a plurality of endonucleases that recognize distinct target sequences, at least nineteen times over a period of time using a plurality of endonucleases that recognize distinct target sequences, or at least twenty times over a period of time using a plurality of endonucleases that recognize distinct target sequences.

In one embodiment, introducing step is mediated by electroporation, by intracytoplasmic injection, by an adenovirus, by lentivirus, by retrovirus, by transfection, by lipid-mediated transfection or is mediated via Nucleofection™.

In one embodiment, the method further comprises introducing an exogenous nucleic acid into the genetically modified pluripotent rat cell. In one embodiment, the exogenous nucleic acid is a transgene. In one embodiment, the exogenous nucleic acid is introduced into an endogenous locus. In one embodiment, the exogenous nucleic acid is introduced ectopically (e.g., at a locus different from its endogenous locus).

In one aspect, a method for making a genetically modified rat is provided, comprising modifying a genomic locus of interest in a pluripotent rat cell employing RNA-guided genome engineering to introduce a modification at a rat genomic locus of interest to form a modified pluripotent rat cell, maintaining the modified pluripotent rat cell under conditions sufficient to maintain pluripotency, employing the modified pluripotent rat cell as a donor cell in a rat host embryo, and gestating the host embryo comprising the modified pluripotent rat cell in a surrogate mother, wherein the host embryo is gestated by the surrogate mother and a genetically modified rat progeny is born.

In one embodiment, the method has a targeting rate ranging from about 2% to about 80%.

In one embodiment, the method comprises co-introducing a plurality of the second expression construct comprising distinct genomic target sequences for multiplex editing of distinct genomic loci. In on embodiment, the method comprises introducing a plurality of the second expression construct comprising distinct genomic target sequences for multiplex editing of distinct genomic loci over a period of time.

In one embodiment, introducing step is performed multiple times over a period of time. In one embodiment, introducing step (b) is performed at least two times over a period of time, at least three times over a period of time, at least four times over a period of time, at least five times over a period of time, at least six times over a period of time, at least seven times over a period of time, at least eight times over a period of time, at least nine times over a period of time, at least ten times over a period of time, at least eleven times over a period of time, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, at least twenty times over a period of time.

In one embodiment, the first expression construct and the second expression construct are expressed from a same plasmid.

In one embodiment, introducing step is mediated by electroporation, by intracytoplasmic injection, by an adenovirus, by lentivirus, by retrovirus, by transfection, by lipid-mediated transfection or is mediated via Nucleofection™.

In one embodiment, the method further comprises introducing an exogenous nucleic acid into the pluripotent rat cell comprising the mutant allele.

In one embodiment, the exogenous nucleic acid is a transgene. In one embodiment, the exogenous nucleic acid is introduced into an endogenous locus. In one embodiment, the exogenous nucleic acid is placed ectopically (e.g., at a locus different from its endogenous locus).

In one embodiment, the method further comprises introducing an exogenous nucleic acid into the genetically modified pluripotent rat cell. In one embodiment, the exogenous nucleic acid is a transgene. In one embodiment, the exogenous nucleic acid is introduced into an endogenous locus. In one embodiment, the exogenous nucleic acid is introduced ectopically (e.g., at a locus different from its endogenous locus).

In one aspect, a method for making a humanized rat is provided, comprising modifying a genome of a pluripotent rat cell with an LTVEC comprising an insert that comprises a human sequence of at least 5 kb, and employing the pluripotent rat cell as a donor cell, introducing the donor cell into a host embryo, and gestating the host embryo in a surrogate mother, wherein the surrogate mother births a rat progeny that comprises the humanization.

Other methods for making a genetically modified rat comprising in its germline one or more genetic modifications as described herein is provided, comprising: (a) modifying a targeted rat locus contained in a prokaryotic cell employing the various methods described herein; (b) selecting a modified prokaryotic cell comprising the genetic modification at the targeted rat locus; (c) isolating the genetically modified targeting vector from the genome of the modified prokaryotic cell; (d) introducing the genetically modified targeting vector into a pluripotent rat cell to generate a genetically modified pluripotent cell comprising the insert nucleic acid at the targeted genomic locus; (e) selecting the genetically modified rat pluripotent cell; (f) introducing the genetically modified pluripotent rat cell into a host rat embryo at a pre-morula stage; and (g) implanting the host rat embryo comprising the genetically modified pluripotent rat cell into a surrogate mother to generate an F0 generation derived from the genetically modified pluripotent rat cell. In such methods the targeting vector can comprise a large targeting vector. The pluripotent rat cell can be a rat ES cell. In further methods, the isolating step (c) further comprises (c1) linearizing the genetically modified targeting vector (i.e., the genetically modified LTVEC). In still further embodiments, the introducing step (d) further comprises (d1) introducing a nuclease agent as described herein into the pluripotent rat cell. In one embodiment, selecting steps (b) and/or (e) are carried out by applying a selectable agent as described herein to the prokaryotic cell or the pluripotent rat cell. In one embodiment, selecting steps (b) and/or (e) are carried out via a modification of allele (MOA) assay as described herein.

Further methods for modifying a target genomic locus of a mammalian cell via bacterial homologous recombination (BHR) in a prokaryotic cell are provided and comprise: (a) providing a prokaryotic cell comprising a target locus comprising a rat nucleic acid, (b) introducing into the prokaryotic cell a targeting vector comprising an insert nucleic acid flanked with a 5' rat homology arm and a 3' rat homology arm, wherein the insert nucleic acid comprises a mammalian region (including, for example, a. DNA insert from a human), and (c) selecting a targeted prokaryotic cell comprising the insert nucleic acid at the target rat locus, wherein the prokaryotic cell is capable of expressing a recombinase that mediates the BHR. Step (a1) can comprise providing a prokaryotic cell comprising a target locus comprising a rat nucleic acid comprising a first polynucleotide comprising a first recognition site for a first nuclease agent, and step (hi) can further comprise expressing in the prokaryotic cell a nuclease agent that makes a nick or double-strand break at or near the first recognition site. Steps (a)-(c) can be serially repeated as disclosed herein to allow the introduction of multiple insert nucleic acids at the targeted rat locus in the prokaryotic cell. Once the targeted genomic locus is "built" with the prokaryotic cell, a targeting vector comprising the modified target rat locus can be isolated from the prokaryotic cell and introduced into a target genomic locus within a pluripotent rat cell. Pluripotent rat cells (i.e., rat ES cells) comprising the modified genomic locus can then be made into genetically modified rats.

In some embodiments, various genetic modifications of the target genomic loci described herein can be carried out by a series of homologous recombination reactions (BHR) in bacterial cells using an LTVEC derived from Bacterial Artificial Chromosome (BAC) DNA using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, Nature Biotechnology 21(6): 652-659, which is incorporated herein by reference in their entireties).

In some embodiments, targeted rat ES cells comprising various genetic modifications as described herein are used as insert ES cells and introduced into a pre-morula stage embryo from a corresponding organism, e.g., an 8-cell stage mouse embryo, via the VELOCIMOUSE® method (see, e.g., U.S. Pat. Nos. 7,576,259, 7,659,442, 7,294,754, and US 2008-0078000 A1, all of which are incorporated by reference herein in their entireties). The rat embryo comprising the genetically modified rat ES cells is incubated until the blastocyst stage and then implanted into a surrogate mother to produce an F0. Rats bearing the genetically modified genomic locus can be identified via modification of allele (MOA) assay as described herein. The resulting F0 generation rat derived from the genetically modified ES rat cells is crossed to a wild-type rat to obtain F1 generation offspring. Following genotyping with specific primers and/or probes, F1 rats that are heterozygous for the genetically modified genomic locus are crossed to each other to produce rats that are homozygous for the genetically modified genomic locus. Alternatively, an F0 female rat and an F0 male rat each having the genetic modification can be crossed to obtain an F1 rat homozygous for the genetic modification.

In one aspect, a genetically modified rat genome is provided, comprising a targeted modification of an endogenous rat nucleic acid sequence with a homologous or orthologous non-rat nucleic acid sequence.

In one embodiment, the homologous or orthologous non-rat nucleic acid sequence is of a length from about 5 kb to about 200 kb. In one embodiment, the homologous or orthologous non-rat nucleic acid sequence ranges from about 5 kb to about 10 kb. In one embodiment, the homologous or orthologous non-rat nucleic acid sequence ranges from about 10 kb to about 20 kb. In one embodiment, the homologous or orthologous non-rat nucleic acid sequence ranges from about 20 kb to about 30 kb. In one embodiment, the homologous or orthologous non-rat nucleic acid sequence ranges from about 30 kb to about 40 kb. In one embodiment, the homologous or orthologous non-rat nucleic acid sequence ranges from about 40 kb to about 50 kb. In one embodiment, the homologous or orthologous non-rat nucleic acid sequence ranges from about 50 kb to about 60 kb. In one embodiment, the homologous or orthologous non-rat nucleic acid sequence ranges from about 60 kb to about 70 kb. In one embodiment, the homologous or orthologous non-rat nucleic acid sequence ranges from about 70 kb to about 80 kb. In one embodiment, the homologous or orthologous non-rat nucleic acid sequence ranges from about 80 kb to about 90 kb. In one embodiment, the homologous or orthologous non-rat nucleic acid sequence ranges from about 90 kb to about 100 kb. In one embodiment, the homologous or orthologous non-rat nucleic acid sequence ranges from about 100 kb to about 110 kb. In one embodiment, the homologous or orthologous non-rat nucleic acid sequence ranges from about 110 kb to about 120 kb. In one embodiment, the homologous or orthologous non-rat nucleic acid sequence ranges from about 120 kb to about 130 kb. In one embodiment, the homologous or orthologous non-rat nucleic acid sequence ranges from about 140 kb to about 150 kb. In one embodiment, the homologous or orthologous non-rat nucleic acid sequence ranges from about 150 kb to about 160 kb. In one embodiment, the homologous or orthologous non-rat nucleic acid sequence ranges from about 160 kb to about 170 kb. In one embodiment, the homologous or orthologous non-rat nucleic acid sequence ranges from about 170 kb to about 180 kb. In one embodiment, the homologous or orthologous non-rat nucleic acid sequence ranges from about 180 kb to about 190 kb. In one embodiment, the homologous or orthologous non-rat nucleic acid sequence ranges from about 190 kb to about 200 kb. Various polynucleotides of interest that can be employed in the insert nucleic acid are described elsewhere herein.

6. Cells

The various methods and compositions described herein employ a genomic locus targeting system in a cell. In one embodiment, the cell is a pluripotent cell. In one embodiment, the pluripotent cell is a non-human pluripotent cell. In one embodiment, the non-human pluripotent cell is a mammalian pluripotent cell. In one embodiment, the pluripotent cell is a human induced pluripotent stem (iPS) cell.

In one embodiment, the pluripotent cell is a pluripotent rat cell. In one embodiment, the pluripotent rat cell is a rat embryonic stem (ES) cell. In one embodiment, the pluripotent rat cell is an induced pluripotent stem (iPS) cell or is a developmentally restricted progenitor cell. In other embodiments, the pluripotent rat cell is able to sustain its pluripotency following at least one targeted genetic modification of its genome and is able to transmit the targeted modification to a germline of an F1 generation.

In one embodiment, the pluripotent cell is a non-human fertilized egg at the single cell stage. In one embodiment, the non-human fertilized egg is a mammalian fertilized egg. In one embodiment, the mammalian fertilized egg is a rodent fertilized egg at the single cell stage. In one embodiment, the mammalian fertilized egg is a rat or mouse fertilized egg at the single cell stage.

The various cells employed in the method and compositions disclosed herein can also comprise prokaryotic cells, such as a bacterial cell, including E. coli. In specific embodiments, the prokaryotic cell is a recombination-competent strain of E. coli. In one embodiment, the prokaryotic cell comprises a nucleic acid that encodes the recombinase, while in other instances, the prokaryotic cell does not comprise the nucleic acid that encodes the recombinase, and the nucleic acid encoding the recombinase is introduced into the prokaryotic cell. In one embodiment, the nucleic acid encoding the recombinase comprises a DNA or an mNA. In some embodiments, the nucleic acid encoding the recombinase is pABG. In one embodiment, the recombinase is expressed under the control of an inducible promoter. In one embodiment, expression of the recombinase is controlled by arabinose.

A. Rat Embryonic Stem (ES) Cells

As outlined in detail above, the various compositions and methods provided herein can employ embryonic stem (ES) cells from rat. In one embodiment, the pluripotent rat cell is a rat ES cell. In one embodiment, the rat ES cell is derived from a rat strain is a Wistar rat, an LEA strain, a Sprague Dawley strain, a Fischer strain, F344, 1'6, and Dark Agouti or ACI. In one embodiment, the rat strain is a mix of two or more of a strain selected from the group consisting of Wistar, LEA, Sprague Dawley, Fischer, F344, F6, and Dark Agouti. In one embodiment, the rat ES cell is derived from an inbred strain. In one embodiment, the rat ES cell is derived from a strain selected from a DA strain and an ACI strain. In a specific embodiment, the rat ES cell is derived from an ACI strain. In one embodiment, the rat ES cell is derived from a rat blastocyst.

In other embodiments, the rat ES cell is characterized by expression of at least one pluripotency marker. In specific embodiments, the rat ES cell is characterized by expression of a pluripotency marker comprising Oct-4, Sox-2, alkaline phosphatase, or a combination thereof. In one embodiment, the rat ES cell is a male (XY) rat ES cell or a female (XX) rat ES cell.

In one embodiment, following the one to 15 serial genetic modifications, the genetically modified rat ES cells upon exposure to differentiation medium are capable of differentiation into a plurality of cell types.

In one embodiment, following the one to 15 serial genetic modifications, the genetically modified rat ES cells are capable of being maintained in an undifferentiated state in culture. In one embodiment, the genetically modified and cultured rat ES cells in the undifferentiated state, when employed as donor cells in a rat host embryo, populate the embryo and form a blastocyst comprising the one to fifteen genetic modifications. In one embodiment, the blastocyst, when implanted into a surrogate mother under conditions suitable for gestation, develops into an F0 rat progeny that comprises the one to 15 genetic modifications.

In one aspect, an isolated rat ES cell is provided that is capable of sustaining pluripotency following one or more genetic modifications in vitro, and that is capable of transmitting a genetically modified genome to a germline of an F1 generation.

In one embodiment, the rat ES cell maintains its pluripotency to develop into a plurality of cell types following the one or more serial genetic modifications in vitro (e.g., two, three, four, five, or six or more serial genetic modifications). In one embodiment, the genetic modification is mediated by an electroporation, by intracytoplasmic injection, by a viral infection, by an adenovirus, by lentivirus, by retrovirus, by transfection, by lipid-mediated transfection, or by Nucleofection™.

In one embodiment, the rat ES cell maintains its pluripotency to develop into a plurality of cell types following a single round of electroporation with an exogenous nucleic acid. In one embodiment, the rat ES cell maintains its pluripotency to develop into a plurality of cell types following a $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, or $15^{th}$ round of electroporation with an exogenous nucleic acid.

In other embodiments, the rat ES cells employed are those described in US 2014-0235933, herein incorporated by reference in its entirety.

The pluripotent rat cell employed in the various methods and compositions disclosed herein can be characterized by expression of at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, and/or a combination thereof. In other instances, the pluripotent rat cell employed in the various methods and compositions disclosed herein is characterized by one or more of the following features: (a) lack of expression of one or more pluripotency markers comprising c-Myc, Ecat1, and/or Rexo1; (b) lack of expression of one or more mesodermal markers comprising Brachyury and/or Bmpr2; (c) lack of expression of one or more endodermal markers comprising Gata6, Sox17, and/or Sox7; or (d) lack of expression of one or more neural markers comprising Nestin and/or Pax6. As used herein, "lack of expression" as it relates to expression of a pluripotency marker means that the expression of the pluripotency marker is at or below the experimental background as determined for each individual experiment.

In one non-limiting embodiment, the rat ES cells provided herein have one or more of any of the following properties:

(a) have germ-line competency, meaning when the rat ES cell is implanted into a rat host embryo, the genome of the rat ES cell line is transmitted into an offspring;

(b) have germ-line competency following at least one targeted genetic modification, meaning when the rat ES cell having the targeted genetic modification is implanted into a rat host embryo, the targeted genetic modification within the genome of the rat ES cell line is transmitted into an offspring;

(c) have pluripotency in vitro;

(d) have totipotency in vitro;

(e) when cultured in vitro loosely adhere to a feeder cell layer;

when cultured in vitro form sphere-like colonies when plated on a feeder cell layer in vitro;

(g) maintain pluripotency when cultured in vitro under conditions comprising a feeder cell layer that is not genetically modified to express leukemia inhibitory factor (LIF), wherein the culture media comprises a sufficient concentration of LIF;

(h) maintain pluripotency when cultured in vitro under conditions comprising a feeder cell layer, wherein the culture media comprises mouse LIF or an active variant or fragment thereof;

(i) comprise a molecular signature that is characterized by
   i) the expression of one or more of rat ES cell-specific genes comprising Adheres Junctions Associate Protein (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta(Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof;

ii) the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes comprising Adheres Junctions Associate Protein (Ajap1), Claudin 5 (Cldn5), Cdc42 guanine nucleotide exchange factor 9 (Arhgef9), Calcium/calmodulin-dependent protein kinase IV (Camk4), ephrin-A1 (Efna1), EPH receptor A4 (Epha4), gap junction protein beta 5 (Gjb5), Insulin-like growth factor binding protein-like 1 (Igfbpl1), Interleukin 36 beta(Il1f8), Interleukin 28 receptor, alpha (Il28ra), left-right determination factor 1 (Lefty1), Leukemia inhibitory factor receptor alpha (Lifr), Lysophosphatidic acid receptor 2 (Lpar2), Neuronal pentraxin receptor (Ntm), Protein tyrosine phosphatase non-receptor type 18 (Ptpn18), Caudal type homeobox 2 (Cdx2), Fibronectin type III and ankyrin repeat domains 1 (Fank1), Forkhead box E1 (thyroid transcription factor 2) (Foxe1), Hairy/enhancer-of-split related with YRPW motif 2 (Hey2), Forkhead box E1 (thyroid transcription factor 2) (Foxe1), Hairy/enhancer-of-split related with YRPW motif 2 (Hey2), Lymphoid enhancer-binding factor 1 (Lef1), Sal-like 3 (*Drosophila*) (Sall3), SATB homeobox 1 (Satb1), miR-632, or a combination thereof;

iii) at least a 20-fold increase in the expression of one or more of the rat ES cell-specific genes as set forth in Table 9 when compared to a F1H4 mouse ES cell;

iv) at least a 20-fold increase in the expression of at least 2, 3, 4, 5, 6, 7, 8, 9, 10, 11, 12, 13, 14, 15, 16, 17, 18, 19, 20, 21, 22, 23, 24, 25 or more of the rat ES cell-specific genes as set forth in Table 9 when compared to a F1H4 mouse ES cell;

v) the expression of one or more of rat ES cell-specific genes as set forth in Table 10;

vi) the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 10;

vii) at least a 20-fold increase in the expression of one or more of the rat ES cell-specific genes as set forth in Table 10 when compared to a F1H4 mouse ES cell;

viii) at least a 20-fold increase in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 10 when compared to a F1H4 mouse ES cell;

ix) at least a 20-fold decrease in the expression of one or more of the rat ES cell-specific genes as set forth in Table 8 when compared to a F1H4 mouse ES cell;

x) at least a 20-fold decrease in the expression of at least 2, 3, 4, 5, 6, 7, 8, 9, 10, 11, 12, 13, 14, 15, 16, 17, 18, 19, 20, 21, 22, 23, 24, 25, 30, 35, 40, 45, 50 or more of the rat ES cell-specific genes as set forth in Table 8 when compared to a F1H4 mouse ES cell;

xi) any combination of expression of the rat ES cell-specific genes of parts (i)-(x);

xii) a relative expression level of pluripotency markers as shown in Table 11 for at least 2, 3, 4, 5, 6, 7, 8, 9, 10, 11, 12, 13, 14, 15, 16, 17 or 18 of the listed pluripotency markers. See, pluripotency ranking column of Table 11 for relative expression levels;

xiii) a relative expression level of the mesodermal markers as shown in Table 11 for at least 2, 3, or 4 of the listed mesodermal markers. See, mesodermal ranking column in Table 11 for relative expression levels;

xiv) a relative expression level of endodermal markers as shown in Table 11 for at least 2, 3, 4, 5, or 6 of the listed endodermal markers. See, endodermal ranking column in Table 11 for relative expression levels;

xv) a relative expression level of neural markers as shown in Table 11 for at least 2 and 3 of the listed neural markers. See, neural ranking column in Table 11 for relative expression levels;

xvi) a relative expression level of trophectoderm markers as shown in Table 11 for the listed trophectoderm markers. See, trophectoderm ranking column in Table 11 for relative expression levels;

xvii) any relative expression level of one or more (2, 3, 4, 5, 6, 7, 8, 9, 10, 11, 12, 13, 14, 15, 16, 17, 18, 19, 20, 21, 22, 23, 24, 25, 26, 27, 28, 29 or 30) of the pluripotency markers, mesodermal markers, endodermal markers, neural markers and/or trophectoderm markers set forth in Table 11;

xviii) the relative expression level of each of the markers set forth in Table 11;

xix) any combination of the signatures set forth in xii-xiix; and/or xx) any combination of the signature set forth in i-xiix;

(j) have the ability to produce a F0 rat;

(k) are capable of being subcultured and maintaining the undifferentiated state;

(l) have the same number of chromosomes as a normal rat cell;

(m) maintain pluripotency in vitro without requiring paracrine LIF signaling;

(n) have self-renewal, meaning they divide indefinitely while maintaining pluripotency;

(o) the rat ES cells express at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, and/or a combination thereof;

(p) the rat ES cells do not express one or more differentiation markers comprising c-Myc, Ecat1, and/or Rexo1;

(q) the rat ES cells do not express one or more mesodermal markers comprising Brachyury, Bmpr2, and/or a combination thereof;

(r) the rat ES cells do not express one or more endodermal markers comprising Gata6, Sox17, Sox7, and/or combination thereof; and/or (s) the rat ES cells do not express one or more neural markers comprising Nestin, Pax6, and/or combination thereof.

One or more of the characteristics outlined in (a)-(s) can be present in a rat ES cell, a rat ES cell population or a rat ES cell line employed in the methods and compositions provided herein, wherein the rat ES cells have not undergone a targeted genetic modification. Moreover, following the one or more genetic modification to the rat target locus as described in detail above, the one or more of the characteristics outlined in (a)-(s) can be retained in the rat ES cell following the genetic modification of the target locus.

In one embodiment, the rat ES cell exhibits a homologous recombination efficiency of at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, at least 50%, at least 55%, at least 60%, at least 65%, at least 70%, at least 75%, or at least 80%.

In one embodiment, the homologous recombination efficiency employing the rat ES cell is greater than 4%.

In one embodiment, the rat ES cell has a doubling time ranging from 24 hours to 36 hours. In one embodiment, the rat ES cell has a doubling time of 25 hours.

In one embodiment, the rat ES cell can be passaged up to at least 15 times in 2i medium (Millipore Cat. SF016-200). In one embodiment, the rat ES cell can be passaged at least 14 times in 2i medium (Millipore Cat. No. SF016-200). In one embodiment, the rat ES cell can be passaged at least 13, 12, 11, 10, 9, 8, 7, 6, or 5 times in 2i medium.

In one embodiment, when transplanted into a pre-morula stage rat embryo, the rat ES cell can contribute to at least 90% of the cells in an F0 generation. In one embodiment, when transplanted into a pre-morula stage rat embryo, the rat ES cell can contribute to at least 95%, 96%, 97%, 98%, or 99% of the cells in an F0 generation.

In specific embodiments, the various rat ES cells and cell lines employed in the various methods and compositions provided herein are used to generate a targeted modification at a target locus. The rat ES cell having these targeted genetic modifications can be germ-line competent, meaning when the rat ES cell having the targeted genetic modification is implanted into a rat host embryo, the targeted genetic modification of the rat ES cell is transmitted to the offspring (i.e., the F1 population). Thus, in various aspects, the rat ES cells in the various methods and compositions are employed to obtain a high frequency, or high efficiency, of germline transmission of a rat cell genome from rat ES cells that have undergone a targeted genetic modification. In various embodiments, the frequency of germline transmission is greater than 1:600, greater than 1:500, greater than 1:400, greater than 1:300, greater than 1:200, and greater than 1:100. In various embodiments, the frequency of germline transmission is greater than 1%, greater than 2%, greater than 3%, greater than 4%, greater than 5%, greater than 6%, greater than 7%, greater than 8%, greater than 9%, greater than 10%, up to about 16%, greater than 25%, greater than 50%, greater than 60%, greater than 65%, greater than 70%, greater than 75% or greater. In various embodiments, the frequency of germline transmission ranges from 9% to 16%. In various aspects, percent of donor rESC-derived progeny in the F1 generation is 1% or more, 2% or more, 3% or more, 10% or more, 20% or more, 30% or more, 40% or more, 50% or more, 60% or more, from 3% to about 10% or more; from 3% or more to about 63%, from about 10% to about 30%, from about 10% to about 50%, from about 30% to about 70%, from about 30% to about 60%, from about 20% to about 40%, from about 20% to 65%, or from about 40% to 70%. Thus, a rat ES cell that has a targeted genetic modification have the ability to transmit their genome into the F1 population.

Figure 2:
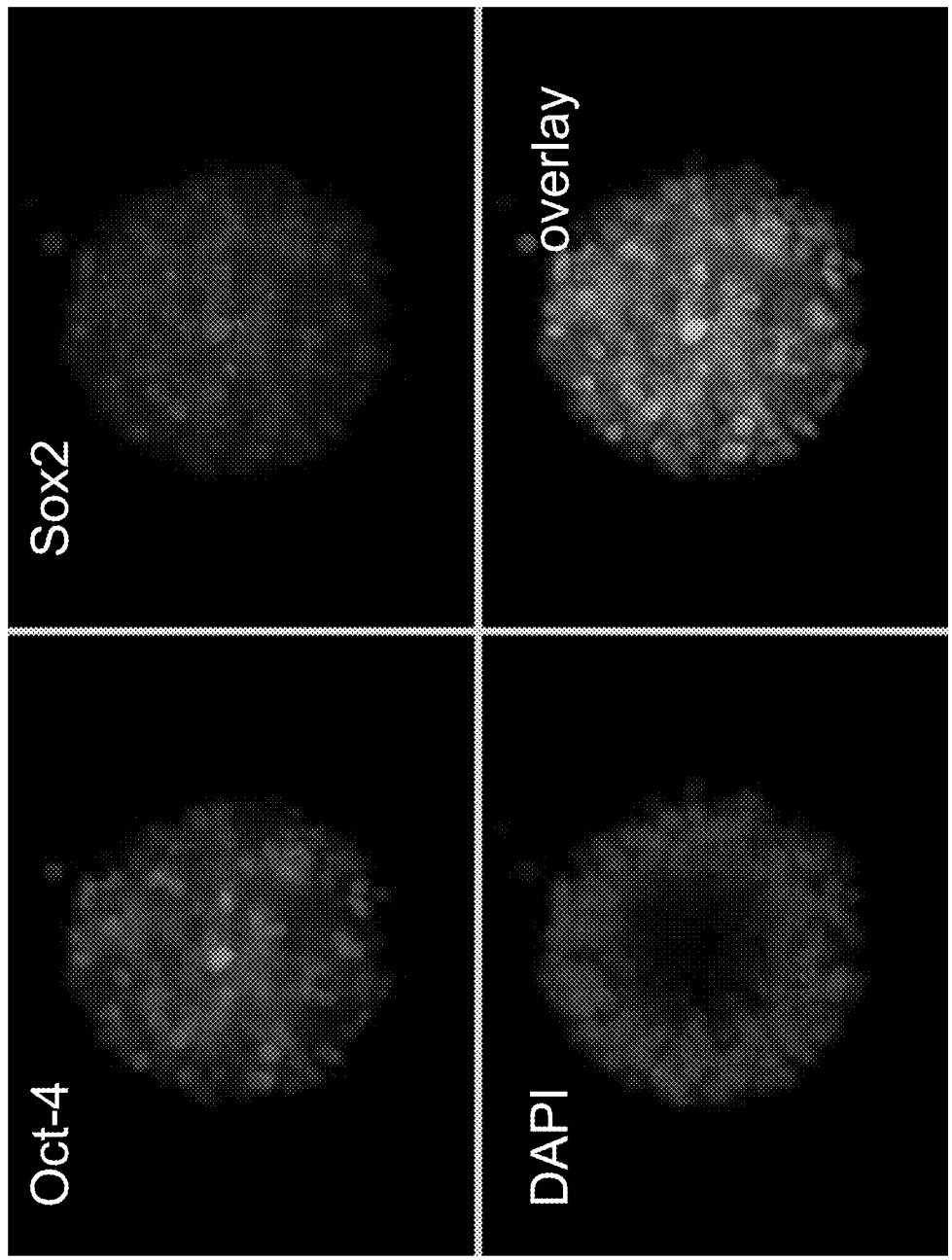
FIGS. 2A through 2D depict various pluripotency markers expressed by rat ESCs.
Figure 3:
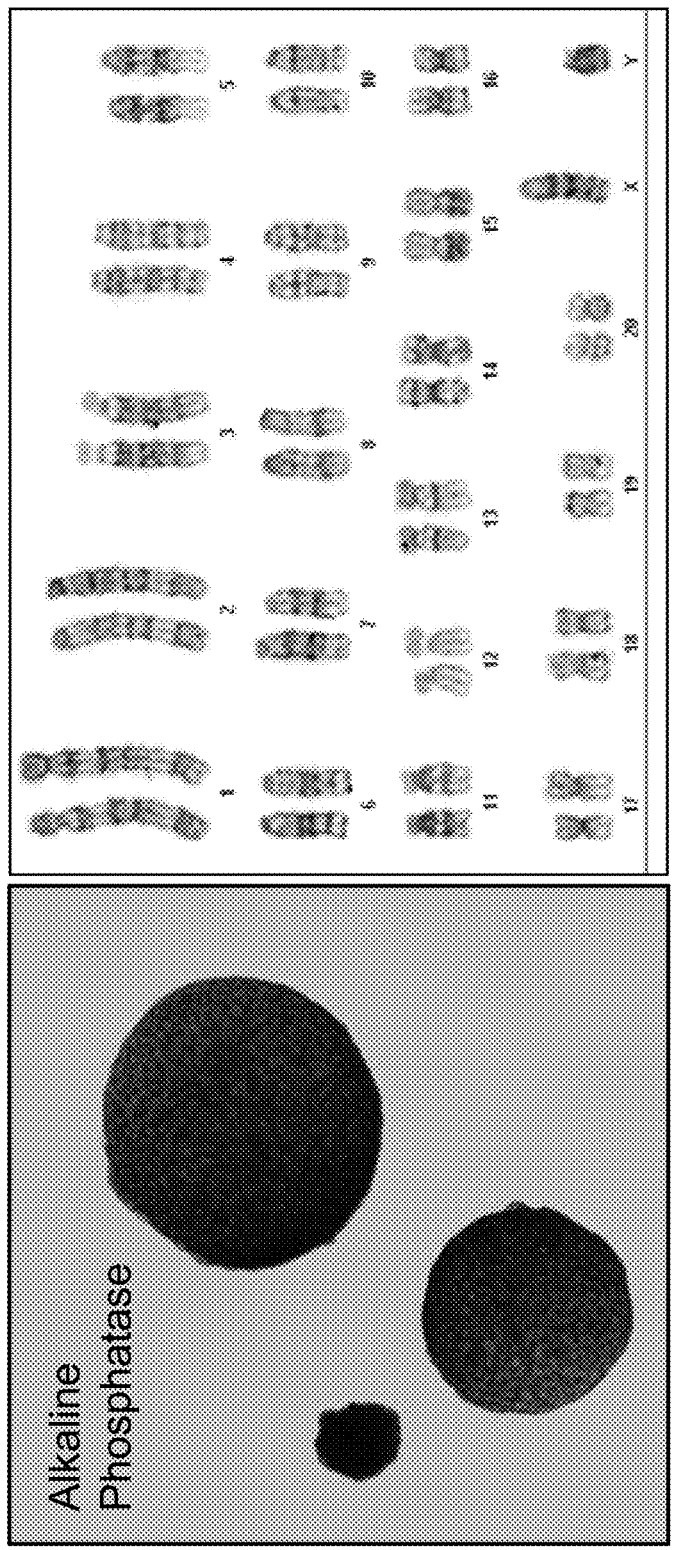
FIG. 3 depicts that the rat ESCs express light levels of alkaline phosphatase (a pluripotency marker)(left), and the karyotype for line DA.2B is 42X,Y (right). Karyotyping was done because rat ESCs often become tetraploid; lines were thus pre-screened by counting metaphase chromosome spreads, and lines with mostly normal counts were then formally karyotyped.

A rat ES cell that has a targeted genetic modification can be pluripotent and/or totipotent. Various methods can be used to determine if a rat ES cell is pluripotent. For example, the ES cell can be assayed for the expression of various pluripotent markers including, but not limited to, Oct-4, Sox2, alkaline phosphatase, or a combination thereof. See, for example, Okamoto, K. et al., *Cell*, 60: 461-472 (1990), Scholer, H. R. et al., *EMBO J.* 9: 2185-2195 (1990)) and Nanog (Mitsui, K. et al., *Cell*, 113: 631-642 (2003), Chambers, I. et al., *Cell*, 113: 643-655 (2003) for various methods of assaying for the presence or the level of such markers. See, also FIGS. 2 and 3 provided herein. Other pluripotency markers include, for example, the presence of at least 1, 2, 3, 4, or 5 pluripotency marker comprising Nanog, Klf4, Dppa2, Fgf4, Rex1, Eras, Err-beta and/or Sall3. Other pluripotency markers include, for example, the absence of at least 1, 2, 3, 4, 5, 6, 7, 8, 9 or 10 pluripotency marker comprising T/Brachyury, Flk1, Nodal, Bmp4, Bmp2, Gata6, Sox17, Hhex1, Sox7, and/or Pax6.

In specific embodiments, the expression and/or the level of expression of these markers can be determined using RT-PCR. Various kits are available to determine the level and/or presence of alkaline phosphatase, including, for example, an ALP tissue staining kit (Sigma) and Vector Red Alkaline Phosphatase Substrate Kit I (Funakoshi) and the like. Additional assays include in situ hybridization, immunohistochemistry, and immunofluorescence. In specific embodiments, the rat ES cell is characterized by expression of at least one pluripotency marker, including for example expression of Oct-4, Sox2, alkaline phosphatase, or a combination thereof, and preferably all three of these markers.

The various rat ES cells employed in the method and compositions provided herein are capable of maintaining pluripotency and/or totipotency while being maintained in in vitro culturing conditions. Thus, the various rat ES cells provide herein can, in some embodiments, be subcultured while still maintaining the undifferentiated state. Various methods of culturing the rat ES cells are discussed in further detail elsewhere herein and in US 2014-0235933, herein incorporated by reference in its entirety.

In some embodiments, the rat embryonic stem cells employed herein have been isolated from the rat embryo employing various isolation, purification, and culture expansion techniques which are discussed in detail in US 2014-0235933, herein incorporated by reference in its entirety.

An "isolated" rat ES cell or rat embryo has been removed from its natural environment. The term "isolated" can mean free from 70%, 80%, 90%, 95%, 96%, 97%, 98% or 99% of the constituents with which a component is found in its natural state. As used herein, a rat ES "cell line" comprises a population of isolated rat cells that were developed from a single rat ES cell and therefore the population of cells within a given cell line have a uniform genetic makeup other than for mutations or karyotypic changes occurring during propagation or during targeted genetic modifications. For example, rat ES cells can be characterized by a high level of euploidy. Nevertheless, in some cell lines the level of euploidy is less than 100% due to karyotypic changes in propagation of the line from a single cell. Moreover, a given population of rat ES cells can comprise at least $1 \times 10^3$, $1 \times 10^4$, $1 \times 10^5$, $1 \times 10^6$, $1 \times 10^7$, $1 \times 10^8$, $1 \times 10^9$, or $1 \times 10^{10}$ cells or greater. Some cell populations have sufficient cells to permit selection of a desired modified cell but not an excessively greater number so as to reduce the possibility of mutations or karyotypic changes developing in the cell line. For example, some cell populations have $1 \times 10^3$ to $1 \times 10^6$ cells.

As discussed elsewhere herein, various methods are provided for the targeted genetic modification of a rat ES cell line. When such methods are carried out, at least one cell within a rat ES cell line contains the targeted genetic modification. Through various culturing and/or selection techniques rat ES cell lines having one or more desired targeted genetic modifications are produced.

In specific embodiments, a rat ES cell, a population of rat ES cell or a rat ES cell line (that have not undergone a targeted genetic modification and/or have a targeted genetic modification) are euploid, and thus have a chromosome number that is an exact multiple of the haploid number. In further embodiment, a rat ES cell, a population of rat ES cells or a rat ES cell line (that have not undergone a targeted genetic modification and/or have a targeted genetic modification) are diploid, and thus have two haploid sets of homologous chromosomes. When referring to a rat ES cell population or a population of cells from a given population of rat ES cells or a rat ES cell line (that have not undergone a targeted genetic modification and/or have a targeted genetic modification), at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the cells with the given population are euploid and/or diploid. In other instances, when referring to a rat ES cell population or a population of cells from a given rat ES cell line (that have not undergone a targeted genetic modification and/or have a targeted genetic modification), at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the cells within the given population are euploid and/or diploid.

In still further embodiments, a rat ES cell, a population of rat ES cells or a rat ES cell line (that have not undergone a targeted genetic modification and/or have a targeted genetic modification) have 42 chromosomes. When referring to a rat ES cell population or a population of cells from a given rat ES cell line (that have not undergone a targeted genetic modification and/or have a targeted genetic modification) at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the cells with the given population have 42 chromosomes. In other instances, when referring to a rat ES cell population or a population of cells from a given rat ES cell line (that have not undergone a targeted genetic modification and/or have a targeted genetic modification) at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the cells within the given population have 42 chromosomes.

In further embodiments, a rat ES cell, a population of rat ES cells or a rat ES cell line (that have not undergone a targeted genetic modification and/or have a targeted genetic modification) provided herein form sphere-like colonies when plated on a feeder cell layer in vitro. The "sphere-like" morphology refers to the shape of rat ES cell colonies in culture, rather than the shape of individual ES cells. The rat ES cell colonies are spherical-like. Colonies, which are loosely attached to the feeder cells appear circular (have a circular-like morphology). Free-floating colonies are spherical-like. The rat ES cell colonies are spherical-like and very compact, meaning: the boundaries between cells are very hard to see. The edge of the colony appears bright and sharp. Individual nuclei are difficult to distinguish because the cells are very small (so that the nucleus takes up most of the volume of the cell). Mouse ES Cells form elongated colonies and attach strongly to feeder cells. mESC morphology can vary with strain; e.g. B6 colonies are rounder and more domed than F1H4 colonies but are still more elongated than rESC. Human ES cell colonies are flatter and more spread out than mESC colonies. The instant rat ES colonies are not flat and do not resemble human ES cell colonies.

In still further embodiments, a rat ES cell, a population of rat ES cells or a rat ES cell line (that have not undergone a targeted genetic modification and/or have a targeted genetic modification) have a circular morphology. A morphology scale for a circle is provided below, where a score of a 10 represents a perfect circle and a score of a 1 represents an ellipse.

Morphology Scale of a Circle:

10=A circle with a structure having a longitudinal axis and a vertical axis that run through the center of the structure and are of equal length.

9=A structure having a longitudinal axis and vertical axis that run through the center of the structure, wherein one of the axis is between 0.9999 to 0.9357 the length of the other axis.

8=A structure having a longitudinal axis and vertical axis that run through the center of the structure, wherein one of the axis is between 0.9357 to 0.875 the length of the other axis.

7=A structure having a longitudinal axis and vertical axis that run through the center of the structure, wherein one of the axis is between 0.875 to about 0.8125 the length of the other axis.

6=A structure having a longitudinal axis and vertical axis that run through the center of the structure, wherein one of the axis is between 0.8125 to 0.750 the length of the other axis.

5=A structure having a longitudinal axis and vertical axis that run through the center of the structure, wherein one of the axis is between 0.750 to 0.6875 the length of the other axis.

4=A structure having a longitudinal axis and vertical axis that run through the center of the structure, wherein one of the axis is between 0.6875 to 0.625 the length of the other axis.

3=A structure having a longitudinal axis and vertical axis that run through the center of the structure, wherein one of the axis is between 0.625 to 0.5625 the length of the other axis.

2=A structure having a longitudinal axis and vertical axis that run through the center of the circle, wherein one of the axis is between 0.5625 to 0.523 the length of the other axis.

1=An ellipse is defined as having a longitudinal axis and vertical axis that run through the center of the structure, wherein one of the axis is between 0.523 to 0.500 the length of the other axis.

In one non-limiting embodiment, the rat ES cell population or a population of cells from a given rat ES cell line (that have not undergone a targeted genetic modification and/or have a targeted genetic modification) have at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the cells with the given population have a circular morphology score of a 10, 9 or 8. In other embodiments, the rat ES cell population or a population of cells from a given rat ES cell line (that have not undergone a targeted genetic modification and/or have a targeted genetic modification) have at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the cells within the given population have a circular morphology score of a 10, 9, or 8.

In another non-limiting embodiment, the rat ES cell population or a population of cells from a given rat ES cell line (that have not undergone a targeted genetic modification and/or have a targeted genetic modification) have at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the cells with the given population have a circular morphology score of a 7, 6, 5, 4 or 3. In other non-limiting embodiments, the rat ES cell population or a population of cells from a given rat ES cell line (that have not undergone a targeted genetic modification and/or have a targeted genetic modification) have at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the cells within the given population have a circular morphology score of a 7, 6, 5, 4, or 3.

In still further embodiments, sphere-like colonies form when the rat ES cells (that have not undergone a targeted genetic modification and/or have a targeted genetic modification) are plated on a feeder cell layer in vitro. A morphology scale for a sphere is provided below, where a score of a 10 represents a perfect sphere and a score of a 1 represents a three dimensional elliptical structure.

Morphology scale of a sphere-like structure:

10=A sphere is a structure having an X-axis and a Y-axis and a Z-axis each of which runs through the center of the structure and are of equal length.

9=A structure having an X axis and a Y-axis and a Z-axis that run through the center of the structure, wherein one of the axis is between 0.9999 to 0.9357 the length of at least one of the other axes.

8=A structure having an X axis and a Y-axis and a Z-axis that run through the center of the structure, wherein one of the axis is between 0.9357 to 0.875 the length of at least one or both of the other axes.

7=A structure having an X axis and a Y-axis and a Z-axis that run through the center of the structure, wherein one of the axis is between 0.875 to 0.8125 the length of at least one or both of the other axes.

6=A structure having an X axis and a Y-axis and a Z-axis that run through the center of the structure, wherein one of the axis is between 0.8125 to 0.750 the length of at least one or both of the other axes.

5=A structure having an X axis and a Y-axis and a Z-axis that run through the center of the structure, wherein one of the axis is 0.750 to 0.6875 the length of at least one or both of the other axes.

4=A structure having an X axis and a Y-axis and a Z-axis that run through the center of the structure, wherein one of the axis is 0.6875 to 0.625 the length of at least one or both of the other axes.

3=A structure having an X axis and a Y-axis and a Z-axis that run through the center of the structure, wherein one of the axis is between 0.625 to 0.5625 the length of at least one or both of the other axes.

2=A structure having an X axis and a Y-axis and a Z-axis that run through the center of the structure, wherein one of the axis is between 0.5625 to 0.523 the length of at least one or both of the other axes.

1=A structure having an X axis and a Y-axis and a Z-axis that run through the center of the structure, wherein one of the axis is between 0.523 to 0.500 the length of at least one or both of the other axes.

In one non-limiting embodiment, the rat ES cell population or a population of cells from a given rat ES cell line (that have not undergone a targeted genetic modification and/or have a targeted genetic modification) have at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the colonies that form when the cells are plated on a feeder cell layer in vitro have a sphere-like morphology of a 10, 9 or 8. In other embodiments, the rat ES cell population or a population of cells from a given rat ES cell line (that have not undergone a targeted genetic modification and/or have a targeted genetic modification) have at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 95%, about 80% to about 90%, about 90% to about 100%, about 90% to about 99%, about 90% to about 98%, about 90% to about 97%, about 90% to about 95% of the colonies that form when the cells are plated on a feeder cell layer in vitro have a sphere-like morphology of a 10, 9 or 8.

In another non-limiting embodiment, the rat ES cell population or a population of cells from a given rat ES cell line (that have not undergone a targeted genetic modification and/or have a targeted genetic modification) have at least about 50%, 60%, 65%, 70%, 75%, 80%, 85%, 86%, 87%, 88%, 89%, 90%, 91%, 92%, 93%, 94%, 95%, 96%, 97%, 98%, 99% or 100% of the colonies that form when the cells are plated on a feeder cell layer in vitro have a sphere-like morphology of a 7, 6, 5, 4, or 3. In other embodiments, the rat ES cell population or a population of cells from a given rat ES cell line (that have not undergone a targeted genetic modification and/or have a targeted genetic modification) have at least about 50% to 95%, about 60% to 90%, about 60% to 95%, about 60% to 85%, about 60% to 80%, about 70% to 80%, about 70% to 85%, about 70% to about 90%, about 70% to about 95%, about 70% to about 100%, about 80% to about 100%, about 80% to about 95%, about 80% to about 90%, about 90% to about 100%, about 90% to about 99%, about 90% to about 98%, about 90% to about 97%, about 90% to about 95% of the colonies that form when the cells are plated on a feeder cell layer in vitro have a sphere-like morphology of a 7, 6, 5, 4, or 3.

A given rat ES cell, employed in the various methods and compositions provided herein can be a male (XY) rat ES cell, a male (XY) population of rat ES cells, or a male (XY) rat ES cell line. In other embodiments, a population of rat ES cells or a rat ES cell line employed herein can be a female (XX) rat ES cell, a female (XX) population of rat ES cells, or a female (XX) rat ES cell line. Any such rat ES cell, population of rat ES cells or rat ES cell line can comprise the euploidy and/or diploidy as described above.

The various rat ES cells employed in the methods and compositions can be from any rat strain, including but not limited to, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. The various rat ES cells can also be obtained from a strain derived from a mix of two or more strains recited above. In one embodiment, the rat ES cell is derived from a strain selected from a DA strain and an ACI strain. In a specific embodiment, the rat ES cell is derived from an ACI strain. The ACI rat strain is are characterized as having black agouti, with white belly and feet and an RT1av1 haplotype. Such strains are available from a variety of sources including Harlan Laboratories. In other embodiments, the various rat ES cells are from a Dark Agouti (DA) rat strain, which is characterized as having an agouti coat and an RT1av1 haplotype. Such rats are available from a variety of source including Charles River and Harlan Laboratories. In a further embodiment, the various rat ES cells employed herein are from an inbred rat strain.

In specific embodiments the rat ES cell line is from an ACI rat and comprises the ACI.G1 rat ES cell as described in detail in US 2014-0235933, herein incorporated by reference in its entirety. In another embodiment, the rat ES cell line is from a DA rat and comprises the DA.2B rat ES cell line or the DA.2C rat ES cell line as described in detail in US 2014-0235933, herein incorporated by reference in its entirety.

A given rat ES cell provided herein can be obtained from a rat embryo at various stages of rat embryo development. The rat embryos employed to derive the rat ES cells can be a morula-stage embryo, a blastocyst-stage embryo, or a rat embryo at a developmental stage between a morula-stage embryo and a blastocyst-stage embryo. Thus, in specific embodiments, the rat embryo employed is at or between the Witschi stages of 5 and 7. In other embodiments, the rat embryo employed is at the Witschi stage 5, 6, or 7.

In one embodiment, the rat ES cell is obtained from a rat blastocyst. In other embodiments, the rat ES cell is obtained from a blastocyst from a superovulated rat. In other embodiments, the rat ES cells are obtained from an 8-cell stage embryo, which is then cultured in vitro until it develops into a morula-stage, blastocyst stage, an embryo between the Witschi stages 5 and 7, or into an embryo at the Witschi stage 5, 6, or 7. At which time the embryos are then plated. Morula-stage embryos comprise a compact ball of cells with no internal cavity. Blastocyst-stage embryos have a visible internal cavity (the blastocoel) and contain an inner cell mass (ICM). The ICM cells form ES cells.

B. Derivation and Propagation of Rat Embryonic Stem (ES) Cells

Methods of derivation and propagation of rat embryonic stem cells are known in the art and are disclosed, for example, in US 2014-0235933, herein incorporated by reference in its entirety. In specific embodiments, such methods comprise (a) providing an in vitro culture comprising a feeder cell layer and a population of isolated rat embryonic stem (ES) cells; (b) culturing in vitro under conditions which are sufficient to maintain pluripotency and/or totipotency of the isolated rat ES cell. Such methods thereby allow for the propagation of a rat ES cell population and/or a rat ES cell line.

Methods for culturing a rat embryonic stem cell line is provided. Such methods comprise culturing in vitro a feeder cell layer and a rat ES cell line, wherein the culture conditions maintain pluripotency of the rat ES cells and comprise a media having mouse leukemia inhibitory factor (LIF) or an active variant or fragment thereof. The methods can further comprise passaging and culturing in vitro the cells of the rat ES cell line, wherein each subsequent in vitro culturing comprises culturing the rat ES cells on the feeder cell layer under conditions that maintain pluripotency of the rat ES cells and comprises a media having mouse LIF or an active variant or fragment thereof.

The culture media employed in the various methods and compositions can maintain the rat ES cells. The terms "maintaining" and "maintenance" refer to the stable preservation of at least one or more of the characteristics or phenotypes of the rat ES cells outline herein. Such phenotypes can include maintaining pluripotency and/or totipotency, cell morphology, gene expression profiles and the other functional characteristics of the rat stem cells described herein. The term "maintain" can also encompass the propagation of stem cells, or an increase in the number of stem cells being cultured. The term further contemplates culture conditions that permit the stem cells to remain pluripotent, while the stem cells may or may not continue to divide and increase in number.

The term "feeder cell" or "feeder cell layer" comprises a culture of cells that grow in vitro and secrete at least one factor into the culture medium that is used to support the growth of another cell of interest in the culture. The feeder cells employed herein aid in maintaining the pluripotency of the rat ES cells, and in specific embodiments, one or more of the other characteristics or phenotypes described herein. Various feeder cells can be used including, for example, mouse embryonic fibroblasts, including mouse embryonic fibroblasts obtained between the $12^{th}$ and $16^{th}$ day of pregnancy. In specific embodiments, feeder cell layer comprises a monolayer of mitotically inactivated mouse embryonic fibroblasts (MEFs).

The in vitro cultures of the rat ES cells further comprise an effective amount of Leukemia Inhibitory Factor (LIF) or an active variant or fragment thereof. Leukemia inhibitory factor (LIF) belongs to the IL-6 receptor family. LIF binds to a heterodimeric membrane receptor made up of a LIF-specific subunit, gp190 or LIFR, and the subunit gp130, which is shared with the other members of the IL-6 family. LIF inhibits the differentiation of embryonic stem cells in mice and contribute to stem cell self-renewal. Human and mouse LIF share 79% sequence homology and exhibit cross-species activity. Rat LIF (rtLIF) is a 22.1 kDa protein containing 202 amino acid residues that exhibits 91% amino acid sequence identity with murine LIF (Takahama et al. 1998). There are six possible asparagine-linked glycosylation (N-glycosylation) sites which are conserved among the LIF polypeptide from the various species and an additional site of Asn150 which is specific for rat LIF. The tertiary structure of the mouse LIF and its function is described in further detail in Aikawa et al. (1998) *Biosci. Biotechnol. Biochem.* 62 1318-1325 and Senturk et al. (2005) *Immunology of Pregnancy*, editor Gil Mor., U.S. Pat. No. 5,750,654 and D P Gearing (1987) *EMBO Journal* 1987-12-20, each of which is herein incorporated by reference in their entirety. A partial mouse LIF sequence is reported on the SwissProt website under the accession number P09056.

Mouse LIF activity is assessed by its ability to induce differentiation of M1 myeloid leukemia cells. The specific activity is $1 \times 10^6$ units/ml (Cat. No. 03-0011 from Stemgent) and $1 \times 10^7$ units/ml (Cat. No. 03-0011-100 from Stemgent), where 50 units is defined as the amount of mouse LIF required to induce differentiation in 50% of the M1 colonies in 1 ml of medium. See, also, Williams, R. L. et al. (1988) Nature 336: 684-687.; Metcalf, D. et al. (1988) Leukemia 2: 216-221; Niwa, H. et al. (2009) Nature 460: 118-122; Xu, J.

et al. (2010) *Cell Biol Int.* 34: 791-797; Fukunaga, N. et al. (2010) *Cell Reprogram.* 12: 369-376; and, Metcalf D. (2003) *Stem Cells* 21: 5-14, each of which is herein incorporated by reference in their entirety. An "effective amount of LIF" comprises a concentration of LIF that allows the rat ES cells of an in vitro culture to remain in an undifferentiated pluripotent state. Various markers that can be used to assay for the cells remaining in a pluripotent state are discussed elsewhere herein.

The LIF polypeptide employed in the various methods and compositions provided herein can be from any organism, including from a mammal, a rodent, a human, a rat or a mouse. In one embodiment, the LIF polypeptide is from a mouse. In still further embodiments, the mouse LIF polypeptide comprises the amino acid sequence set forth in SwissProt Accession number: P09056, which is herein incorporated by reference in its entirety and is also set forth in SEQ ID NO: 9.

In other embodiments, an active variant or fragment of the mouse LIF polypeptide as set forth in SEQ ID NO: 9 or in SwissProt Accession number: P09056 can be used. Such active variants and fragments (including active variants having at least 75%, 80%, 85%, 90%, 91%, 92%, 93%, 94%, 95%, 96%, 97%, 98%, or 99% sequence identity to SEQ ID NO: 9 are discussed in further detail elsewhere herein.

LIF polypeptide or the active variant or fragment thereof can be provided to the in vitro culture in a variety of ways. In one embodiment, the effective amount of the LIF polypeptide or the active variant or fragment thereof is added to the culture media. In other embodiments, the feeder cells have been genetically modified to overexpress the LIF polypeptide or the active variant or fragment thereof. Such feeder cells include feeder cells prepared from gamma-irradiated or mitomycin-C treated DIA-M mouse fibroblasts that express matrix-associated LIF. Method of generating and using such genetically modified feeder cells can be found, for example, in See, Buehr et al. (2003) *Biol Reprod* 68:222-229, Rathjen et al. (1990) *Cell* 62 1105-1115, and Buehr et al. (2008) *Cell* 135:1287-1298, each of which is herein incorporated by reference. The heterologous LIF expressed in the feeder cells can be from the same organism as the feeder cells or from an organism that is different from that of the feeder cell. In addition, the heterologous LIF expressed in the feeder cells can be from the same or from a different organism than the ES cells the feeder layer is supporting.

In still other embodiments, the feeder cells employed in the various methods disclosed herein are not genetically modified to express a heterologous LIF polypeptide or an active variant or fragment thereof. Thus, in particular embodiments, the monolayer of mitotically inactivated mouse embryonic fibroblast employed in the methods has not been genetically modified to express a heterologous LIF polypeptide.

In other embodiments, the LIF polypeptide or the active variant or fragment thereof is added to the culture media. When LIF is added to the culture media, the LIF can be from any organism, including from a mammal, a rodent, a human, a rat or a mouse. In one embodiment, the LIF present in the culture media is from a mouse. In still further embodiments, the mouse LIF polypeptide comprises the amino acid sequence set forth in SEQ ID NO:9. In other embodiments, an active variant or fragment of the mouse LIF polypeptide as set forth in SEQ ID NO:9 can be used. Such active variants and fragments (including active variants having at least 75%, 80%, 85% 90%, 91%, 92%, 93%, 94%, 95%, 96%, 97%, 98%, or 99% sequence identity to SEQ ID NO: 9) are discussed in further detail elsewhere herein.

In specific embodiments, the rat ES cells and rat ES cell lines provided herein maintain pluripotency in vitro without requiring paracrine LIF signaling.

In specific embodiments, LIF or an active variant or fragment thereof is present in the culture media at any concentration that maintains the rat ES cells. LIF polypeptide or active variant or fragment thereof is present in the culture media at about 25 U/ml to about 50 U/ml, at about 50 U/ml to about 100 U/ml, at about 100 U/ml to about 125 U/ml, at about 125 U/ml to about 150 U/ml, at about 150 U/ml to about 175 U/ml, at about 175 U/ml to about 200 U/ml, at about 200 U/ml to about 225 U/ml, at about 225 U/ml to about 250 U/ml, at about 250 U/ml to about 300 U/ml, to about 300 U/ml to about 325 U/ml, at about 325 U/ml to about 350 U/ml, at about 350 U/ml to about 400 U/ml, at about 400 U/ml to about 425 U/ml, at about 425 U/ml to about 450 U/ml, at about 450 U/ml to about 475 U/ml, at about 475 U/ml to about 500 U/ml, at about 75 U/ml to about 500 U/ml or greater. In other embodiments, LIF polypeptide or active variant or fragment thereof is present in the culture media at about 25 U/ml to about 50 U/ml, at about 25 U/ml to about 100 U/ml, at about 75 U/ml to about 125 U/ml, at about 50 U/ml to about 150 U/ml, at about 90 U/ml to about 125 U/ml, at about 90 U/ml to about 110 U/ml, at about 80 U/ml to about 150 U/ml, or at about 80 U/ml to about 125 U/ml. In a specific embodiment, LIF polypeptide or active variant or fragment thereof is present in the culture media at about 100 U/ml.

When mouse LIF is employed, the mouse LIF polypeptide or active variant or fragment thereof is present in the culture media at any concentration that maintains the rat ES cells. Mouse LIF polypeptide or active variant or fragment thereof is present at about 25 U/ml to about 50 U/ml, at about 50 U/ml to about 100 U/ml, at about 100 U/ml to about 125 U/ml, at about 125 U/ml to about 150 U/ml, at about 150 U/ml to about 175 U/ml, at about 175 U/ml to about 200 U/ml, at about 200 U/ml to about 225 U/ml, at about 225 U/ml to about 250 U/ml, at about 250 U/ml to about 300 U/ml, to about 300 U/ml to about 325 U/ml, at about 325 U/ml to about 350 U/ml, at about 350 U/ml to about 400 U/ml, at about 400 U/ml to about 425 U/ml, at about 425 U/ml to about 450 U/ml, at about 450 U/ml to about 475 U/ml, at about 475 U/ml to about 500 U/ml, at about 75 U/ml to about 500 U/ml or greater. In other embodiments, mouse LIF polypeptide or active variant or fragment thereof is present at about 25 U/ml to about 50 U/ml, at about 25 U/ml to about 100 U/ml, at about 75 U/ml to about 125 U/ml, at about 50 U/ml to about 150 U/ml, at about 90 U/ml to about 125 U/ml, at about 90 U/ml to about 110 U/ml, at about 80 U/ml to about 150 U/ml, or at about 80 U/ml to about 125 U/ml. In a specific embodiment, mouse LIF polypeptide or active variant or fragment thereof is present in the culture media at about 100 U/ml.

The culture media employed maintains rat ES cells. As such, in specific embodiments, the culture media employed in the various method and compositions will maintain the pluripotency of all or most of (i.e., over 50%) of the rat ES cells in a cell line for a period of a at least 5, 10 or 15 passages. In one embodiment, the culture media comprises one or more compounds that assist in maintaining pluripotency. In one embodiment, the culture media comprises a MEK pathway inhibitor and a glycogen synthase kinase-3 (GSK-3) inhibitor. The media can further comprise additional components that aid in maintaining the ES cells, including for example, FGF receptor inhibitors, ROCK inhibitors, and/or ALK (TGFb receptor) inhibitors. A non-limiting example of an FGF receptor inhibitors includes PD184352. A non-limiting example of a ROCK inhibitor includes Y-27632, and non-limiting example of an ALK (TGFb receptor) inhibitor includes A-83-01. In specific embodiments, 2i media is used with 10 uM ROCKi when thawing cryopreserved rESC or when re-plating rESC after dissociation with trypsin.

In other embodiments, the media comprises a combination of inhibitors consisting of a MEK pathway inhibitor and a glycogen synthase kinase-3 (GSK-3) inhibitor.

In one non-limiting embodiment, the culture media comprises a GSK-3 inhibitor comprising CHIR99021 and/or comprises a MEK inhibitor comprising PD0325901. In other embodiments, the media comprises a combination of inhibitors consisting of CHIR99021 and PD0325901. Either of these compounds can be obtained, for example, from Stemgent. In specific embodiments, CHIR99021 is present in the culture media at a concentration of about 0.5μ to about 3 μM, about 0.5μ to about 3.5 μM, about 0.5 μM to about 4 μM, about 0.5 μM to about 1 μM, about 1 μM to about 1.5 μM, about 1.5 μM to about 2 μM, about 2 μM to about 2.5 μM, about 2.5 to about 3 μM, 3 μM to about 3.5 μM. In further embodiments, CHIR99021 is present in the culture media at a concentration of about 3 μM. In other embodiments, PD0325901 is present in the culture media at a concentration of about 0.4 μM to about 1 uM, about 0.4 μM to about 1.5 uM, about 0.4 μM to about 2 μM, about 0.4 μM to about 0.8 μM, 0.8 μM to about 1.2 μM, about 1.2 to about 1.5 μM. In further embodiments, PD0325901 is present in the culture media at a concentration of about 1 μM. In specific embodiments, CHIR99021 is present in the culture media at a concentration of about 3 μM and PD0325901 is present at a concentration of about 1 μM.

In one non-limiting embodiment, the culture media employed in the various methods and compositions disclosed herein is a 2i media which comprises: DMEM/F12 basal media (at a concentration of 1× (50%)); Neurobasal media (at a concentration of 1× (50%)); Penicillin/streptomycin (at a concentration of 1%); L-Glutamine (at a concentration of 4 mM); 2-Mercaptoethanol (at a concentration of 0.1 mM); N2 supplement (at a concentration of 1×); B27 supplement (at a concentration 1×); LIF (at a concentration of 100 U/ml); PD0325901 (MEK inhibitor) (at a concentration of 1 μM) and CHIR99021 (GSK inhibitor) (at a concentration of 3 μM).

Additional media that can be employed include those disclosed in Li et al. (2008) *Cell* 135:1299-1310, Yamamoto et al. (2012) *Transgenic Rats* 21:743-755, Ueda et al. (2008) *PLoS ONE* 3(6):e2800, Meek et al. (2010) *PLoS ONE* 4 (12): e14225; Tong et al. (2010) *Nature* 467:211-213; US Patent Publication 2012/0142092, Buehr et al. (2008) Cell 135:1287-1298, Li et al. (135) *Cell* 1299-1310, each of which is herein incorporated by reference in their entirety. When employing such media, the concentration and the source of LIF can be modified as outlined herein. In specific embodiments, the various culture medias are used in combination with mouse LIF or an active variant or fragment thereof, and in even further embodiments, the various culture medias comprise a mouse LIF or an active variant or fragment thereof at a concentration of about 50 U/ml to about 100 U/ml, about 50 U/ml to 150 U/ml, or about 100 U/ml.

The temperature of the cultures of rat ES cells, both for the production of the ES cell line and for the culturing and maintaining of the ES line it typically carried out at about 35° C. to about 37.5° C. In specific embodiment, the temperature is 37.0° C. The culture is typically carried out at 7.5% $CO_2$.

7. Sequence Identity

The methods and compositions provided herein employ a variety of different components of the targeted genomic integration system (i.e. nuclease agents, recognition sites, insert nucleic acids, polynucleotides of interest, targeting vectors, selection markers and other components). It is recognized throughout the description that some components of the targeted genomic integration system can have active variants and fragments. Such components include, for example, nuclease agents (i.e. engineered nuclease agents), nuclease agent recognition sites, polynucleotides of interest, target sites and corresponding homology arms of the targeting vector. Biological activity for each of these components is described elsewhere herein.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" means any sequence comparison program that, for any two sequences in question, generates an alignment having identical nucleotide or amino acid residue matches and an identical percent sequence identity when compared to the corresponding alignment generated by GAP Version 10.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the described invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates, which may need to be independently confirmed.

The described invention may be embodied in other specific forms without departing from the spirit or essential attributes thereof and, accordingly, reference should be made to the appended claims, rather than to the foregoing specification, as indicating the scope of the invention.

Non-limiting embodiments include:

1. A method for targeted modification of a genomic locus of interest in a pluripotent rat cell, comprising (a) introducing into the pluripotent rat cell a large targeting vector (LTVEC) comprising an insert nucleic acid flanked with a 5' rat homology arm and a 3' rat homology arm, wherein the sum total of the 5' and the 3' homology arms is at least 10 kb but less than 150 kb; and (b) identifying a genetically modified pluripotent rat cell comprising the targeted genetic modification at the genomic locus of interest, wherein the targeted genetic modification is capable of being transmitted through the germline.

2. The method of embodiment 1, wherein the targeted genetic modification is biallelic.

3. The method of embodiment 1 or 2, wherein the pluripotent rat cell is a rat embryonic stem (ES) cell.

4. The method of embodiment 1, 2 or 3, wherein the pluripotent rat cell is derived from a DA strain or an ACI strain.

5. The method of any one of embodiments 1-4, wherein the pluripotent rat cell is characterized by expression of at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof.

6. The method of any one of embodiments 1-4 wherein the pluripotent rat cell is characterized by one of more of the following characteristics:
  (a) lack of expression of one or more pluripotency markers comprising c-Myc, Ecat1, and/or Rexo1; (b) lack of expression of mesodermal markers comprising Brachyury and/or Bmpr2; (c) lack of expression of one or more endodermal markers comprising Gata6, Sox17 and/or Sox7; or (d) lack of expression of one or more neural markers comprising Nestin and/or Pax6.

7. The method of any one of embodiments 1-6, wherein the sum total of the 5' and the 3' homology arms of the LTVEC is from about 10 kb to about 30 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

8. The method of any one of embodiments 1-6, wherein the sum total of the 5' and the 3' homology arms of the LTVEC is from about 16 Kb to about 150 Kb.

9. The method of any one of embodiments 1-8, wherein the targeted genetic modification comprises: (a) a replacement of an endogenous rat nucleic acid sequence with a homologous or an orthologous nucleic acid sequence; (b) a deletion of an endogenous rat nucleic acid sequence; (c) a deletion of an endogenous rat nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (e) an exogenous nucleic acid sequence comprising a homologous or an orthologous nucleic acid sequence; (f) a chimeric nucleic acid sequence comprising a human and a rat nucleic acid sequence; (g) a conditional allele flanked with site-specific recombinase target sequences; or, (h) a reporter gene operably linked to a promoter active in a rat cell.

10. The method of any one of embodiments 1-9, wherein the genomic locus of interest comprises (i) a first nucleic acid sequence that is complementary to the 5' rat homology arm; and (ii) a second nucleic acid sequence that is complementary to the 3' rat homology arm.

11. The method of embodiment 10, wherein the first and the second nucleic acid sequence is separated by at least 5 kb but less than 3 Mb.

12. The method of embodiment 10, wherein the first and the second nucleic acid sequence is separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb.

13. The method of any one of embodiment 1-12, wherein introducing step (a) further comprises introducing a second nucleic acid encoding a nuclease agent that promotes a homologous recombination between the targeting construct and the genomic locus of interest in the pluripotent rat cell.

14. The method of embodiment 13, wherein the nuclease agent comprises (a) a chimeric protein comprising a zinc finger-based DNA binding domain fused to a FokI endonuclease; or, (b) a chimeric protein comprising a Transcription Activator-Like Effector Nuclease (TALEN) fused to a FokI endonuclease.

15. The method of any one of embodiments 1-12, wherein introducing step (a) further comprises introducing into the pluripotent rat cell: (i) a first expression construct comprising a first promoter operably linked to a first nucleic acid sequence encoding a Clustered Regularly Interspaced Short Palindromic Repeats (CRISPR)-associated (Cas) protein, (ii) a second expression construct comprising a second promoter operably linked to a genomic target sequence linked to a guide RNA (gRNA), wherein the genomic target sequence is immediately flanked on the 3' end by a Protospacer Adjacent Motif (PAM) sequence.

16. The method of embodiment 15, wherein the genomic locus of interest comprises the nucleotide sequence of SEQ ID NO: 1.

17. The method of embodiment 15 or 16, wherein the gRNA comprises a third nucleic acid sequence encoding a Clustered Regularly Interspaced Short Palindromic Repeats (CRISPR) RNA (crRNA) and a trans-activating CRISPR RNA (tracrRNA).

18. The method of embodiment 15, 16 or 17, wherein the Cas protein is Cas9.

19. The method of embodiment 15, 16, 17, or 18, wherein the gRNA comprises: (a) the chimeric RNA of the nucleic acid sequence of SEQ ID NO: 2; or, (b) the chimeric RNA of the nucleic acid sequence of SEQ ID NO: 3.

20. The method of embodiment 17, wherein the crRNA comprises SEQ ID NO: 4; SEQ ID NO: 5; or SEQ ID NO: 6.

21. The method of embodiment 17, wherein the tracrRNA comprises SEQ ID NO: 7 or SEQ ID NO: 8.

22. A modified rat genomic locus comprising: (i) an insertion of a homologous or orthologous human nucleic acid sequence; (ii) a replacement of an endogenous rat nucleic acid sequence with the homologous or orthologous human nucleic acid sequence; or (iii) a combination thereof, wherein the modified rat genomic locus is capable of being transmitted through the germline.

23. The modified rat genomic locus of embodiment 22, wherein the size of the insertion or replacement is from about 5 kb to about 400 kb.

24. The rat genomic locus of embodiment 22, wherein the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

25. A method for making a humanized rat, comprising: (a) targeting a genomic locus of interest in a pluripotent rat cell with a targeting construct comprising a human nucleic acid to form a genetically modified pluripotent rat cell; (b) introducing the genetically modified pluripotent rat cell into a host rat embryo; and (c) gestating the host rat embryo in a surrogate mother; wherein the surrogate mother produces rat progeny comprising a modified genomic locus that comprises: (i) an insertion of a human nucleic acid sequence; (ii) a replacement of the rat nucleic acid sequence at the genomic locus of interest with a homologous or orthologous human nucleic acid sequence; (iii) a chimeric nucleic acid sequence comprising a human and a rat nucleic acid sequence; or (iv) a combination thereof, wherein the modified genomic locus is capable of being transmitted through the germline.

26. The method of embodiment 25, wherein the targeting construct is a large targeting vector (LTVEC), and the sum total of the 5' and the 3' homology arms of the LTVEC is at least 10 kb but less than 150 kb.

27. The method of embodiment 26, wherein the sum total of the 5' and the 3' homology arms of the targeting construct is from about 10 kb to about 30 kb, from about 20 kb to 40 kb, from about 40 kb to about 60 kb, from about 60 kb to about 80 kb, or from about 80 kb to about 100 kb, from about 100 kb to about 120 kb, or from about 120 kb to 150 kb.

28. The method of embodiment 25, 26 or 27, wherein the human nucleic acid sequence is at least 5 kb but less than 400 kb.

29. The method of embodiment 25, 26, or 27, wherein the human nucleic acid sequence is at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, at least 150 kb but less than 200 kb, at least 200 kb but less than 250 kb, at least 250 kb but less than 300 kb, at least 300 kb but less than 350 kb, or at least 350 kb but less than 400 kb.

30. The method of any one of embodiments 25-29, wherein the pluripotent rat cell is a rat embryonic stem (ES) cell.

31. The method of any one of embodiments 25-30, wherein the pluripotent rat cell is derived from a DA strain or an ACI strain.

32. The method of any one of embodiments 25-31, wherein the pluripotent rat cell is characterized by expression of at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof.

33. The method of any one of embodiment 25-31, wherein the pluripotent rat cell is characterized by one or more of the following features: (a) lack of expression of one or more pluripotency markers comprising c-Myc, Ecat1, and/or Rexo1; (b) lack of expression of one or more mesodermal markers comprising Brachyury and/or Bmpr2; (c) lack of expression of one or more endodermal markers comprising Gata6, Sox17, and/or Sox7; or (d) lack of expression of one or more neural markers comprising Nestin and/or Pax6.

34. A modified rat comprising a humanized genomic locus, wherein the humanized genomic locus comprises: (i) an insertion of a homologous or orthologous human nucleic acid sequence; (ii) a replacement of a rat nucleic acid sequence at an endogenous genomic locus with a homologous or orthologous human nucleic acid sequence; (iii) a chimeric nucleic acid sequence comprising a human and a rat nucleic acid sequence or, (iv) a combination thereof, wherein the humanized genomic locus is capable of being transmitted through the germline.

35. A rat or rat cell comprising a targeted genetic modification in its genomic locus, wherein the genomic locus is an Interleukin-2 receptor gamma locus, an ApoE locus, a Rag1 locus, a Rag2 locus, or a Rag2/Rag1 locus, wherein the targeted genetic modification comprises: (a) a deletion of an endogenous rat nucleic acid sequence at the genomic locus; (b) an insertion of a homologous nucleic acid, an orthologous nucleic acid, or a chimeric nucleic acid comprising a human and a rat nucleic acid sequence, or (c) a combination thereof, wherein the targeted genetic modification is transmissible through the germline of the rat or a rat propagated from the rat cell.

36. The rat or rat cell of embodiment 35, wherein (a) the deletion of the endogenous rat nucleic acid at the genomic locus is at least about 10 kb; or, (b) the deletion of the endogenous rat nucleic acid at the genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (c) the insertion of the exogenous nucleic acid sequence at the genomic locus is at least about 5 kb; or, (d) the insertion of the exogenous nucleic acid sequence at the genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

37. The rat or rat cell of embodiment 35 or 36, wherein (a) the targeted genetic modification at the Interleukin-2 receptor gamma locus results in a decrease in or absence of Interleukin-2 receptor gamma protein activity; (b) the targeted genetic modification at the ApoE locus results in a decrease in or absence of ApoE protein activity; (c) the targeted genetic modification at the Rag1 locus results in a decrease in or absence of Rag1 protein activity; (d) the targeted genetic modification at the Rag2 locus results in a decrease in or absence of Rag2 protein activity; or, (e) the targeted genetic modification at the Rag2/Rag1 locus results in a decrease in or absence of Rag2 protein activity and Rag1 activity.

38. The rat or rat cell of embodiment 35, 36, or 37, wherein the targeted genetic modification of the Interleukin-2 receptor gamma locus comprises: (a) a deletion of the entire rat Interleukin-2 receptor gamma coding region or a portion thereof; (b) a replacement of the entire rat Interleukin-2 receptor gamma coding region or a portion thereof with a human Interleukin-2 receptor gamma coding region or a portion thereof; (c) a replacement of an ecto-domain of the rat Interleukin-2 receptor gamma coding region with the ecto-domain of a human Interleukin-2 receptor gamma; or, (d) at least a 3 kb deletion of the Interleukin-2 receptor gamma locus.

39. The rat or rat cell of any one of embodiments 35-37, wherein the targeted genetic modification of the ApoE locus comprises: (a) a deletion of the entire ApoE coding region or a portion thereof; or, (b) at least a 1.8 kb deletion of the ApoE locus comprising the ApoE coding region.

40. The rat or rat cell of any one of embodiments 35-37, wherein the targeted genetic modification of the Rag2 locus comprises: (a) a deletion of the entire Rag2 coding region or a portion thereof; (b) at least a 5.7 kb deletion of the Rag2 locus comprising the Rag2 coding region.

41. The rat or rat cell of any one of embodiments 35-37, wherein the targeted genetic modification of the Rag2/Rag1 locus comprises: (a) a deletion of the entire Rag2 coding region or a portion thereof and a deletion of the entire Rag1 coding region or portion thereof; or, (b) a deletion of at least 16 kb of the Rag2/Rag1 locus comprising the Rag2 coding region.

42. The rat or rat cell of any one of embodiment 35-41, wherein the targeted genetic modification comprises an insertion of an expression cassette comprising a selective marker at the Interleukin-2 receptor gamma locus, the ApoE locus, the Rag1 locus, the Rag2 locus, or the Rag2/Rag1 locus.

43. The rat or rat cell of any one of embodiments 42, wherein the expression cassette comprises a lacZ gene operably linked to the endogenous promoter at the genomic locus and a human ubiquitin promoter operably linked to a selective marker.

44. The rat or rat cell of any one of embodiments 35-43, wherein the targeted genetic modification in the Interleukin-2 receptor gamma locus, the ApoE locus, the Rag1 locus, the Rag2 locus or the Rag2/Rag1 locus comprises the insertion of a self-deleting selection cassette.

45. The rat or rat cell of embodiment 44, wherein the self-deleting selection cassette comprises a selective marker gene operably linked to a promoter active in the rat cell and a recombinase gene operably linked to a male germ cell-specific promoter, wherein the self-deleting cassette is flanked by recombination recognition sites recognized by the recombinase.

46. The rat or rat cell of embodiment 45, wherein (a) the male germ cell-specific promoter is a Protamine-1 promoter; or, (b) the recombinase gene encodes Cre, and the recombination recognition sites are loxP sites.

47. The rat or rat cell of any one of embodiments 35-46, wherein the insertion of the exogenous nucleic acid sequence at the genomic locus comprises a reporter nucleic acid operably linked to an endogenous Interleukin-2 receptor gamma promoter, an endogenous ApoE promoter, an endogenous Rag1 promoter, or an endogenous Rag2 promoter.

48. The rat or rat cell of embodiment 47, wherein the reporter nucleic acid encodes a reporter comprising β-galactosidase, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, or a combination thereof.

49. The rat cell of any one of embodiments 35-48, wherein the rat cell is a pluripotent rat cell or a rat embryonic stem (ES) cell.

50. The rat cell of embodiment 49, wherein the pluripotent rat cell or the rat embryonic stem (ES) cell (a) is derived from a DA strain or an ACI strain; (b) is characterized by expression of at least one pluripotency marker comprising Dnmt3L, Eras, Err-beta, Fbxo15, Fgf4, Gdf3, Klf4, Lef1, LIF receptor, Lin28, Nanog, Oct4, Sox15, Sox2, Utf1, or a combination thereof; or (c) is characterized by one or more of the following characteristics: (i) lack of expression of one or more pluripotency markers comprising c-Myc, Ecat1, and/or Rexo1; (ii) lack of expression of mesodermal markers comprising Brachyury and/or Bmpr2; (iii) lack of expression of one or more endodermal markers comprising Gata6, Sox17 and/or Sox7; or (iv) lack of expression of one or more neural markers comprising Nestin and/or Pax6.

51. A method for modifying a target genomic locus in an Interleukin-2 receptor gamma locus, an ApoE locus, a Rag1 locus, a Rag2 locus or a Rag2/Rag1 locus in a pluripotent rat cell, the method comprising: (a) introducing into the pluripotent rat cell a targeting vector comprising an insert nucleic acid flanked with 5' and 3' rat homology arms homologous to the target genomic locus, (b) identifying a genetically modified pluripotent rat cell comprising a targeted genetic modification at the target genomic locus, wherein the targeted genetic modification is capable of being transmitted through the germline of a rat propagated from the pluripotent rat cell.

52. The method of embodiment 51, wherein the targeting vector is a large targeting vector (LTVEC) wherein the sum total of the 5' and the 3' rat homology arms is at least about 10 kb but less than about 150 kb.

53. The method of embodiment 51 or 52, wherein introducing the targeting vector into the pluripotent rat cell leads to: (i) a deletion of an endogenous rat nucleic acid sequence at the target genomic locus; (ii) an insertion of an exogenous nucleic acid sequence at the target genomic locus; or (iii) a combination thereof.

54. The method of embodiment 53, wherein (a) the deletion of the endogenous rat nucleic acid at the genomic locus is at least about 10 kb; or, (b) the deletion of the endogenous rat nucleic acid at the genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (c) the insertion of the exogenous nucleic acid sequence at the genomic locus is at least about 5 kb; or. (d) the insertion of the exogenous nucleic acid sequence at the genomic locus is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

55. The method of any one of embodiment 51-54, wherein (a) the targeted genetic modification at the Interleukin-2 receptor gamma locus results in a decrease in or absence of Interleukin-2 receptor gamma protein activity; (b) the targeted genetic modification at the ApoE locus results in a decrease in or absence of ApoE protein activity; (c) the targeted genetic modification at the Rag1 locus results in a decrease in or absence of Rag1 protein activity; (d) the targeted genetic modification at the Rag2 locus results in a decrease in or absence of Rag2 protein activity; or, (e) the targeted genetic modification at the Rag2/Rag1 locus results in a decrease in or absence of Rag2 protein activity and i Rag1 protein activity.

56. The method of any one of embodiment 51-54, wherein the targeted genetic modification of the Interleukin-2 receptor gamma locus comprises (a) a deletion of the entire rat Interleukin-2 receptor gamma coding region or a portion thereof; (b) a replacement of the entire rat Interleukin-2 receptor gamma coding region or a portion thereof with a human Interleukin-2 receptor gamma coding region or a portion thereof; (c) a replacement of an ecto-domain of the rat Interleukin-2 receptor gamma coding region with the ecto-domain of a human Interleukin-2 receptor gamma; or, (d) at least a 3 kb deletion of the Interleukin-2 receptor gamma locus comprising the Interleukin-2 receptor gamma coding region.

57. The method of any one of embodiment 51-55, wherein the targeted genetic modification of the ApoE locus comprises: (a) a deletion of the entire ApoE coding region or a portion thereof; or, (b) at least a 1.8 kb deletion of the ApoE locus comprising the ApoE coding region.

58. The method of any one of embodiment 51-55, wherein the targeted genetic modification of the Rag2 locus comprises: (a) a deletion of the entire Rag2 coding region or a portion thereof; or, (b) at least a 5.7 kb deletion of the Rag2 locus comprising the Rag2 coding region.

59. The method of any one of embodiment 51-55, wherein the targeted genetic modification of the Rag1/Rag2 locus comprises: (a) a deletion of the entire Rag2 coding region or a portion thereof and a deletion of the entire Rag1 coding region or portion thereof; or, (b) a deletion of at least 16 kb of the Rag2/Rag1 locus comprising the Rag2 and Rag1 coding regions.

60. The method of any one of embodiment 51-59, wherein the insert nucleic acid comprises an expression cassette comprising a polynucleotide encoding a selective marker.

61. The method embodiment 60, wherein the expression cassette comprises a lacZ gene operably linked to an endogenous promoter at the genomic locus and a human ubiquitin promoter operably linked to a selective marker gene.

62. The method of any one of embodiments 51-60, wherein the insert nucleic acid comprises a self-deleting selection cassette.

63. The method of embodiment 62, wherein the self-deleting selection cassette comprises a selective marker operably linked to a promoter active in the rat pluripotent cell and a polynucleotide encoding a recombinase operably linked to a male germ cell-specific promoter, wherein the self-deleting cassette is flanked by recombination recognition sites recognized by the recombinase.

64. The method of embodiment 63, wherein (a) the male germ cell-specific promoter is a Protamine-1 promoter; or, (b) the recombinase gene encodes Cre and the recombination recognition sites are loxP sites.

65. The method of embodiment 53, wherein the insertion of the exogenous nucleic acid sequence at the genomic locus comprises a reporter nucleic acid sequence operably linked to an endogenous Interleukin-2 receptor gamma promoter, an endogenous ApoE promoter, an endogenous Rag1 promoter, or an endogenous Rag2 promoter.

66. The method of embodiment 65, wherein the reporter nucleic acid sequence encodes a reporter comprising β-galactosidase, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, or a combination thereof.

67. The method of any one of embodiment 51-66, wherein the pluripotent rat cell is a rat embryonic stem (ES) cell.

68. The method of any one of embodiment 51-67, wherein the pluripotent rat cell (a) is derived from a DA strain or an ACI strain; or, (b) is characterized by expression of a pluripotency marker comprising Oct-4, Sox-2, alkaline phosphatase, or a combination thereof; or, (c) is characterized by one or more of the following characteristics: (i) lack of expression of one or more pluripotency markers comprising c-Myc, Ecat1, and/or Rexo1; (ii) lack of expression of mesodermal markers comprising Brachyury and/or Bmpr2; (iii) lack of expression of one or more endodermal markers comprising Gata6, Sox17 and/or Sox7; or (iv) lack of expression of one or more neural markers comprising Nestin and/or Pax6.

69. The method of any one of embodiment 51-68, further comprising identifying the targeted genetic modification at the target genomic locus, wherein the identification step employs a quantitative assay for assessing a modification of allele (MOA) at the target genomic locus.

70. The method of any one of embodiment 51-69, wherein introducing step (a) further comprises introducing a second nucleic acid encoding a nuclease agent that promotes a homologous recombination between the targeting vector and the target genomic locus in the pluripotent rat cell.

71. The method of embodiment 70, wherein the nuclease agent comprises a chimeric protein comprising a zinc finger-based DNA binding domain fused to a FokI endonuclease.

72. The method of embodiment 71, wherein the method results in bi-allelic modification of the target genomic locus.

73. The method of any one of embodiment 51-70, wherein introducing step (a) further comprises introducing into the pluripotent rat cell: (i) a first expression construct comprising a first promoter operably linked to a first nucleic acid sequence encoding a Clustered Regularly Interspaced Short Palindromic Repeats (CRISPR)-associated (Cas) protein, (ii) a second expression construct comprising a second promoter operably linked to a genomic target sequence linked to a guide RNA (gRNA), wherein the genomic target sequence is immediately flanked on the 3' end by a Protospacer Adjacent Motif (PAM) sequence.

74. The method of embodiment 73, wherein the genomic locus of interest comprises the nucleotide sequence of SEQ ID NO: 1.

75. The method of embodiment 73 or 74, wherein the gRNA comprises a third nucleic acid sequence encoding a Clustered Regularly Interspaced Short Palindromic Repeats (CRISPR) RNA (crRNA) and a trans-activating CRISPR RNA (tracrRNA).

76. The method of embodiment 73, wherein the Cas protein is Cas9.

77. The method of embodiment 73, 74, or 75, wherein the gRNA comprises: (a) the chimeric RNA of the nucleic acid sequence of SEQ ID NO: 2; or, (b) the chimeric RNA of the nucleic acid sequence of SEQ ID NO: 3.

78. The method of embodiment 75, wherein the crRNA comprises SEQ ID NO: 4; SEQ ID NO: 5; or SEQ ID NO: 6.

79. The method of embodiment 75, wherein the tracrRNA comprises SEQ ID NO: 7 or SEQ ID NO: 8.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Figure 7:
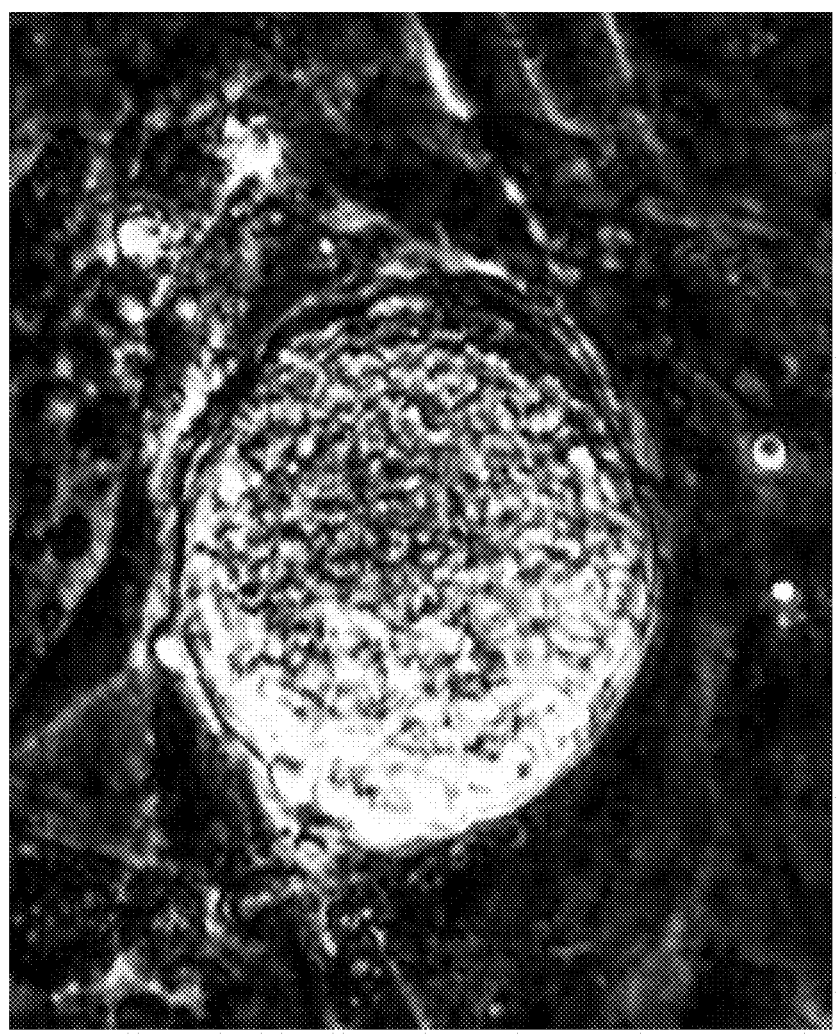
FIG. 7 depicts a closer view of a rat ESC of FIG. 1.

Example 1. Rat ES Cell Derivation and Characterization 1.1. Rat ES Cell Characterization As shown in FIG. 1, rat ESCs grow as compact spherical colonies, which routinely detach and float in the dish (close-up, FIG. 7). Rat ESCs express pluripotency markers including Oct-4 (FIG. 2A) and Sox2 (FIG. 2B), and express high levels of alkaline phosphatase (FIG. 3, left panel). Karyotype for line DA.2B is 42X,Y (FIG. 3, right panel). Rat ESCs often become tetraploid; thus, lines were pre-screened by counting metaphase chromosome spreads; lines with mostly normal counts were then formally karyotyped.

ACI blastocysts were collected from super-ovulated females obtained commercially. DA blastocysts were cultured from frozen 8-cell embryos obtained commercially. Zona pellucidae were removed with Acid Tyrodes; and blastocysts were plated onto mitotically inactivated MEFs. Outgrowths were picked and expanded using standard methods. All blastocysts were plated, cultured and expanded using 2i media (Li et al. (2008) Germline competent embryonic stem cells derived from rat blastocysts, Cell 135:1299-1310; incorporated herein by reference in its entirety).

TABLE 1

Rat ES Cell Derivation

|  | ACI | DA |
| --- | --- | --- |
| Embryo source | Blastocysts (Superovulation) | Frozen 8-cell embryos cultured to blastocyst |
| Blastocysts plated: | 107 | 22 |
| Outgrowths: | 32 (30% of blasts) | 10 (45% of blasts) |
| Lines: | 16 (50% of outgrowths) | 9 (90% of outgrowths) |
| Karyotyped: | 3; all 42X, Y | 6: 3 42X, X<br>3 42X, Y |
| GLT validated: | 1 (ACI.G1) | 1 42X, X (DA.2C)<br>1 42X, Y (DA.2B) |

1.2. Rat Production

Figure 8:
FIG. 8 depicts production of chimeras by blastocyst injection and transmission of the rat ESC genome through the germline; chimeras produced by blastocyst injection using parental ACI.G1 rat ESCs; high percentage chimeras usually have albino snouts.
Figure 9:
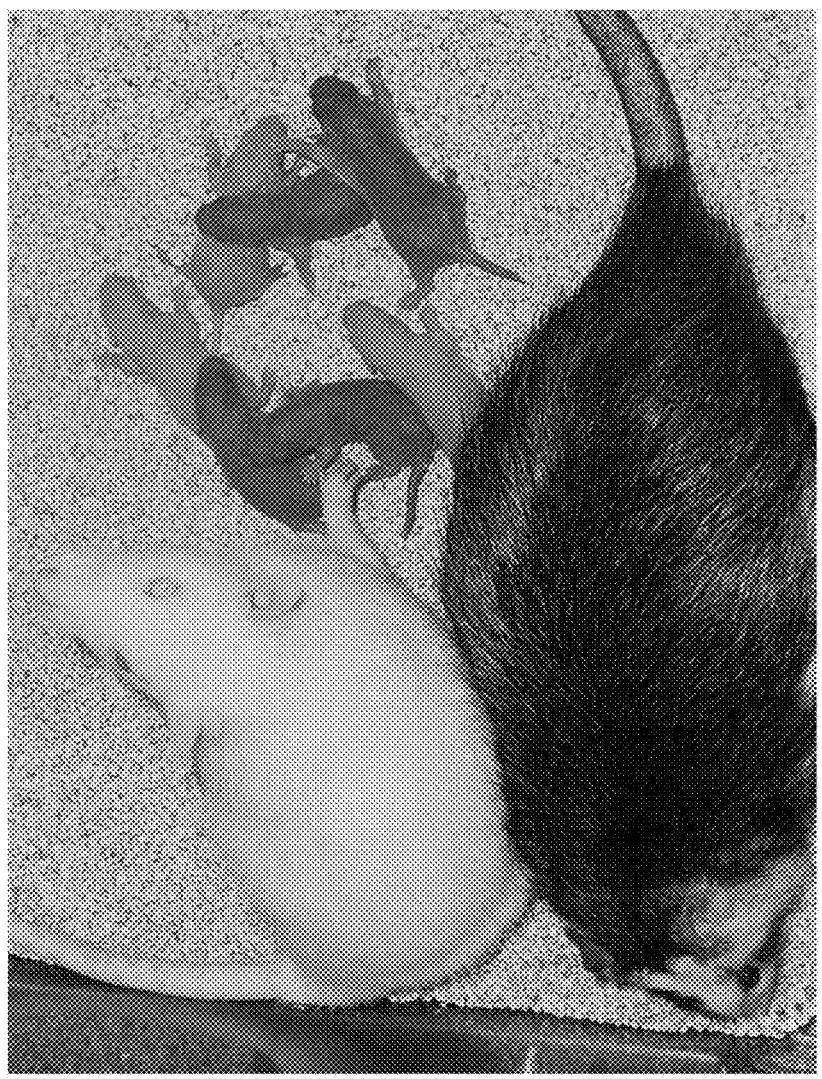
FIG. 9 depicts F1 agouti pups with albino littermates, sired by ACI/SD chimera labeled with an asterisk (*) in FIG. 8.

Chimeric rats were produced by blastocyst injection and transmission of the rat ESC genome. Chimeras produced by blastocyst microinjection using parental ACI.G1 rat ESCs are shown in FIG. 8. F1 agouti pups with albino littermates, sired by the ACI/SD chimera labeled with an asterisk (*) in FIG. 8 are shown in FIG. 9.

Germline Transmission of Parental Rat ESC.

Three euploid rat ESC lines were evaluated for pluripotency by microinjection into albino SD blastocysts. Chimeras were identified by agouti coat color, which indicates rat ESC contribution. For each line, a majority of chimeras transmitted the rESC genome to F1 offspring (Table 2).

TABLE 2

Germline Transmission of Parental rESC

| Line | Chimeras bred | Germline transmitters | Total pups from GLT chimeras | rESC-derived pups | GLT efficiency (%) |
| --- | --- | --- | --- | --- | --- |
| ACI.G1 | 5 | 3 (60%) | 103 | 11 | 11 |
| DA.2B | 5 | 4 (80%) | 129 | 11 | 9 |
| DA.2C (XX) | 3 | 2 (66%) | 45 | 7 | 16 |

1.3. Derivation of Rat Embryonic Stem Cells.

Superovulation protocol, rats

Day 0: injected with pregnant mare serum: IP, 20 U (0.4 ml).

Day 1: no action

Day 2: (46 hr. later): injected with hCG, IP, 50 U (1 ml). set up single female matings.

Day 3: checked plugs. Females were plugged. This is day 0.5.

Day 6 (e3.5): Euthanized females and flushed embryos.
ES Cell Derivation Protocol (Superovulation)
Day 0:
1) Euthanized female rat with $CO_2$.
2) Swabbed ventral abdomen with 70% ethanol; using scissors, opened the ventral body wall to expose the viscera.
3) Dissected out the oviducts and uterine horns and placed them into a tissue culture dish containing warm N2B27 media. Washed out as much blood as possible and transferred to a new dish with N2B27.
4) Using a 1 ml syringe and a blunt 27 g needle, flushed media through the uterine horns and oviducts to eject blastocysts into the media.
5) Collected the blastocysts with a mouth pipet and transfer to embryo culture dish containing KSOM+2i (1 µMPDW0325901, 3 µM CHIR99021). KSOM is a culture medium produced by Millipore. Catalog number is MR-106-D.
6) Cultured overnight at 37°; 7.5% $CO_2$.
ES Cell Derivation Protocol (Frozen Embryos)
Day 0:
1) Thawed frozen 8-cell embryos (commercially obtained) into M2 medium. Cultured 10 minutes at room temperature.
2) Transferred to KSOM+2i and culture overnight.
ES Cell Derivation Protocol (Same for Both)
Day 1:
1) Transferred cavitated embryos to 2i medium & culture overnight.
2) Continued culturing un-cavitated embryos in KSOM+2i
Day 2:
1) Transferred all remaining embryos to 2i medium (whether or not they've cavitated).
2) Cultured overnight; continued culturing earlier embryos in 2i medium.
Day 3:
1) Transferred embryos for 30-60 seconds with Acid Tyrodes to remove the zona pellucida.
2) Washed embryos 3× in 2i medium to remove Acid Tyrodes.
3) Deposited each embryo into a separate well of a 96-well feeder plate (the well contains a monolayer of mitotically inactivated mouse embryonic fibroblasts (MEFs).
4) Cultured overnight in 2i medium.
Day 4-5:
1) Monitored plated embryos for the presence of an outgrowth (an amorphous undifferentiated mass of cells). Outgrowths are ready for transfer when they are approximately twice the size of the plated embryo.
2) Each day: remove spent media with a micropipette and replace with fresh 2i media.
3) Transferred outgrowths to new feeder wells:
   a. Removed spent media and gently wash well with PBS.
   b. Removed PBS and add 30 µl 0.05% trypsin; incubate for 10 minutes.
   c. Stopped trypsin reaction by adding 30 µl 2i+10% FBS.
   d. Gently dissociated the cells with a micropipettor and transferred entire contents of the well to a new well in a 24-well feeder plate. This was Passage 1 (P1).
   e. Cultured overnight in 2i medium.
Day 5-8: (timing depends on how fast each line expands)
1) Changed media each day (2i media) and monitored for the presence of colonies with an ESC morphology.
2) When colonies appear, continued culturing until colonies expand to ~50% confluency.
Ongoing:
1) Continued feeding and monitoring each line until approximately 50% confluent.
2) Trypsinized cells as usual.
3) stopped trypsin with 2i+10% FBS; pelleted the cells by centrifugation (5', 1200 rpm in Beckman-Coulter table-top centrifuge).
4) Aspirated the supernatant and gently resuspend the cells in 400 µl Freezing Medium (70% 2i, 20% FBS, 10% DMSO).
5) Distributed the cells into 2 vials and freeze at −80°. This was Passage 3 (P3).
6) For long-term storage, transferred the vials to liquid N2 storage.

The 2i media was prepared as follows in Table 3.

| Reagent | Vendor | Concentration |
|---|---|---|
| DMEM/F12 basal media | Invitrogen/Life Technologies | 1x |
| Neurobasal media | Invitrogen/Life Technologies | 1x |
| Penicillin/streptomycin | Invitrogen/Life Technologies | 1% |
| L-Glutamine | Invitrogen/Life Technologies | 4 mM |
| 2-Mercaptoethanol | Invitrogen/Life Technologies | 0.1 mM |
| N2 supplement | Invitrogen/Life Technologies | 1x |
| B27 supplement | Invitrogen/Life Technologies | 1x |
| LIF | Millipore | 100 U/ml |
| PD0325901 (MEK inhibitor). | Stemgent | 1 uM |
| CHIR99021 (GSK inhibitor). | Stemgent | 3 uM |

Materials:
Pregnant Mare's Serum Gonadotropin (PMSG)
Human Pregnancy Urine Chorionic Gonadotropin (HCG)
Female Rats (5-12 weeks old)
Male rats (12 wks. to 8 mos. old), one per cage
Syringes/needles
Animal room with lights on 6:00-18:00
Procedure:
Day 1: 8:00-10:00 AM
Inject females with 20 IU PMSG (0.4 ml), IP
Discard unused PMSG.
Day 3: 8:00-10:00 AM (48 hours after PMSG injection)
Inject females with 50 IU HCG (1 ml), IP
Place one female per male in mating cage.
Discard unused HCG.
Day 4: 8:00-10:00 AM (24 hrs. after HCG injection)
Check females for plugs.
Hormone Suppliers
PMSG: Sigma #G-4877 (1000 IU). Resuspend in PBS to a final [ ] of 50 IU/ml. Store at −20° in 1 ml aliquots.
HCG: Sigma #CG-5 (5000 IU). Resuspend in PBS to a final [ ] of 50 IU/ml. Store at −20° in 1 ml aliquots.
1.4.: Karyotyping of Rat Embryonic Stem Cell Lines
The rat ES cell lines generated herein were karyotyped, and the results are summarized in Tables 4-7.

TABLE 4

| ACI.G1 Karyotyping Results | Number of cells |
|---|---|
| Number of cells karyotyped | 7 |
| Number of cells analyzed | 20 |
| Number of 42, XY cells | 18 |
| Number of abnormal cells | 2 |
| 40, XY, −5, −9 | 1 |
| 41, XY, −14 | 1 |
| 42, XY | 18 |

Figure 4A:
FIGS. 4A-4B provide photographs showing the analysis of the chromosome number of the ACI.G1 rat ES cell line.
Figure 4B:
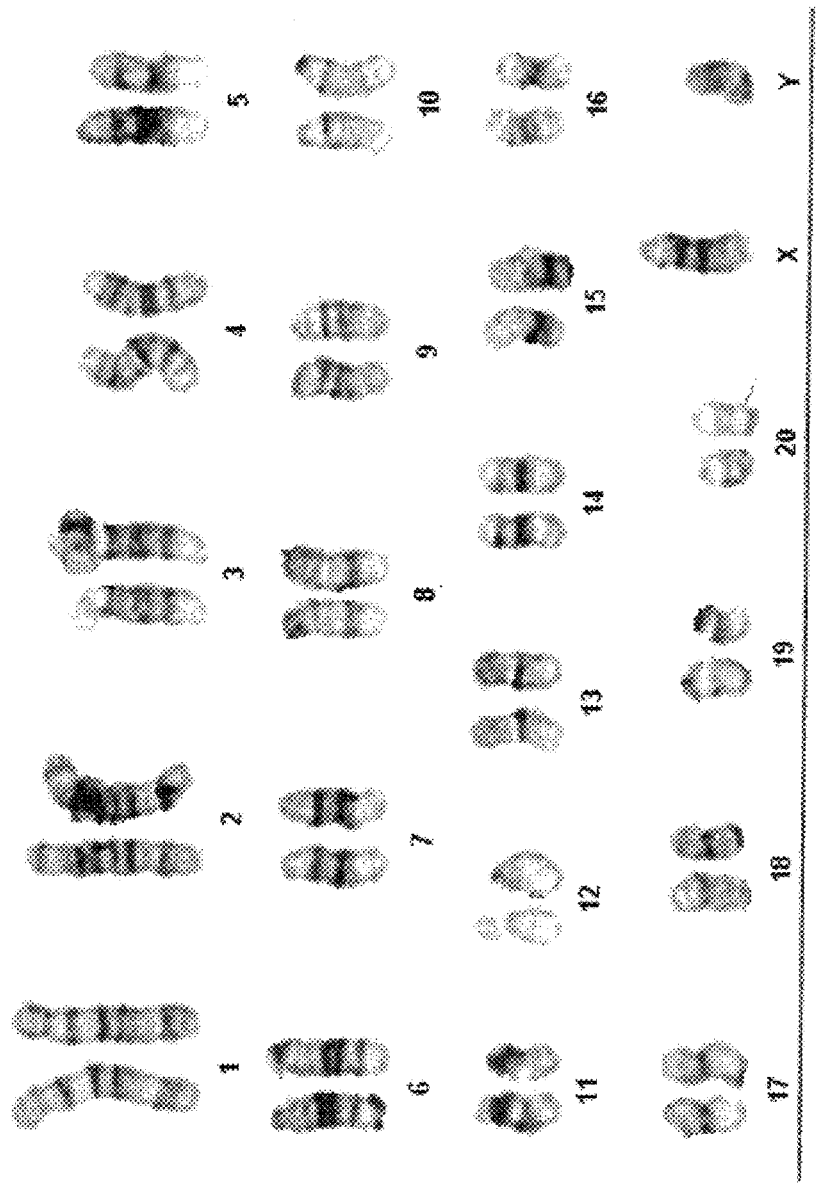

Other notes:
Two analyzed cells were missing different autosomes, which may be a sporadic occurrence due to technical artifact. 90% of analyzed cells had a normal male 42, XY karyotype.
FIG. 4 provides a photograph showing the analysis of the chromosome number of the ACI.G1 rat ES cell line.

TABLE 5

| DA.2B Karyotyping Results | Number of cells |
|---|---|
| Number of cells karyotyped | 6 |
| Number of cells analyzed | 20 |
| Number of 42, XY cells | 20 |
| Number of abnormal cells | 0 |
| 42, XY | 20 |

Figure 5A:
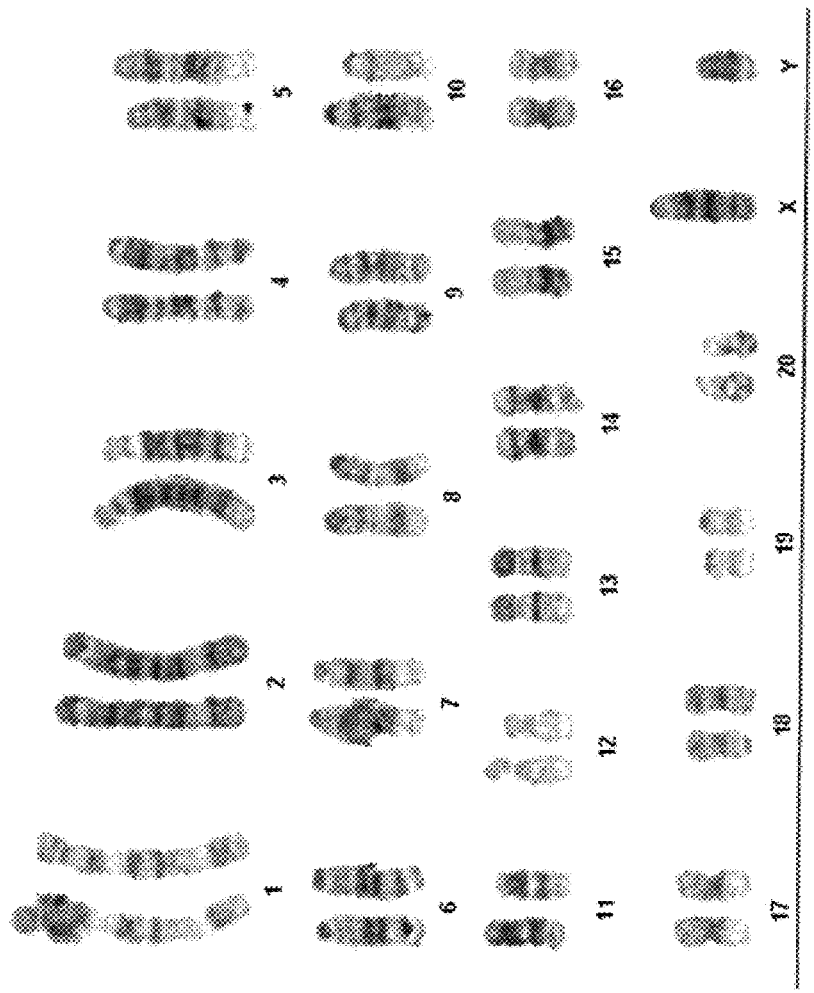
FIGS. 5A-5B provide photographs showing the analysis of the chromosome number of the DA.2B rat ES cell line.
Figure 5B:

Other notes:
All analyzed cells had a normal diploid 42, XY karyotype.
FIG. 5 provides a photograph showing the analysis of the chromosome number of the DA.2B rat ES cell line.

TABLE 6

| DA.C2 Karyotyping Results | Number of cells |
|---|---|
| Number of cells karyotyped | 5 |
| Number of cells analyzed | 20 |
| Number of 42, XY cells | 20 |
| Number of abnormal cells | 0 |
| 42, XX | 20 |

Figure 6A:
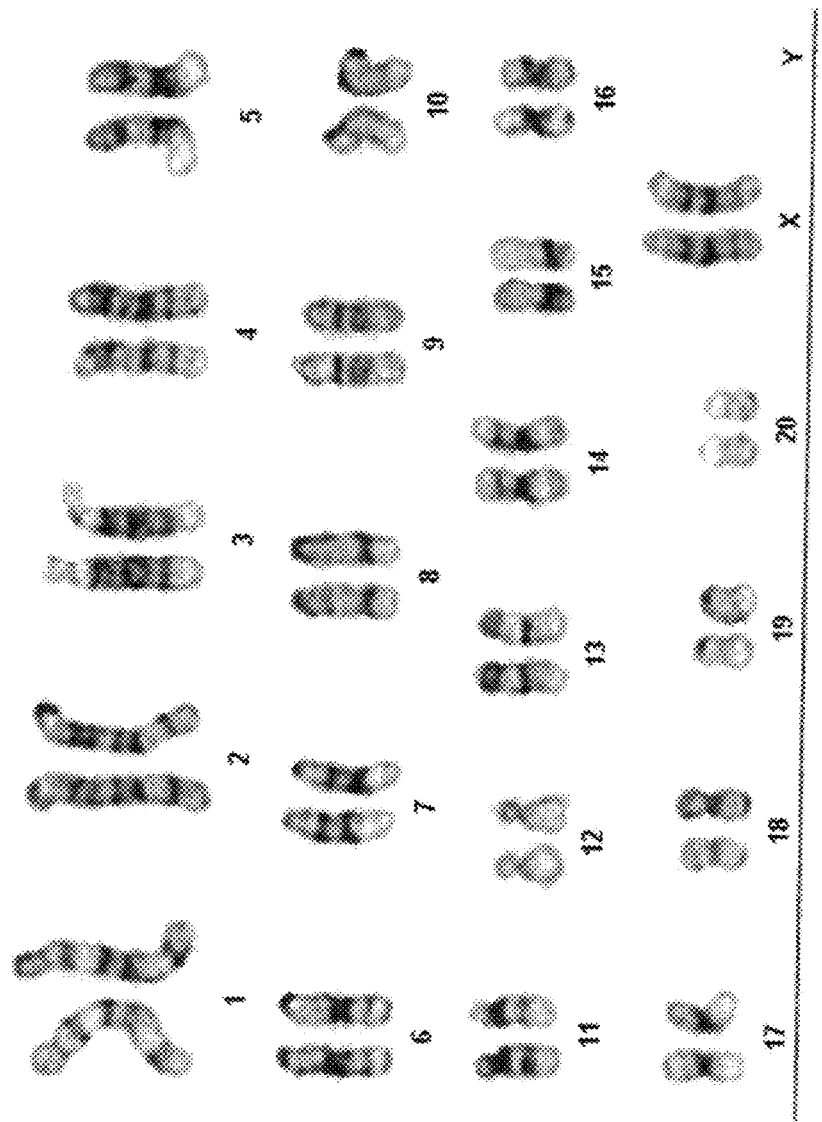
FIGS. 6A-6B provide photographs showing the analysis of the chromosome number of the DA.C2 rat ES cell line.
Figure 6B:

Other notes:
100% of analyzed cells had normal female XX rat karyotype.
FIG. 6 provides a photograph showing the analysis of the chromosome number of the DA.C2 rat ES cell line.

TABLE 7

| strain | Blastocysts plated | Lines established | Lines Karyotyped | Karyotypes |
|---|---|---|---|---|
| BN × SD F1 | 41 | 8 (20%) | 5 | all lines were high % complex polyploid |
| ACI | 27 | 16 (60%) | 3 | G1: 90% 42 XY; others were 70-85% euploid |
| DA | 20 | 9 (45%) | 6 | 2B: 100% 42 XY; 2C: 100% 42 XX; others were 95-100% euploid |
| F344 | 4 | 1 (25%) | 0 | |
| Totals | 92 | 34 (37%) | | |

1.5.: Electroporation of Vector into Rat Embryonic Stem Cell
1. Passaged rat ES cells 24-48 hrs prior to electroporation.
2. Changed media to RVG2i+ROCKi (10 μM Y-27632) 24 hr. prior to electroporation
3. Changed media 30' prior to trypsinization.
4. Aliquoted DNA to be electroporated.
5. Allowed DNA to warm at RT for >10 min.
6. Heated DNA for 5' @ 62° C. Place DNA on ice.
7. Trypsinized cells:
   a. Collected floating colonies. Washed plate to collect as many floaters as possible.
   b. Pelleted colonies: 3' @ 750 rpm.
   c. Washed pellet 1× with 5-10 ml PBS and re-spin/pellet
   d. Aspirated supernatant; add 500λ trypsin, 0.05%+1% chicken serum.
      i. Did not pool more than 1 10 cm plate of colonies per tube. If there are too many colonies packed into the bottom of the tube during trypsinization they will clump and most of the cells will be lost.
   e. 4' @ 37°. Pipetted colonies several times to minimize clumping.
   f. Repeated steps 1-2×: 4' @ 37°.
   g. Stopped trypsin with 500λ RVG2i+10% FBS.
8. Pelleted cells: 5' @ 1200 rpm.
9. Resuspend cells in 10 ml PBS. Count two 20λ aliquots to determine total cell number.
10. Pelleted cells (5'/1200 rpm); calculate total cell number and total resuspension volume to achieve correct cell concentration (target #175 μl EP buffer).
11. Resuspend in a minimal volume of EP buffer; measure total volume and adjust to target volume with EP buffer. Electroporation buffer is sold by Millipore. The catalog # is ES-003-D. See, Valenzuela et al. (2003) Nature Biotechnology 21:652-659, which is herein incorporated by reference.
12. Add 75λ cells to 50λ DNA; transfer the 125λ cells/DNA solution to one well of a BTX 48-well cuvette.
    a. Filled the empty wells in the same column with 125λ EP buffer.
13. Pulsed the cuvette once in the BTX electroporator:
    a. Settings: 400V; Ω; 100 μF (settings may vary)
14. Placed cuvette on ice for 15' to recover.
15. Removed cells into 5 ml RVG2i+10 μM ROCKi.
16. Added to 15 cm plate with 20 ml RVG2i+1004 ROCKi. Plate has 2× neoR MEFs (or other MEFs depending on project). The neoR selectable marker is the neomycin phosphotransferase (neo) gene of Beck et al. (1982) Gene, 19:327-36 or in U.S. Pat. No. 7,205,148 or 6,596,541, each of which are herein incorporated by reference.
17. Incubated @ 37°. Begin selection 48 hrs later.
ROCK inhibitor used was Y-27632.

1.6: Selecting a Targeted Genetic Modification in a Rat Embryonic Stem Cell
1. Passaged cells for 24-48 hrs prior to electroporation.
2. Changed media to RVG2i+ROCKi (1004 Y-27632) 24 hr. prior to electroporation
3. Changed media 30' prior to trypsinization.
4. Aliquoted DNA to be electroporated.
5. Allowed DNA warm at RT for >10 min.
6. Heated DNA for 5' @ 62° C. Place DNA on ice.
7. Trypsinized cells:
   a. Collected floating colonies. Washed plate to collect as many floaters as possible.
   b. Pelleted colonies: 3' @ 750 rpm.
   c. Washed pellet 1× with 5-10 ml PBS and re-spin/pellet
   d. Aspirated supernatant; add 500λ trypsin, 0.05%+1% chicken serum.
      i. Did not pool more than 1 10 cm plate of colonies per tube. If there are too many colonies packed into the bottom of the tube during trypsinization they will clump and most of the cells will be lost.
   e. 4' @ 37°. Pipetted colonies several times to minimize clumping
   f. Repeated 1-2×: 4' @ 37°.
   g. Stopped trypsin with 500λ RVG2i+10% FBS.
8. Pelleted cells: 5' @ 1200 rpm.
9. Resuspended cells in 10 ml PBS. Count two 20λ aliquots to determine total cell number.

10. Pelleted cells (5'/1200 rpm); calculate total cell number and total resuspension volume to achieve correct cell concentration (target #/75 µl EP buffer).
11. Resuspend in a minimal volume of EP buffer; measured total volume and adjusted to target volume with EP buffer.
12. Added 75λ cells to 50λ DNA; transfer the 125λ cells/DNA solution to one well of a BTX 48-well cuvette.
   a. Filled the empty wells in the same column with 125λ EP buffer.
13. Pulsed the cuvette once in the BTX electroporator:
   a. Settings: 400V; 100 µF (settings may vary)
14. Placed cuvette on ice for 15' to recover.
15. Removed cells into 5 ml RVG2i+10 µM ROCKi.
16. Added to 15 cm plate with 20 ml RVG2i+10 µM ROCKi. Plate had 2× neoR MEFs (or other MEFs depending on project).
17. Incubated @ 37°. Began selection 48 hrs later.
18. G418 selection protocol was as follows:
   a. Day 2 ($2^{nd}$ day after EP): incubated cells in 2i media+G418, 75 µg/ml.
   b. Day 3: incubated cells in 2i media without G418
   c. Day 4: incubated cells in 2i media+G418, 75 µg/ml.
   d. Day 5: incubated cells in 2i media without G418
   e. Day 6: incubated cells in 2i media+G418, 75 µg/ml.
   f. Day 7: incubated cells in 2i media without G418
   g. Day 8: incubated cells in 2i media+G418, 75 µg/ml.
   h. Day 9: incubated cells in 2i media without G418
   i. Day 10: incubated cells in 2i media+G418, 75 µg/ml.
   j. Day 11: incubated cells in 2i media without G418
   k. Day 12: picked colonies to expand for screening. Each colony was dissociated in 0.05% trypsin+1% chicken serum for 10 minutes and then plated into 1 well of a 96-well feeder plate.
19. Expanded colonies for 3 days in 2i media.
20. Passaged clones 1:1 to new 96-well feeder plates.
21. Expanded clones for 3 days in 2i media.
22. For each clone, dissociated colonies in trypsin. Froze ⅔ of each clone and store at −80°; plated the remaining ⅓ onto laminin plates (96-well plates coated with 10 µg/ml laminin).
23. When the laminin plates were confluent, passed off to the screening lab for genotyping of the clones.

1.7. Molecular Signature of the Rat Embryonic Stem Cells

The genes listed in Table 8 were expressed at 20-fold lower in rat ES cells than the corresponding genes in mouse ES cells. The genes listed in Table 9 were expressed at levels 20-fold higher in rat ES cells than the corresponding genes in mouse ES cells.

The microarray data in Tables 8 and 9 were generated as follows. Rat ES cells (ACI.G2 and DA.2B) and mouse ES cells (F1H4) were cultured in 2i media for 3 passages until confluent. F1H4 cells were cultured on gelatin-coated plates in the absence of feeders. F1H4 mouse ES cells were derived from 12956/SvEvTac and C57BL/6NTac heterozygous embryos (see, e.g., U.S. Pat. No. 7,294,754 and Poueymirou, W. T., Auerbach, W., Frendewey, D., Hickey, J. F., Escaravage, J. M., Esau, L., Dore, A. T., Stevens, S., Adams, N.C., Dominguez, M. G., Gale, N. W., Yancopoulos, G. D., DeChiara, T. M., Valenzuela, D. M. (2007), incorporated by reference herein in its entirety).

The following protocol was used for sample prep: The 1.5 mL Eppendorf tubes were labeled with the Sample ID. Cells grown on a plate were rinsed in 37° C. Phosphate-Buffered Saline (PBS). PBS was removed and 300 ul of Trizol® was added. A scraper was used to break the cells in Trizol® (Life Technology). The lysed cells were collected in Trizol® in a 1.5 mL Eppendorf tube. For cells grown on suspension, the cells were rinsed in 37° C. PBS and collected in a 1.5 mL tube. The cells were spun down; PBS was removed; and 300 ul of Trizol® was added to the cells. The cell membranes were broken by pipetting. Samples were sorted for FACS with 10 to $10^5$ cells, the volume was concentrated to less than 100 uL. 4 volumes of RNA Lysis buffer were added and mixed by pipetting. For sample, 320 uL RNA Lysis buffer was added to 80 uL sample. Samples were stored at −20° C.

RNA-Seq was used to measure the expression level of mouse and rat genes. Sequencing reads were mapped to mouse and rat reference genome by Tophat, and RPKM (fragments per kilobase of exon per million fragments mapped) were calculated for mouse and rat genes. Homology genes based on gene symbol were selected, and then used t-test to compare the expression level of each gene between mouse and rat. miR-632 was in the top 10 highest expressed in rat ESCs but was not expressed in mouse ES cells. Although no comparative data exist from miR-632, based on the level of its expression compared to other genes expressed in rat ESCs and their known function in embryonic development, miR-632 was selected as a marker for rat ES cells.

TABLE 8

The genes listed were expressed at levels 20-fold lower in rat ES cells than the corresponding genes in mouse ES cells.

| ID | Symbol | Entrez Gene Name | Location | Type(s) |
|---|---|---|---|---|
| Abcb1b | Abcb1b | ATP-binding cassette, sub-family B (MDR/TAP), member 1B | Plasma Membrane | transporter |
| Acta2 | ACTA2 | actin, alpha 2, smooth muscle, aorta | Cytoplasm | other |
| Actg2 | ACTG2 | actin, gamma 2, smooth muscle, enteric | Cytoplasm | other |
| Aebp1 | AEBP1 | AE binding protein 1 | Nucleus | peptidase |
| Angptl2 | ANGPTL2 | angiopoietin-like 2 | Extracellular Space | other |

TABLE 8-continued

The genes listed were expressed at levels 20-fold lower in rat
ES cells than the corresponding genes in mouse ES cells.

| ID | Symbol | Entrez Gene Name | Location | Type(s) |
|---|---|---|---|---|
| Ankrd1 | ANKRD1 | ankyrin repeat domain 1 (cardiac muscle) | Cytoplasm | transcription regulator |
| Anxa1 | ANXA1 | annexin A1 | Plasma Membrane | other |
| Anxa6 | ANXA6 | annexin A6 | Plasma Membrane | other |
| Anxa8 | ANXA8L2 | annexin A8-like 2 | Plasma Membrane | other |
| Arhgef25 | ARHGEF25 | Rho guanine nucleotide exchange factor (GEF) 25 | Cytoplasm | other |
| Axl | AXL | AXL receptor tyrosine kinase | Plasma Membrane | kinase |
| Basp1 | BASP1 | brain abundant, membrane attached signal protein 1 | Nucleus | transcription regulator |
| Bgn | BGN | biglycan | Extracellular Space | other |
| Bst2 | BST2 | bone marrow stromal cell antigen 2 | Plasma Membrane | other |
| Btf3 | BTF3 | basic transcription factor 3 | Nucleus | transcription regulator |
| Btg2 | BTG2 | BTG family, member 2 | Nucleus | transcription regulator |
| Capsl | CAPSL | calcyphosine-like | Other | other |
| Cav1 | CAV1 | caveolin 1, caveolae protein, 22 kDa | Plasma Membrane | transmembrane receptor |
| Ccdc80 | CCDC80 | coiled-coil domain containing 80 | Nucleus | other |
| Ccnd2 | CCND2 | cyclin D2 | Nucleus | other |
| Cd248 | CD248 | CD248 molecule, endosialin | Plasma Membrane | other |
| Cd44 | CD44 | CD44 molecule (Indian blood group) | Plasma Membrane | enzyme |
| Cd97 | CD97 | CD97 molecule | Plasma Membrane | G-protein coupled receptor |
| Cdc42ep5 | CDC42EP5 | CDC42 effector protein (Rho GTPase binding) 5 | Cytoplasm | other |
| Cdh11 | CDH11 | cadherin 11, type 2, OB-cadherin (osteoblast) | Plasma Membrane | other |
| Cdkn2a | CDKN2A | cyclin-dependent kinase inhibitor 2A | Nucleus | transcription regulator |
| Cdo1 | CDO1 | cysteine dioxygenase type 1 | Cytoplasm | enzyme |
| Clip3 | CLIP3 | CAP-GLY domain containing linker protein 3 | Cytoplasm | other |
| Cln5 | CLN5 | ceroid-lipofuscinosis, neuronal 5 | Cytoplasm | other |
| Cnn1 | CNN1 | calponin 1, basic, smooth muscle | Cytoplasm | other |
| Col1a1 | COL1A1 | collagen, type I, alpha 1 | Extracellular Space | other |
| Col1a2 | COL1A2 | collagen, type I, alpha 2 | Extracellular Space | other |
| Col3a1 | COL3A1 | collagen, type III, alpha 1 | Extracellular Space | other |
| Col5a2 | COL5A2 | collagen, type V, alpha 2 | Extracellular Space | other |
| Col6a2 | COL6A2 | collagen, type VI, alpha 2 | Extracellular Space | other |
| Cryab | CRYAB | crystallin, alpha B | Nucleus | other |
| Csf1 | CSF1 | colony stimulating factor 1 (macrophage) | Extracellular Space | cytokine |

TABLE 8-continued

The genes listed were expressed at levels 20-fold lower in rat
ES cells than the corresponding genes in mouse ES cells.

| ID | Symbol | Entrez Gene Name | Location | Type(s) |
|---|---|---|---|---|
| Cth | CTH | cystathionase (cystathionine gamma-lyase) | Cytoplasm | enzyme |
| Cthrc1 | CTHRC1 | collagen triple helix repeat containing 1 | Extracellular Space | other |
| Ctsc | CTSC | cathepsin C | Cytoplasm | peptidase |
| Cyr61 | CYR61 | cysteine-rich, angiogenic inducer, 61 | Extracellular Space | other |
| Ddx58 | DDX58 | DEAD (Asp-Glu-Ala-Asp) box polypeptide 58 | Cytoplasm | enzyme |
| Dkk3 | DKK3 | dickkopf WNT signaling pathway inhibitor 3 | Extracellular Space | cytokine |
| Dmc1 | DMC1 | DNA meiotic recombinase 1 | Nucleus | enzyme |
| Dpysl3 | DPYSL3 | dihydropyrimidinase-like 3 | Cytoplasm | enzyme |
| Dse | DSE | dermatan sulfate epimerase | Cytoplasm | enzyme |
| Dusp1 | DUSP1 | dual specificity phosphatase 1 | Nucleus | phosphatase |
| Dusp27 | DUSP27 | dual specificity phosphatase 27 (putative) | Other | phosphatase |
| Dusp9 | DUSP9 | dual specificity phosphatase 9 | Nucleus | phosphatase |
| Ece2 | ECE2 | endothelin converting enzyme 2 | Plasma Membrane | peptidase |
| Ecm1 | ECM1 | extracellular matrix protein 1 | Extracellular Space | transporter |
| Egr1 | EGR1 | early growth response 1 | Nucleus | transcription regulator |
| Emp1 | EMP1 | epithelial membrane protein 1 | Plasma Membrane | other |
| Emp3 | EMP3 | epithelial membrane protein 3 | Plasma Membrane | other |
| Ephx2 | EPHX2 | epoxide hydrolase 2, cytoplasmic | Cytoplasm | enzyme |
| F3 | F3 | coagulation factor III (thromboplastin, tissue factor) | Plasma Membrane | transmembrane receptor |
| Fau | FAU | Finkel-Biskis-Reilly murine sarcoma virus (FBR-MuSV) ubiquitously expressed | Cytoplasm | other |
| Fbn1 | FBN1 | fibrillin 1 | Extracellular Space | other |
| Fbxo15 | FBXO15 | F-box protein 15 | Other | transcription regulator |
| Fhl2 | FHL2 | four and a half LIM domains 2 | Nucleus | transcription regulator |
| Flnc | FLNC | filamin C, gamma | Cytoplasm | other |
| Fos | FOS | FBJ murine osteosarcoma viral oncogene homolog | Nucleus | transcription regulator |
| Fundc2 | FUNDC2 | FUN14 domain containing 2 | Cytoplasm | other |
| Gjb3 | GJB3 | gap junction protein, beta 3, 31 kDa | Plasma Membrane | transporter |
| Gpa33 | GPA33 | glycoprotein A33 (transmembrane) | Plasma Membrane | other |
| Gpbp1l1 | GPBP1L1 | GC-rich promoter binding protein 1-like 1 | Other | other |
| Gpc3 | GPC3 | glypican 3 | Plasma Membrane | other |
| Grb10 | GRB10 | growth factor receptor-bound protein 10 | Cytoplasm | other |

TABLE 8-continued

The genes listed were expressed at levels 20-fold lower in rat
ES cells than the corresponding genes in mouse ES cells.

| ID | Symbol | Entrez Gene Name | Location | Type(s) |
| --- | --- | --- | --- | --- |
| Gstm1 | GSTM5 | glutathione S-transferase mu 5 | Cytoplasm | enzyme |
| Hap1 | HAP1 | huntingtin-associated protein 1 | Cytoplasm | other |
| Hist1h2bc | HIST2H2BE (includes others) | histone cluster 2, H2be | Nucleus | other |
| Hmga2 | HMGA2 | high mobility group AT-hook 2 | Nucleus | enzyme |
| Hmgn3 | Hmgn3 | high mobility group nucleosomal binding domain 3 | Nucleus | other |
| Hormad1 | HORMAD1 | HORMA domain containing 1 | Nucleus | other |
| Hsd17b14 | HSD17B14 | hydroxysteroid (17-beta) dehydrogenase 14 | Cytoplasm | enzyme |
| Hspb1 | HSPB1 | heat shock 27 kDa protein 1 | Cytoplasm | other |
| Hspb8 | HSPB8 | heat shock 22 kDa protein 8 | Cytoplasm | kinase |
| Htra1 | HTRA1 | HtrA serine peptidase 1 | Extracellular Space | peptidase |
| Ifi204 | Ifi204 (includes others) | interferon activated gene 204 | Nucleus | transcription regulator |
| Ifi44 | IFI44 | interferon-induced protein 44 | Cytoplasm | other |
| Ifit1 | IFIT1B | interferon-induced protein with tetratricopeptide repeats 1B | Cytoplasm | other |
| Ifitm3 | IFITM2 | interferon induced transmembrane protein 2 | Cytoplasm | other |
| Igf2 | IGF2 | insulin-like growth factor 2 (somatomedin A) | Extracellular Space | growth factor |
| Igfbp7 | IGFBP7 | insulin-like growth factor binding protein 7 | Extracellular Space | transporter |
| Il1rl1 | IL1RL1 | interleukin 1 receptor-like 1 | Plasma Membrane | transmembrane receptor |
| Inhba | INHBA | inhibin, beta A | Extracellular Space | growth factor |
| Inhbb | INHBB | inhibin, beta B | Extracellular Space | growth factor |
| Irf7 | IRF7 | interferon regulatory factor 7 | Nucleus | transcription regulator |
| Isg15 | ISG15 | ISG15 ubiquitin-like modifier | Extracellular Space | other |
| Itga5 | ITGA5 | integrin, alpha 5 (fibronectin receptor, alpha polypeptide) | Plasma Membrane | transmembrane receptor |
| Jun | JUN | jun proto-oncogene | Nucleus | transcription regulator |
| Junb | JUNB | jun B proto-oncogene | Nucleus | transcription regulator |
| Lgals3bp | LGALS3BP | lectin, galactoside-binding, soluble, 3 binding protein | Plasma Membrane | transmembrane receptor |
| Lgals9 | LGALS9 | lectin, galactoside-binding, soluble, 9 | Extracellular Space | other |
| Lmna | LMNA | lamin A/C | Nucleus | other |
| Lox | LOX | lysyl oxidase | Extracellular Space | enzyme |
| Loxl2 | LOXL2 | lysyl oxidase-like 2 | Extracellular Space | enzyme |
| Loxl3 | LOXL3 | lysyl oxidase-like 3 | Extracellular Space | enzyme |
| Lrp1 | LRP1 | low density lipoprotein receptor-related protein 1 | Plasma Membrane | transmembrane receptor |

TABLE 8-continued

The genes listed were expressed at levels 20-fold lower in rat
ES cells than the corresponding genes in mouse ES cells.

| ID | Symbol | Entrez Gene Name | Location | Type(s) |
|---|---|---|---|---|
| Mageb16 | MAGEB16 | melanoma antigen family B, 16 | Other | other |
| Mcam | MCAM | melanoma cell adhesion molecule | Plasma Membrane | other |
| Mgp | MGP | matrix Gla protein | Extracellular Space | other |
| Mmp2 | MMP2 | matrix metallopeptidase 2 (gelatinase A, 72 kDa gelatinase, 72 kDa type IV collagenase) | Extracellular Space | peptidase |
| Mxra8 | MXRA8 | matrix-remodelling associated 8 | Other | other |
| Myl9 | MYL9 | myosin, light chain 9, regulatory | Cytoplasm | other |
| Mylpf | MYLPF | myosin light chain, phosphorylatable, fast skeletal muscle | Cytoplasm | other |
| Nab2 | NAB2 | NGFI-A binding protein 2 (EGR1 binding protein 2) | Nucleus | transcription regulator |
| Ndufb4 | NDUFB4 | NADH dehydrogenase (ubiquinone) 1 beta subcomplex, 4, 15 kDa | Cytoplasm | transporter |
| Npm1 | NPM1 | nucleophosmin (nucleolar phosphoprotein B23, numatrin) | Nucleus | transcription regulator |
| Nr0b1 | NR0B1 | nuclear receptor subfamily 0, group B, member 1 | Nucleus | ligand-dependent nuclear receptor |
| Nr4a1 | NR4A1 | nuclear receptor subfamily 4, group A, member 1 | Nucleus | ligand-dependent nuclear receptor |
| Nrp2 | NRP2 | neuropilin 2 | Plasma Membrane | kinase |
| Oas1a | OAS1 | 2'-5'-oligoadenylate synthetase 1, 40/46 kDa | Cytoplasm | enzyme |
| Oasl2 | Oasl2 | 2'-5' oligoadenylate synthetase-like 2 | Other | enzyme |
| P4ha2 | P4HA2 | prolyl 4-hydroxylase, alpha polypeptide II | Cytoplasm | enzyme |
| Parp3 | PARP3 | poly (ADP-ribose) polymerase family, member 3 | Nucleus | enzyme |
| Pcolce | PCOLCE | procollagen C-endopeptidase enhancer | Extracellular Space | other |
| Pcyt1b | PCYT1B | phosphate cytidylyltransferase 1, choline, beta | Cytoplasm | enzyme |
| Pdgfc | PDGFC | platelet derived growth factor C | Extracellular Space | growth factor |
| Phlda1 | PHLDA1 | pleckstrin homology-like domain, family A, member 1 | Cytoplasm | other |
| Phlda2 | PHLDA2 | pleckstrin homology-like domain, family A, member 2 | Cytoplasm | other |
| Pla2g1b | PLA2G1B | phospholipase A2, group IB (pancreas) | Extracellular Space | enzyme |

TABLE 8-continued

The genes listed were expressed at levels 20-fold lower in rat
ES cells than the corresponding genes in mouse ES cells.

| ID | Symbol | Entrez Gene Name | Location | Type(s) |
|---|---|---|---|---|
| Pla2g4a | PLA2G4A | phospholipase A2, group IVA (cytosolic, calcium-dependent) | Cytoplasm | enzyme |
| Porcn | PORCN | porcupine homolog (Drosophila) | Cytoplasm | other |
| Postn | POSTN | periostin, osteoblast specific factor | Extracellular Space | other |
| Prrx1 | PRRX1 | paired related homeobox 1 | Nucleus | transcription regulator |
| Prss23 | PRSS23 | protease, serine, 23 | Extracellular Space | peptidase |
| Psmb8 | PSMB8 | proteasome (prosome, macropain) subunit, beta type, 8 | Cytoplasm | peptidase |
| Ptgs2 | PTGS2 | prostaglandin-endoperoxide synthase 2 (prostaglandin G/H synthase and cyclooxygenase) | Cytoplasm | enzyme |
| Ptn | PTN | pleiotrophin | Extracellular Space | growth factor |
| Ptrf | PTRF | polymerase I and transcript release factor | Nucleus | transcription regulator |
| Rarg | RARG | retinoic acid receptor, gamma | Nucleus | ligand-dependent nuclear receptor |
| Rgs16 | RGS16 | regulator of G-protein signaling 16 | Cytoplasm | other |
| Rn45s | Rn45s | 45S pre-ribosomal RNA | Other | other |
| Rpl10a | RPL10A | ribosomal protein L10a | Other | other |
| Rpl31 | RPL31 | ribosomal protein L31 | Other | other |
| Rpl37a | RPL37A | ribosomal protein L37a | Cytoplasm | other |
| Rps10 | RPS10-NUDT3 | RPS10-NUDT3 readthrough | Cytoplasm | other |
| Rps14 | RPS14 | ribosomal protein S14 | Cytoplasm | translation regulator |
| Rps20 | Rps20 | ribosomal protein S20 | Cytoplasm | other |
| Rps26 | RPS26 | ribosomal protein S26 | Cytoplasm | other |
| Rps9 | RPS9 | ribosomal protein S9 | Cytoplasm | translation regulator |
| S100a4 | S100A4 | S100 calcium binding protein A4 | Cytoplasm | other |
| S100a6 | S100A6 | S100 calcium binding protein A6 | Cytoplasm | transporter |
| Schip1 | SCHIP1 | schwannomin interacting protein 1 | Cytoplasm | other |
| Sdc2 | SDC2 | syndecan 2 | Plasma Membrane | other |
| Serpine1 | SERPINE1 | serpin peptidase inhibitor, clade E (nexin, plasminogen activator inhibitor type 1), member 1 | Extracellular Space | other |
| Serpine2 | SERPINE2 | serpin peptidase inhibitor, clade E (nexin, plasminogen activator inhibitor type 1), member 2 | Extracellular Space | other |

TABLE 8-continued

The genes listed were expressed at levels 20-fold lower in rat
ES cells than the corresponding genes in mouse ES cells.

| ID | Symbol | Entrez Gene Name | Location | Type(s) |
|---|---|---|---|---|
| Serpinf1 | SERPINF1 | serpin peptidase inhibitor, clade F (alpha-2 antiplasmin, pigment epithelium derived factor), member 1 | Extracellular Space | other |
| Sh3gl2 | SH3GL2 | SH3-domain GRB2-like 2 | Plasma Membrane | enzyme |
| Slc19a2 | SLC19A2 | solute carrier family 19 (thiamine transporter), member 2 | Plasma Membrane | transporter |
| Slc25a5 | SLC25A5 | solute carrier family 25 (mitochondrial carrier; adenine nucleotide translocator), member 5 | Cytoplasm | transporter |
| Slc29a1 | SLC29A1 | solute carrier family 29 (equilibrative nucleoside transporter), member 1 | Plasma Membrane | transporter |
| Slc35f2 | SLC35F2 | solute carrier family 35, member F2 | Other | other |
| Snrpn | SNRPN | small nuclear ribonucleoprotein polypeptide N | Nucleus | other |
| Snx22 | SNX22 | sorting nexin 22 | Other | transporter |
| Sparc | SPARC | secreted protein, acidic, cysteine-rich (osteonectin) | Extracellular Space | other |
| Spp1 | SPP1 | secreted phosphoprotein 1 | Extracellular Space | cytokine |
| Sult4a1 | SULT4A1 | sulfotransferase family 4A, member 1 | Cytoplasm | enzyme |
| Tagln | TAGLN | transgelin | Cytoplasm | other |
| Tcea3 | TCEA3 | transcription elongation factor A (SII), 3 | Nucleus | transcription regulator |
| Tgfb3 | TGFB3 | transforming growth factor, beta 3 | Extracellular Space | growth factor |
| Thbs1 | THBS1 | thrombospondin 1 | Extracellular Space | other |
| Thbs2 | THBS2 | thrombospondin 2 | Extracellular Space | other |
| Tm4sf1 | TM4SF1 | transmembrane 4 L six family member 1 | Plasma Membrane | other |
| Tmbim1 | TMBIM1 | transmembrane BAX inhibitor motif containing 1 | Cytoplasm | other |
| Tmem176b | TMEM176B | transmembrane protein 176B | Other | other |
| Tnc | TNC | tenascin C | Extracellular Space | other |
| Tpd52l1 | TPD52L1 | tumor protein D52-like 1 | Cytoplasm | other |
| Tpm2 | TPM2 | tropomyosin 2 (beta) | Cytoplasm | other |
| Usp18 | USP18 | ubiquitin specific peptidase 18 | Cytoplasm | peptidase |
| Vim | VIM | vimentin | Cytoplasm | other |
| Wfdc2 | WFDC2 | WAP four-disulfide core domain 2 | Extracellular Space | other |
| Wisp2 | WISP2 | WNT1 inducible signaling pathway protein 2 | Extracellular Space | growth factor |

TABLE 8-continued

The genes listed were expressed at levels 20-fold lower in rat ES cells than the corresponding genes in mouse ES cells.

| ID | Symbol | Entrez Gene Name | Location | Type(s) |
|---|---|---|---|---|
| Ybx1 | YBX1 | Y box binding protein 1 | Nucleus | transcription regulator |

TABLE 9

The genes listed were expressed at levels 20-fold higher in rat ES cells than the corresponding genes in mouse ES cells.

| ID | Symbol | Entrez Gene Name | Location | Type(s) |
|---|---|---|---|---|
| Ajap1 | Ajap1 | adherens junction associated protein 1 | Other | other |
| Amd1 | AMD1 | adenosylmethionine decarboxylase 1 | Cytoplasm | enzyme |
| Ankrd2 | ANKRD2 | ankyrin repeat domain 2 (stretch responsive muscle) | Nucleus | transcription regulator |
| Arhgef9 | ARHGEF9 | Cdc42 guanine nucleotide exchange factor (GEF) 9 | Cytoplasm | other |
| Atp5h | Atp5h | ATP synthase, H+ transporting, mitochondrial F0 complex, subunit d | Cytoplasm | enzyme |
| Btg3 | BTG3 | BTG family, member 3 | Nucleus | other |
| Car6 | CA6 | carbonic anhydrase VI | Extracellular Space | enzyme |
| Camk4 | CAMK4 | calcium/calmodulin-dependent protein kinase IV | Nucleus | kinase |
| Capn12 | CAPN12 | calpain 12 | Other | peptidase |
| Cct6b | CCT6B | chaperonin containing TCP1, subunit 6B (zeta 2) | Cytoplasm | transporter |
| Cdx2 | CDX2 | caudal type homeobox 2 | Nucleus | transcription regulator |
| Cldn5 | CLDN5 | claudin 5 | Plasma Membrane | other |
| Clec3a | CLEC3A | C-type lectin domain family 3, member A | Other | other |
| Clic6 | CLIC6 | chloride intracellular channel 6 | Plasma Membrane | ion channel |
| Dhrsx | DHRSX | dehydrogenase/reductase (SDR family) X-linked | Other | enzyme |
| Dpysl2 | DPYSL2 | dihydropyrimidinase-like 2 | Cytoplasm | enzyme |
| Dusp26 | DUSP26 | dual specificity phosphatase 26 (putative) | Cytoplasm | enzyme |
| Eci3 | Eci3 | enoyl-Coenzyme A delta isomerase 3 | Other | enzyme |
| Eef2k | EEF2K | eukaryotic elongation factor-2 kinase | Cytoplasm | kinase |
| Efna1 | EFNA1 | ephrin-A1 | Plasma Membrane | other |
| Epha4 | EPHA4 | EPH receptor A4 | Plasma Membrane | kinase |
| Fank1 | FANK1 | fibronectin type III and ankyrin repeat domains 1 | Nucleus | transcription regulator |
| Fhit | FHIT | fragile histidine triad | Cytoplasm | enzyme |
| Filip1 | FILIP1 | filamin A interacting protein 1 | Cytoplasm | other |
| Fmod | FMOD | fibromodulin | Extracellular Space | other |

TABLE 9-continued

The genes listed were expressed at levels 20-fold higher in rat ES cells than the corresponding genes in mouse ES cells.

| ID | Symbol | Entrez Gene Name | Location | Type(s) |
|---|---|---|---|---|
| Foxe1 | FOXE1 | forkhead box E1 (thyroid transcription factor 2) | Nucleus | transcription regulator |
| Fry | FRY | furry homolog (Drosophila) | Extracellular Space | other |
| Gjb5 | GJB5 | gap junction protein, beta 5, 31.1 kDa | Plasma Membrane | transporter |
| Gpx2 | GPX2 | glutathione peroxidase 2 (gastrointestinal) | Cytoplasm | enzyme |
| Grxcr2 | GRXCR2 | glutaredoxin, cysteine rich 2 | Other | other |
| Hecw2 | HECW2 | HECT, C2 and WW domain containing E3 ubiquitin protein ligase 2 | Extracellular Space | enzyme |
| Hey2 | HEY2 | hairy/enhancer-of-split related with YRPW motif 2 | Nucleus | transcription regulator |
| Icos | Icos | inducible T-cell co-stimulator | Plasma Membrane | other |
| Ifitm1 | IFITM1 | interferon induced transmembrane protein 1 | Plasma Membrane | transmembrane receptor |
| Il1f8 | IL1F8 (IL36B) | Interleukin-1 family member (Interleukin 36 beta) | Extracellular space | cytokine |
| Il28ra | IL-28RA | Interleukin 28 receptor, alpha | Plasma membrane | Cytokine receptor |
| Igfbpl1 | IGFBPL1 | insulin-like growth factor binding protein-like 1 | Other | other |
| Ipcef1 | IPCEF1 | interaction protein for cytohesin exchange factors 1 | Cytoplasm | enzyme |
| Lctl | Lctl | lactase-like | Cytoplasm | other |
| Ldhd | LDHD | lactate dehydrogenase D | Cytoplasm | enzyme |
| Lef1 | LEF1 | lymphoid enhancer-binding factor 1 | Nucleus | transcription regulator |
| Lefty1 | LEFTY1 | left-right determination factor 1 | Extracellular Space | growth factor |
| Lifr | LIFR | leukemia inhibitory factor receptor alpha | Plasma Membrane | transmembrane receptor |
| Lpar2 | LPAR2 | lysophosphatidic acid receptor 2 | Plasma Membrane | G-protein coupled receptor |
| Mog | MOG | myelin oligodendrocyte glycoprotein | Extracellular Space | other |
| Morn5 | MORN5 | MORN repeat containing 5 | Other | other |
| Pigz | NCBP2 | nuclear cap binding protein subunit 2, 20 kDa | Nucleus | other |
| Nptxr | NPTXR | neuronal pentraxin receptor | Plasma Membrane | transmembrane receptor |
| Ntm | NTM | neurotrimin | Plasma Membrane | other |
| Nutf2 | NUTF2 | nuclear transport factor 2 | Nucleus | transporter |
| Ocln | OCLN | occludin | Plasma Membrane | enzyme |
| Olr1 | OLR1 | oxidized low density lipoprotein (lectin-like) receptor 1 | Plasma Membrane | transmembrane receptor |
| Pabpc4 | PABPC4 | poly(A) binding protein, cytoplasmic 4 (inducible form) | Cytoplasm | translation regulator |
| Pde11a | PDE11A | phosphodiesterase 11A | Cytoplasm | enzyme |
| Pdyn | PDYN | prodynorphin | Extracellular Space | transporter |

TABLE 9-continued

The genes listed were expressed at levels 20-fold higher in rat ES cells than the corresponding genes in mouse ES cells.

| ID | Symbol | Entrez Gene Name | Location | Type(s) |
|---|---|---|---|---|
| Per3 | PER3 | period circadian clock 3 | Nucleus | other |
| Pllp | PLLP | plasmolipin | Plasma Membrane | transporter |
| Ppp1r14c | PPP1R14C | protein phosphatase 1, regulatory (inhibitor) subunit 14C | Cytoplasm | other |
| Pramel6 | Pramel6 | preferentially expressed antigen in melanoma like 6 | Other | other |
| Ptpn18 | PTPN18 | protein tyrosine phosphatase, non-receptor type 18 (brain-derived) | Nucleus | phosphatase |
| Pycr1 | PYCR1 | pyrroline-5-carboxylate reductase 1 | Cytoplasm | enzyme |
| Rab26 | RAB26 | RAB26, member RAS oncogene family | Plasma Membrane | enzyme |
| Ramp2 | RAMP2 | receptor (G protein-coupled) activity modifying protein 2 | Plasma Membrane | transporter |
| Rbm24 | RBM24 | RNA binding motif protein 24 | Other | other |
| Rhag | RHAG | Rh-associated glycoprotein | Plasma Membrane | peptidase |
| Rpl3 | RPL3 | ribosomal protein L3 | Cytoplasm | other |
| Sall3 | SALL3 | sal-like 3 (Drosophila) | Nucleus | other |
| Satb1 | SATB1 | SATB homeobox 1 | Nucleus | transcription regulator |
| Scg2 | SCG2 | secretogranin II | Extracellular Space | cytokine |
| Slc15a1 | SLC15A1 | solute carrier family 15 (oligopeptide transporter), member 1 | Plasma Membrane | transporter |
| Slc1a1 | SLC1A1 | solute carrier family 1 (neuronal/epithelial high affinity glutamate transporter, system Xag), member 1 | Plasma Membrane | transporter |
| Slc24a5 | Slc24a5 | solute carrier family 24 (sodium/potassium/calcium exchanger), member 5 | Other | other |
| Slc37a2 | SLC37A2 | solute carrier family 37 (glucose-6-phosphate transporter), member 2 | Other | transporter |
| 40424 | SNTB1 | syntrophin, beta 1 (dystrophin-associated protein A1, 59 kDa, basic component 1) | Plasma Membrane | other |
| St6galnac3 | ST6GALNAC3 | ST6 (alpha-N-acetyl-neuraminyl-2,3-beta-galactosyl-1,3)-N-acetylgalactosaminide alpha-2,6-sialyltransferase 3 | Cytoplasm | enzyme |
| Tex12 | TEX12 | testis expressed 12 | Nucleus | other |
| Tex15 | TEX15 | testis expressed 15 | Extracellular Space | other |

TABLE 9-continued

The genes listed were expressed at levels 20-fold higher in rat ES cells than the corresponding genes in mouse ES cells.

| ID | Symbol | Entrez Gene Name | Location | Type(s) |
|---|---|---|---|---|
| Tfap2a | TFAP2A | transcription factor AP-2 alpha (activating enhancer binding protein 2 alpha) | Nucleus | transcription regulator |
| Tmc1 | TMC1 | transmembrane channel-like 1 | Plasma Membrane | other |
| Tmem130 | TMEM130 | transmembrane protein 130 | Other | other |
| Tmem30b | TMEM30B | transmembrane protein 30B | Other | other |
| Tomm20 | TOMM20 | translocase of outer mitochondrial membrane 20 homolog (yeast) | Cytoplasm | transporter |
| Tox3 | TOX3 | TOX high mobility group box family member 3 | Other | other |
| Ttc25 | TTC25 | tetratricopeptide repeat domain 25 | Cytoplasm | other |
| Tymp | TYMP | thymidine phosphorylase | Extracellular Space | growth factor |
| Ubb | Ubb | ubiquitin B | Cytoplasm | other |
| Vamp7 | VAMP7 | vesicle-associated membrane protein 7 | Cytoplasm | transporter |
| Wfdc12 | Wfdc12 | WAP four-disulfide core domain 12 | Extracellular Space | other |
| Wfdc15a | Wfdc15a | WAP four-disulfide core domain 15A | Other | other |
| Wfdc6a | Wfdc6a | WAP four-disulfide core domain 6A | Other | other |

TABLE 10

A subset of genes from Table 9, which are expressed at levels 20-fold higher in rat ES cells than the corresponding genes in mouse ES cells.

| ID | Entrez Gene Name |
|---|---|
| Ajap1 | Adheres Junctions Associate Protein |
| Cldn5 | Claudin 5 |
| Arhgef9 | Cdc42 guanine nucleotide exchange factor 9 |
| Camk4 | Calcium/calmodulin-dependent protein kinase IV |
| Efna1 | ephrin-A1 |
| Epha4 | EPH receptor A4 |
| Gjb5 | gap junction protein beta 5 |
| Igfbpl1 | Insulin-like growth factor binding protein-like 1 |
| Il1f8 | Interleukin 36 beta |
| Il28ra | Interleukin 28 receptor, alpha |
| Lefty1 | left-right determination factor 1 |
| Lifr | Leukemia inhibitory factor receptor alpha |
| Lpar2 | Lysophosphatidic acid receptor 2 |
| Ntm | Neuronal pentraxin receptor |
| Ptpn18 | Protein tyrosine phosphatase non-receptor type 18 |
| Cdx2 | Caudal type homeobox 2 |
| Fank1 | Fibronectin type III and ankyrin repeat domains 1 |
| Foxe1 | Forkhead box E1 (thyroid transcription factor 2) |
| Hey2 | Hairy/enhancer-of-split related with YRPW motif 2 |
| Lef1 | Lymphoid enhancer-binding factor 1 |
| Sall3 | Sal-like 3 (*Drosophila*) |
| Satb1 | SATB homeobox 1 |

An additional molecular signature employing the pluripotency markers/genes for the rat ES cells has also been developed. Table 11 provides a gene list and their expression ranks from the RNA profiling data. mRNA was isolated from rat ES cells and the expression level of various markers were compared relative to each other. The term "rank" means the comparative expression levels of individual genes: the higher the rank (1 is highest), the higher the expression. For example, Oct4's rank of 13 means that, of all the genes assayed, it was expressed higher than all but 12 genes. Background in this experiment was any expression value below 30; 6107 genes had expression values of 30 or higher.

TABLE 11

Rat ES cell molecular signature employing various pluripotency, mesodermal, endodermal, neural and trophectoderm markers/genes.

| Pluripotency | Pluripotency Rank | Mesodermal | Mesodermal Rank | Endodermal | Endodermal Rank | Neural | Neural Rank | Trophectoderm | Trophectoderm Rank |
|---|---|---|---|---|---|---|---|---|---|
| c-Myc | 8248 | Brachyury | 7542 | Gata6 | 11195 | Nestin | 7761 | Cdx2 | 739 |
| Dnmt3L | 127 | Flk1 | Not tested | Sox17 | 11418 | Pax6 | 13570 | | |

TABLE 11-continued

Rat ES cell molecular signature employing various pluripotency, mesodermal, endodermal, neural and trophectoderm markers/genes.

| Pluripotency | Pluripotency Rank | Mesodermal | Mesodermal Rank | Endodermal | Endodermal Rank | Neural | Neural Rank | Trophectoderm | Trophectoderm Rank |
|---|---|---|---|---|---|---|---|---|---|
| Dppa2 | Not tested | Nodal | 3050 | Hhex1 | 4571 | Sox2 | 681 | | |
| Dppa5 | Not tested | Bmp4 | 3072 | Nodal | 3050 | | | | |
| Ecat1 | 9714 | Bmpr2 | 6382 | Ext1 | 6091 | | | | |
| Eras | 2541 | | | Sox7 | 10284 | | | | |
| Err-beta | 1368 | | | | | | | | |
| Fbxo15 | 1369 | | | | | | | | |
| Fgf4 | 3440 | | | | | | | | |
| Fthl17 | Not tested | | | | | | | | |
| Gdf3 | 2771 | | | Rank >6107 = bkg expression | | | | | |
| Klf4 | 836 | | | | | | | | |
| Lef1 | 1313 | | | | | | | | |
| LIF receptor | 724 | | | | | | | | |
| Lin28 | 828 | | | | | | | | |
| Nanog | 774 | | | | | | | | |
| Oct4 | 13 | | | | | | | | |
| Rexo1 | 6119 | | | | | | | | |
| Sox15 | 4524 | | | | | | | | |
| Sox2 | 681 | | | | | | | | |
| SSEA1 | Not tested | | | | | | | | |
| SSEA4 | Not tested | | | | | | | | |
| Stella | Not tested | | | | | | | | |
| Tcl1 | Not tested | | | | | | | | |
| Utf1 | 1501 | | | | | | | | |

Example 2: Inactivation of Genomic Loci in Rats 2.1: Inactivation of Endogenous Genomic Loci Using an Endonuclease Agent In order to introduce a mutant allele at an endogenous rat genomic locus, the rat ES cells described herein are electroporated with expression vectors (or mRNA) that express ZFNs 1 and 2 (or TALENs 1 and 2). These proteins bind their target sequences on opposite strands, separated by about 6 bp to about 40 bp. A double-stranded break is formed within the target locus, which the cell attempts to repair by Non-Homologous End-Joining (NHEJ). In many cases, NHEJ results in creation of a deletion, which often disrupts the function of the gene (most often by producing a frameshift mutation). In order to identify a positive clone comprising a mutant allele, the electroporated cells are plated at low density, because no drug selection is done. Colonies are picked and assayed at the target site to see if a mutation was produced (e.g., using a modification of allele (MOA) assay described above). The selected ES cells comprising the mutant allele are then introduced into a host rat embryo, for example, a pre-morula stage or blastocyst stage rat embryo, and implanted in the uterus of a surrogate mother to generate a founder rat (F0 rat). Subsequently, the founder rat is bred to a wild-type rat to create F1 progeny heterozygous for the mutant allele. Mating of the heterozygous F1 rat can produce progeny homozygous for the mutant allele.

2.2.: Rat ESC Targeting for the Inactivation of the Rat Apolipoprotein E (ApoE) Gene Using Zinc Finger Nucleases Zinc finger nucleases use sequence specific modular DNA binding domains to direct endonuclease activity to unique target sequence in the genome. ZFNs are engineered as a pair of monomers. Each monomer contains nonspecific cleavage domain from FokI endonuclease fused to 3 or more zinc finger DNA-binding domains. Each zinc finger binds a 3 bp subsite and specificity is achieved by the combined target sites of both monomers. ZFNs produce double-stranded breaks (DSB'S) in DNA, and mutations (insertions or deletions) frequently occur during non-homologous end joining (NHEJ). DSBs also stimulate homology-directed repair (HDR) by homologous recombination if a donor sequence is provided with ZFN.

Such ZFNs were employed in combination with the various methods and compositions described herein to improve targeting efficiency. The rat Apolipoprotein E (ApoE) locus was targeted as described in Example 3.2(a)(i), except expression vectors that express ZFNs 1 and 2 were also introduced into the rat ES cells. See FIG. 10 which provides a schematic of the ApoE targeting event in combination with rTZFN1P and rTZFN2P. The targeting efficiency was determined as discussed below in Example 6 and results are shown in FIG. 11. Surprisingly, the targeting efficiency went up 8-10 fold.

A plasmid targeting vector was built with a self-deleting drug selection cassette and a lacZ gene as a reporter gene. Good targeting efficiency was achieved and a high % chimeras were produced. Zinc finger nucleases (ZFNs) were also tested in combination with targeting vectors to examine its effect on improving targeting efficiency. The targeting vector was co-expressed with the expression vectors for 2 ZFN pairs that cut the ApoE locus. The rat ESC clones electroporated with both the targeting vector and a set of the ZFNs showed a targeting efficiency of 8-10 fold higher than that of rat ESC clones electroporated with a targeting vector alone. Moreover, bi-allelic homozygous targeting in about 2% of our clones was detected. High % chimeras from two of these targeted clones were obtained.

Figure 17:
FIG. 17 provides a summary of the chimera production and germline transmission of the modified rat ApoE locus. The targeted modification was assisted by zinc finger nucleases.

The ApoE-targeted (with ZFN assistance) rat ESC clones were microinjected into SD blastocysts, which were then transferred to pseudopregnant SD recipient females, using standard techniques. Chimeras were identified by coat color; male F0 chimeras were bred to SD females. Germline F1 pups were genotyped for the presence of the targeted ApoE allele (FIG. 17). There was a high % chimeras from two of these targeted clones.

An ApoE knockout rat provides a means to study various types of disorders and diseases. In humans, Apolipoprotein is found in chylomicron, HDL, LDL and VLDL. ApoE is essential for the normal catabolism of triglyceride-rich lipoprotein constituents. Defects in APOE result in numerous disease states including, for example, familial hypercholesterolemia, hyperlipemia, betalipoproteinemia, familial dysbetalipoproteinemia, type III hyperlipoproteinemia (HLP III), risk of coronary artery disease. One isoform (ApoE4) is associated with late-onset familial and sporadic Alzheimer's disease, possibly with MS as well.

In mice, ApoE is primarily found in HDL; transports cholesterol, as in humans. ApoE-deficient mice (2 independent KOs) have 5 times normal plasma cholesterol; developed foam cell-rich depositions in their proximal aortas by age 3 months (comparable to human syndrome).

ApoE knockouts in rats offer an animal model to study endothelial function, including, but not limited to, plaque formation, transcriptional changes (RNA-Seq), ex vivo function. Moreover, larger size of rats would facilitate all these assays and potentially improve the quality of the RNA-Seq data.

Figure 18:
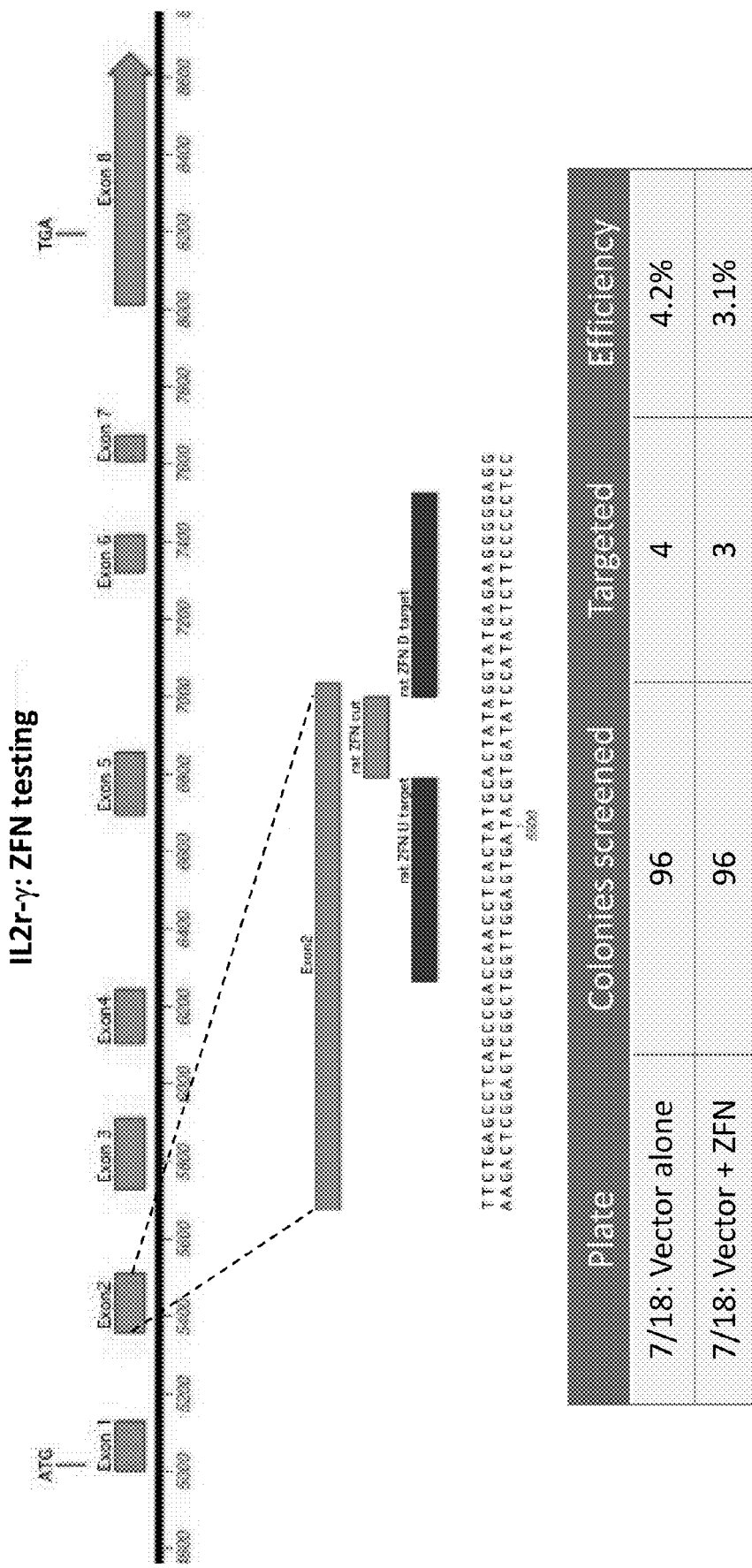
FIG. 18 provides a schematic of the IL2r-γ targeting event in combination with zinc finger nucleases that target ZFN U and ZFN D. ZFN cut sites are noted in the figure.

2.3. Inactivation of the Rat Interleukin-2 Receptor Gamma (IL2r-γ) Locus Using Zinc Finger Nucleases The rat Interleukin-2 receptor gamma (IL2r-γ) locus was targeted as described in Example 3.3(a), except that expression vectors that express ZFN U (ZFN upstream) and ZFN D (ZFN downstream) were also introduced into the rat ES cells. FIG. 18 provides a schematic of the IL2r-γ targeting event in combination with ZFN U and ZFN D. The sequence of the IL2r-γ locus which these zinc fingers bind is denoted in FIG. 18. The targeting efficiency was determined as discussed below in Example 3.3(a) and the results are shown in FIG. 18. Briefly, homozygously targeted clones were confirmed by PCR. For the ZFN1 pair: 173 mutant clones out of 192 screened (90%) and for the ZFN2 pair: 162 clones out of 192 (84%) screened.

The IL2r-γ-targeted (with ZFN assistance) rat ESC clones were microinjected into SD blastocysts, which were then transferred to pseudopregnant SD recipient females, using standard techniques. Chimeras were identified by coat color; male F0 chimeras were bred to SD females. Germline F1 pups were genotyped for the presence of the targeted IL2r-γ allele.

2.4.: Inactivation of the Rat Interleukin-2 Receptor Gamma (IL2r-γ) Using CRISPR/Cas9

Figure 19:
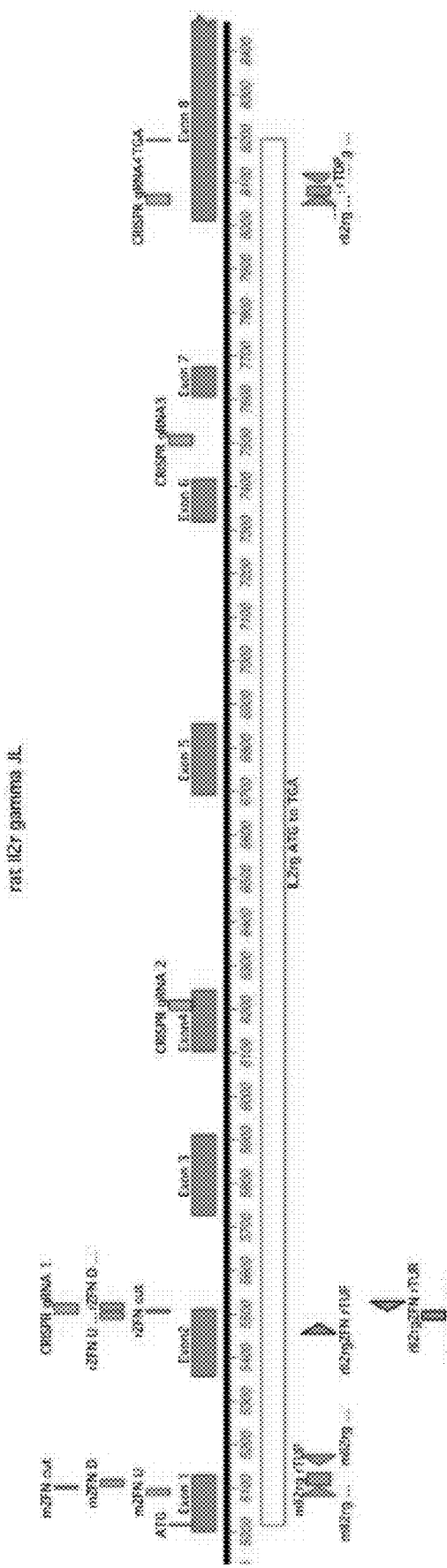
FIG. 19 provides the targeting efficiency when targeting IL2r-γ in combination with the CRISPR/Cas9 system.

The rat IL2r-γ locus was targeted as described in Example 3.3(a), except that the CRISPR/Cas9 system was also introduced into the rat ES cells to aid in targeting efficiency. SBI: System Biosciences Cas9 "SmartNuclease" all-in-one vectors were employed and Cas9 expression was driven by CAG, EF1a, PGK, or CMV promoter. Custom gRNA was ligated into a vector and expressed by H1 promoter. 4 gRNAs against Il2rg were designed. The targeting efficiency when employing the various guide RNAs is shown in FIG. 19.

Example 3: Targeted Modification of Rat Genomic Loci 3.1: Rat ESC Targeting: The Rat Rosa 26 Locus.

The rat Rosa26 locus lies between the Setd5 and Thumpd3 genes as in mouse, with the same spacing. The rat Rosa 26 locus (FIG. 12, Panel B) differs from the mouse Rosa 26 locus (FIG. 12, Panel A). The mouse Rosa26 transcripts consist of 2 or 3 exons. The rat locus contains a 2nd exon 1 (Ex1b) in addition to the homologous exon to mouse exon1 (Ex1a). No 3rd exon has been identified in rat. Targeting of a rat Rosa26 allele is depicted in FIG. 12 (bottom), where homology arms of 5 kb each were cloned by PCR using genomic DNA from DA rat ESC. The targeted allele contains a SA (splicing acceptor)-lacZ-hUb-neo cassette replacing a 117 bp deletion in the rat Rosa26 intron.

Targeting efficiency at the rat Rosa 26 locus was determined (Table 12). Linearized vector was electroporated into DA or ACI rat ESCs, and transfected colonies were cultured in 2i media+G418, using standard techniques. Individual colonies were picked and screened using a Loss of Allele (LOA) assay (Valenzuela, D. et al. (2003) High-throughput engineering of the mouse genome coupled with high-resolution expression analysis, Nature Biotech. 21:652-660, incorporated herein by reference).

TABLE 12

| | rat Rosa26 Targeting Efficiency | | |
|---|---|---|---|
| Cell line | Colonies picked | Reconfirmed positives | Targeting efficiency (%) |
| DA.2B | 192 | 4 | 2.1 |
| ACI.G1 | 96 | 4 | 4.2 |

Chimera Production and Germline Transmission Using Rosa26-Targeted Rat ESC Clones.

Reconfirmed Rosa26-targeted rat ESC clones were microinjected into SD blastocysts, which were then transferred to pseudopregnant SD recipient females, using standard techniques. Chimeras were identified by coat color; male F0 chimeras were bred to SD females. Germline (agouti) F1 pups were genotyped for the presence of the targeted Rosa26 allele; nine of 22 agouti pups genotyped as heterozygous at the Rosa26 locus (Table 13).

TABLE 13

| Germline Transmission Using Targeted Rosa26 rESC | | | | | | |
|---|---|---|---|---|---|---|
| Cell line | R26 clones injected | Clones producing Chimeras | Germline Transmitting Clones | Total Pups | rESC-derived Pups | ESC-derived pups (%) |
| DA.2B | 4 | 3 | 2 | AH7: 64 AE3: 112 DE9: 39 | AH7: 41 AE3: 6 DE9: 4 | AH7: 63 AE3: 3 10 |
| ACI.G1 | 4 | 4 | 1 | | | |

3.2. (a)(i): Targeting of the Rat Apolipoprotein E (ApoE) Locus.

Figure 20:
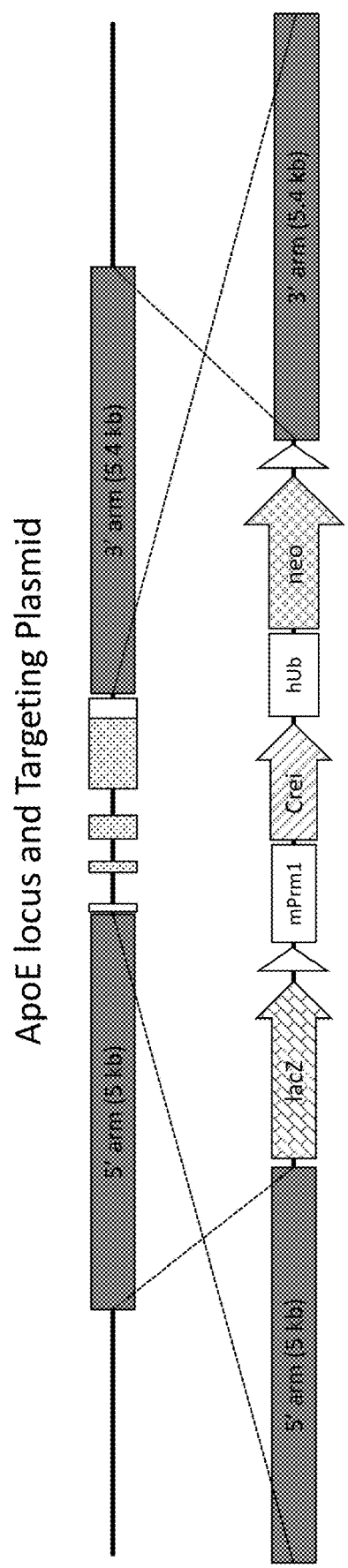
FIG. 20 provides a schematic of the rat ApoE locus and a targeting plasmid. The upper schematic shows the genomic structure of the rat ApoE locus and the genomic regions corresponding to the 5' and 3' homology arms (5 kb and 5.4 kb respectively; dark grey boxes). Exon 1 of the ApoE gene is non-coding and is shown as an open box closest to the 5' homology arm. The three introns of the ApoE gene are denoted as lines. Exons 2 and 3 comprise coding regions and are shown as stippled grey boxes. Exon 4 contains both coding and non-coding sequences as denoted by the stippled grey shading and the open box. The lower panel shows the targeting plasmid. The 5' and 3' homology arms (5 kb and 5.4 kb, respectively) are denoted by the dark grey boxes. The targeting vector comprises a reporter gene (lacZ) and a self-deleting cassette flanked by loxP sites (open arrows). The self-deleting cassette comprises a mouse Prm1 promoter operably linked to the Crei gene and a drug selection cassette comprising a human ubiquitin promoter operably linked to a neomycin resistance gene.

The rat Apolipoprotein E (ApoE) locus was targeted to disrupt ApoE function. Targeting of the ApoE locus was done using a targeting vector comprising a lacZ-hUb-neo cassette flanked with a 5' and 3' homology arms homologous to the ApoE locus. FIG. 20 depicts a genetically modified rat ApoE locus that has been disrupted by a 1.8 kb deletion and the insertion of a lacZ-hUb-neo cassette, which further includes a self-deleting Cre cassette comprising a Crei gene driven by a protamine promoter. The electroporation conditions were as follows: 6 ug DNA; 2.05×10$^6$ cells; 400V; 200 uF: 342 V, 593 usec; plate on 15 cm 2× dense neoR MEFs in 2i+10 uM ROCKi.

Targeting efficiency at the ApoE locus was determined and is shown in Table 14. Linearized vector was electroporated into DA.2B rat ESCs derived from the DA strain, and transfected colonies were cultured using standard techniques. Individual colonies were picked and screened using a Loss of Allele (LOA) assay.

TABLE 14 rat ApoE Targeting Efficiency

| Cell line | Vector | Colonies picked | Targeted | Targeting efficiency (%) |
|---|---|---|---|---|
| DA.2B | ApoE-mSDC | 192 | 7 | 3.7 |
| DA.2B | ApoE-mSDC | 192 | 15 | 7.8 |

Chimera production and germline transmission using ApoE-targeted rat ESC clones was performed. ApoE-targeted rat ESC clones were microinjected into SD blastocysts, which were then transferred to pseudopregnant SD recipient females, using standard techniques. Chimeras were identified by coat color; male F0 chimeras were bred to SD females. F1 pups were genotyped for the presence of the targeted ApoE allele (Table 15).

TABLE 15

Microinjection Results

| Exp | Clone | pups | Chimeras |
|---|---|---|---|
| 1 | ApoE-AF5 | 4 | 3 (90, 90, 90) |
| 2 | ApoE-BC4 | 5 | 0 |

Figure 21:
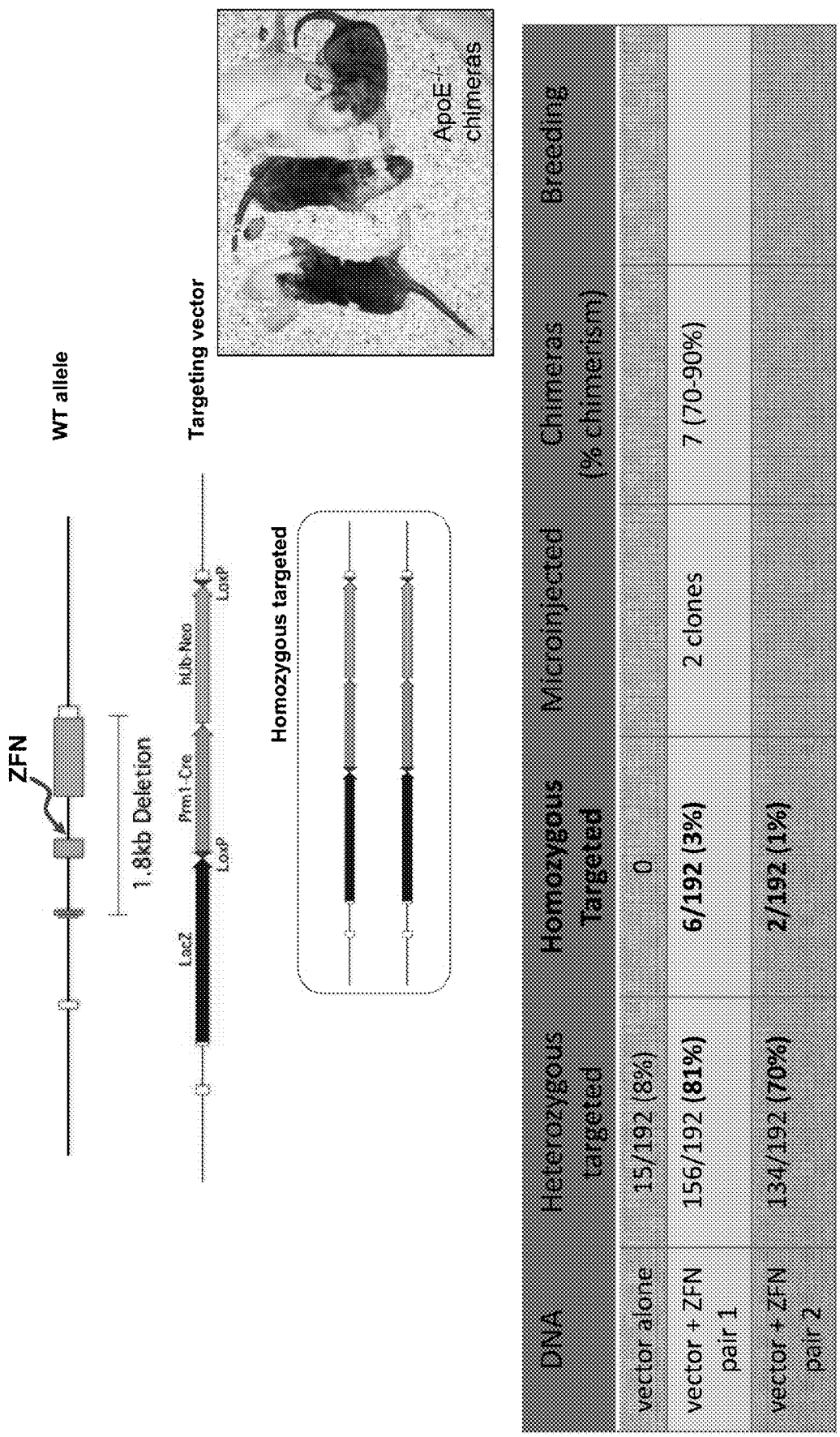
FIG. 21 provides a schematic for targeting the ApoE locus in rat ES cells using zinc-finger nucleases and a targeting vector comprising a reporter gene (LacZ) and a self-deleting cassette comprising a mouse Prm1 promoter operably linked to the Crei gene and a drug selection cassette comprising a human ubiquitin promoter operably linked to a neomycin resistance gene.

Additional targeting data for ApoE is also provided in FIG. 21.

3.2.(a)(ii). Targeting ApoE in Rats with a Targeting Vector

FIG. 20 provides a schematic of the rat ApoE locus and a targeting plasmid. The upper schematic of FIG. 20 shows the genomic structure of the rat ApoE locus and the genomic regions corresponding to 5' and 3' homology arms (5 kb and 5.4 kb, respectively; dark grey boxes). Exon 1 of ApoE is non-coding and is shown as an open box closest to the 5' homology arm. The 3 introns of ApoE are denoted as lines and exons 2 and 3 comprise coding regions and are shown as stippled grey boxes. Exon 4 contains both coding and non-coding sequences as denoted by the stippled grey shading and the open box.

The lower schematic in FIG. 20 is the targeting vector. The 5' and 3' homology arms (5 kb and 5.4 kb respectively) are denoted by the dark grey boxes. The targeting vector comprises a reporter gene (lacZ) and a self-deleting cassette flanked by loxP sites (open arrows). The self-deleting cassette comprises the Crei gene operably linked to a mouse Prm1 promoter and a selection cassette comprising a neomycin resistance gene operably linked to a human ubiquitin promoter.

The Crei gene comprises two exons encoding a Cre recombinase, which are separated by an intron (Crei) to prevent its expression in a prokaryotic cell. See, See, for example, U.S. Pat. No. 8,697,851 and U S Application Publication 2013-0312129, which describe the self-deleting cassette in detail and are hereby incorporated by reference in their entirety. By employing the Prm1 promoter, the self-deleting cassette can be deleted specifically in male germ cells of F0 rats. The targeting vector was electroporated into the rat ES cells obtained in Example 1 and the cells were plated on 15 cm 2× dense neomycin-resistant MEFs in 2i+10 uM ROCKi. The transformed rat ES cells were cultured, selected, and maintained as described in Example 1.

As shown in Table 23, 384 colonies were screened and 23 targeted clones were obtained. The targeting efficiency was 5.99%. 3 clones were injected into blastocysts as described herein in Example 1. 3 clones producing chimeras were obtained and 2 of the clones transmitted the targeted modification through the germline.

3.2.(a)(iii). Targeting ApoE in Rats with a Targeting Vector in Combination with Zinc Finger Nucleases The targeting vector employed in Example 3.2(a)(ii) was used in combination with zinc finger nucleases to target the rat ApoE locus. Table 16 provides a summary of the genomic organization of the rat ApoE locus. The positions shown in the Table 16 were taken from build 5.0 of the Reference Sequence of the rat genome (ENSMBL). ApoE is on chromosome 1 on the (−) strand.

TABLE 16

Summary of the rat ApoE locus and the positions of the zinc finger nuclease binding sites and cutting sites.

| Feature | Start | End | length | Notes |
|---|---|---|---|---|
| Exon 1 | 81881110 | 81881182 | 73 | 5' non-coding |
| Exon2 | 81880269 | 81880332 | 64 | contains ATG |
| ATG | 81880309 | 81880311 | 3 | start codon |
| Exon3 | 81879607 | 81879775 | 169 | |
| ZFN1a binding site | 81879707 | 81879693 | 15 | CAGGCCCTGAACCGC (SEQ ID NO: 10) |
| ZFN1 cutting site | 81879692 | 81879687 | 6 | TTCTGG (SEQ ID NO: 11) |
| ZFN1b binding site | 81879686 | 81879671 | 16 | GATTACCTGCGCTGGG (SEQ ID NO: 12) |
| Intron 3-4 | 81879776 | 81879207 | 400 | |
| ZF21a binding site | 81879591 | 81879577 | 15 | TTCACCCTCCGCACC (SEQ ID NO: 13) |
| ZFN2 cutting site | 81879576 | 81879570 | 7 | TGCTGAG (SEQ ID NO: 14) |
| ZF21b binding site | 81879569 | 81879552 | 18 | TATCCAGATCCAGGGGTT (SEQ ID NO: 15) |

TABLE 16-continued

Summary of the rat ApoE locus and the positions of the zinc
finger nuclease binding sites and cutting sites.

| Feature | Start | End | length | Notes |
|---|---|---|---|---|
| Exon 4 | 81878371 | 81879208 | 838 | contains TGA |
| TGA | 81878482 | 81878484 | 3 | |
| ApoE deletion | 81878482 | 81880311 | 1830 | |

Figure 10:
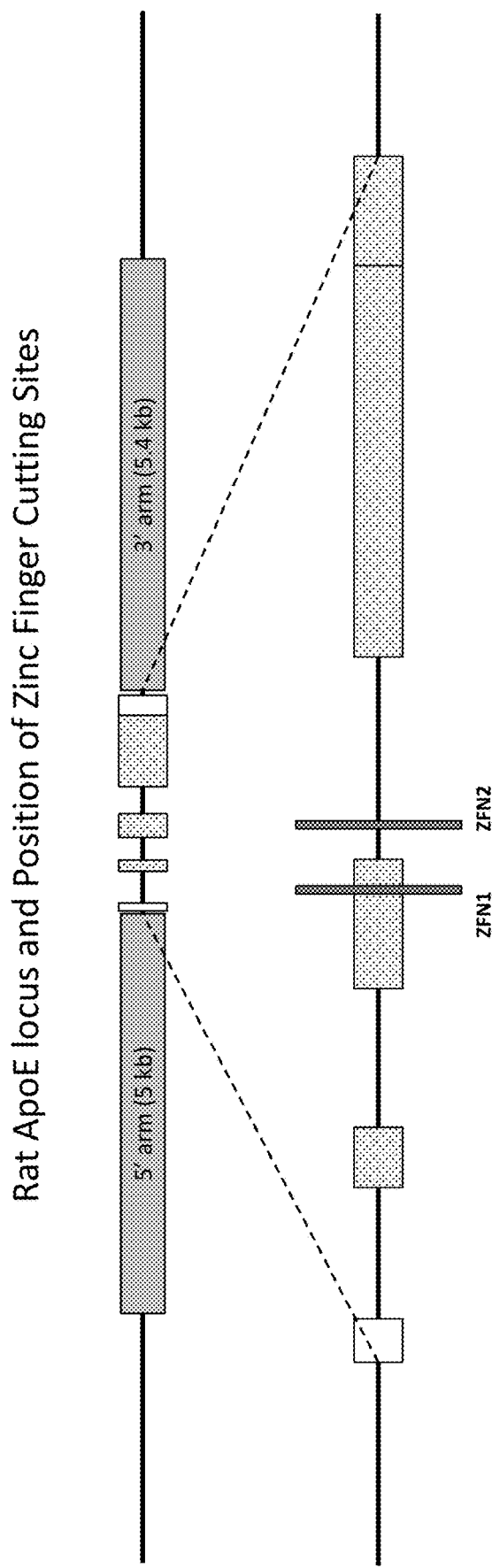
FIG. 10 provides a schematic of the rat ApoE locus and denotes with grey bars the cutting site for zinc finger nucleases (ZFN1 and ZFN2). The genomic regions corresponding to the 5' and 3' homology arms (5 kb and 5.4 kb, respectively) are denoted by the dark grey boxes. Exon 1 of the ApoE gene is non-coding and is shown as an open box closest to the 5' homology arm. The three introns of the ApoE gene are denoted as lines. Exons 2 and 3 comprise coding regions and are shown as stippled grey boxes. Exon 4 contains both coding and non-coding sequences as denoted by the stippled grey shading and the open box.
Figure 13A:
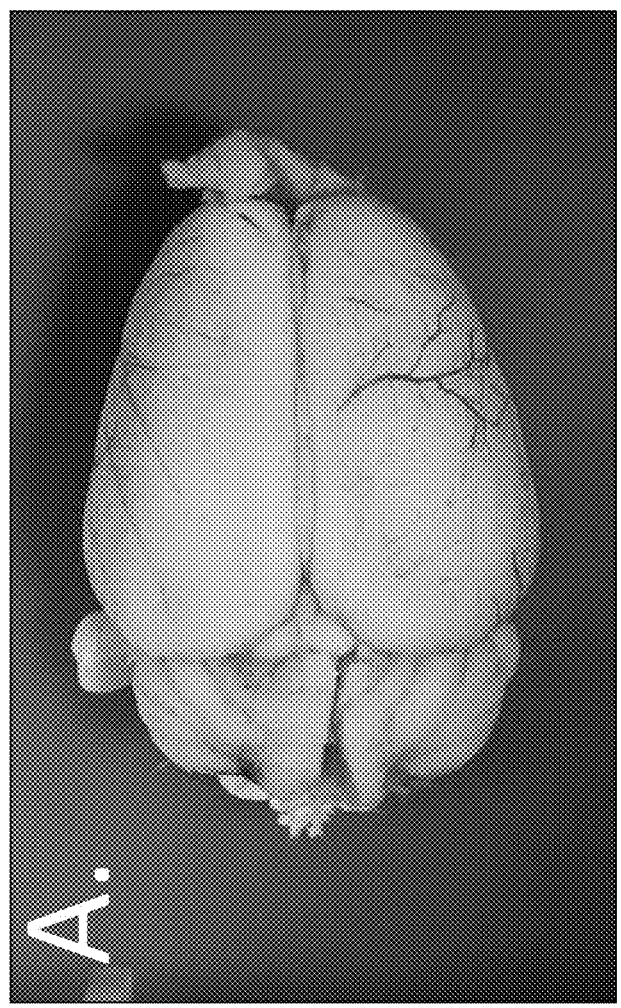
FIG. 13A depicts a control brain of a 14-week-old wild type rat, which was stained with X-gal. The control brain showed a low level of background staining for LacZ (dorsal view).
Figure 13B:
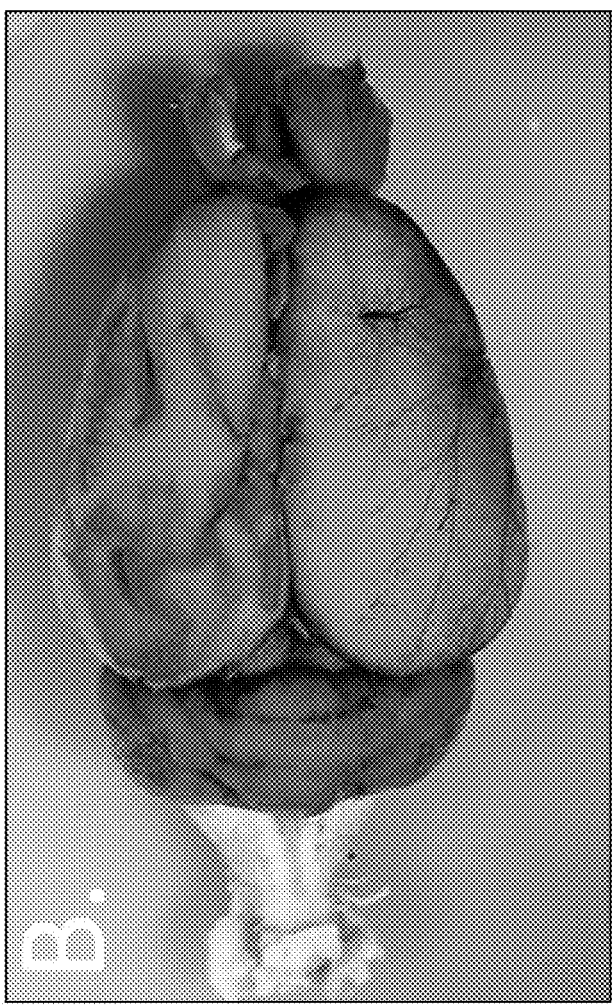
FIG. 13B depicts LacZ expression in the brain of an rRosa26 heterozygous rat (14-week old). The lacZ reporter was expressed ubiquitously throughout the brain of the rRosa26 heterozygote.
Figure 13C:
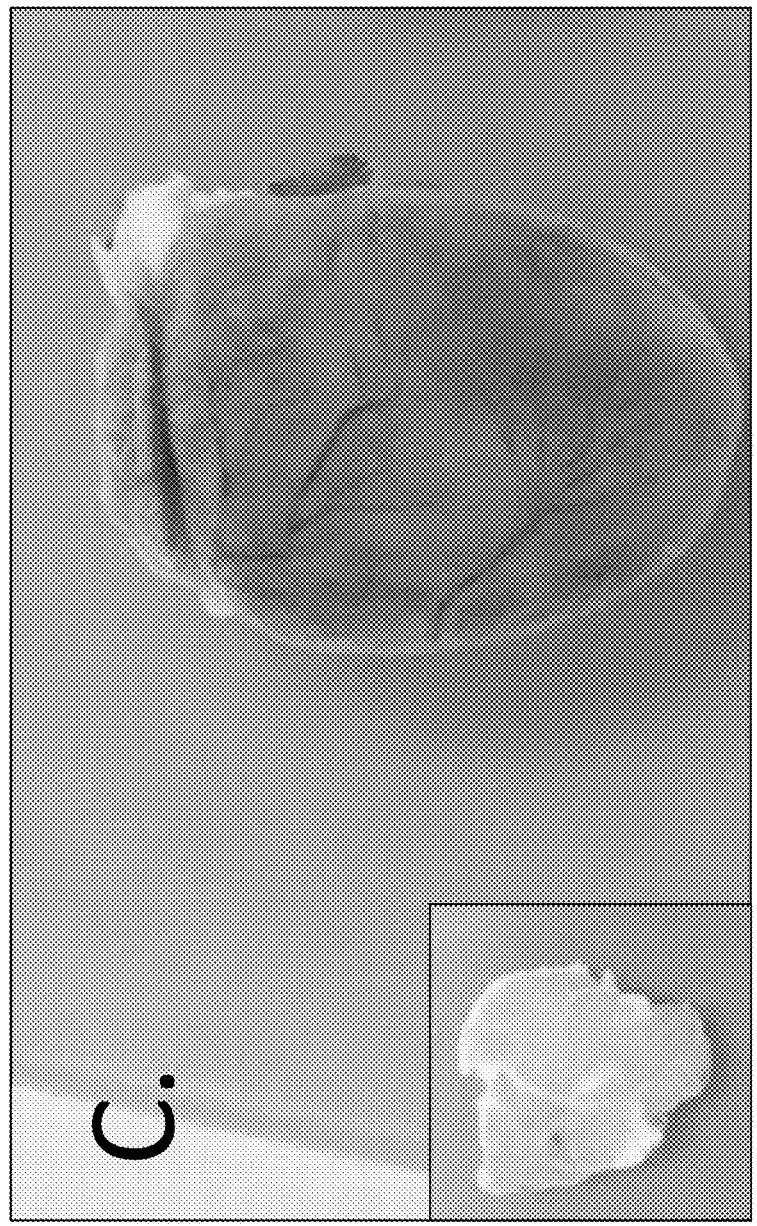
FIG. 13C depicts a control heart and thymus (inset) of a 14-week-old wild type rat, which were treated with X-gal. The control heart and thymus showed a low level of background staining for LacZ.
Figure 13D:
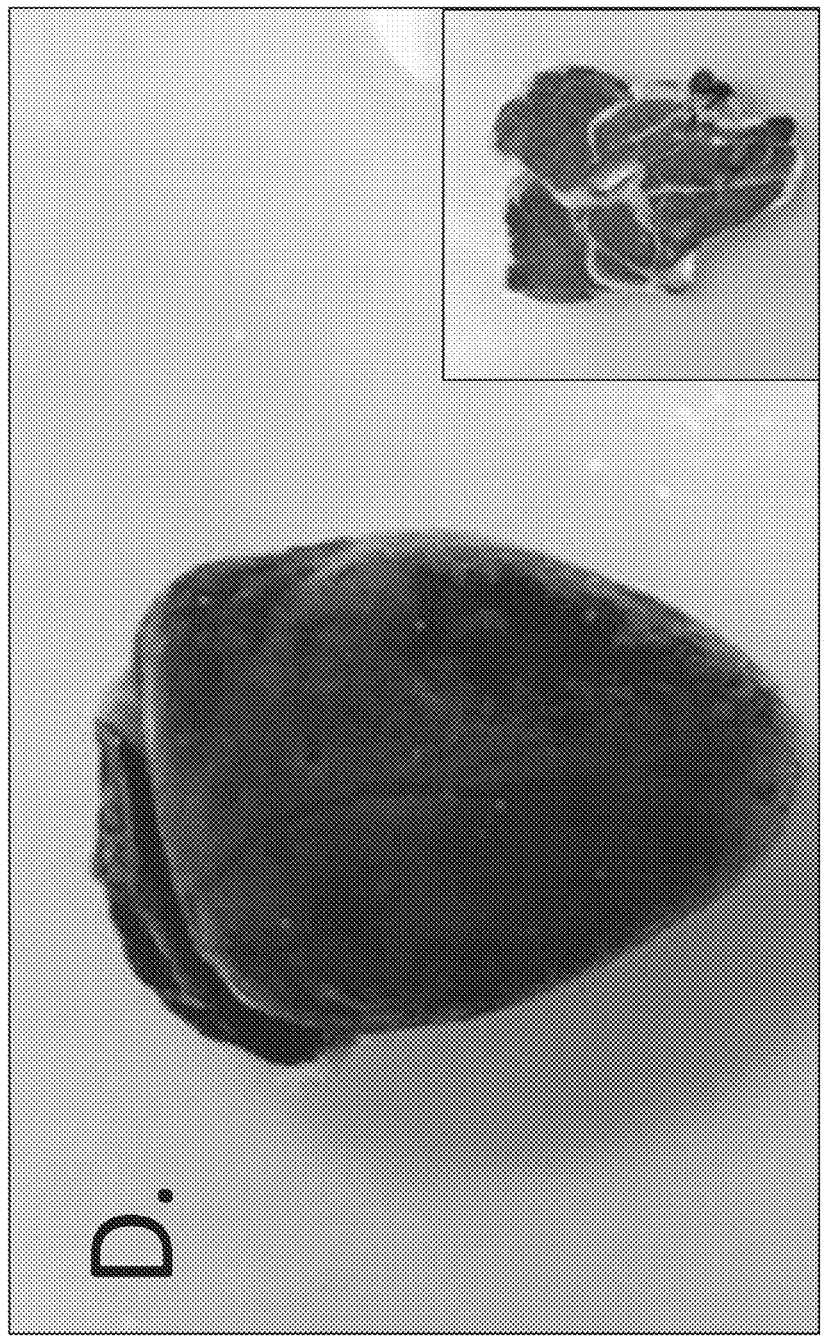
FIG. 13D depicts LacZ expression in the heart and thymus (inset) of a 14-week-old rRosa26 heterozygous rat. The lacZ reporter was expressed ubiquitously throughout the heart and thymus of the rROSA26 heterozygote.
Figure 13E:
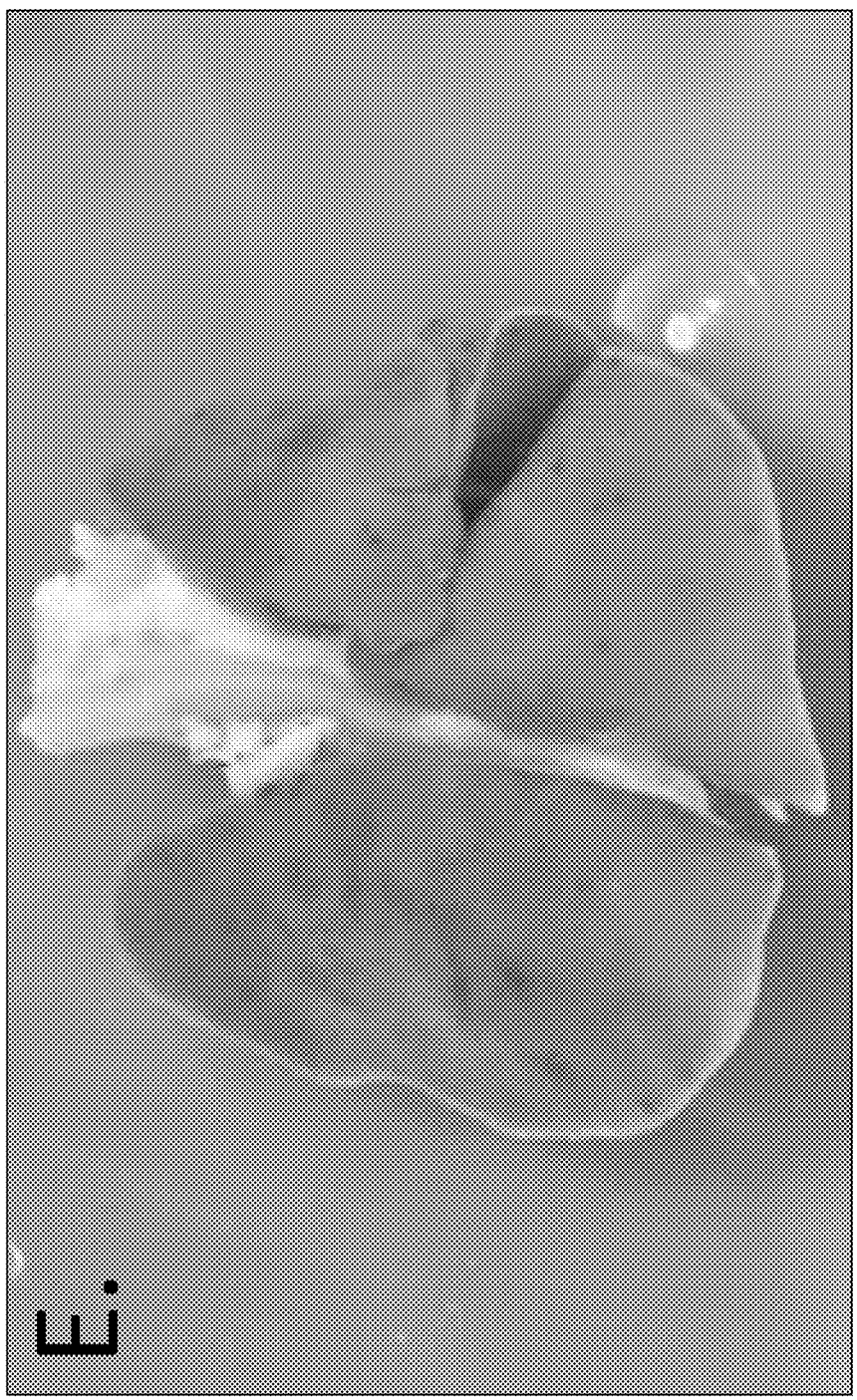
FIG. 13E depicts a control lung of a 14-week-old wild type rat, which was treated with X-gal. The control lung showed a low level of background staining for LacZ.
Figure 13F:
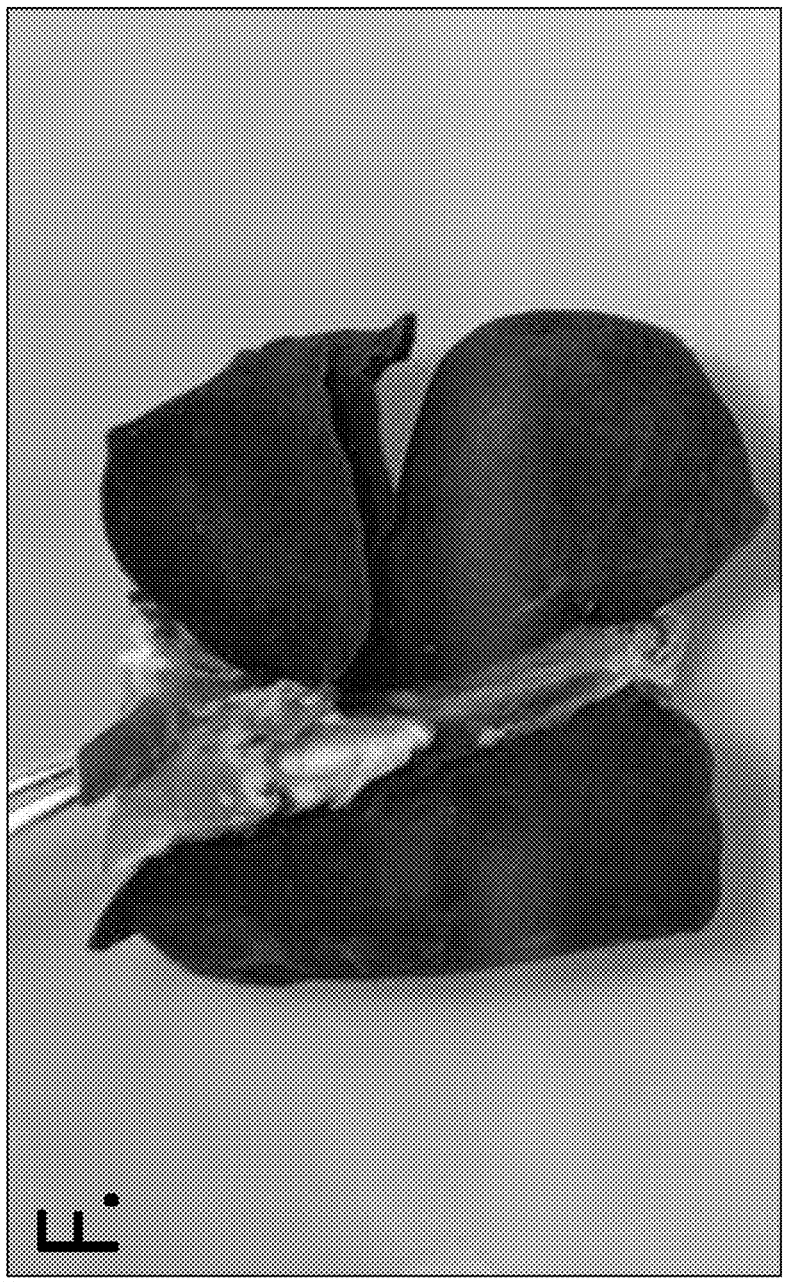
FIG. 13F depicts LacZ expression in the lung of a 14-week-old rRosa26 heterozygote rat. The lacZ reporter was expressed ubiquitously throughout the lung of the rRosa26 heterozygote.
Figure 14:
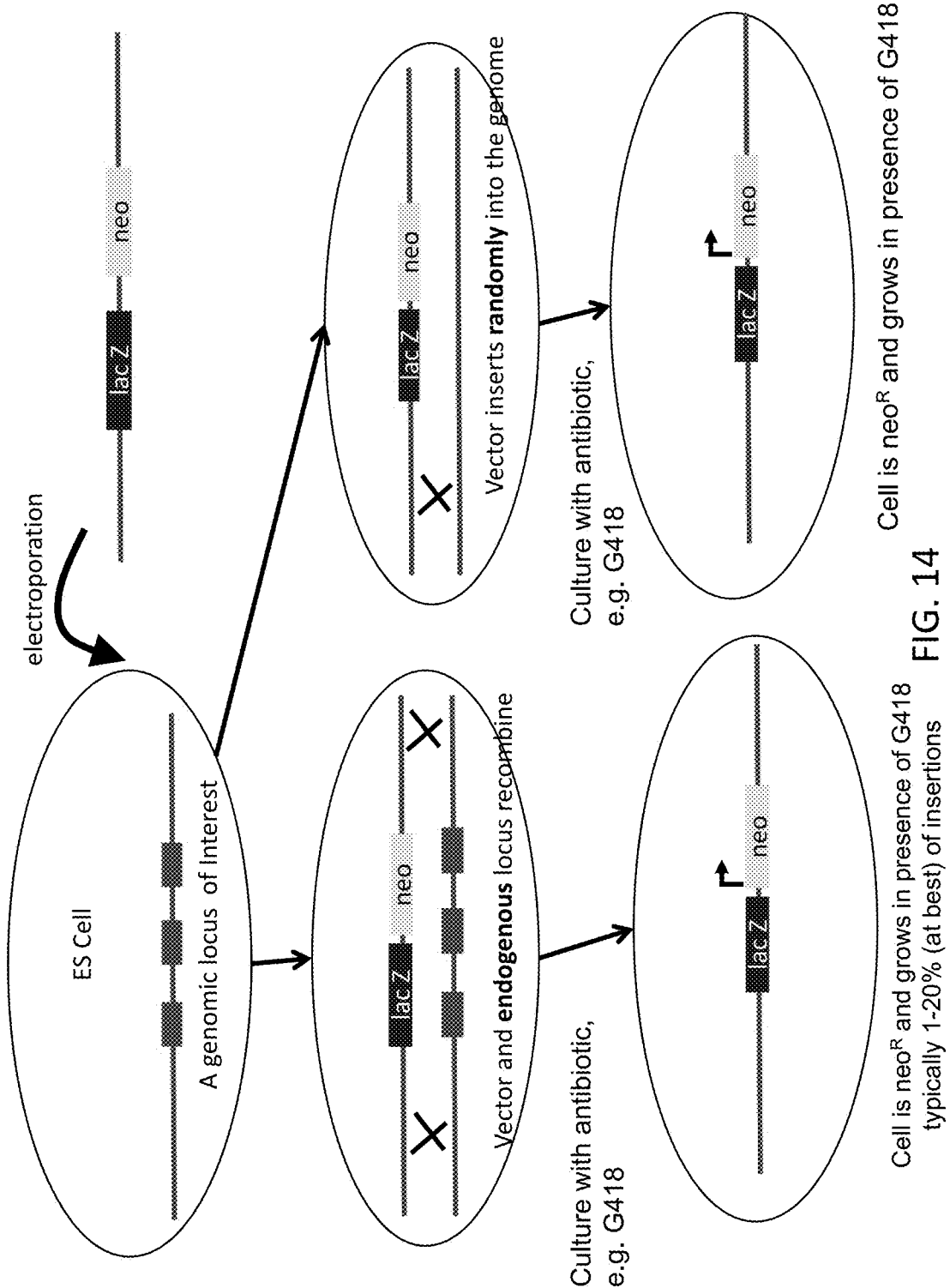
FIG. 14 illustrates a homologous or non-homologous recombination event that occurs inside a rat ES cell following an electroporation of a targeting vector comprising a selection cassette (lacZ-neo cassette).
Figure 15:
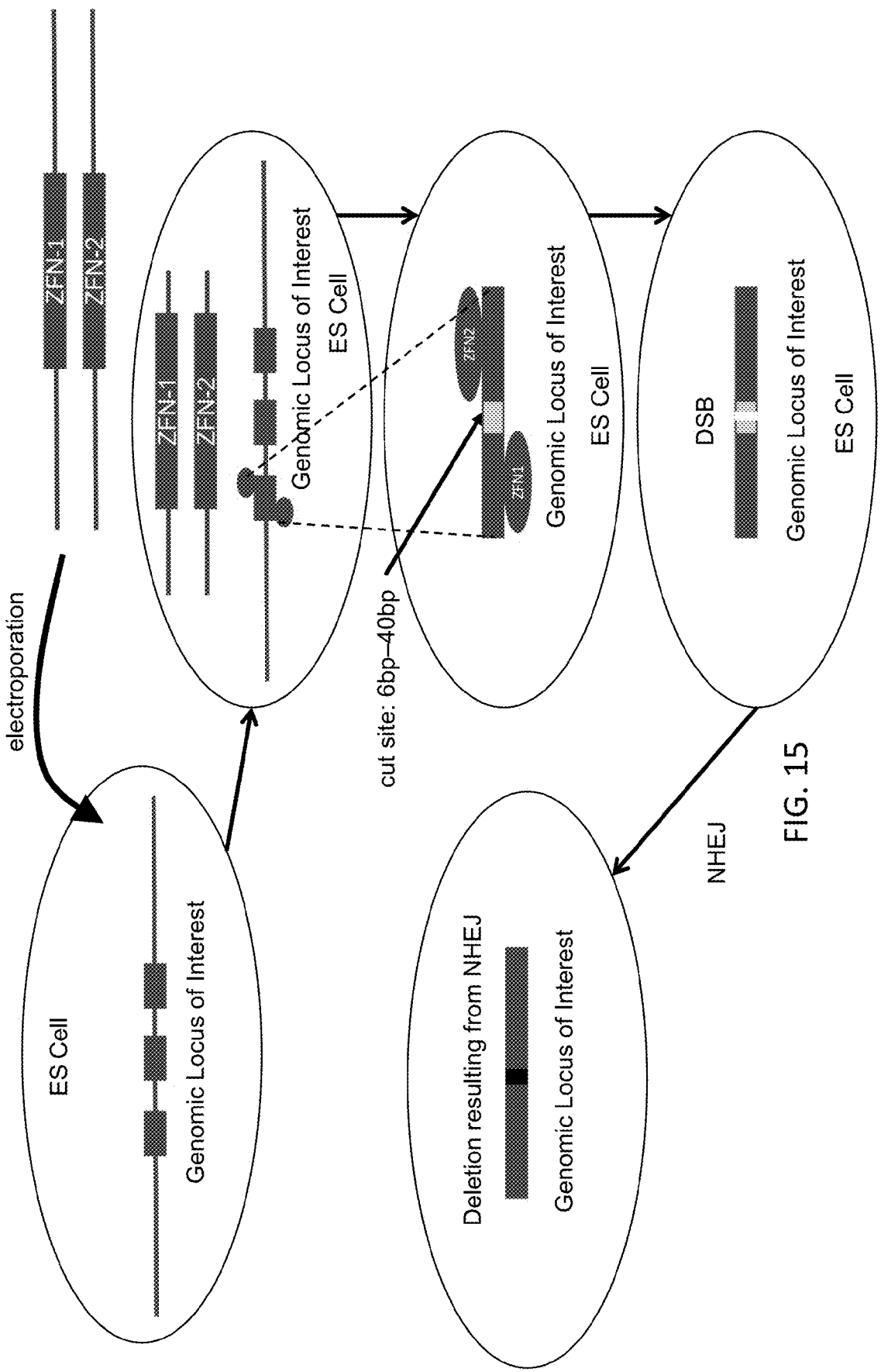
FIG. 15 illustrates the mechanism by which genome-editing endonucleases (e.g., ZFNs and TALENs) introduce a double strand break (DSB) in a target genomic sequence and activate non-homologous end-joining (NHEJ) in an ES cell.
Figure 16:
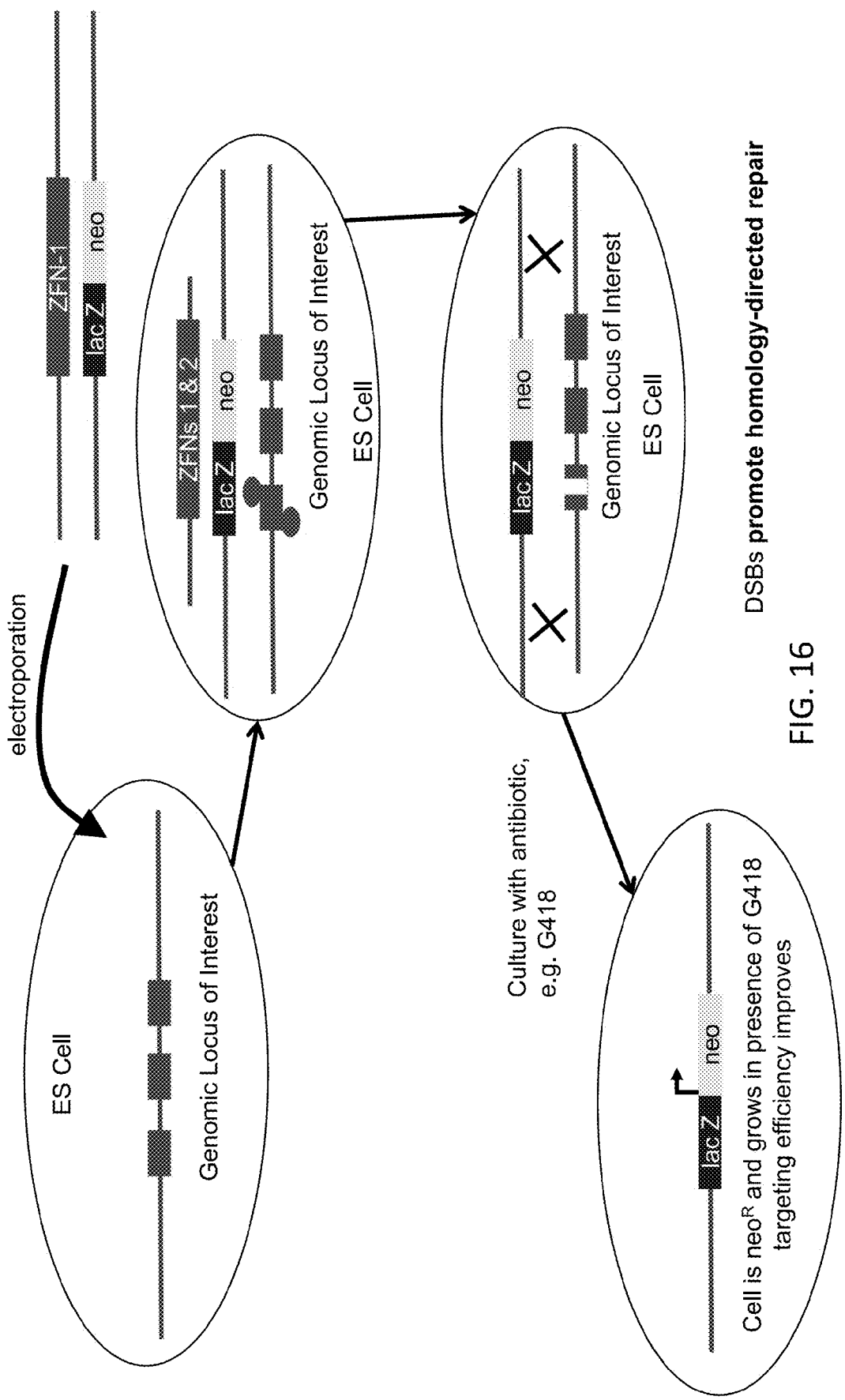
FIG. 16 illustrates a gene targeting technique that utilizes ZFN/TALENs to improve the efficiency of homologous recombination of a targeting vector. DSB represents double strand break.

FIG. 10 provides a schematic of the rat ApoE locus and denotes with grey bars the cutting site for ZFN1 and ZFN2. The cutting site for ZFN1 is in exon 3 and the cutting site for ZNF2 is in intron 3. The exact position of the both ZFN sites is set forth in Table 16. The genomic regions corresponding to the 5' and 3' homology arms (5 kb and 5.4 kb, respectively) are denoted by the dark grey boxes. Exon 1 of ApoE is non-coding and is shown as an open box closest to the 5' homology arm. The three introns of the ApoE gene are denoted as lines and exons 2 and 3 comprise coding regions and are shown as stippled grey boxes. Exon 4 contains both coding and non-coding sequences as denoted by the stippled grey shading and the open box.

The employed targeting vector was the same as that in Example 3.2(a)(ii) and shown in FIG. 20. The ZFNs were introduced as two expression plasmids, one for each half of the ZFN pair. 20 ug of the plasmid for ZFN1 and 20 ug of the plasmid for ZFN2 was used. ZFNs were purchased from Sigma. The expression of each ZFN was driven by the CMV promoter.

The targeting vector were electroporated into the rat ES cells obtained in Example 1 and the cells were plated on 15 cm 2× dense neoR MEFs in 2i+10 uM ROCKi. The transformed rat ES cells were cultured, selected and maintained as described in Example 1.

As shown in Table 23, 384 colonies were screened and 290 targeted clones were obtained. The targeting efficiency was 75.52%. 2 clones were injected into blastocysts as described herein in Example 1. Two clones producing chimeras were obtained and one of the clones transmitted the targeted modification through the germline.

Moreover, employing ZFN1 and ZFN2 produced 8 biallelic targeted clones with an efficiency of 2.08%.

3.2. (b)(i): Targeted Modification of the Rat Apolipoprotein E (ApoE) Locus Using a Large Targeting Vector (LTC).

Figure 22:
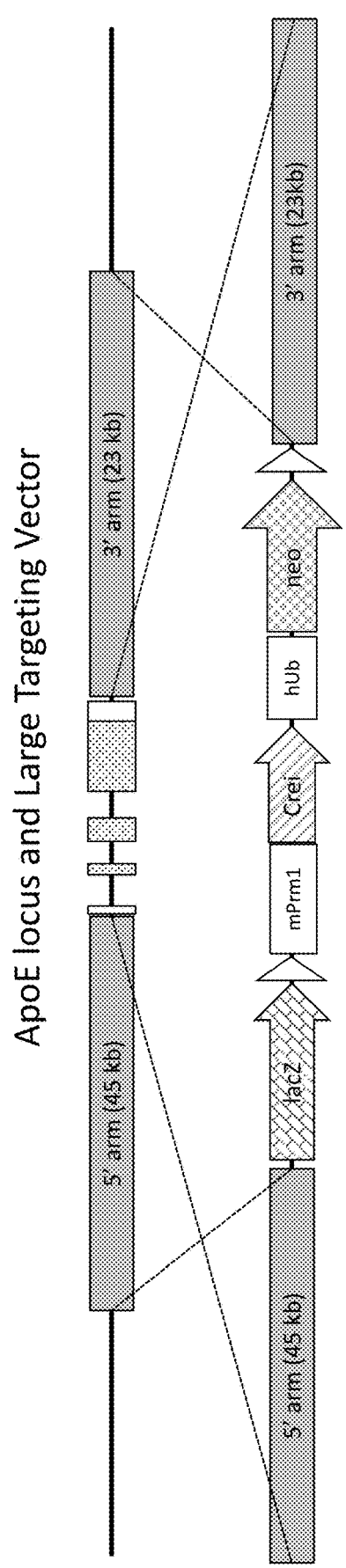
FIG. 22 provides a schematic of the rat ApoE locus and a large targeting vector (LTVEC). The upper panel shows the genomic organization of the rat ApoE locus and the genomic regions corresponding to the 5' and 3' homology arms (45 kb and 23 kb, respectively; the dark grey boxes). Exon 1 of ApoE is non-coding and is shown as an open box closet to the 5' homology arm. The three introns of the ApoE gene are denoted as lines and exons 2 and 3 comprise coding regions and are shown as stippled grey boxes. Exon 4 contains both coding and non-coding sequences as denoted by the stippled grey shading and the open box. The lower panel shows the LTVEC for modifying the rat ApoE locus. The 5' and 3' homology arms (45 kb and 23 kb, respectively) are denoted by the dark grey boxes. The LTVEC comprises a reporter gene (lacZ) and a self-deleting cassette flanked by loxP sites (open arrows), which comprises a mouse Prm1 promoter operably linked to the Crei gene and a drug selection cassette comprising a human ubiquitin promoter operably linked to a neomycin resistance gene.

Targeting of the ApoE locus is done using a large targeting vector (LTVEC) comprising a lacZ-mouse Prm1-Crei cassette flanked with a 5' homology arm to the ApoE locus of about 45 kb and a 3' homology arm to the ApoE locus of about 23 Kb. FIG. 22 depicts the rat ApoE locus in which the ApoE locus has been disrupted by a 1.83 kb deletion and the insertion of the lacZ gene and a self-deleting cassette comprising mPrm1-Crei cassette and a hUb-neo selection cassette. Methods employed in example 3.2(a)(i) can be used to introduce this vector into rat ES cells.

Example 3.2. (b)(ii). Targeting of the Rat ApoE Locus with a Large Targeting Vector (LTVEC)

FIG. 22 provides a schematic of the rat ApoE locus and a large targeting vector (LTVEC). The upper schematic of FIG. 22 shows the genomic organization of the rat ApoE locus and the genomic regions corresponding to the 5' and 3' homology arms (45 kb and 23 kb, respectively; dark grey boxes). Exon 1 of ApoE is non-coding and is shown as an open box closest to the 5' homology arm. The 3 introns of ApoE are denoted as lines and exons 2 and 3 comprise coding regions and are shown as stippled grey boxes. Exon 4 contains both coding and non-coding sequences as denoted by the stippled grey shading and the open box.

The lower schematic in FIG. 22 is the LTVEC. The 5' and 3' homology arms (45 kb and 23 kb, respectively) are denoted by the dark grey boxes. The targeting vector comprises a reporter gene (lacZ) and a self-deleting cassette flanked by loxP sites (open arrows), which comprises the Crei gene operably linked to a mouse Prm1 promoter and a drug selection cassette comprising a neomycin resistance gene operably linked to a human ubiquitin promoter. The Crei comprises two exons encoding the Cre recombinase which are separated by an intron (Crei) to prevent its expression in a prokaryotic cell. See, for example, U.S. Pat. No. 8,697,851 and U.S. Application Publication 2013-0312129, which describes the self-deleting cassette in detail and is hereby incorporated by reference in their entirety. By employing a mouse Prm1 promoter, the self-deleting cassette can be deleted specifically in male germ cells of F0 rat.

The LTVEC was electroporated into the rat ES cells obtained in Example 1 and the cells were plated on 15 cm 2× dense neoR MEFs in 2i+10 uM ROCKi. The transformed rat ES cells were cultured, selected, and maintained as described in Example 1.

As shown in Table 23, 288 colonies were screened and 8 targeted clones were obtained. The targeting efficiency was 2.78%. 3 clones were injected into a host embryo at a blastocyst stage as described herein in Example 2 to produce chimeric rats (F0). Moreover, one biallelic targeted clone was produced providing a biallelic efficiency of 0.35%.

3.2. (b)(iii). Targeting ApoE in Rats with a Large Targeting Vector (LTVEC) in Combination with Zinc Finger Nucleases The LTVEC employed in Example 3.2.(b)(ii) was used in combination with zinc finger nucleases to target the rat ApoE locus. Table 16 provides a summary of the genomic organization of the rat ApoE locus and the positions shown were taken from build 5.0 of the Reference Sequence of the rat genome (ENSMBL).

Figure 23:
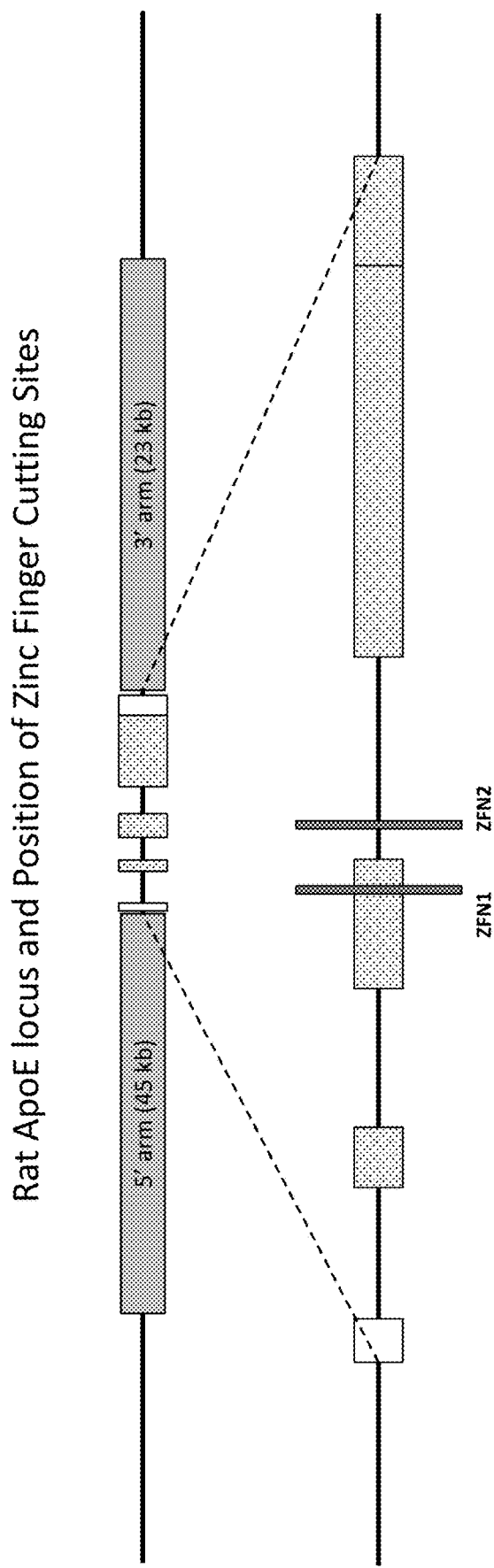
FIG. 23 provides a schematic of the rat ApoE locus and denotes with grey bars the cutting sites for zinc finger nucleases (ZFN1 and ZFN2) used together with the large targeting vector (LTVEC) to enhance homologous recombination between the targeting vector and the target cognate chromosomal region.
Figure 24:
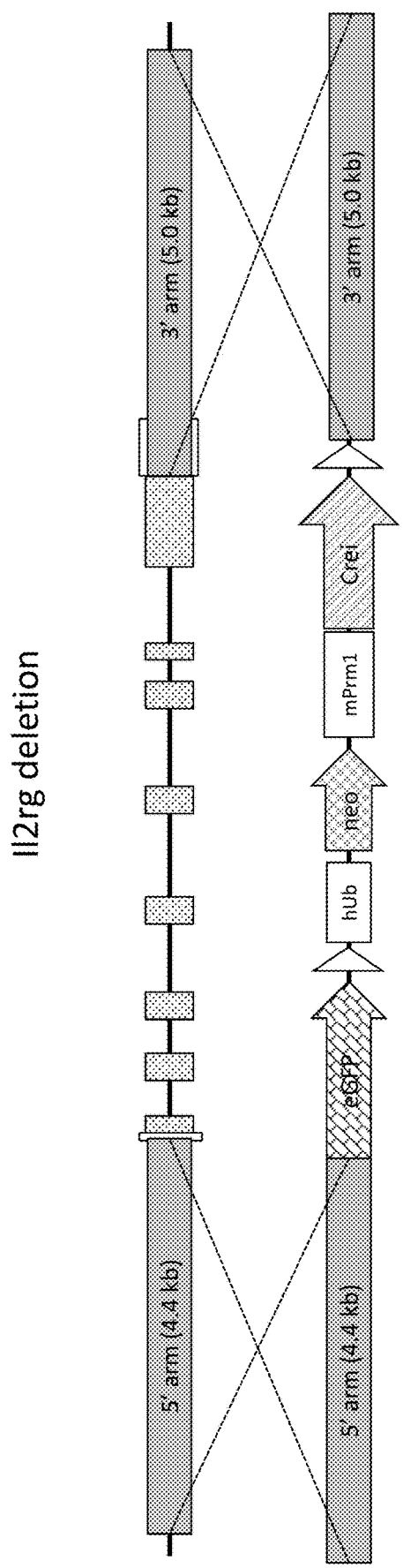
FIG. 24 depicts the rat IL2r-γ locus that has been disrupted by a 3.2 kb deletion and the insertion of a reporter gene (eGFP) and a self-deleting cassette comprising a drug selection cassette (hUb-neo) and the Crei gene operably linked to a mouse Prm1 promoter.

FIG. 23 provides a schematic of the rat ApoE locus and denotes with grey bars the cutting site for ZFN1 and ZFN2. The cutting site for ZFN1 is in t exon 3 and the cutting site for ZNF2 is in intron 3. The exact position of the both ZFN sites is set forth in Table 16. The 5' and 3' homology arms (45 kb and 23 kb, respectively) are denoted by the dark grey boxes. Exon 1 of the ApoE gene is non-coding and is shown as an open box closest to the 5' homology arm. The three introns of the ApoE gene are denoted as lines. Exons 2 and 3 comprise coding regions and are shown as stippled grey boxes. Exon 4 contains both coding and non-coding sequences as denoted by the stippled grey shading and the open box.

The LTVEC employed was the same as that in Example 3.2(b)(ii) and shown in FIG. 22. The ZFNs were introduced as two expression plasmids, one for each half of the ZFN pair. 20 ug of the plasmid for ZFN 1 and 20 ug of the plasmid for ZFN2 was used. ZFNs were purchased from Sigma. The expression of each ZFN was driven by the CMV promoter.

The targeting vector was electroporated into the rat ES cells obtained in Example 1 and the cells were plated on 15 cm 2× dense neoR MEFs in 2i+10 uM ROCKi. The transformed rat ES cells were cultured, selected, and maintained as described in Example 1.

As shown in Table 23, 288 colonies were screened and 16 targeted clones were obtained. The targeting efficiency was 5.56%. One clone was injected into blastocysts as described herein in Example 2.

Moreover, the employment of ZFN1 and ZFN2 produced one biallelic targeted clone, with an efficiency of 0.35%.

3.3(a): Targeting of the Rat Interleukin-2 Receptor Gamma (IL2r-γ) Locus

The rat Interleukin-2 receptor gamma (IL2r-γ) locus was targeted to disrupt IL2r-γ function. IL2r-γ plays an important role for signaling by IL-2, IL-4, IL-7, IL-9, IL-15, IL-21 and mutations in IL2r-γ are associated with severe defects in T, B and NK cell development.

Figure 26:
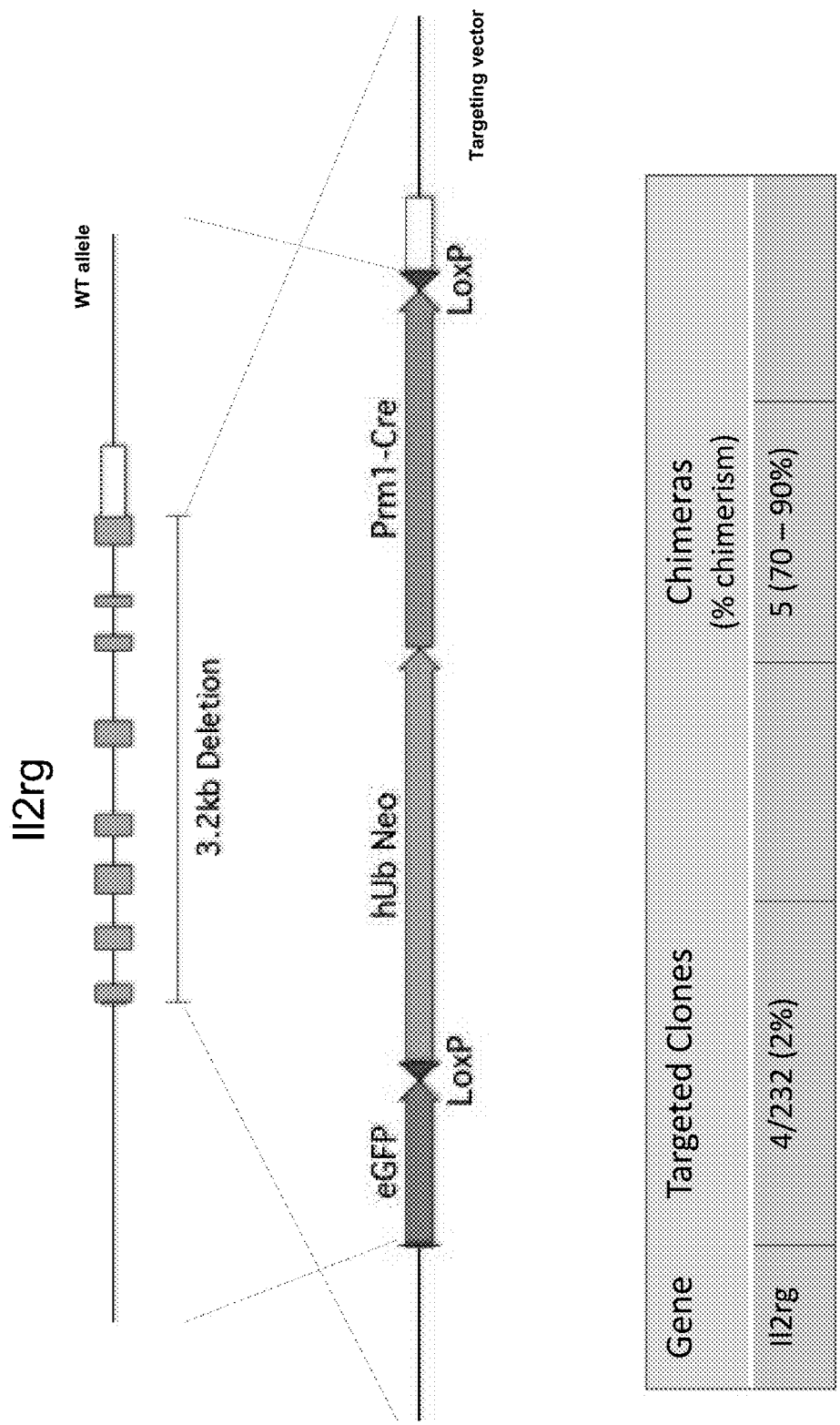
FIG. 26 provides another depiction of the rat IL2r-γ locus that has been disrupted by a 3.2 kb deletion and the insertion of a reporter gene (eGFP) and a self-deleting cassette comprising the Crei gene operably linked to a mouse Prm1 promoter and a drug selection cassette (hUb-Neo).

Targeting of the IL2r-γ locus was done using a targeting vector comprising an eGFP-hUb-neo cassette flanked with a 5' and 3' homology arms homologous to the IL2r-γ locus. FIG. 26 depicts the genomic structure of the rat IL2r-γ locus in which the IL2r-γ locus has been disrupted by a 3.2 kb deletion. The targeted IL2r-γ locus also comprised an eGFP gene and a self-deleting cassette containing Crei operably linked to a mouse Protamine1 promoter and a drug selection cassette comprising a hUb promoter operably linked to a neomycin resistance gene.

Targeting efficiency at the IL2r-γ locus was determined and shown in Table 17. Linearized vector was electroporated into DA.2B rat ESCs, and transfected colonies were cultured using standard techniques. Individual colonies were picked and screened using a Loss of Allele (LOA) assay.

TABLE 17 rat IL2r-γ Targeting Efficiency

| Cell line | Vector | Colonies picked | Targeted | Targeting efficiency (%) |
|---|---|---|---|---|
| DA.2B | Il2rg-floxed neo | 136 | 1 | 0.7 |
| DA.2B | Il2rg-mSDC | 96 | 4 | 4.2 |

Chimera production and germline transmission using IL2r-γ-targeted rat ESC clones was performed. IL2r-γ-targeted rat ESC clones were microinjected into SD blastocysts, which were then transferred to pseudopregnant SD recipient females, using standard techniques. Chimeras were identified by coat color; male F0 chimeras were bred to SD females. Germline F1 pups were genotyped for the presence of the targeted IL2r-γ allele (Table 18).

TABLE 18

Microinjection Results

| Exp | Clone | pups | Chimeras |
|---|---|---|---|
| 1 | Il2rg-AA1 | 5 | 2 (90, 70) |
| 2 | Il2rg-AA1 | 10 | 3 (90, 90, 80) |

The phenotype of Il2rg$^{-/Y}$ chimera #3 was further studied. The peripheral blood mononuclear cells (PBMCs) were stained with antibodies that recognize antigens in several lymphoid lineages. GFP-positive PBMCs were detected from 2 of the chimeras. Moreover, the GFP+ cells were negative for the T-cell marker CD3, and were mostly negative for the B-cell marker B220 and the NK cell marker CD161a. See, FIG. 30. The small double-positive populations are consistent with the published Il2rg knockout phenotype in mice. These data were obtained from a chimeric rat, which contains IL2 receptor gamma-positive cells, and this may complicate the analysis of the phenotype.

3.3(b): Targeted Modification of the Rat Interleukin-2 Receptor Gamma (IL2r-γ) Locus The rat Interleukin-2 receptor gamma (IL2r-γ) locus was targeted to disrupt the IL2r-γ function in rats. FIG. 26 shows the genomic structure of the rat Il2rg locus and the targeting vector introduced into the locus. eGFP was chosen as a reporter so that the immunophenotype of the genetically modified rats could be examined using FACS. The self-deleting cassette (hUb-Neo; Prm1-Cre) was used to delete the drug section cassette and the Cre gene specifically in male germ cells of the F0 rat. Additionally, the targeting vector was designed to delete the entire coding region (about 3.2 kb) of the rat Il2rg gene.

Figure 30:
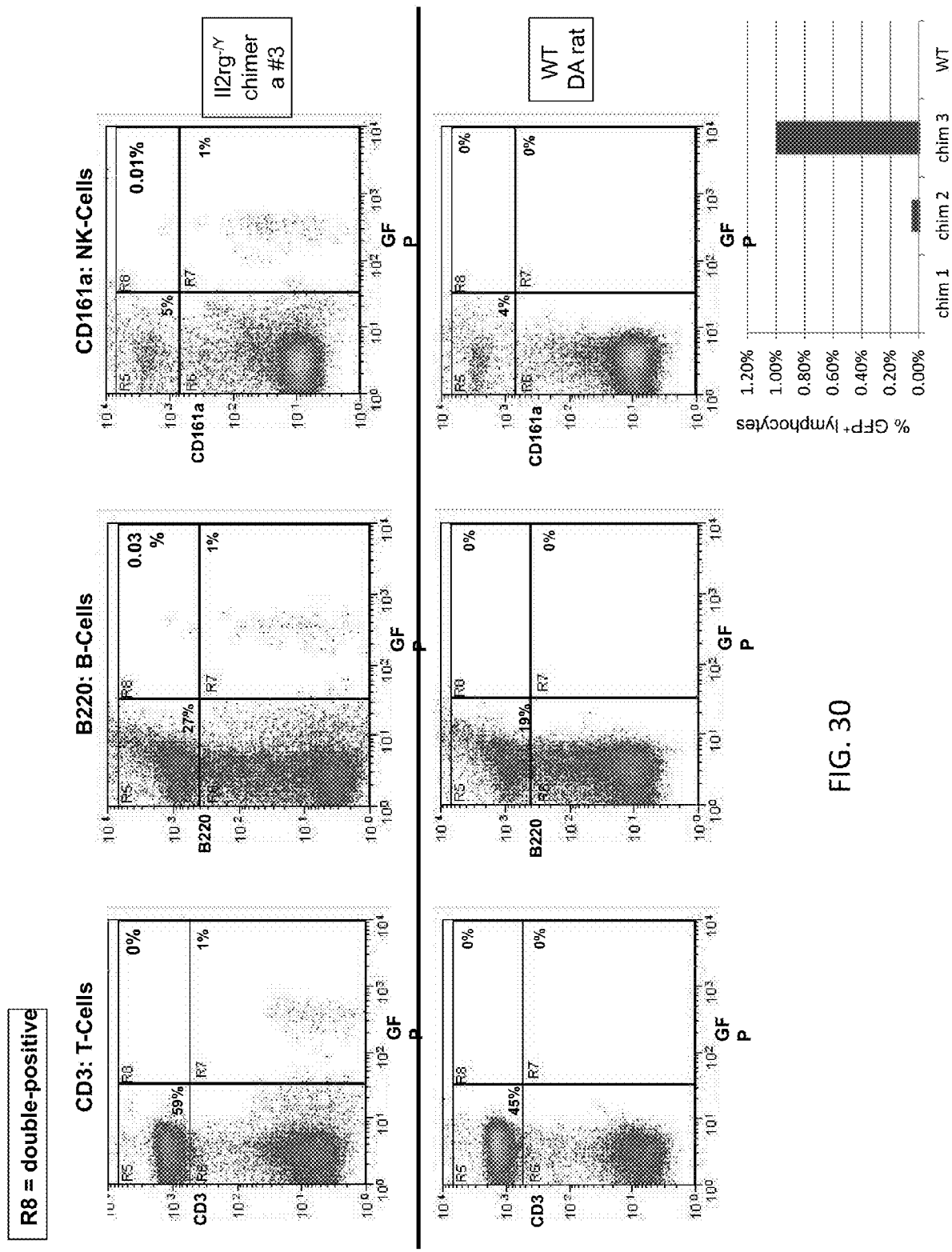
FIG. 30 shows that Il2rg−/y PBMC do not express mature lymphocyte markers. GFP-positive lymphocytes were detected in peripheral blood in 2 of the 3 chimeras.

The size of the deletion in rat ESCs was confirmed by PCR using primers specific to the rat Il2rg locus. Upon microinjection of the targeted clones into host embryos at a blastocyst stage, high percentage of chimeras were obtained. Those chimeras have been set up for breeding. To determine if the targeting worked as expected, the peripheral blood from the chimeras were collected prior to breeding, and the phenotype of the immune cells in the peripheral blood was analyzed via FACS. As shown in FIG. 30, GFP-positive cells were detected in the peripheral blood in 2 of the 3 chimeras examined (upper right panel), and the chimeric rats contained less than 1% of T cells, less than 1% of B cells, and less than 1% of NK-cells, which are positive for GFP (i.e., Il2rg KO cells).

3.4(a). Targeting the Rag2 Locus in Rats with a Large Targeting Vector (LTVEC)

Table 19 provides a summary of the genomic organization of the rat Rag2 locus and the positions shown were taken from build 5.0 of the Reference Sequence of the rat genome (ENSMBL). Rag2 is on chromosome 3 on the (+) strand.

TABLE 19

Genomic organization summary of the rat Rag2 locus.

| Feature | Start | End | length | Notes |
|---|---|---|---|---|
| Exon 1 | 97,851,317 | 97,851,448 | 132 | |
| Exon 2 | 97,854,635 | 97,854,693 | 59 | |
| Exon 3 | 97,858,260 | 97,859,615 | 1,356 | contains entire coding sequence |
| ATG | 97,856,286 | 97,856,288 | 3 | start codon |
| TGA | 97,857,867 | 97,857,869 | 3 | stop codon |
| Rag2 deletion | 97,856,289 | 97,859,784 | 3,496 | |

Figure 27:
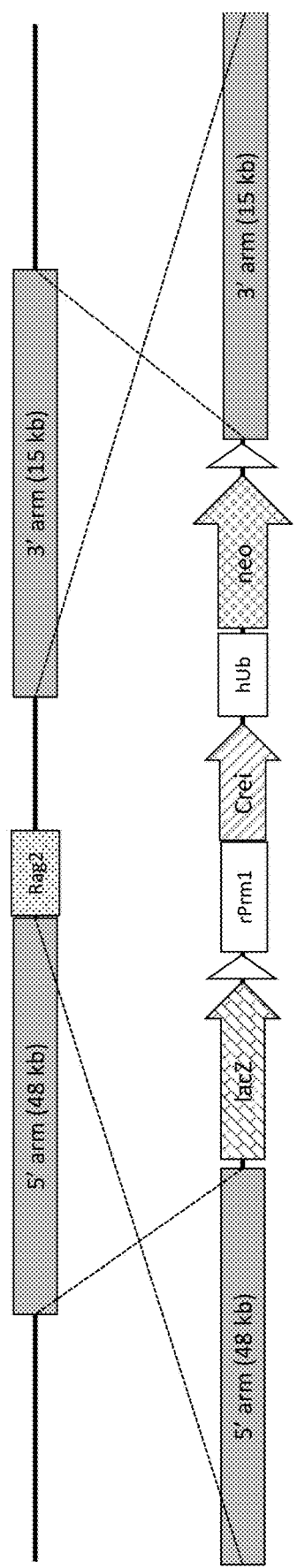
FIG. 27 provides a schematic of the rat Rag2 locus and a large targeting vector (LTVEC) for modifying the rat Rag2 locus. The upper panel shows the genomic organization of the rat Rag2 locus and the cognate genomic regions corresponding to the 5' and 3' homology arms (48 kb and 15 kb, respectively; dark grey boxes). Rag2 comprises single exon denoted by the stippled grey shading. The lower panel is the LTVEC. The 5' and 3' homology arms (48 kb and 15 kb, respectively) are denoted by the dark grey boxes. The LTVEC comprises a reporter gene (lacZ) and a self-deleting cassette flanked by loxP sites (open arrows) that contains a rat Prm1 promoter operably linked to the Crei gene and a drug selection cassette containing a human ubiquitin promoter operably linked to a neomycin resistance gene.

FIG. 27 provides a schematic of the rat Rag2 locus and a large targeting vector (LTVEC). The upper schematic of FIG. 27 shows the genomic organization of the rat ApoE locus and the genomic regions corresponding to the 5' and 3' homology arms (48 Kb and 15 Kb, respectively; dark grey boxes). Rag2 comprises a single exon denoted by the stippled grey shading.

The lower schematic in FIG. 27 is the LTVEC. The 5' and 3' homology arms (48 kb and 15 kb, respectively) are denoted by the dark grey boxes. The LTVEC comprises a reporter gene (lacZ) and a self-deleting cassette flanked by loxP sites (open arrows). The self-deleting cassette comprises a mouse Prm1 promoter operably linked to the Crei gene and a drug selection cassette comprising a human ubiquitin promoter operably linked to a neomycin resistance gene. The Crei comprises two exons encoding the Cre recombinase are separated by an intron (Crei) to prevent its expression in a prokaryotic cell. See, for example, U.S. Pat. No. 8,697,851 and U.S. Application Publication 2013-0312129, which describe the self-deleting cassette in detail and are hereby incorporated by reference in their entirety. By employing a mouse Prm1 promoter, the self-deleting cassette can be deleted specifically in male germ cells of F0 rats.

The LTVEC was electroporated into the rat ES cells obtained in Example 1 and the cells were plated on 15 cm 2× dense neoR MEFs in 2i+10 uM ROCKi. The transformed rat ES cells were cultured and maintained as described in Example 1. Colonies are screened as described elsewhere herein and targeted clones are obtained. The targeted clones are then injected into a host embryo as described elsewhere herein to produce an F0 rat.

3.4. (b). Targeting the Rag1 and the Rag 2 Locus in Rats

Figure 28:
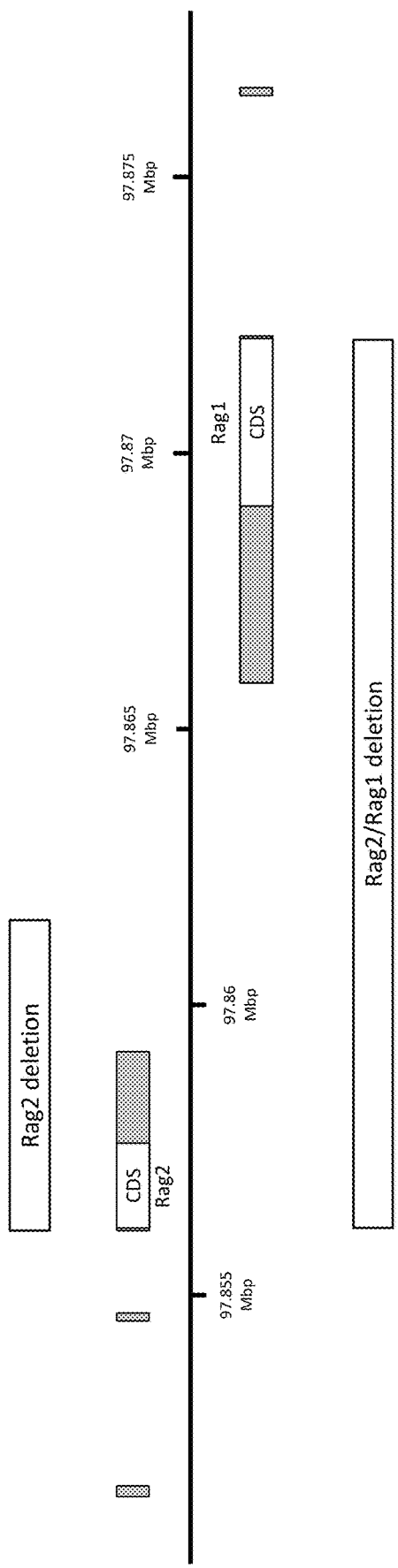
FIG. 28 provides the genomic structure of the rat Rag1/Rag2 locus and the genomic regions deleted by either Rag2 targeting (Rag2 deletion) or Rag2/Rag1 double targeting (Rag2/Rag1 deletion).

FIG. 28 provides the genomic structure of the rat Rag1/Rag2 locus. CDS denotes the coding sequence and grey boxes represent exons. Rag2 is on the "plus" strand with transcription to the right. Rag1 is on the "minus" strand with transcription to the left. Mbp=million base pairs.

Table 20 provides a summary of the genomic organization of the rat Rag2 and Rag1 locus and the positions shown were taken from build 5.0 of the Reference Sequence of the rat genome (ENSMBL). Rag1 is on chromosome 3 on the (−) strand.

TABLE 20

Genomic organization summary of the rat Rag1 locus.

| Feature | Start | End | length | Notes |
|---|---|---|---|---|
| Exon 1 | 97,877,145 | 97,877,066 | 80 | |
| Exon 2 | 97,872,503 | 97,866,047 | 6,457 | contains entire coding sequence |
| ATG | 97,872,489 | 97,872,487 | 3 | start codon |
| TAA | 97,869,369 | 97,869,367 | 3 | stop codon |
| Rag1-2 deletion | 97,856,289 | 97,872,486 | 16,198 | |

Figure 29:
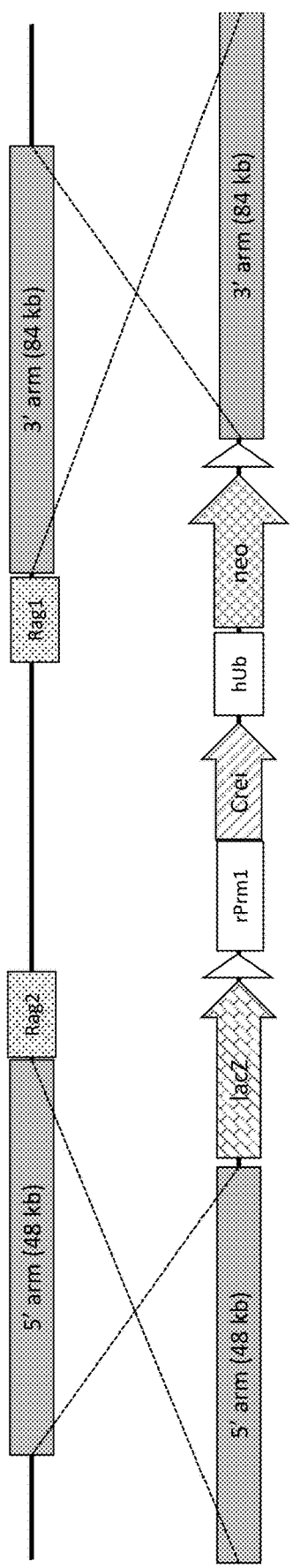
FIG. 29 provides a schematic of the rat Rag2 and Rag1 loci and a large targeting vector (LTVEC) used for modifying the loci. The upper panel shows the genomic organization of the Rag1 and Rag2 loci and the cognate genomic regions corresponding to the 5' and 3' homology arms (48 kb and 84 kb, respectively; dark grey boxes). Rag2 and Rag1 each comprise a single exon denoted by the stippled grey shading. The lower panel is the LTVEC. The 5' and 3' homology arms (48 kb and 84 kb, respectively) are denoted by the dark grey boxes. The LTVEC comprises a reporter gene (lacZ) and a self-deleting cassette flanked by loxP sites (open arrows), which comprises a rat Prm1 promoter operably linked to the Crei gene and a drug selection cassette comprising a human ubiquitin promoter operably linked to a neomycin resistance gene.

FIG. 29 provides a schematic of the rat Rag2 and Rag1 locus and a large targeting vector (LTVEC). The upper schematic of FIG. 29 shows the genomic organization of the Rag1 and Rag2 loci and the genomic regions corresponding to the 5' and 3' homology arms (48 kb and 84 kb, respectively; dark grey boxes). Rag2 and Rag 1 each comprises a single exon denoted by the stippled grey shading. The lower schematic in FIG. 29 is the LTVEC. The 5' and 3' homology arms (48 kb and 84 kb, respectively) are denoted by the dark grey boxes. The LTVEC comprises a reporter gene (lacZ) and a self-deleting cassette flanked by loxP sites (open arrows). The self-deleting cassette comprises a rat Prm1 promoter operably linked to the Crei gene and a drug selection cassette comprising a human ubiquitin promoter operably linked to a neomycin resistance gene. The Crei comprises two exons encoding the Cre recombinase are separated by an intron (Crei) to prevent its expression in a prokaryotic cell. See, for example, U.S. Pat. No. 8,697,851 and U.S. Application Publication 2013-0312129, which describes the self-deleting cassette in detail and is hereby incorporated by reference in their entirety. By employing a rat Prm1 promoter that drives expression of Crei specifically in male germ cells, the self-deleting cassette can be deleted from the male germ cells of F0 rats.

The LTVEC was electroporated into the rat ES cells obtained in Example 1 and the cells were plated on 15 cm 2× dense neoR MEFs in 2i+10 uM ROCKi. The transformed rat ES cells were cultured and maintained as described in Example 1.

Colonies are screened as described elsewhere herein and targeted clones are obtained. The targeted clones are then injected into a host embryo as described elsewhere herein to produce an F0 rat.

Example 4. Humanization 4.1. Humanization of Rat Genomic Loci

Humanization of rat genomic loci is carried out employing the rat ES cells described herein, which are capable of sustaining their pluripotency following one or more electroporations in vitro, and are capable of transmitting the targeted genetic modifications to subsequent generations. In addition, in order to circumvent the limitations of plasmids in accommodating a large genomic DNA fragment, and to overcome the low efficiency of introducing a targeted genetic modification into an endogenous locus in rat ES cells, one or more targeted genetic modifications are carried out in bacteria, e.g., E. coli, by utilizing bacterial homologous recombination (BHR) and employing a large targeting vector (LTVEC). The LTVEC described herein, for example, includes a large fragment of an endogenous rat genomic sequence with one or more modifications or comprises an exogenous nucleic acid (e.g., a homologous or orthologous human nucleic acid) flanked with rat homology arms complementary to specific genomic regions.

4.2. Humanization of Rat Immunoglobulin Loci

Humanization of an endogenous rat immunoglobulin heavy chain locus is carried out by removing one or more endogenous rat immunoglobulin heavy chain nucleic acid sequences (e.g., one or more endogenous $V_H$ gene segments, one or more human D gene segments, and one or more human $J_H$ gene segments); and introducing into the modified immunoglobulin locus a targeting vector, e.g., a large targeting vector (LTVEC) comprising: (i) one or more unrearranged human variable region nucleic acid sequences (e.g., one or more human $V_H$ gene segments, one or more human D gene segments, and one or more human $J_H$ gene segments), or one or more rearranged human variable region nucleic acid sequences (e.g., one or more human rearranged V-D-J gene segments); (ii) a selection cassette (e.g., neomycin resistance gene flanked with loxP sites); and (iii) 5' and 3' rat homology arms.

Briefly, one or more endogenous rat immunoglobulin heavy chain variable region gene segments (i.e., one or more $V_H$ gene segments, one or more human D gene segments, and one or more human $J_H$ gene segments) in a rat BAC clone are removed or inactivated by targeting the endogenous rat immunoglobulin heavy chain locus with a selection cassette flanked by rat homology arms. More specifically, a targeting vector is constructed to contain a selection cassette (e.g., a neomycin resistance gene flanked with loxP sites) flanked with 5' and 3' rat homology arms that are complementary to target rat genomic sequences (e.g., upstream and downstream rat genomic DNA sequences encompassing one or more rat $V_H$ gene segments, one or more human D gene segments, and one or more human $J_H$ gene segments).

Next, bacterial cells containing a large rat genomic DNA fragment encompassing a rat immunoglobulin heavy chain locus are selected and introduced with a plasmid (e.g., pABG) encoding a recombinase operably linked to a transiently inducible promoter. The targeting vector constructed above is then introduced into the recombination-competent bacterial cells. Following electroporation, the bacterial cells are treated with an inducer (e.g., arabinoside) to initiate homologous recombination between the targeting vector and the target rat genomic sequence in the BAC clone. Transformed cells are plated at a high density and subjected to drug selection to find colonies that are drug-resistant. Drug-resistant colonies are picked and screened for the targeted modification.

In order to facilitate identification of the targeted genetic modification, a high-throughput quantitative assay, namely, modification of allele (MOA) assay, is employed, which allows a large-scale screening of a modified allele(s) in a parental chromosome following a genetic modification. The MOA assay can be carried out via various analytical techniques, including, but not limited to, a quantitative PCR, e.g., a real-time PCR (qPCR). For example, the real-time PCR comprises a first primer set that recognizes the target locus and a second primer set that recognizes a non-targeted reference locus. In addition, the primer set can comprise a fluorescent probe that recognizes the amplified sequence. Alternatively, the quantitative assay can be carried out via a variety of analytical techniques, including, but not limited to, fluorescence-mediated in situ hybridization (FISH), comparative genomic hybridization, isothermic DNA amplification, quantitative hybridization to an immobilized probe(s), Invader Probes®, MMP Assays®, TaqMan® Molecular Beacon, and Eclipse™ probe technology. (See, for example, US2005/0144655, incorporated by reference herein in its entirety).

The bacterial cells comprising the modified rat BAC clone, i.e., a BAC clone containing a rat genomic DNA sequence wherein one or more endogenous heavy chain variable region gene segments ($V_H$, D, and/or $J_H$ gene segments) have been deleted or inactivated, are then electroporated with a large targeting vector (LTVEC) comprising: (i) one or more unrearranged human variable region nucleic acid sequences (e.g., one or more unrearranged human $V_H$ gene segments, one or more human D gene segments, and one or more human $J_H$ gene segments), or one or more rearranged human variable region nucleic acid sequences (e.g., one or more rearranged human V-D-J gene segments).

Initiation of homologous recombination in the bacterial cells and the selection of positive clones are performed as described above. The unrearranged or rearranged human immunoglobulin heavy chain variable region nucleic acid sequences, when targeted into the endogenous immunoglobulin heavy chain locus, become operably linked to an endogenous rat immunoglobulin heavy chain constant region nucleic acid sequence. Alternatively, endogenous rat heavy chain constant region locus can be inactivated, for example, by deleting one or more rat heavy chain constant region gene segments (CH) from the endogenous heavy chain constant region locus, and can be replaced with a human heavy chain constant region nucleic acid sequence.

Likewise, humanization of an endogenous rat immunoglobulin κ or λ light chain locus is carried out by removing one or more endogenous rat immunoglobulin κ and/or λ light chain variable region nucleic acid sequences (e.g., one or more endogenous κ rat $V_\kappa$ gene segments and one or more endogenous rat $J_\kappa$ gene segments); and targeting the modified immunoglobulin light chain locus with a targeting vector, e.g., a large targeting vector (LTVEC), comprising: (i) one or more unrearranged human immunoglobulin light chain variable region nucleic acid sequences (e.g., one or more human $V_\kappa$ gene segments and one or more human $J_\kappa$ gene segments), or one or more rearranged human variable region nucleic acid sequences (e.g., one or more human rearranged $V_\kappa$-$J_\kappa$ gene segments); (ii) a selection cassette (e.g., neomycin resistance gene flanked with loxP sites); and (iii) 5' and 3' rat homology arms.

The unrearranged or rearranged human immunoglobulin light chain variable region nucleic acid sequences, when targeted into the endogenous immunoglobulin light chain locus, become operably linked to the endogenous rat immunoglobulin light chain constant region nucleic acid sequence.

The LTVEC so produced in the bacterial cells comprises, for example, an insert nucleic acid that contains a humanized rat immunoglobulin heavy chain or light chain locus in which one or more endogenous rat heavy or light chain variable region gene segments have been replaced with one or more human heavy or light chain variable region gene segments; and rat homologous arms (e.g., ranging from 5 kb to 150 kb) complementary to specific genomic target sequences. The LTVEC comprising the genetic modification described above is then linearized and electroporated into the rat ES cells. Electroporated rat ES cells are plated at a high density to select drug-resistant ES cells comprising the targeting vector. The drug selection process removes the majority of the plated cells (~99%), leaving behind individual colonies, each of which is a clone derived from a single cell. Of the remaining cells, most cells (~80-100%) contain the targeting vector integrated at a random location in the genome. Therefore, the colonies are picked and genotyped individually in order to identify rat ES cells comprising the targeting vector at the correct genomic location (e.g., using the modification of allele (MOA) assay described above).

In order to increase the efficiency of the targeted genetic modification, the rat ES cells are electroporated with expression vectors (or mRNA) that express ZFNs 1 and 2 (or TALENs 1 and 2) together with the LTVEC. The targeting vector's homology arms lie outside the ZFN target site, therefore, the targeting vector is not cleaved by the ZFNs. The double strand break produced by the ZFNs stimulates homology-directed repair (HDR), which otherwise accounts for a very small percentage of repairs occurred normally in mammalian cells (compared to non-homologous end-joining; NHEJ).

Alternatively, expression vectors containing a type II CRISPR-associated nuclease (e.g., Cas9), a guide RNA (including CRISPR-RNA (cr-RNA) and trans-activating CRISPR RNA (tracrRNA)), as described herein, can be introduced into the bacterial cells together with the LTVEC to increase the efficiency of homologous recombination at the target genomic locus. Electroporated cells are plated at a high density and subjected to drug selection to find colonies that are drug-resistant. Drug-resistant colonies are picked and screened for the targeted modification using the modification of allele (MOA) assay as described herein. Following these procedures, improvement in the targeting efficiency can be achieved. For example, the amount of improvement can be small (e.g., improve from 10% to 15%) or large (e.g., improve from 10% to 80%).

The selected rat ES cells comprising the targeted genetic modification are then introduced into a host rat embryo, for example, a pre-morula stage or blastocyst stage rat embryo, and implanted in the uterus of a surrogate mother to generate a founder rat (F0 rat). Subsequently, the founder rat is bred to a wild-type rat to create F1 progeny heterozygous for the genetic modification. Mating of the heterozygous F1 rat can produce progeny homozygous for the genetic modification.

4.3(a). Replacing Rat IL2rg with Human IL2 Receptor Gamma

Table 21 provides a summary of the genomic organization of the rat Interleukin 2 receptor gamma locus and the positions shown were taken from build 5.0 of the Reference Sequence of the rat genome (ENSMBL). IL2rg is on chromosome X on the (−) strand.

of the human IL-2rg protein (SEQ ID NO: 20; NP_000197.1); the rat IL-2rg protein (SEQ ID NO: 21; NP_543165.1); and the chimeric IL-2rg protein (SEQ ID NO: 22) comprising the human ecto-domain of IL-2rg fused to the remainder of the rat IL-2rg protein. The junction between the human and rat IL-2rg is noted by the vertical line.

TABLE 21

Summary of the genomic organization of the rat Il2rg locus

| Feature | Start | End | length | Notes |
|---|---|---|---|---|
| Exon 1 | 72,021,388 | 72,021,516 | 129 | contains ATG |
| ATG | 72,017,500 | 72,017,502 | 3 | start codon |
| Exon2 | 72,021,007 | 72,021,160 | 154 | |
| ZFN1a binding site | 72,021,014 | 72,021,028 | 15 | CAGGCCCTGAACCGC (SEQ ID NO: 17) |
| ZFN1 cutting site | 72,021,008 | 72,021,013 | 6 | TTCTGG (SEQ ID NO: 18) |
| ZFN1b binding site | 72,020,993 | 72,021,007 | 15 | GATTACCTGCGCTGGG (SEQ ID NO: 20) |
| Exon3 | 72,020,606 | 72,020,790 | 185 | |
| Exon4 | 72,020,274 | 72,020,413 | 140 | |
| Exon5 | 72,019,662 | 72,019,824 | 163 | |
| Exon6 | 72,019,101 | 72,019,197 | 97 | |
| Exon7 | 72,018,844 | 72,018,910 | 67 | |
| Exon8 | 72,017,856 | 72,018,506 | 651 | contains TGA |
| TGA | 72,018,321 | 72,018,323 | 3 | stop codon |
| Il2rg deletion | 72,018,323 | 72,021,502 | 3,180 | |

The lower schematic in FIG. 26 is the targeting vector for the IL2rg 3.2 kb deletion. The targeting vector comprises a reporter gene (eGFP) operably linked to the endogenous promoter and a self-deleting cassette flanked by loxP sites (open arrows). The self-deleting cassette comprises the Crei gene operably linked to a mouse Prm1 promoter and a selection cassette comprising a neomycin resistance gene operably linked to a human ubiquitin promoter.

The Crei gene comprises two exons encoding a Cre recombinase, which are separated by an intron (Crei) to prevent its expression in a prokaryotic cell. See, See, for example, U.S. Pat. No. 8,697,851 and U.S. Application Publication 2013-0312129, which describe the self-deleting cassette in detail and are hereby incorporated by reference in their entirety. By employing the mouse Prm1 promoter the Cre expression cassette and the drug selection cassette can be deleted specifically in male germ cells of F0 rats. The targeting vector was electroporated into the rat ES cells obtained in Example 1 and the cells were plated on 15 cm 2× dense neomycin-resistant MEFs in 2i+10 uM ROCKi. The transformed rat ES cells were cultured, selected, and maintained as described in Example 1.

As shown in Table 23, 168 colonies were screened and 6 targeted clones were obtained. The targeting efficiency was 3.57%.

Clones are injected into blastocysts as described herein in Example 1. Clones producing F0 rats are obtained and F0 rats that transmit the targeted modification through the germline are obtained.

Example 4.3(b). Replacing Rat IL2rg Ecto-Domain with Human IL2rg Ecto-Domain The full-length humanization of IL 2 receptor gamma is useful because rats having this modified locus will produce human Il2rg; and this would allow for the detection of human Il2rg in rats with antibodies specific to human Il2rg.

Figure 33:
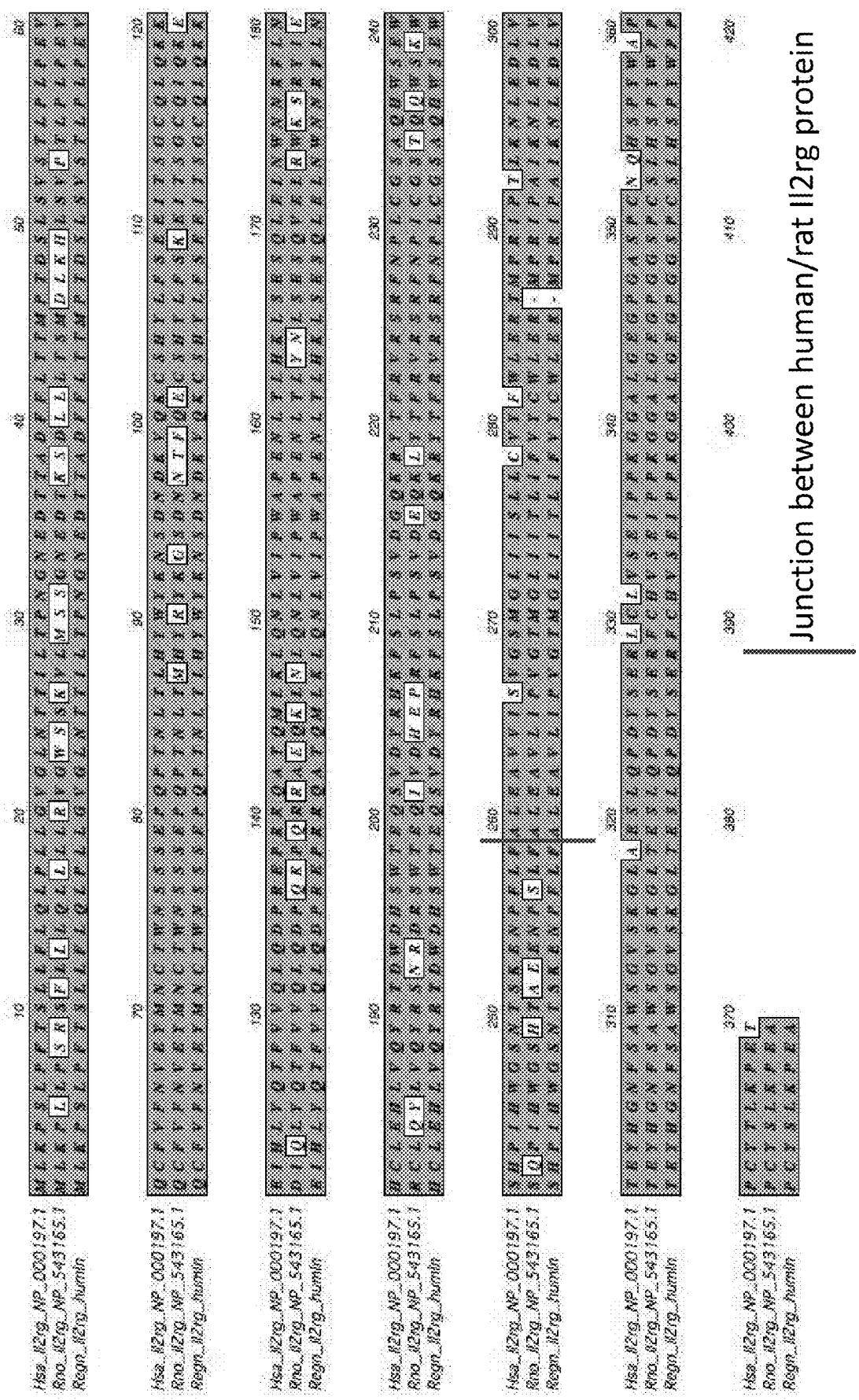
FIG. 33 provides a sequence alignment of the human IL-2rg protein (SEQ ID NO: 20; NP 000197.1); the rat IL-2rg protein (SEQ ID NO: 21; NP 543165.1); and the chimeric IL-2rg protein (SEQ ID NO: 22) comprising the human ecto-domain of IL-2rg fused to the remainder of the rat IL-2rg protein. The junction between the human and rat IL-2rg is noted by the vertical line.

The ecto-humanization (i.e., replacing the rat ecto-domain of Il2rg with the human ecto-domain of Il2rg) will result in an Il2rg polypeptide that will bind the human ligands for Il2rg, but because the cytoplasmic domain is still rat, it ecto-humanized form of Il2rg will also interact with the rat signaling machinery. FIG. 33 provides a sequence alignment Table 22 provides a summary of the genomic organization of the rat Interleukin 2 receptor gamma locus and the positions shown were taken from build 5.0 of the Reference Sequence of the rat genome (ENSMBL). IL2rg is on chromosome X on the (−) strand. Further noted is the position of the ecto-domain of IL2rg.

TABLE 22

Summary of the genomic organization of the rat Il2rg locus

| Feature | Start | End | length | Notes |
|---|---|---|---|---|
| Exon 1 | 71,111,444 | 71,111,543 | 100 | contains ATG |
| ATG | 71,111,537 | 71,111,539 | 3 | start codon |
| Exon2 | 71,110,897 | 71,111,050 | 154 | |
| Exon3 | 71,110,504 | 71,110,688 | 185 | |
| Exon4 | 71,110,156 | 71,110,295 | 140 | |
| Exon5 | 71,109,228 | 71,109,390 | 163 | |
| Exon6 | 71,108,599 | 71,108,645 | 47 | contains transmembrane domain |
| Exon7 | 71,108,277 | 71,108,346 | 70 | |
| Exon8 | 71,107,404 | 71,107,921 | 518 | contains TGA |
| TGA | 71,108,736 | 71,108,738 | 3 | stop codon |
| full-length humanization: | 71,107,404 | 71,111,539 | 4,136 | (ATG to TGA plus 3′ poly-A) |
| ecto-humanization | 71,108,679 | 71,111,539 | 2,861 | (ATG to beginning of transmembrane domain) |

Figure 31:
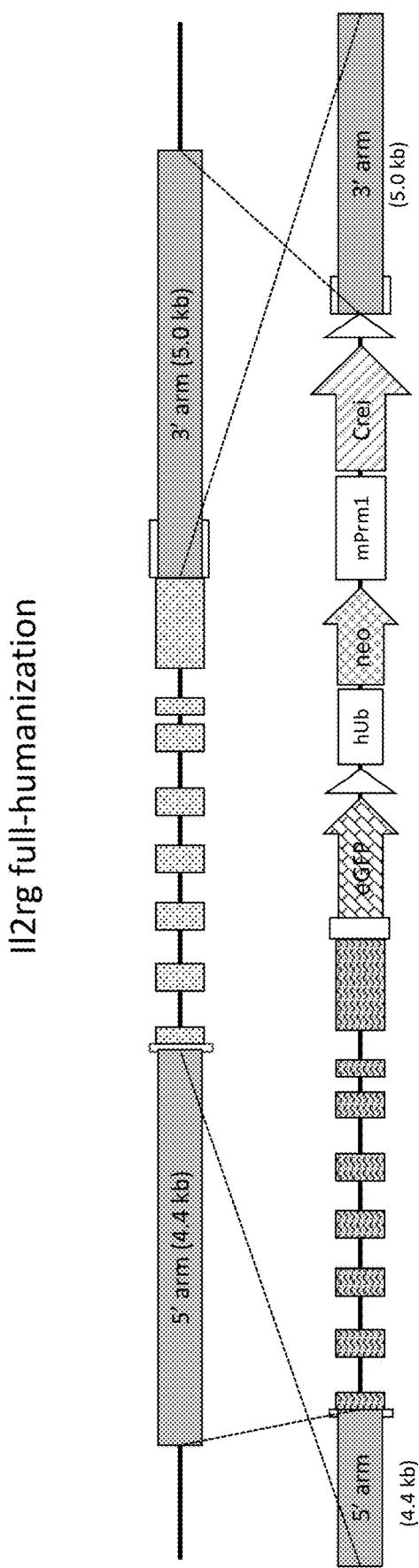
FIG. 31 provides a schematic of the rat IL-2rg locus and a targeting plasmid for the full humanization of the rat IL-2rg locus. The upper panel shows the genomic organization of the rat IL-2rg locus and the cognate genomic regions corresponding to the 5' and 3' homology arms (4.4 kb and 5.0 kb, respectively; dark grey boxes). The lower panel is the targeting plasmid. The 5' and 3' homology arms (4.4 kb and 5.0 kb, respectively) are denoted by the dark grey boxes. The targeting plasmid comprises the human IL-2rg genomic region, a reporter gene (GFP) and a self-deleting cassette flanked by loxP sites (open arrows) that contains a mouse Prm1 promoter operably linked to the Crei gene and a drug selection cassette containing a human ubiquitin promoter operably linked to a neomycin resistance gene.
Figure 32:
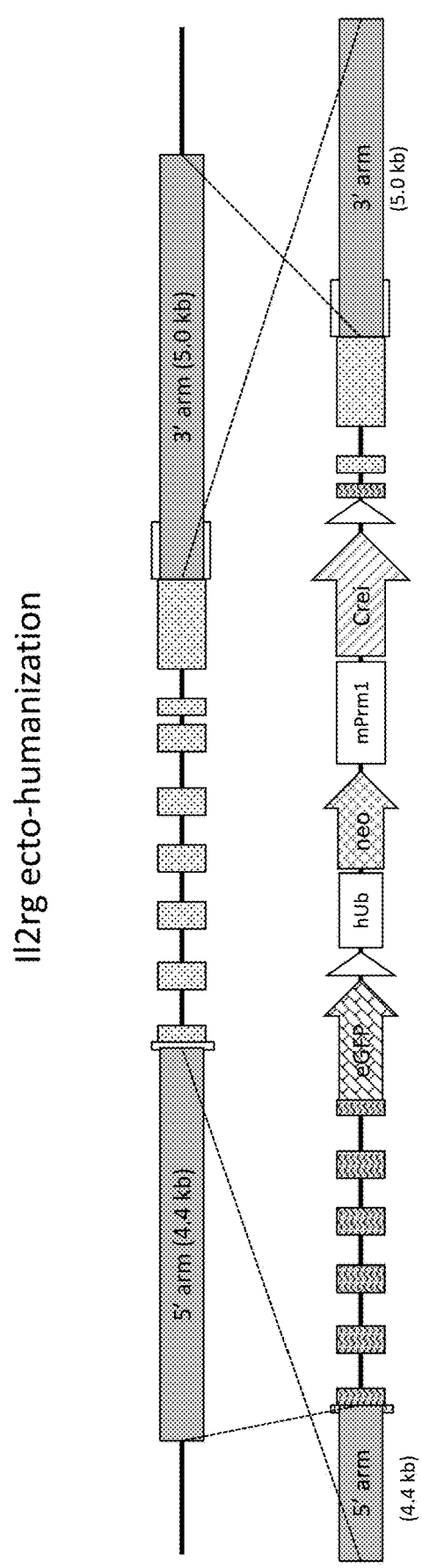
FIG. 32 provides a schematic of the rat IL-2rg locus and a targeting plasmid for the ecto-domain humanization of the rat IL-2rg locus. The upper panel shows the genomic organization of the rat IL-2rg locus and the cognate genomic regions corresponding to the 5' and 3' homology arms (4.4 kb and 5.0 kb, respectively; dark grey boxes). The lower panel is the targeting plasmid. The 5' and 3' homology arms (4.4 kb and 5.0 kb, respectively) are denoted by the dark grey boxes. The targeting plasmid comprises the human ecto-domain of the IL-2Rg genomic region, a reporter gene (GFP) and a self-deleting cassette flanked by loxP sites (open arrows) that contains a mouse Prm1 promoter operably linked to the Crei gene and a drug selection cassette a human ubiquitin promoter operably linked to a neomycin resistance gene.

A plasmid targeting vectors were constructed to replace the rat ecto-domain of the interleukin 2 receptor gamma coding region with the human ecto domain as shown in FIG. 31. The targeting vector was electroporated into the rat ES cells obtained in Example 1 and the cells were plated on 15 cm 2× dense neomycin-resistant MEFs in 2i+10 uM ROCKi. The transformed rat ES cells were cultured, selected, and maintained as described in Example 1.

As shown in Table 23, 192 colonies were screened and 13 targeted clones were obtained. The targeting efficiency was 6.77%.

Clones are injected into blastocysts as described herein in Example 1. Clones producing F0 rats are obtained and F0 rats that transmit the targeted modification through the germline are obtained.

Example 5. Summary

TABLE 23

Summary of rat targeting with various vector types and nuclease agents discussed in Examples 3 and 4.
Table 23 Targeting Summary

| Example # | Locus | Vector | Colonies screened | Targeted Clones | Targeting efficiency | Biallelic targeted | Biallelic efficiency | Clones Injected | Clones producing chimeras | Clones transmitting through germline | Notes |
|---|---|---|---|---|---|---|---|---|---|---|---|
| 3.2(a)(ii) | ApoE | plasmid | 384 | 23 | 5.99% | | | 3 | 3 | 2 | |
| 3.2(a)(iii) | ApoE + ZFN | plasmid | 384 | 290 | 75.52% | 8 | 2.08% | 2 | 2 | 1 | These 2 clones are biallelic targeted |
| 3.3(a) | Il2rg | plasmid | 232 | 5 | 2.16% | | | 6 | 5 | | |
| 3.2(b)(ii) | ApoE LTVEC | LTVEC | 288 | 8 | 2.78% | 1 | 0.35% | 3 | 1 | | |
| 3.2(b)(iii) | ApoE LTVEC + ZFN | LTVEC | 288 | 16 | 5.56% | 1 | 0.35% | 1 | N/A | | This clone is biallelic targeted |
| 4.3(a) | Il2rg Humanization 1 | plasmid | 168 | 6 | 3.57% | | | | | | replaces entire rat Il2rg with human Il2rg |
| 4.3(b) | Il2rg Humanization 2 | plasmid | 192 | 13 | 6.77% | | | 2 | N/A | | replaces rat Il2rg ecto-domain with human Il2rg ecto-domain |
| 3.4(a) | Rag2 | LTVEC | 270 | N/A | | | | | | | Predicted 5.7 KB deletion |
| 3.4(b) | Rag1-2 | LTVEC | 256 | N/A | | | | | | | Predicted 16.2 kb deletion |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Unless otherwise apparent from the context of any embodiment, aspect, step or feature of the invention can be used in combination with any other. Reference to a range includes any integers within the range, any subrange within the range. Reference to multiple ranges includes composites of such ranges.

We claim:

1. A method for making a genetically modified rat pluripotent stem cell clone capable of generating a genetically modified rat comprising a targeted genetic modification and transmitting the targeted genetic modification through the germline, comprising:
   (a) culturing a population of rat pluripotent stem cells on a layer of feeder cells that is not modified to express leukemia inhibitory factor (LIF) with a medium comprising about 50 U/mL to about 150 U/mL LIF, N2 supplement, B27 supplement, and a combination of inhibitors consisting of MEK inhibitor PD0325901 and GSK3 inhibitor CHIR99021;
   (b) introducing into the rat pluripotent stem cells a large targeting vector (LTVEC) comprising an insert nucleic acid flanked by a 5' homology arm homologous to a first nucleic acid sequence at a genomic locus of interest and a 3' homology arm homologous to a second nucleic acid sequence at the genomic locus of interest to produce the targeted genetic modification via homologous recombination, wherein the sum total of the 5' and the 3' homology arms is at least 10 kb; and
   (c) obtaining a rat pluripotent stem cell clone comprising the targeted genetic modification at the genomic locus of interest, wherein the obtaining consists of identifying in a single cloning step a rat pluripotent stem cell clone comprising the targeted genetic modification at the genomic locus of interest and capable of generating a genetically modified rat comprising the targeted genetic modification and transmitting the targeted genetic modification through the germline.

2. The method of claim 1, wherein the rat pluripotent stem cells in step (a) are rat embryonic stem (ES) cells.

3. The method of claim 2, wherein the rat ES cells are male (XY) rat ES cells or female (XX) rat ES cells.

4. The method of claim 2, wherein the rat ES cells are diploid and/or form spherical, free-floating colonies in culture.

5. The method of claim 1, wherein the rat pluripotent stem cells in step (a) are derived from a DA strain or an ACI strain.

6. The method of claim 1, wherein the rat pluripotent stem cells in step (a) are characterized by one or more of the following characteristics:

(I) expression of at least one pluripotency marker selected from the group consisting of Dnmt3L, Eras, Err-beta, Fbxo15, Fgf4, Gdf3, Klf4, Lef1, LIF receptor, Lin28, Nanog, Oct4, Sox15, Sox2, and Utf1;
(II) lack of expression of one or more of the pluripotency markers c-Myc, Ecat1, and Rexo1;
(III) lack of expression of one or more of the mesodermal markers Brachyury and Bmpr2;
(IV) lack of expression of one or more of the endodermal markers Gata6, Sox17, and Sox7; and
(V) lack of expression of one or more of the neural markers Nestin and Pax6.

7. The method of claim 1, wherein the medium comprises about 75 U/mL to about 125 U/mL LIF.

8. The method of claim 7, wherein the medium comprises about 90 U/mL to about 110 U/mL LIF.

9. The method of claim 8, wherein the medium comprises about 100 U/mL LIF.

10. The method of claim 1, wherein the LIF is a mouse LIF.

11. The method of claim 1, wherein the concentration of MEK inhibitor PD0325901 is 0.8 µM to about 1.2 µM, and the concentration of GSK3 inhibitor CHIR99021 is about 2.5 µM to about 3.5 µM.

12. The method of claim 11, wherein the concentration of MEK inhibitor PD0325901 is about 1 µM, and the concentration of GSK3 inhibitor CHIR99021 is about 3 µM.

13. The method of claim 9, wherein the concentration of the MEK inhibitor PD0325901 is about 1 µM, and the concentration of GSK3 inhibitor CHIR99021 is about 3 µM.

14. The method of claim 1, wherein the feeder cells comprise mitotically inactivated mouse embryonic fibroblasts.

15. The method of claim 1, wherein the feeder cells comprise mitotically inactivated mouse embryonic fibroblasts, and the medium is a 2i medium comprising DMEM/F12 basal medium at a concentration of 1×; neurobasal medium at a concentration of 1×; penicillin/streptomycin at a concentration of 1%; L-Glutamine at a concentration of 4 mM; 2-mercaptoethanol at a concentration of 0.1 mM; N2 supplement at a concentration of 1×; B27 supplement at a concentration 1×; LIF at a concentration of 100 U/mL; MEK inhibitor PD0325901 at a concentration of 1 µM, and GSK3 inhibitor CHIR99021 at a concentration of 3 µM.

16. The method of claim 1, wherein:
(I) the sum total of the 5' and the 3' homology arms of the LTVEC is from 10 kb to 150 kb,
(II) the 5' homology arm ranges from 5 kb to 100 kb or the 3' homology arm ranges from 5 kb to 100 kb; or
(III) the LTVEC is from 20 kb to 400 kb.

17. The method of claim 1, wherein the insert nucleic acid is from about 5 kb to about 400 kb.

18. The method of claim 1, wherein the insert nucleic acid:
(i) comprises a polynucleotide of interest comprising a genomic nucleic acid sequence that encodes a human immunoglobulin heavy chain variable region amino acid sequence;
(ii) comprises a polynucleotide of interest comprising a genomic nucleic acid sequence that encodes a human immunoglobulin light chain variable region amino acid sequence;
(iii) comprises a polynucleotide of interest comprising a polynucleotide encoding at least a region of a T cell receptor; or
(iv) comprises a polynucleotide of interest comprising at least one disease allele.

19. The method of claim 18, wherein the insert nucleic acid comprises a polynucleotide of interest comprising a polynucleotide encoding at least a region of a T cell receptor alpha.

20. The method of claim 1, wherein the insert nucleic acid:
(i) is from a human;
(ii) comprises a knock-in allele of at least one exon of an endogenous gene;
(iii) comprises a regulatory element;
(iv) comprises a conditional allele;
(v) comprises a nucleic acid flanked by site-specific recombination target sequences;
(vi) comprises a polynucleotide encoding a selection marker; or
(vii) comprises a reporter gene operably linked to a promoter.

21. The method of claim 20, wherein the insert nucleic acid comprises a polynucleotide encoding a selection marker and/or a reporter gene flanked by site-specific recombination target sequences or comprises a self-deleting selection cassette.

22. The method of claim 1, wherein introducing step (b) further comprises introducing a nuclease agent or a nucleic acid encoding the nuclease agent, wherein the nuclease agent promotes homologous recombination between the LTVEC and the genomic locus of interest in the rat pluripotent stem cells.

23. The method of claim 22, wherein the nuclease agent comprises:
(I) a chimeric protein comprising a zinc finger-based DNA binding domain fused to a FokI endonuclease;
(II) a chimeric protein comprising a Transcription Activator-Like Effector Nuclease (TALEN); or
(III) a CRISPR/Cas system.

24. The method of claim 23, wherein the nuclease agent comprises the CRISPR/Cas system, wherein the CRISPR/Cas system comprises a Cas9 nuclease and a guide RNA.

25. The method of claim 24, wherein the guide RNA comprises the sequence set forth in SEQ ID NO: 2, 3, 4, 5, 6, 7, or 8.

26. The method of claim 1, wherein the targeted genetic modification is biallelic.

27. The method of claim 1, wherein the targeted genetic modification comprises deletion of an endogenous rat nucleic acid sequence, wherein the deletion ranges from about 5 kb to about 3 Mb.

28. The method of claim 1, wherein the targeted genetic modification comprises insertion of an exogenous nucleic acid sequence ranging from 5 kb to 400 kb.

29. The method of claim 1, wherein the targeted genetic modification comprises:
(I) replacement of an endogenous rat nucleic acid sequence with an exogenous sequence;
(II) replacement of an endogenous rat nucleic acid sequence with a homologous or an orthologous nucleic acid sequence;
(III) deletion of an endogenous rat nucleic acid sequence;
(IV) insertion of an exogenous nucleic acid sequence comprising a nucleic acid sequence that is homologous or orthologous to an endogenous rat nucleic acid sequence;
(V) insertion of a chimeric nucleic acid sequence comprising a human nucleic acid sequence and a rat nucleic acid sequence;
(VI) insertion of a conditional allele flanked by site-specific recombinase target sequences; or
(VII) insertion of a reporter gene operably linked to a promoter active in a rat cell.

30. The method of claim 1, wherein the targeted genetic modification comprises:
(I) an insertion of the insert nucleic acid, wherein the insert nucleic acid comprises a human nucleic acid sequence;
(II) a replacement of a rat nucleic acid sequence at the genomic locus of interest with a human nucleic acid sequence, wherein the replaced rat nucleic acid sequence is homologous or orthologous to the human nucleic acid sequence;
(III) a chimeric nucleic acid sequence comprising a human nucleic acid sequence and a rat nucleic acid sequence; or
(IV) a combination thereof.

31. The method of claim 30, wherein the size of the insertion is from 5 kb to 500 kb, or wherein the size of the replacement is from 5 kb to 500 kb.

32. The method of claim 1, wherein the genomic locus of interest comprises:
(i) an Il2rg locus, an ApoE locus, a Rag1 locus, a Rag2 locus, or a Rag2/Rag1 locus;
(ii) an immunoglobulin locus; or
(iii) a T cell receptor locus.

33. The method of claim 32, wherein the immunoglobulin locus is an immunoglobulin heavy chain locus or an immunoglobulin light chain locus.

34. The method of claim 33, wherein the immunoglobulin light chain locus is a λ or κ immunoglobulin light chain locus.

35. The method of claim 32, wherein the genomic locus of interest comprises a T cell receptor alpha locus.

36. The method of claim 1, wherein the introducing step is mediated by electroporation.

37. The method of claim 1, wherein steps (a)-(c) are sequentially repeated to allow for the targeted integration of at least two insert nucleic acids into the genomic locus of interest.

38. The method of claim 1, wherein a modification-of-allele assay is used to identify the rat pluripotent stem cell clone comprising the targeted genetic modification at the genomic locus of interest.

39. A method for producing a genetically modified rat whose genome comprises a targeted genetic modification that is transmitted through the germline, comprising:
   performing steps (a)-(c) of claim 1;
   (d) introducing the rat pluripotent stem cell clone into a rat host embryo;
   (e) gestating the rat host embryo comprising the rat pluripotent stem cell clone in a surrogate mother, wherein the surrogate mother produces an F0 progeny genetically modified rat comprising the targeted genetic modification; and
   (f) breeding the F0 progeny genetically modified rat with another rat to produce an F1 progeny genetically modified rat comprising the targeted genetic modification, wherein the targeted genetic modification is transmitted through the germline.

40. The method of claim 1, wherein the medium is between 50 U/mL and 150 U/mL.

41. The method of claim 1, wherein the medium is between 75 U/mL and 125 U/mL.

42. The method of claim 1, wherein the medium is between 90 U/mL and 110 U/mL.

43. The method of claim 1, wherein the medium is 100 U/mL.

44. The method of claim 1, wherein the concentration of MEK inhibitor PD0325901 is 0.8 μM to 1.2 μM, and the concentration of GSK3 inhibitor CHIR99021 is 2.5 μM to 3.5 μM.

45. The method of claim 44, wherein the concentration of MEK inhibitor PD0325901 is 1 μM, and the concentration of GSK3 inhibitor CHIR99021 is 3 μM.

46. The method of claim 43, wherein the concentration of the MEK inhibitor PD0325901 is 1 μM, and the concentration of GSK3 inhibitor CHIR99021 is 3 μM.

* * * * *

UNITED STATES PATENT AND TRADEMARK OFFICE
CERTIFICATE OF CORRECTION

PATENT NO. : 10,975,390 B2  
APPLICATION NO. : 16/451859  
DATED : April 13, 2021  
INVENTOR(S) : Jeffrey D. Lee et al.

Page 1 of 1

It is certified that error appears in the above-identified patent and that said Letters Patent is hereby corrected as shown below:

In the Claims

Column 155, Claim 17, Line 8: delete "about 5 kb to about 400 kb" and insert --5 kb to 400 kb--

Column 156, Claim 27, Line 4: delete "about 5 kb to about 3 Mb" and insert --5 kb to 3 Mb--

Column 157, Claim 40, Line 17: after "wherein" insert --the concentration of LIF in--

Column 158, Claim 41, Line 1: after "wherein" insert --the concentration of LIF in--

Column 158, Claim 42, Line 3: after "wherein" insert --the concentration of LIF in--

Column 158, Claim 43, Line 5: after "wherein" insert --the concentration of LIF in--

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*

```
                    SEQUENCE LISTING

<160> NUMBER OF SEQ ID NOS: 23

<210> SEQ ID NO 1
<211> LENGTH: 23
<212> TYPE: DNA
<213> ORGANISM: Artificial Sequence
<220> FEATURE:
<223> OTHER INFORMATION: a genomic target sequence that is linked to a
      guide RNA (gRNA)
<220> FEATURE:
<221> NAME/KEY: misc_feature
<222> LOCATION: 2, 3, 4, 5, 6, 7, 8, 9, 10, 11, 12, 13, 14, 15, 16, 17,
      18, 19, 20, 21
<223> OTHER INFORMATION: n = A,T,C or G

<400> SEQUENCE: 1
gnnnnnnnnn nnnnnnnnnn ngg                                              23

<210> SEQ ID NO 2
<211> LENGTH: 80
<212> TYPE: DNA
<213> ORGANISM: Artificial Sequence
<220> FEATURE:
<223> OTHER INFORMATION: a guide RNA (gRNA)

<400> SEQUENCE: 2
guuuuagagc uagaaauagc aaguuaaaau aaggcuaguc cguuaucaac uugaaaaagu      60
ggcaccgagu cggugcuuuu                                                  80

<210> SEQ ID NO 3
```

```
<211> LENGTH: 42
<212> TYPE: DNA
<213> ORGANISM: Artificial Sequence
<220> FEATURE:
<223> OTHER INFORMATION: a guide RNA (gRNA)

<400> SEQUENCE: 3
guuuuagagc uagaaauagc aaguuaaaau aaggcuaguc cg                              42

<210> SEQ ID NO 4
<211> LENGTH: 30
<212> TYPE: DNA
<213> ORGANISM: Artificial Sequence
<220> FEATURE:
<223> OTHER INFORMATION: a crRNA

<400> SEQUENCE: 4
guuuuagagc uagaaauagc aaguuaaaau                                           30

<210> SEQ ID NO 5
<211> LENGTH: 33
<212> TYPE: DNA
<213> ORGANISM: Artificial Sequence
<220> FEATURE:
<223> OTHER INFORMATION: a crRNA

<400> SEQUENCE: 5
guuuuagagc uagaaauagc aaguuaaaau aag                                       33

<210> SEQ ID NO 6
<211> LENGTH: 26
<212> TYPE: DNA
<213> ORGANISM: Artificial Sequence
<220> FEATURE:
<223> OTHER INFORMATION: a crRNA

<400> SEQUENCE: 6
gaguccgagc agaagaagaa guuuua                                               26

<210> SEQ ID NO 7
<211> LENGTH: 12
<212> TYPE: DNA
<213> ORGANISM: Artificial Sequence
<220> FEATURE:
<223> OTHER INFORMATION: a tracrRNA

<400> SEQUENCE: 7
aaggcuaguc cg                                                              12

<210> SEQ ID NO 8
<211> LENGTH: 50
<212> TYPE: DNA
<213> ORGANISM: Artificial Sequence
<220> FEATURE:
<223> OTHER INFORMATION: a tracrRNA

<400> SEQUENCE: 8
aaggcuaguc cguuaucaac uugaaaaagu ggcaccgagu cggugcuuuu                     50

<210> SEQ ID NO 9
<211> LENGTH: 203
<212> TYPE: PRT
<213> ORGANISM: Mus Musculus

<400> SEQUENCE: 9

Met Lys Val Leu Ala Ala Gly Ile Val Pro Leu Leu Leu Leu Val Leu
```

```
                1               5                  10                 15
              His Trp Lys His Gly Ala Gly Ser Pro Leu Pro Ile Thr Pro Val Asn
                           20                 25                 30

Ala Thr Cys Ala Ile Arg His Pro Cys His Gly Asn Leu Met Asn Gln
                           35                 40                 45

Ile Lys Asn Gln Leu Ala Gln Leu Asn Gly Ser Ala Asn Ala Leu Phe
                           50                 55                 60

Ile Ser Tyr Tyr Thr Ala Gln Gly Glu Pro Phe Pro Asn Asn Val Glu
               65                 70                 75                 80

Lys Leu Cys Ala Pro Asn Met Thr Asp Phe Pro Ser Phe His Gly Asn
                           85                 90                 95

Gly Thr Glu Lys Thr Lys Leu Val Glu Leu Tyr Arg Met Val Ala Tyr
                          100                105                110

Leu Ser Ala Ser Leu Thr Asn Ile Thr Arg Asp Gln Lys Val Leu Asn
                          115                120                125

Pro Thr Ala Val Ser Leu Gln Val Lys Leu Asn Ala Thr Ile Asp Val
                          130                135                140

Met Arg Gly Leu Leu Ser Asn Val Leu Cys Arg Leu Cys Asn Lys Tyr
              145                150                155                160

Arg Val Gly His Val Asp Val Pro Pro Val Pro Asp His Ser Asp Lys
                               165                170                175

Glu Ala Phe Gln Arg Lys Lys Leu Gly Cys Gln Leu Leu Gly Thr Tyr
                          180                185                190

Lys Gln Val Ile Ser Val Val Val Gln Ala Phe
                          195                200

<210> SEQ ID NO 10
<211> LENGTH: 15
<212> TYPE: DNA
<213> ORGANISM: Artificial Sequence
<220> FEATURE:
<223> OTHER INFORMATION: ZFN1a binding site

<400> SEQUENCE: 10
caggccctga accgc                                                       15

<210> SEQ ID NO 11
<211> LENGTH: 6
<212> TYPE: DNA
<213> ORGANISM: Artificial Sequence
<220> FEATURE:
<223> OTHER INFORMATION: ZFN1 cutting site

<400> SEQUENCE: 11 ttctgg                                                                  6

<210> SEQ ID NO 12
<211> LENGTH: 16
<212> TYPE: DNA
<213> ORGANISM: Artificial Sequence
<220> FEATURE:
<223> OTHER INFORMATION: ZFN1b binding  site

<400> SEQUENCE: 12
gattacctgc gctggg                                                      16

<210> SEQ ID NO 13
<211> LENGTH: 15
<212> TYPE: DNA
<213> ORGANISM: Artificial Sequence
```

```
<220> FEATURE:
<223> OTHER INFORMATION: ZF21a binding site

<400> SEQUENCE: 13
ttcaccctcc gcacc                                                    15

<210> SEQ ID NO 14
<211> LENGTH: 7
<212> TYPE: DNA
<213> ORGANISM: Artificial Sequence
<220> FEATURE:
<223> OTHER INFORMATION: ZFN2 cutting site

<400> SEQUENCE: 14 tgctgag                                                              7

<210> SEQ ID NO 15
<211> LENGTH: 18
<212> TYPE: DNA
<213> ORGANISM: Artificial Sequence
<220> FEATURE:
<223> OTHER INFORMATION: ZF21b binding site

<400> SEQUENCE: 15
tatccagatc caggggtt                                                 18

<210> SEQ ID NO 16
<211> LENGTH: 9
<212> TYPE: PRT
<213> ORGANISM: Artificial Sequence
<220> FEATURE:
<223> OTHER INFORMATION: conserved domain of a family of homing
      nucleases

<400> SEQUENCE: 16

Leu Ala Gly Leu Ile Asp Ala Asp Gly
1               5

<210> SEQ ID NO 17
<211> LENGTH: 15
<212> TYPE: DNA
<213> ORGANISM: Artificial Sequence
<220> FEATURE:
<223> OTHER INFORMATION: ZFN1a binding site

<400> SEQUENCE: 17
caggccctga accgc                                                    15

<210> SEQ ID NO 18
<211> LENGTH: 6
<212> TYPE: DNA
<213> ORGANISM: Artificial Sequence
<220> FEATURE:
<223> OTHER INFORMATION: ZFN1 cutting site

<400> SEQUENCE: 18 ttctgg                                                               6

<210> SEQ ID NO 19
<211> LENGTH: 16
<212> TYPE: DNA
<213> ORGANISM: Artificial Sequence
<220> FEATURE:
<223> OTHER INFORMATION: ZFN1b binding site

<400> SEQUENCE: 19
```

```
gattacctgc gctggg                                                     16
```

<210> SEQ ID NO 20
<211> LENGTH: 369
<212> TYPE: PRT
<213> ORGANISM: Homo sapiens

<400> SEQUENCE: 20

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
        355                 360                 365

Thr

<210> SEQ ID NO 21
<211> LENGTH: 368
<212> TYPE: PRT
<213> ORGANISM: Rattus norvegicus

<400> SEQUENCE: 21

```
Met Leu Lys Pro Leu Pro Ser Arg Ser Phe Leu Leu Gln Leu
1               5                   10                  15

Leu Leu Leu Arg Val Gly Trp Ser Ser Lys Val Leu Met Ser Ser Gly
            20                  25                  30

Asn Glu Asp Thr Lys Ser Asp Leu Leu Thr Ser Met Asp Leu Lys
            35                  40                  45

His Leu Ser Val Pro Thr Leu Pro Leu Pro Glu Val Gln Cys Phe Val
        50                  55                      60

Phe Asn Val Glu Tyr Met Asn Cys Thr Trp Asn Ser Ser Ser Glu Pro
65                  70                  75                  80

Gln Pro Thr Asn Leu Thr Met His Tyr Arg Tyr Lys Gly Ser Asp Asn
                85                  90                  95

Asn Thr Phe Gln Glu Cys Ser His Tyr Leu Phe Ser Lys Glu Ile Thr
            100                 105                 110

Ser Gly Cys Gln Ile Gln Lys Glu Asp Ile Gln Leu Tyr Gln Thr Phe
        115                 120                 125

Val Val Gln Leu Gln Asp Pro Gln Lys Pro Gln Arg Arg Ala Glu Gln
130                 135                 140

Lys Leu Asn Leu Gln Asn Leu Val Ile Pro Trp Ala Pro Glu Asn Leu
145                 150                 155                 160

Thr Leu Tyr Asn Leu Ser Glu Ser Gln Val Glu Leu Arg Trp Lys Ser
                165                 170                 175

Arg Tyr Ile Glu Arg Cys Leu Gln Tyr Leu Val Gln Tyr Arg Ser Asn
            180                 185                 190

Arg Asp Arg Ser Trp Thr Glu Gln Ile Val Asp His Glu Pro Arg Phe
        195                 200                 205

Ser Leu Pro Ser Val Asp Glu Gln Lys Leu Tyr Thr Phe Arg Val Arg
    210                 215                     220

Ser Arg Phe Asn Pro Ile Cys Gly Ser Thr Gln Gln Trp Ser Lys Trp
225                 230                 235                 240

Ser Gln Pro Ile His Trp Gly Ser His Thr Ala Glu Glu Asn Pro Ser
                245                 250                 255

Leu Phe Ala Leu Glu Ala Val Leu Ile Pro Val Gly Thr Met Gly Leu
            260                 265                 270

Ile Ile Thr Leu Ile Phe Val Tyr Cys Trp Leu Glu Arg Met Pro Arg
        275                 280                 285

Ile Pro Ala Ile Lys Asn Leu Glu Asp Leu Val Thr Glu Tyr His Gly
    290                 295                 300

Asn Phe Ser Ala Trp Ser Gly Val Ser Lys Gly Leu Thr Glu Ser Leu
305                 310                 315                 320

Gln Pro Asp Tyr Ser Glu Arg Phe Cys His Val Ser Glu Ile Pro Pro
                325                 330                 335

Lys Gly Gly Ala Leu Gly Glu Gly Pro Gly Gly Ser Pro Cys Ser Leu
            340                 345                 350

His Ser Pro Tyr Trp Pro Pro Pro Cys Tyr Ser Leu Lys Pro Glu Ala
        355                 360                 365
```

<210> SEQ ID NO 22
<211> LENGTH: 368
<212> TYPE: PRT
<213> ORGANISM: Artificial Sequence
<220> FEATURE:
<223> OTHER INFORMATION: chimeric IL-2 receptor gamma comprising the rat
IL-2 receptor gamma protein having the ecto domain
of IL-2 gamma receptor from human

<400> SEQUENCE: 22

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Leu Ile Pro Val Gly Thr Met Gly Leu
            260                 265                 270

Ile Ile Thr Leu Ile Phe Val Tyr Cys Trp Leu Glu Arg Met Pro Arg
        275                 280                 285

Ile Pro Ala Ile Lys Asn Leu Glu Asp Leu Val Thr Glu Tyr His Gly
    290                 295                 300

Asn Phe Ser Ala Trp Ser Gly Val Ser Lys Gly Leu Thr Glu Ser Leu
305                 310                 315                 320

Gln Pro Asp Tyr Ser Glu Arg Phe Cys His Val Ser Glu Ile Pro Pro
                325                 330                 335

Lys Gly Gly Ala Leu Gly Glu Gly Pro Gly Gly Ser Pro Cys Ser Leu
            340                 345                 350

His Ser Pro Tyr Trp Pro Pro Pro Cys Tyr Ser Leu Lys Pro Glu Ala

```
<210> SEQ ID NO 23
<211> LENGTH: 23
<212> TYPE: DNA
<213> ORGANISM: Artificial Sequence
<220> FEATURE:
<223> OTHER INFORMATION: a genomic target sequence that is linked to a
      guide RNA (gRNA)
<220> FEATURE:
<221> NAME/KEY: misc_feature
<222> LOCATION: (2)...(21)
<223> OTHER INFORMATION: n= A, T, C or G
<220> FEATURE:
<221> NAME/KEY: misc_feature
<222> LOCATION: (0)...(0)
<223> OTHER INFORMATION: n can be from 1-20 nucleotides

<400> SEQUENCE: 23
gnnnnnnnnn nnnnnnnnnn ngg                                              23
```